United States Patent
Winter et al.

(10) Patent No.: US 12,410,152 B2
(45) Date of Patent: Sep. 9, 2025

(54) OXAZOLE AND THIOAZOLE-TYPE CULLIN RING UBIQUITIN LIGASE COMPOUNDS AND USES THEREOF

(71) Applicant: Proxygen GmbH, Vienna (AT)

(72) Inventors: Georg Winter, Vienna (AT); Cristina Mayor Ruiz, Vienna (AT); Stefan Kubicek, Vienna (AT)

(73) Assignee: PROXYGEN GMBH, Vienna (AT)

( * ) Notice: Subject to any disclaimer, the term of this patent is extended or adjusted under 35 U.S.C. 154(b) by 799 days.

(21) Appl. No.: 17/769,811

(22) PCT Filed: Oct. 16, 2020

(86) PCT No.: PCT/EP2020/079264
§ 371 (c)(1),
(2) Date: Apr. 18, 2022

(87) PCT Pub. No.: WO2021/074414
PCT Pub. Date: Apr. 22, 2021

(65) Prior Publication Data
US 2023/0124700 A1    Apr. 20, 2023

(30) Foreign Application Priority Data

Oct. 16, 2019 (EP) .................................... 19203702
Jun. 8, 2020 (EP) .................................... 20178833

(51) Int. Cl.
| | | |
|---|---|---|
| C07D 401/12 | (2006.01) |
| C07D 235/28 | (2006.01) |
| C07D 417/06 | (2006.01) |
| C07D 417/14 | (2006.01) |
| C07D 471/04 | (2006.01) |

(52) U.S. Cl.
CPC ......... *C07D 401/12* (2013.01); *C07D 235/28* (2013.01); *C07D 417/06* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | |
|---|---|---|
| 2010/0093747 A1 | 4/2010 | Goodhew |
| 2019/0276459 A1 | 9/2019 | Crews et al. |
| 2019/0300521 A1 | 10/2019 | Crew et al. |

FOREIGN PATENT DOCUMENTS

| | | |
|---|---|---|
| WO | WO2005/037845 | 4/2005 |
| WO | WO2012/135296 | 10/2012 |

OTHER PUBLICATIONS

Lai, et al., "Modular PROTAC Design for the degradation of Oncogenic BCR-ABL", *Angewandt Chemi, International Edition*, 55(2):807-810, 2016.
Partial European Search Report for EP Application No. 19 203 702.6 dated Mar. 24, 2020, 13 pages.
International Search Report and Written Opinion for PCT/EP2020/079264 dated Jan. 25, 2021, 20 pages.
Communication pursuant to Article 94(3) EPC for corresponding European Application No. 20 792 419.2 dated Feb. 8, 2024.
Daniels, Danette L., et al.; "Monitoring and deciphering protein degradation pathways inside cells"; Drug Discovery Today: Technologies 2019; 31:61-68.

*Primary Examiner* — Brian Gangle
(74) *Attorney, Agent, or Firm* — Heslin Rothenberg Farley & Mesiti P.C.

(57) ABSTRACT

The present invention relates to compounds with the ability to stimulate/induce ubiquitination of a target protein/target proteins. The compounds of the present invention may stimulate/induce ubiquitination of a target protein/target proteins; i.e. via degradation of a target protein/target proteins by the cullin-RING ubiquitin ligase (CRL). Such target protein/target proteins may be proteins involved in diseases, like cancer, metabolic disorder, infectious disease and/or neurological disorder. The invention further relates to a method for identifying/obtaining and/or testing a compound able to induce ubiquitination of a target protein/target proteins. The invention also relates to the compounds and composition for use as medicaments as well as pharmaceutical compositions comprising these compounds. Particularly, the compounds of the present invention may degrade proteins associated with cancer, metabolic disorder, infectious disease and/or neurological disorder. Furthermore, the present invention relates the compounds for use as a medicament, such as for use in treating cancer, metabolic disorder, infectious disease and/or neurological disorder and to a method for treating a disease, such as cancer, metabolic disorder, infectious disease and/or neurological disorder, comprising administering the compound of the present invention.

18 Claims, 38 Drawing Sheets
Specification includes a Sequence Listing.

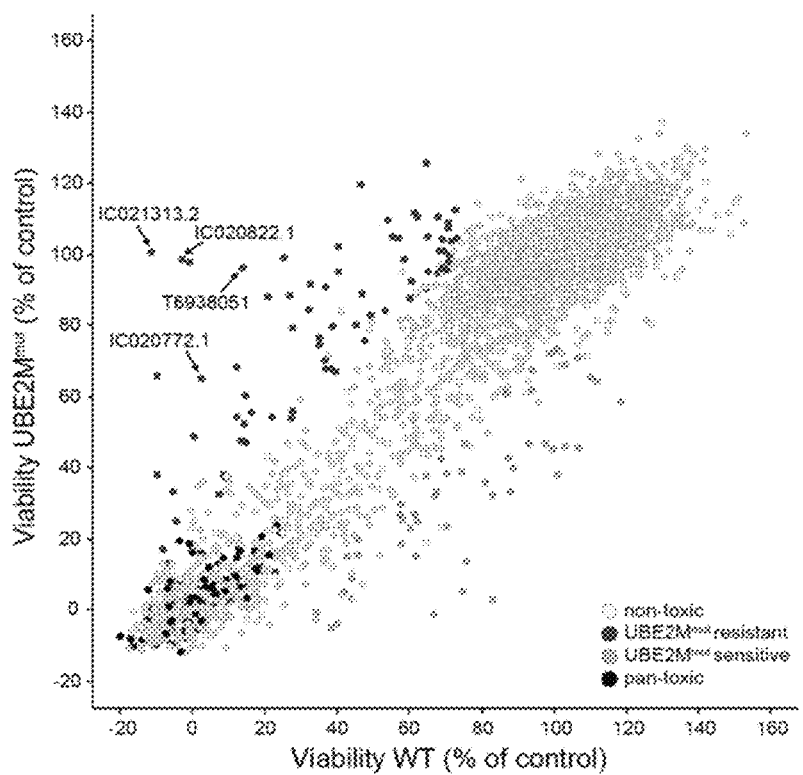
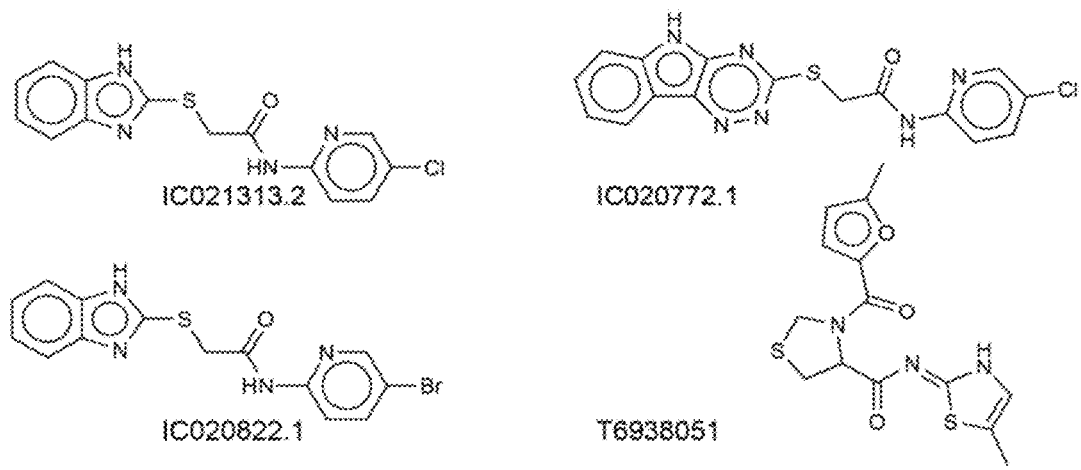
FIG. 3

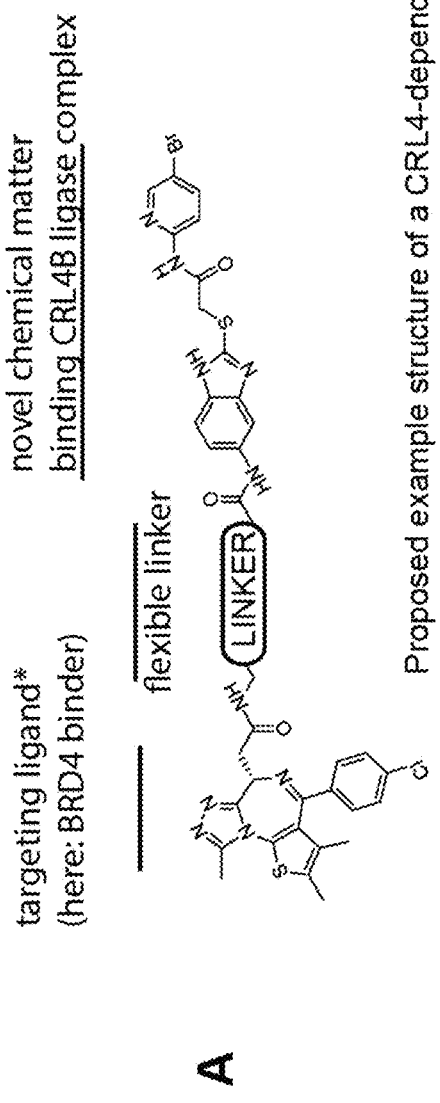
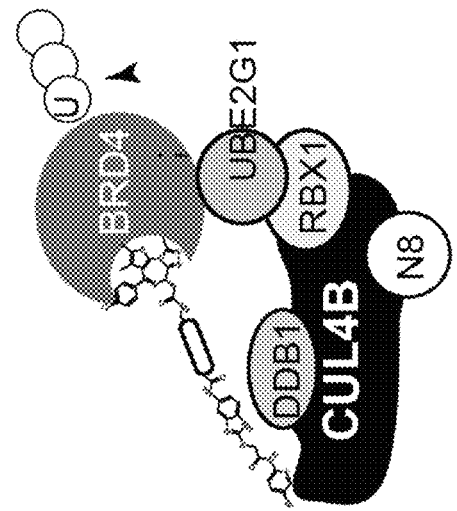
FIG. 11

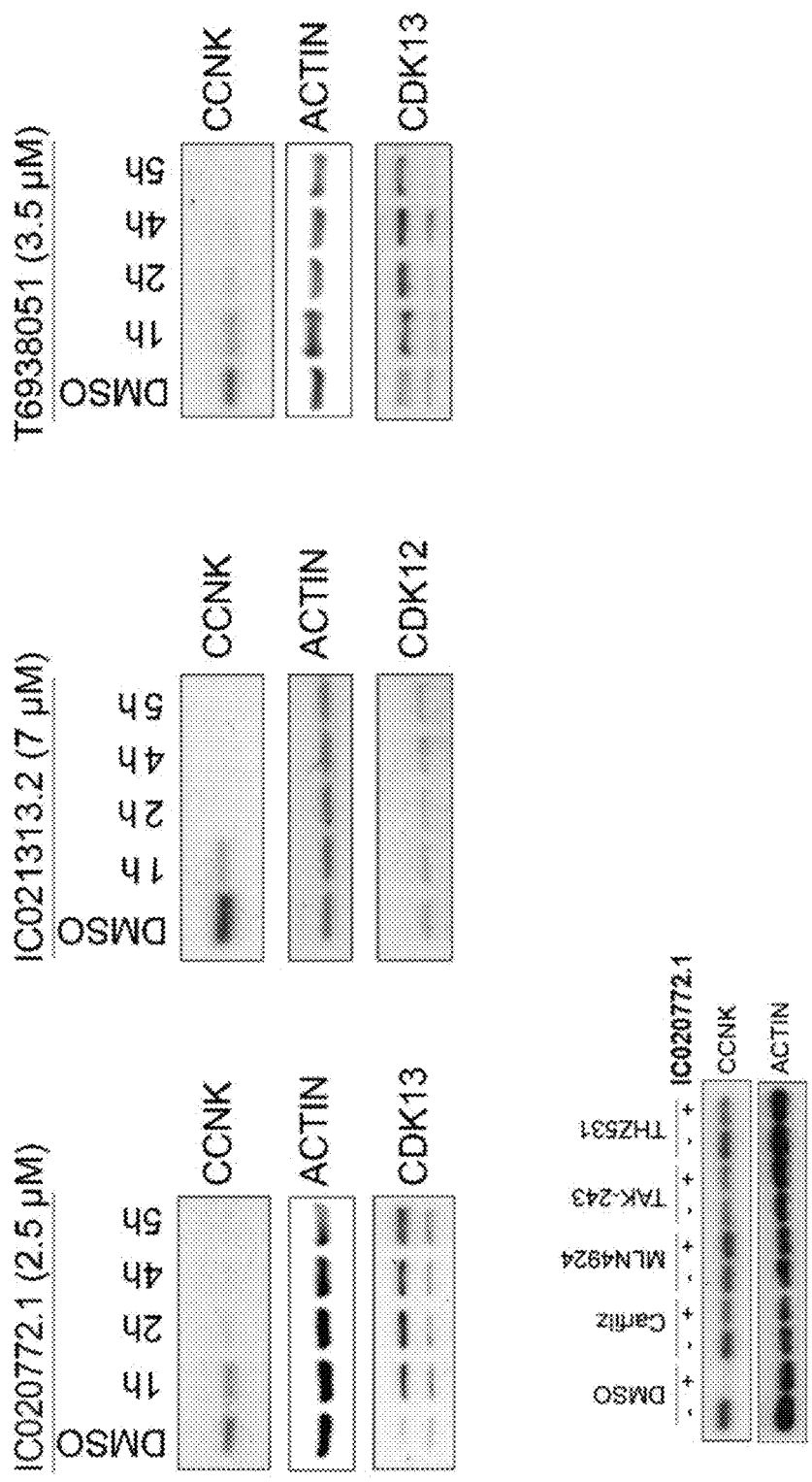
FIG. 19C-D

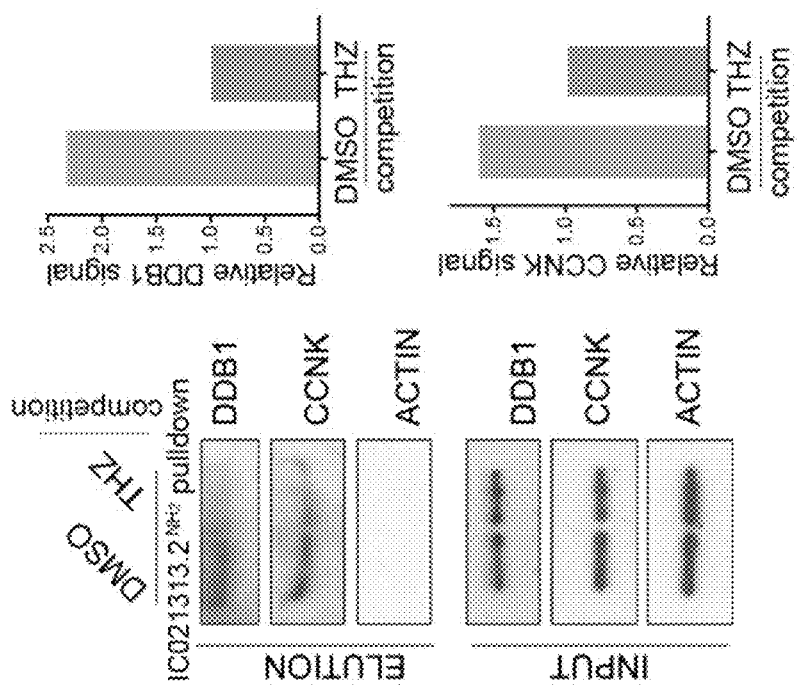
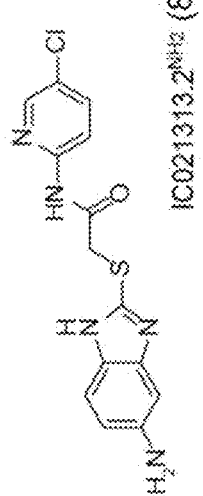
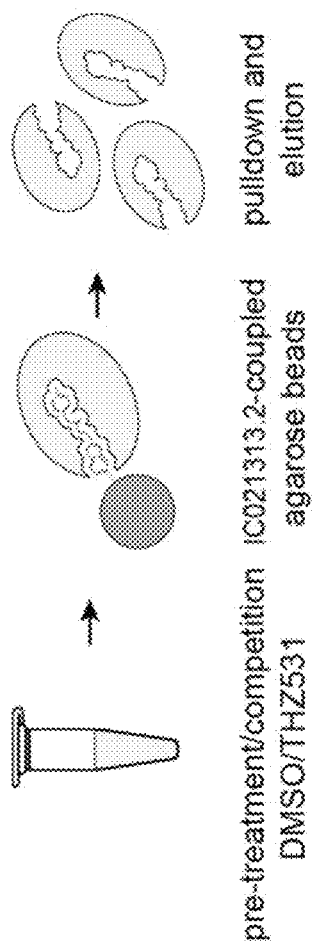
FIG. 20A-C

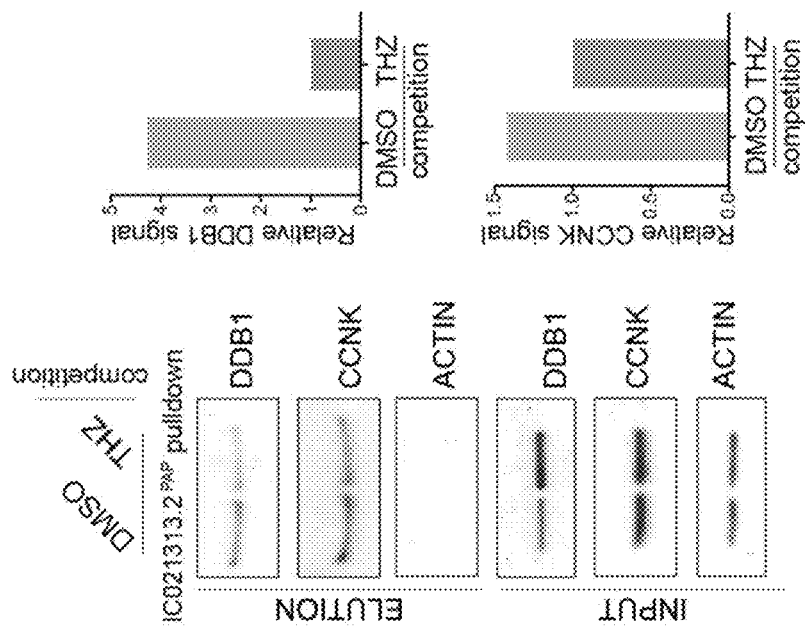
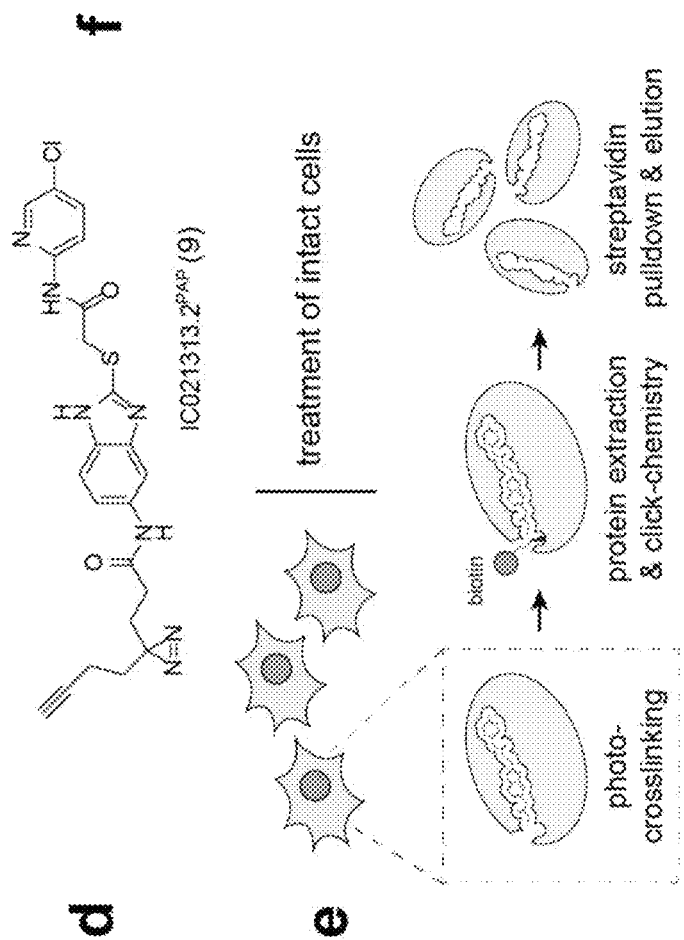
FIG. 20D-F

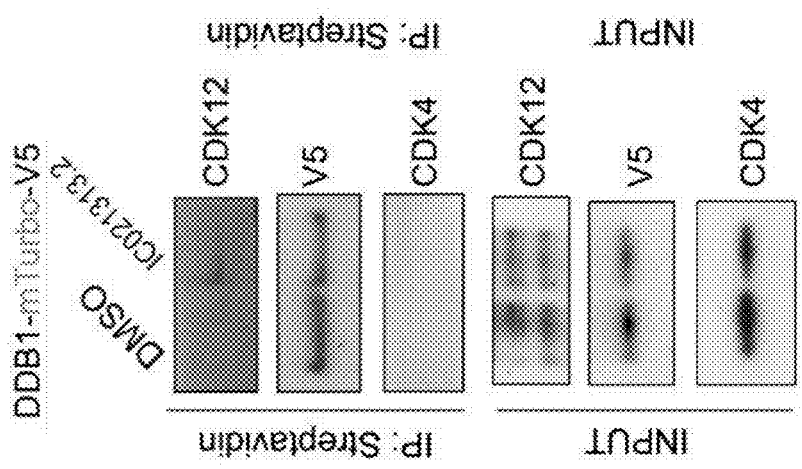
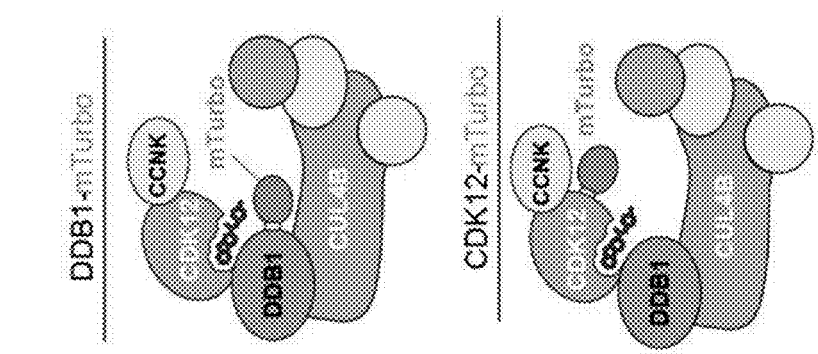
FIG. 20G-H

Figure 21C:
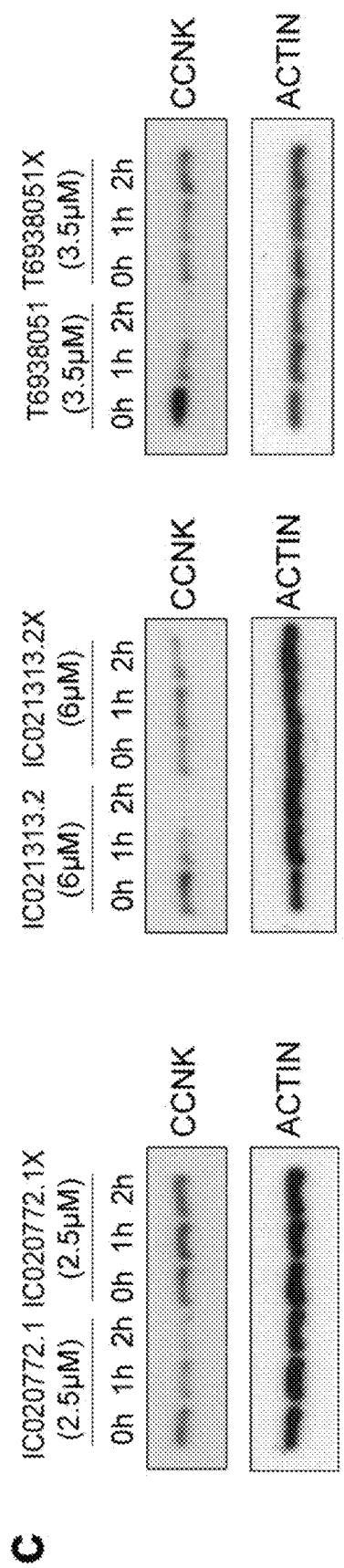

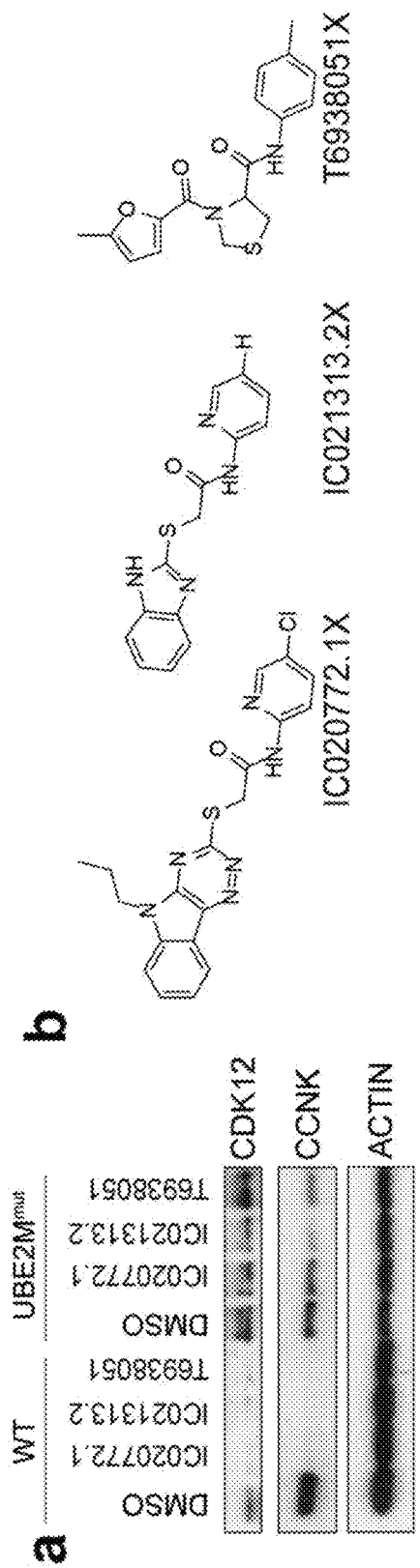
FIG. 21A-B

Figure 23A:
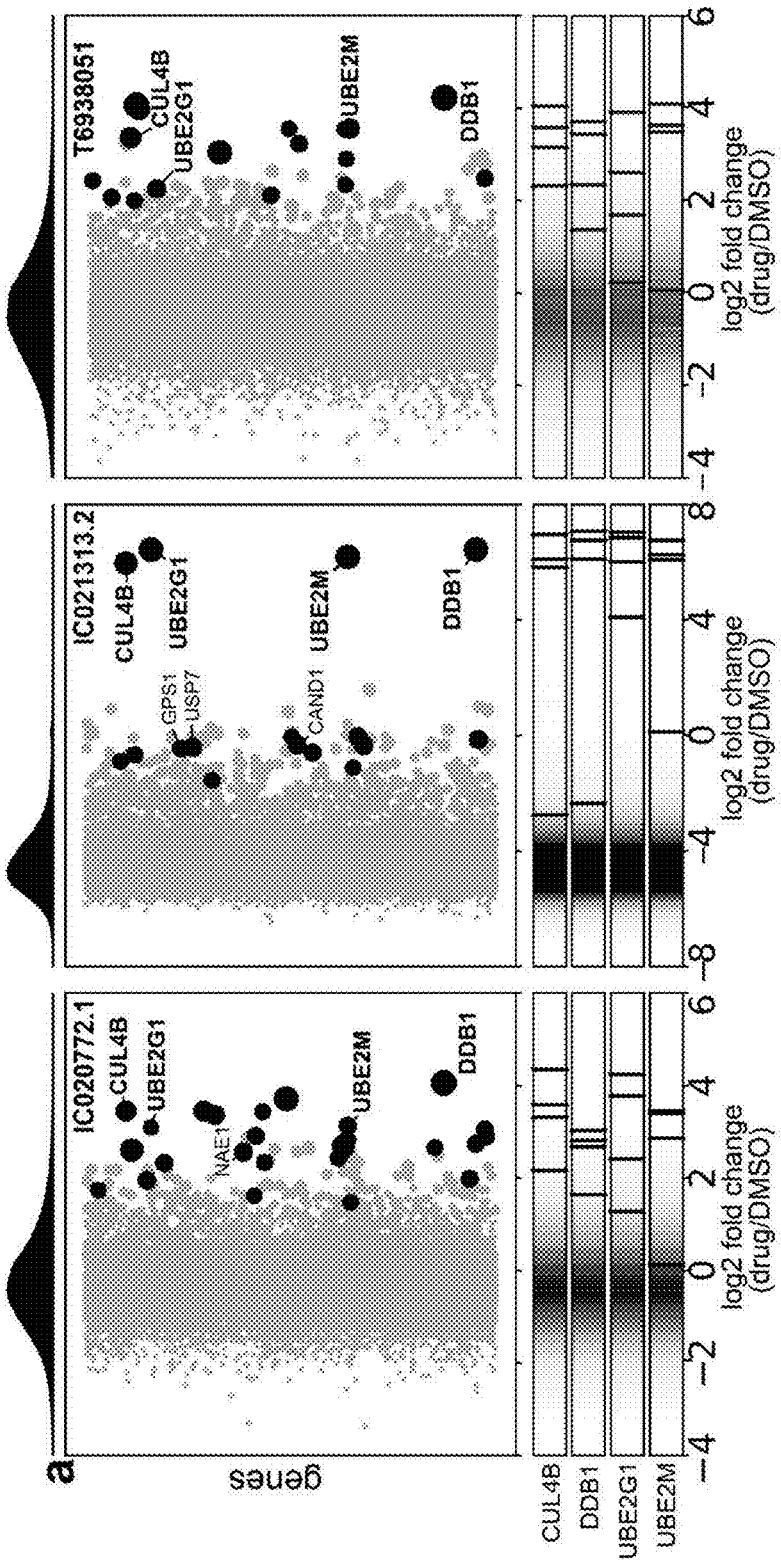

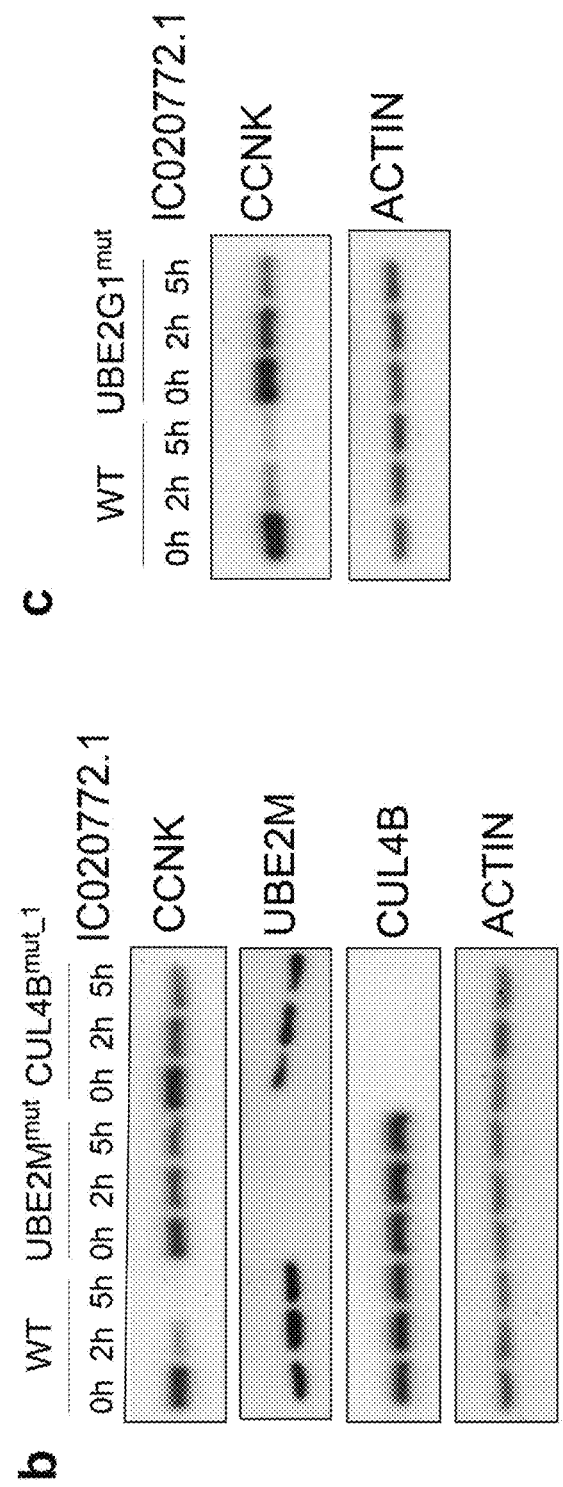
FIG. 23B-C

SEQUENCE LISTING

```
<160> NUMBER OF SEQ ID NOS: 6

<210> SEQ ID NO 1
<211> LENGTH: 35
<212> TYPE: DNA
<213> ORGANISM: Homo sapiens
<220> FEATURE:
<223> OTHER INFORMATION: wild-type UBE2M

<400> SEQUENCE: 1
agacgttgcc ctcgaggtca atgttggggt gatag                              35

<210> SEQ ID NO 2
<211> LENGTH: 17
<212> TYPE: DNA
<213> ORGANISM: Artificial Sequence
<220> FEATURE:
<223> OTHER INFORMATION: mutated UBE2M

<400> SEQUENCE: 2
agacgttggg gtgatag                                                  17

<210> SEQ ID NO 3
<211> LENGTH: 20
<212> TYPE: RNA
<213> ORGANISM: Artificial Sequence
<220> FEATURE:
<223> OTHER INFORMATION: sgUBE2M

<400> SEQUENCE: 3
tcaccccaac attgacctcg                                               20

<210> SEQ ID NO 4
<211> LENGTH: 20
<212> TYPE: RNA
<213> ORGANISM: Artificial Sequence
<220> FEATURE:
<223> OTHER INFORMATION: sgUBE2G1

<400> SEQUENCE: 4
atgacaatga tctctaccga                                               20

<210> SEQ ID NO 5
<211> LENGTH: 20
<212> TYPE: RNA
<213> ORGANISM: Artificial Sequence
<220> FEATURE:
<223> OTHER INFORMATION: sgCUL4A

<400> SEQUENCE: 5
agttctgcag cacataggtg                                               20

<210> SEQ ID NO 6
<211> LENGTH: 20
<212> TYPE: RNA
<213> ORGANISM: Artificial Sequence
<220> FEATURE:
<223> OTHER INFORMATION: sgCUL4B

<400> SEQUENCE: 6
agcatgtggt acttactggg                                               20
```

OXAZOLE AND THIOAZOLE-TYPE CULLIN RING UBIQUITIN LIGASE COMPOUNDS AND USES THEREOF

The present application is a national phase application under 35 U.S.C. § 371 of International Application No. PCT/EP2020/079264, filed Oct. 16, 2020, the entire contents of which are hereby incorporated by reference, and which claims the priority benefit of European Application No. 19203702.6, filed Oct. 16, 2019, and European Application No. 20178833.8, filed Jun. 8, 2020.

This application contains a Sequence Listing which has been submitted electronically in ASCII format and is hereby incorporated by reference in its entirety. The ASCII copy, created on Oct. 24, 2022, is named VOSSP0128US_ST25.txt and is 1,511 bytes in size.

FIELD OF THE INVENTION

The present invention relates to compounds with the ability to modulate/stimulate/induce, particularly induce ubiquitination of a target protein/target proteins. The compounds of the present invention may stimulate/induce ubiquitination of a target protein/target proteins; i.e. via degradation of a target protein/target proteins by the cullin-RING ubiquitin ligase (CRL). Such target protein/target proteins may be proteins involved in diseases, like cancer, metabolic disorder, infectious disease and/or neurological disorder. The invention further relates to a method for identifying/obtaining and/or testing a compound able to induce ubiquitination of a target protein/target proteins. The invention also relates to the compounds and composition for use as medicaments as well as pharmaceutical compositions comprising these compounds. Particularly, the compounds of the present invention may facilitate degradation of proteins associated with cancer, metabolic disorder, infectious disease and/or neurological disorder. Furthermore, the present invention relates the compounds for use as a medicament, such as for use in treating cancer, metabolic disorder, infectious disease and/or neurological disorder and to a method for treating a disease, such as cancer, metabolic disorder, infectious disease and/or neurological disorder, comprising administering the compound of the present invention.

BACKGROUND OF THE INVENTION

Protein degradation plays a central role in many cellular functions such as for cell maintenance and normal function. Accordingly, degradation of proteins, such as proteins which are associated with cellular functions, e.g., maintenance function, has implications for the cell's proliferation, differentiation, and death. In this context, the chemical induction of targeted protein degradation (TPD), thereby reducing the activity of a protein by removing the target protein, is a highly promising paradigm in drug discovery compared to inhibitors of proteins which would reduce the activity of a protein by simply blocking said protein. Utilizing a cell's protein degradation pathway can, therefore, provide means for reducing or removing protein activity.

Until recently, small molecules that induce protein destabilization typically emerged serendipitously. Examples for this are the estrogen receptor (ER) modulator Fulvestran, or the $CRL4^{CRBN}$ modulators thalidomide and related compounds such as lenalidomide or pomalidomide (collectively referred to as "IMiDs" and also known in the art as "molecular glue"). All these cases represent approved drugs, which clinically validates the concept of TPD as a therapeutic reality. Lenalidomide was, in fact, with total revenues of S9.7 billion, one of the commercially most successful drugs of 2018.

Noteworthy, it took several decades of research to decipher the molecular mechanism of IMIDs as small molecule degraders. Rational strategies to generalize the concept of TPD were described by Winter et al. (Winter, G. E.*, Buckley, D. L.*, Paulk, J., Roberts, J., Souza, A., DePhagano, S., and Bradner, J. E. (2015) Phthalimide Conjugation as a Strategy for in vivo Target Protein Degradation. Science 348, 1376-81), describing the formation of heterobifunctional molecules by conjugating IMID-like chemical structures to known targeting ligands via flexible linkers. These heterobifunctional small molecules (often also called "degraders") are shown to function via binding to a protein of interest (via the interchangeable targeting ligand) and the E3 ligase $CRL4C^{RBN}$, i.e. via the IMID-like chemical agent. Thereby, binding induces molecular proximity between the target protein and the E3 ligase, prompting ubiquitination and proteolytic degradation of the former. Particularly, the ubiquitin conjugation on target proteins is mediated by an enzymatic cascade comprised by an E1 ubiquitin-activating enzyme, an E2 ubiquitin-conjugating enzyme and an E3 ubiquitin ligase that attach ubiquitin to the target protein (Hershko et al., Nat. Med. 6, 1073-1081 (2000); Komander et al., Annu. Rev. Biochem. 81, 203-229 (2012)).

Thus, the ubiquitin-proteasome pathway, one of the cell's major degradation pathways and which is a critical pathway that regulates key regulator proteins and degrades misfolded and abnormal proteins, is found to be a valuable tool, in particular in therapeutic applications, for degrading target proteins by covalent attachment of ubiquitin to the said target protein.

The development of heterobifunctional degraders (PROTAC) that have the ability to hijack the CRBN ligase complex is associated with certain caveats. For example, only certain E3 ligases can be harnessed by such heterobifunctional degraders. Thereby, ligands typically bind to CRBN, VHL, cIAIP or MDM2. Furthermore, a part of the heterobifunctional degrader structure of PROTACs is a "ligand to the target (protein)", thereby precluding the application of the technology to "unligandable" proteins (see, e.g., Surade and Blundell (2012); Chemistry & Biology, Volume 19, Issue 1, pp. 42-50; wherein as corresponding examples orphan receptors or other proteins where ligands are unknown are mentioned). Sometimes, the high molecule weight of the resulting heterobifunctional degraders may impact pharmacology and bioavailability.

There is a need for efficient small molecules that are able to bind to E3 ligase components, and which are thus suitable to be to degrade desired target proteins.

Small molecules may modulate E3 ligases and other components of the ubiquitin-proteasome pathway by operating via a "molecular glue" type of mechanism. By this means, such compounds may not rely on the availability of an accessible, hydrophobic binding pocket. For example, IMiDs can induce cooperative associations with target proteins that are naturally not bound by CRBN, i.e. without requiring an additional linkage with a targeting-moiety. This in turn prompts ubiquitination and proteasomal degradation of bound target proteins such as the transcription factors IKZF1 and IKZF3. As another example, aryl sulfonamides can re-direct the activity of the E3 ligase DCAF15 to degrade the splicing factor RBM39 in an analogous manner as IMiDs. Similarly, the phytohormone auxin is known to re-direct the target space of the E3 ligase Tir1 to induce degradation of the Aux/IAA transcriptional repressors.

Until now, targeting proteins which are devoid of a hydrophobic binding pocket or a binding site that leads to inactivation of said target proteins are beyond the reach of commonly used compounds which may be developed for therapeutic uses. In other words, this approach does not allow degradation of target proteins, such as target proteins without an accessible hydrophobic pocket or inhibitory binding site. In this regard, compelling disease-relevant targets such as MYC, RAS, or b-catenin, remain beyond the reach of therapeutic development.

Thus, novel paradigms in drug design are highly needed. Hence, in view of the above, the technical problem underlying the present invention is the provision of compounds and methods for identifying compounds that are able to induce ubiquitination of a target protein/target proteins, in particular a target protein/target proteins desired to be degraded in a cell, like a diseased cell.

The solution to this technical problem is provided by the embodiments as defined herein below and as characterized in the claims.

SUMMARY OF THE INVENTION

The invention relates to the compounds of formulae (I) and (II) as described herein as well as to their use in the treatment of various diseases which can be treated by targeted degradation of certain proteins.

The compounds as disclosed herein and in context of the invention are capable of modulating/stimulating/inducing ubiquitination of a target protein/target proteins, e.g. via degradation of a target protein/target proteins by the ubiquitination system. In context of the invention, the compound has the capacity of modulating/stimulating/inducing, particularly inducing ubiquitination of a target protein/target proteins by enhancing the cullin-RING ubiquitin ligase activity/CRL activity.

The compounds as disclosed herein and in context of the invention may particularly be used as molecular glues as described herein and illustrated in the appended Examples. The compounds of the invention are also envisaged to be used as building blocks for the development of heterobifunctional molecules, such as PROTAC®s (proteolysis targeting chimera).

It is in particular to be understood that for the use as a PROTAC®, the compounds of the present invention (such as the compound of formula (I) or the compound of formula (II)) preferably have the -L-TBM as a substituent on Ring a. Conversely, the compounds of the present invention wherein the group -L-TBM is absent are believed to be in particular suitable (and typically acting) as molecular glue. Molecular glues as well as such PROTACs (heterobifunctional molecules) are in particular useful for medical interventions. Accordingly, the present invention also relates to pharmaceutical compositions comprising the novel and inventive "molecular glues" and/or "heterobifunctional degraders/molecules" comprising (as part, inter alia, EBM) the compounds of the present invention.

It is envisaged that the compounds of the present invention wherein the group -L-TBM is absent can be used in building blocks for the development of PROTAC®s. When being used as building blocks for the development of PROTAC®s, it is preferred that the compounds of the present invention wherein -L-TBM is absent are attached to the rest of the PROTAC® via ring a, for example by the formation of a covalent bond between ring a and the rest of the PROTAC®. The terms "PROTAC®", "PROTAC™", "PROTAC", "PROTAC®s", "PROTAC™s", "PROTACs" or "proteolysis targeting chimera" are used interchangeably and refer in particular to heterobifunctional compounds. As also described herein, PROTACs are known to the person skilled in the art to have advantageous properties such as but not limited to their interchangeable target binding moiety which can bind to a desired target to be degraded. However, certain protein(s) to be degraded are considered "unligandable" and are therefore not degradable by PROTACs. Such "unligandable" protein(s) (yet desired to be degraded) cannot be degraded via the PROTAC mechanism because no target binding moiety (moieties) for the "unligandable" protein(s) are known or available. "Unligandable" proteins are known in the art and include, inter alia, those having featureless binding sites, lack of hydrogen-bind donors and acceptors, the need for adaptive changes in conformation, and the lipophilicity of residues at the protein-ligand interface; see, e.g., Surade and Blundell (2012); Chemistry & Biology, Volume 19, Issue 1, pp. 42-50. Accordingly, and as described herein, the compounds of the present invention, however, can be of advantage because they are able to modulate/induce/stimulate degradation of "unligandable" protein(s), for example as "molecular glue".

Molecular glues can degrade target protein(s) by orchestrating direct interactions between target and cullin-RING ligases (CRLs). Molecular glues have the potential to induce the elimination of disease-relevant proteins otherwise considered "undruggable". The mechanism of action by molecular glues can be exemplified by the clinically approved molecular glues/degraders of thalidomide analogs (IMiDs). Binding of IMiDs to the $CRL4^{CRBN}$ E3 ligase causes recruitment of selected zinc finger transcription factors (TFs), leading to their ubiquitination and subsequent proteasomal degradation (Lu, G. et al. *Science* 343, 305-309, doi:10.1126/science.1244917 (2014); Kronke, J. et al. *Science* 343, 301-305, doi:10.1126/science.1244851 (2014); Sievers, Q. L. et al. *Science* 362, doi:10.1126/science.aat0572 (2018); Gandhi, A. K. et al. *British journal of haematology* 164, 811-821, doi:10.1111/bjh.12708 (2014)).

Noteworthy, IMiDs have per se no measurable binding affinity to the degraded TFs. However, they orchestrate molecular recognition between ligase and TF by inducing several protein-protein interactions proximal to the binding interface. Certain aryl sulfonamides around the clinically tested compound indisulam act as molecular glues between the $CRL4^{DCAF15}$ ligase and the splicing factor RBM39, causing the targeted degradation of the latter (Han, T. et al., *Science*, doi:10.1126/science.aal3755 (2017); Uehara, T. et al. Selective degradation of splicing factor CAPERalpha by anticancer sulfonamides. *Nat Chem Biol* 13, 675-680, doi: 10.1038/nchembio.2363 (2017); Bussiere, D. E. et al. *Nat Chem Biol* 16, 15-23, doi:10.1038/s41589-019-0411-6 (2020); Ting, T. C. et al. *Cell reports* 29, 1499-1510.e1496, doi:10.1016/j.celrep.2019.09.079 (2019); Faust, T. B. et al. *Nat Chem Biol* 16, 7-14, doi:10.1038/s41589-019-0378-3 (2020); Du, X. et al. *Structure* (London, England: 1993) 27, 1625-1633.e1623, doi:10.1016/j.str.2019.10.005 (2019).)

The molecular glue mechanism of action therefore enables the destabilization of target proteins otherwise considered "unligandable" and thus outside the reach of both traditional small-molecule inhibitors and also of heterobifunctional degraders.

The compounds of the invention are able to induce the destabilization of disease associated target proteins, such as cyclin K (CCNK), CDK12 and/or CDK13. The compounds of the invention act, inter alia, as CCNK degraders. As described herein and illustrated in the appended Examples, the compounds of the invention are able to degrade target protein(s), such as cyclin K (CCNK), CDK12 and/or CDK13, independent of a dedicated substrate receptor, which functionally differentiates this mechanism from previously characterized degraders.

As discussed above, the compounds of the invention are also envisaged to be used as PROTACs. The term "PROTAC®" is used interchangeably and refers to heterobifunctional compounds as used herein refer to a compound that induce proteasome-mediated degradation of selected proteins via their recruitment to E3 ubiquitin ligase and subsequent ubiquitination (Crews C, Chemistry & Biology, 2010, 17(6):551-555; Schnnekloth J S Jr., Chembiochem, 2005, 6(1):40-46). The term refers to proteolysis-targeting chimera molecules having generally three components, an E3 ubiquitin ligase binding group (i.e. an E3 Ligase Binding Moiety (EBM)), optionally a linker (L), and a protein binding group of a target (i.e. a target binding moiety (TBM)). A PROTAC/proteolysis-targeting chimera may be illustrated by the following formula:

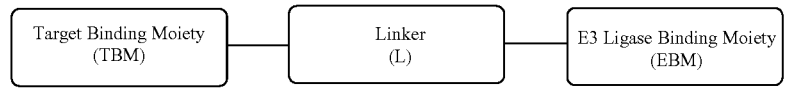

wherein TBM is a moiety binding to a target protein,
preferably wherein the TBM is a moiety binding to a target protein associated with cancer, metabolic disorders, neurologic disorders or infectious diseases;
more preferably wherein the one or more protein(s) associated with cancer is selected from the group consisting of DNA-binding proteins including transcription factors such as ESR1, AR, MYB, MYC; RNA binding proteins; scaffolding proteins; GTPases such as HRAS, NRAS, KRAS; solute carriers; kinases such as CDK4, CDK6, CDK9, EGFR, SRC, PDGFR, ABL1, HER2, HER3, BCR-ABL, MEK1, ARAF, BRAF, CRAF, phosphatases, bromodomain- and chromodomain containing proteins such as BRD2, BRD3, BRD4, CBP, p300, ATAD2, SMARCA2, SMARCA4, PBRM1, G-protein coupled receptors; anti-apoptotic proteins such as SHP2, PTPN1, PTPN12; immune regulators such as PDL1 and combinations thereof;
even more preferably wherein the one or more protein(s) associated with cancer is selected from the group consisting of BRD2, BRD3, BRD4, CBP, p300, ATAD2, SMARCA2, SMARCA4, PBRM1, CDK4, CDK6, CDK9, CDK12 and/or CDK13, EWS-FL1, CDC6, CENPE, EGFR, SRC, PDGFR, ABL1, HER2, HER3, BCR-ABL, MEK1, ARAF, BRAF, CRAF, HRAS, NRAS, KRAS, BCL2, MCL2, SHP2, PTPN1, PTPN12, ESR1, AR, MYB, MYC, PDL1 and combinations thereof;
even more preferably wherein the one or more protein(s) associated with cancer are selected from the group consisting of KRAS, NRAS, MYC, MYB, ESR1, AR, EGFR, HER2, BCR-ABL1 and BRAF;
most preferably the one or more protein(s) associated with cancer are selected from the group consisting of KRAS, NRAS, MYC and MYB.

more preferably wherein the one or more protein(s) associated with metabolic disorders are selected from the group consisting of ARX, SUR, DPP4 and SGLT;
more preferably wherein the one or more protein(s) associated with neurologic disorders are selected from the group consisting of Tau and beta-amyloid; and wherein the one or more protein(s) associated with infectious diseases are selected from the group consisting of CCR5 and PLA2G16:
wherein L is a linker moiety; and
wherein EBM is a moiety modifying the function of the E3 ligase and/or binding to at least one regulator or member of the E3 ligase complex;
preferably wherein the at least one member of the E3 ligase complex (CRL) is selected from the group consisting of CUL4B; DDB1; RBX1; UBE2G1; and CUL4A; and wherein the at least one regulator of the E3 ubiquitin ligase complex is selected from the group consisting of, UBE2M; UBA3; UBE2F; NAE1; COPS1, COPS2, COPS3, COPS4, COPS5, COPS6, COPS7A, COPS7B, COPS8; DCUN1D1; DCUN1D2; DCUN1D3; DCUN1D4; DCUN1D5;
more preferably wherein the at least one member or regulator of the E3 ubiquitin ligase complex is CUL4B or DDB1;
even more preferably wherein the EBM is comprised in a structure selected from the group consisting of any of compounds of formulae (I) and (II).

It is to be understood that when the EBM comprises a structure selected from the group consisting of any of compounds of formulae (I) and (II), the TBM -L-EBM structure indicated above is formally obtained by establishing a bond between the linker moiety (which is preferably also connected to the TBM) and the EBM comprising the structure selected from any of compounds of formulae (I) and (II), e.g. by formally removing a hydrogen radical from both the linker and the compound selected from any compound of formulae (I) and (II) belonging to the EBM and combining the thus hypothetically obtained radical of the linker with the radical of the structure comprising the compound selected from any compound of formulae (I) and (II) belonging to the EBM so as to form a bond between the two atoms hypothetically having born the two radicals, respectively. Preferably, the EBM is a structure selected from the group consisting of any of compounds of formulae (I) and (II).

In other words, the compound of formula (I) or (II), wherein L-TBM is present, is an example of a PROTAC of the following formula which was referred to hereinabove:

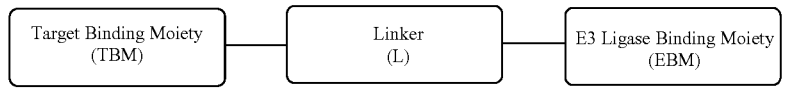

As disclosed herein and in context of the invention, the term "compound" may comprise chemical, biochemical and/or biological molecules. For example, the compound in context of the invention comprises, but is not limited to, compounds which may comprise biological/biochemical parts, like, inter alia, peptide linkers bound to said compounds. As used in context of this invention, the term "identifying" or "to identify" in context of the method of the present invention also comprises "testing" and/or "obtaining" compounds that are able of inducing ubiquitination of (a) proteins of interest/target protein(s).

The compounds as disclosed herein and in context of the invention comprise a E3 ligase binding moiety/EBM (consisting or comprising the compounds of formula (I) or formula (II)), a linker/L and a target binding moiety/TBM and are able of stimulating/inducing ubiquitination of a target protein/target proteins, e.g. via degradation of a target protein/target proteins by the ubiquitination system. In context of the invention, such compound has the capacity of modulating/stimulating/inducing ubiquitination of a target protein/target proteins by enhancing the cullin-RING ubiquitin ligase activity/CRL activity.

Said "target protein" is, in particular a target protein desired to be degraded in particular via (an) ubiquitination(s). The term "target protein" as used in this context also comprises a plurality of proteins of target proteins. This is also illustrated in the appended examples. In one embodiment, the "target protein" in context of this invention is a protein which is desired or is desirable to be degraded in an in vivo or in vitro situation, for example in a diseased cell, like a cancer cell. Particular target proteins are, in one specific embodiment, proteins that are the cause, the driver and/or the maintaining entity of a malignancy, disease, or a diseased status. Such target proteins may comprise proteins that are overexpressed and/or overactive in a diseased cell, like in a cancer cell. Accordingly, in one embodiment, the target protein is involved in the cause, development and/or maintenance of the diseased status of a cell and/or a tissue. Potential target proteins are also discussed herein below and illustrative, non-limited examples are provided herein below. Particular examples of such target proteins are CDK12, CDK13 and/or CCNK. In this context, CDK12, CDK13 and/or CCNK may be desired or desirable to be degraded in an in vivo or in vitro situation, for example in a diseased cell, like a cancer cell. Thus, the target protein(s) as disclosed herein and in the context of the invention may be target protein(s) associated with cancer, wherein the one or more protein(s) associated with cancer may be selected from the groups consisting of CDK12, CDK13 and CCNK. As another particular example, the target protein may be a target protein associated with cancer, wherein the one or more protein(s) associated with cancer may be kinases, such as CDK12 and/or CDK13.

For example, said compound may facilitate the recognition of a target protein by the E3 ligase complex or may facilitate ubiquitination even without physically engaging the target protein at the same time. The compound may also enable said recognition of a target protein by the E3 ligase complex. A further non-limiting option of the "induction of ubiquitination of a target protein" may comprise the conformational change of the target protein that has been induced as a direct consequence of binding/interaction with said compound inducing the ubiquitination of the target protein. For example, binding of a compound as described herein and as illustrated in the appended examples to a target protein may lead to a conformational change of said protein and thereby stabilize an interaction of one or more target protein(s) with one or more component(s) of the E3 ligase complex that results in ubiquitination and degradation of said one or more target protein(s). Particularly, as illustrated in the appended examples, a compound binding to CDK12/13:CCNK prompts interaction with a DDB1:CUL4B E3 ligase complex, leading to the ubiquitination and degradation of CCNK. By this means, a target protein as described herein and illustrated in the appended examples, such as CCNK, may be degraded via an indirect binding mechanism of a compound as described herein, such as by binding of said compound to a protein associated with a target protein. As illustrated in the appended examples, a compound may bind to CDK12/13, which is associated with CCNK, thereby leading to the ubiquitination and degradation of CCNK. This interaction is independent from a particular substrate receptor of an E3 ligase. Thus, a compound as described herein and in context of the invention can degrade one or more target protein(s) via an E3 ligase independent of a particular substrate receptor of said E3 ligase.

In particular, based on the experimental data provided herein, it has been shown that the compounds of the present invention bind in particular to the active site of CDK12/13, thereby prompting a change in structural conformation, which promotes the binding of CDK12:CCNK and CDK13:CCNK, respectively, to DDB1:CUL4B. As such, CDK12 and CDK13 basically serve to present CCNK to the ligase, leading to the degradation of, among others, CCNK, followed by a potentially slightly weaker degradation of CDK12 and CDK13.

Said "enhanced cullin-RING ubiquitin ligase activity"/"enhanced CRL activity" means that said cullin-RING ubiquitin ligase activity/CRL activity is enhanced in the presence of the compound of the present invention compared to the cullin-RING ubiquitin ligase activity/CRL activity in the absence of said compound. Accordingly, the present invention relates to a compound with the capacity to induce and/or stimulate the ubiquitination of a target protein/target proteins via enhancing the CRL activity. The cullin-RING ubiquitin ligase activity/CRL activity may be determined by methods known in the art and provided below as well as illustrated by the appended Examples.

The enhanced CRL activity is induced by the presence of said compound. Said compound may be able to induce molecular proximity between a component of a E3 ligase complex/cullin-RING ubiquitin ligase complex/CRL complex and a target protein/target proteins which may be bound to the compound or which may be part of a ternary complex comprising the E3 ligase complex/cullin-RING ubiquitin ligase complex/CRL complex, the target protein/target proteins and the compound. As is evident from the appended Examples, the compound of the present invention may bind a target protein/target proteins via the target binding moiety/TBM of the compound and bind or modify the function of the E3 ligase complex/cullin-RING ubiquitin ligase complex/CRL complex, for example by recruiting the target protein/target proteins bound to the target binding moiety/TBM of the compound to the E3 ligase complex/cullin-RING ubiquitin ligase complex/CRL complex. For example, the compound may bind to at least one member of the E3 ligase complex/cullin-RING ubiquitin ligase complex/CRL complex and the target protein. As another example, the compound in context of the invention may alter the function of a target protein, for example by modifying posttranslational changes of a target protein. A posttranslational modification may include but is not limited to the phosphorylation status of a protein, e.g. a tyrosine kinase phosphorylating a protein. Thus, the compound may induce ubiquitination of a target protein, e.g., by modifying a target protein in that the target protein becomes accessible for a E3 ligase complex/cullin-RING ubiquitin ligase complex/CRL complex, thereby the compound may not associate with a target protein and/or E3 ligase complex/cullin-RING ubiquitin ligase complex/CRL complex.

The target protein/target proteins may be ubiquitinated by the E3 ligase complex/cullin-RING ubiquitin ligase complex/CRL complex. Particularly, the inventors found that target proteins including those devoid of a hydrophobic binding pocket and/or inhibitory binding site can be recognized by the compounds of the present invention. Such target proteins may further include proteins which are not recognized E3 ligase complex/cullin-RING ubiquitin ligase complex/CRL complex in the absence of the compound of the present invention. Thus, it has been surprisingly found that the compounds of the present invention are able to induce ubiquitination of the target protein/target proteins, i.e. via degradation of the target protein/target proteins by the ubiquitination system.

DESCRIPTION OF THE INVENTION

Several target proteins involved in the cause, development and/or maintenance of a diseased status are devoid of obvious ligand-binding sites, for example inhibitory binding sites, or hydrophobic pockets. Such target proteins include but are not limited to transcription factors, such as the zinc-finger transcription factors IKZF1 and IKZF3, which are devoid of hydrophobic pockets. As another example, such target proteins may include but is not limited to CDK12, CDK13 and/or CCNK. As yet another example, such target protein(s) may include but are not limited to kinases such as CDK12 and/or CDK13. Moreover, target proteins which may not comprise a binding site that results in an altered function of said target protein, such as inhibition or activation upon binding of a compound to said binding site, are "undruggable" drug targets because compounds directed to target proteins involved in the cause, development and/or maintenance of a diseased status comprise compounds that recognize hydrophobic binding pockets and/or a binding site altering the function of said target protein.

Compounds which may act via ubiquitination of the target protein, thereby degrading the target protein by the ubiquitination system could overcome these limitations by connecting a component of the E3 ligase and target protein. These molecules could orchestrate novel interactions between a component of the E3 ligase and a target protein at the dimerization interface to form a trimeric complex comprising the component of the E3 ligase, the molecule and the target protein.

For example, such compounds may be molecular glues as described herein and used in context of the invention. As described herein and illustrated in the appended Examples, said molecular glues are able to degrade "undruggable" and/or "unligandable" proteins.

As used herein and as also discussed herein above, the term "unligandable" refers to a protein that cannot be bound by ligands and/or that does not possess a binding site suitable for binding of said unligandable protein with a ligand. For example, whether a target protein is unligandable may be determined using a structure-based algorithm, wherein the capability of binding of ligands to a protein is assessed based on parameters computed for binding pockets on a protein including parameters such as but not limited to volume, surface area, lipophilic surface area, depth and/or hydrophobic ratio.

As used herein, the term "undruggable" refers to a protein refers to a protein that cannot be bound by a drug compound and/or that does not possess a binding site suitable for binding of said undruggable protein with a drug compound. Thus, an undruggable protein refers to a protein which does not successfully interfere with a drug compound (e.g. a ligand such as an antibody) used in therapy. Therefore, typically, an undruggable protein may be a protein that lacks a binding site for a drug compound or for which, despite having a binding site, successful targeting of said site has proven intractable.

Further, molecular glues as described herein and illustrated in the appended Examples may degrade one or more target protein(s) via interaction with a component of the cullin RING E3 ligase present in several family members of the cullin RING E3 ligase. Particularly, the family members of the cullin RING E3 ligase can be diversified, e.g., by their respective substrate receptors, such as CRBN or DCAF15. The compounds, in particular molecular glues, as described herein can bind to components of the cullin RING E3 ligase family other than the substrate receptor, and thus these compounds may degrade one or more target protein(s) independent from the substrate receptor. Thus, the ability of molecular glues to degrade one or more target protein(s) via interaction with a cullin RING E3 ligase may not be limited to a particular family member of a cullin RING E3 ligase.

For example, a molecular glue as described herein and illustrated in the appended examples may degrade one or more target protein(s) associated with cancer, such as CDK12, CDK13 and/or cyclin K (CCNK). Thereby, the mechanism of action by molecular glues resulting in degradation of one or more target protein(s) such as CDK12, CDK13 and/or cyclin K (CCNK), can be due to the ability of molecular glues to orchestrate protein-protein interactions between a cullin RING E3 ligase and one or more target protein(s) to be degraded. As described herein and illustrated in the appended examples, this can be achieved by stabilizing an interaction of CDK12 and/or CDK13 bound to CCNK with the cullin RING E3 ligase, particularly one or more components of the cullin RING E3 ligase such as CUL4B and/or DDB1.

In particular when using the compounds of the present of formula (I) or (II) and related formulae as molecular glue, it is preferred that -L-TBM is absent, i.e. that at the position where -L-TBM is indicated in the compounds of the present invention, -L-TBM is replaced by a hydrogen. It has been found that the compounds of the present invention can act as molecular glue even in the absence, or particularly well in the absence, of -L-TBM.

In this context, the present invention provides novel compounds that modulate/stimulate/induce ubiquitination of a target protein/target proteins, i.e. via target protein degradation by the cullin RING E3 ligase, wherein the compound has the following formula:

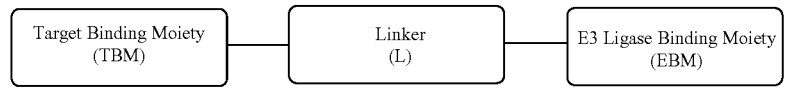

wherein TBM is a moiety binding to a target protein,
  preferably wherein the TBM is a moiety binding to a target protein associated with
  cancer, metabolic disorders, neurologic disorders or infectious diseases;
    more preferably wherein the one or more protein(s) associated with cancer is selected from the group consisting of DNA-binding proteins including transcription factors such as ESR1, AR, MYB, MYC; RNA binding proteins; scaffolding proteins; GTPases such as HRAS, NRAS, KRAS; solute carriers; kinases such as CDK4, CDK6, CDK9, EGFR, SRC, PDGFR, ABL1, HER2, HER3, BCR-ABL, MEK1, ARAF, BRAF, CRAF, phosphatases, bromodomain- and chromodomain containing proteins such as BRD2, BRD3, BRD4, CBP, p300, ATAD2, SMARCA2, SMARCA4, PBRM1, G-protein coupled receptors; anti-apoptotic proteins such as SHP2, PTPN1, PTPN12; immune regulators such as PDL1 and combinations thereof;
      even more preferably wherein the one or more protein(s) associated with cancer is selected from the group consisting of BRD2, BRD3, BRD4, CBP, p300, ATAD2, SMARCA2, SMARCA4, PBRM1, CDK4, CDK6, CDK9, CDK12 and/or CDK13, EWS-FL1, CDC6, CENPE, EGFR, SRC, PDGFR, ABL1, HER2, HER3, BCR-ABL, MEK1, ARAF, BRAF, CRAF, HRAS, NRAS, KRAS, BCL2, MCL2, SHP2, PTPN1, PTPN12, ESR1, AR, MYB, MYC, PDL1 and combinations thereof;
        even more preferably wherein the one or more protein(s) associated with cancer are selected from the group consisting of KRAS, NRAS, MYC, MYB, ESR1, AR, EGFR, HER2, BCR-ABL1 and BRAF;
        most preferably the one or more protein(s) associated with cancer are selected from the group consisting of KRAS, NRAS, MYC and MYB.
    more preferably wherein the one or more protein(s) associated with metabolic disorders are selected from the group consisting of ARX, SUR, DPP4 and SGLT;
    more preferably wherein the one or more protein(s) associated with neurologic disorders are selected from the group consisting of Tau and beta-amyloid; and
    wherein the one or more protein(s) associated with infectious diseases are selected from the group consisting of CCR5 and PLA2G16;
  wherein L is a linker moiety; and
  wherein EBM is a moiety modifying the function of the E3 ligase and/or binding to at least one regulator or member of the E3 ligase complex;
    preferably wherein the at least one member of the E3 ligase complex (CRL) is selected from the group consisting of CUL4B; DDB1; RBX1; UBE2G1; and CUL4A; and wherein the at least one regulator of the E3 ubiquitin ligase complex is selected from the group consisting of, UBE2M; UBA3; UBE2F; NAE1; COPS1, COPS2, COPS3, COPS4, COPS5, COPS6, COPS7A, COPS7B, COPS8; DCUN1D1; DCUN1D2; DCUN1D3; DCUN1D4; DCUN1D5;
      more preferably wherein the at least one member or regulator of the E3 ubiquitin ligase complex is CUL4B or DDB1;
        even more preferably wherein the EBM is selected from the group consisting of any of compounds of formula (I) and (II).

In context of the invention, the compounds are particularly useful as medicaments, for example in the treatment of diseases and/or disorders wherein it is desired to degrade target protein/target proteins via ubiquitination. Accordingly, the present invention also provides for methods of treating such diseases or disorders, said methods comprising the administration to an individual in need of such a treatment with the compound of the invention, i.e. the compound that can stimulating/induce ubiquitination of a target protein/target proteins. Particularly, the inventive compounds provided herein are used in biochemical degradation of misfolded and/or abnormal proteins in vivo as well as in vitro.

In the following, examples of compounds of formulae (I) and (II) are presented. It is to be understood that these also encompass any stereoisomers, tautomers, pharmaceutically acceptable salts, solvates and prodrugs of the compounds presented as Markush formulae or specific formulae.

The term "molecular glue" is generally known in the art and refers to a compound that can bind at least two different molecules at a time by cooperative binding but has no binding affinity to one of the at least two different molecules separately. In other words, a molecular glue refers to a compound that binds to a target protein/target proteins the compound simultaneously binds to the target protein/target proteins and a second protein. In context of the invention, a molecular glue refers to a compound that binds to a target protein/target proteins if the compound may simultaneously bind to the target protein/target proteins and at least one member or regulator of the E3 ligase complex. Examples for molecular glues known in the art include but are not limited to non-chimeric small molecules, lenalidomide, pomalidomide, CC-885 and related immunomodulatory drugs (IMiDs). The compounds of the invention may comprise molecular glues that bind to a target protein/target proteins if the compound may simultaneously bind to the target protein/target proteins and at least one member or regulator of the E3 ligase complex. Such molecular glues of the invention are further described herein below and are illustrated by the appended Examples.

The compounds of the invention may also comprise PROTAC®s (proteolysis targeting chimera). The term "PROTAC®", "PROTAC®s" or "proteolysis targeting chimera" is used interchangeably and refers to heterobifunctional compounds as used herein refer to compound that induce proteasome-mediated degradation of selected proteins via their recruitment to E3 ubiquitin ligase and subsequent ubiquitination (Crews C, Chemistry & Biology, 2010, 17(6):551-555; Schnnekloth J S Jr., *Chembiochem*, 2005, 6(1):40-46). In other words, this term refers to proteolysis-targeting chimera molecules having generally three components, an E3 ubiquitin ligase binding group, optionally a linker, and a protein binding group of a target. Phthalimide conjugation as a strategy for in vivo target protein degradation. Science 348, 1376-1381 (2015), Bondeson, D. P. et al. Catalytic in vivo protein knockdown by small-molecule PROTAC®s. Nat. Chem. Biol. 11, 611-617 (2015)). PROTAC®s operate by inducing molecular proximity between the protein of interest (POI) and a cellular E3 ligase substrate receptor by binding simultaneously to both proteins. This induced proximity leads to ubiquitination and proteasomal degradation of the POI. Of note, the modular design consisting of a warhead binding to the POI, a flexible linker, and a defined E3 ligase ligand renders PROTAC® development very flexible. The list of proteins permissive to targeted degradation now contains a large number of protein kinases, including one instance of a single-pass transmembrane receptor tyrosine kinase. Some proteins with one (1) transmembrane region, like EGFR, HER2, c-Met, ALK and FLT-3 (Cell Chem Biol. 2018 Jan. 18; 25(1):67-77. The Advantages of Targeted Protein Degradation Over Inhibition: An RTK Case Study. Burslem G M, Smith B E, Lai A C, Jaime-Figueroa S, McQuaid D C, Bondeson D P, Toure M, Dong H, Qian Y, Wang J, Crew A P, Hines J, Crews C M./Eur J Med Chem. 2018 May 10; 151:304-314. Proteolysis Targeting Chimeras (PROTAC®s) of Anaplastic Lymphoma Kinase (ALK). Zhang C, Han X R, Yang X, Jiang B, Liu J, Xiong Y, Jin J. J Am Chem Soc. 2018 Dec. 5; 140(48):16428-16432/Enhancing Antiproliferative Activity and Selectivity of a FLT-3 Inhibitor by Proteolysis Targeting Chimera Conversion. Burslem G M, Song J, Chen X, Hines J, Crews C M) have been shown to be degradable by "PROTAC®" induced degradation.

The compounds of the present invention are preferably selected from compounds of the following formula (I):

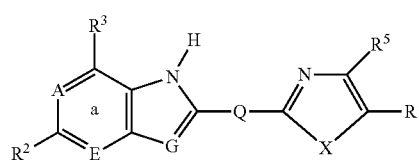

(I)

or a stereoisomer, tautomer, pharmaceutically acceptable salt, solvate or prodrug thereof.

It is to be understood that any reference to a compound of "formula (I)" is also applicable to any more specific examples of compounds of formula (I), such as the compounds of formulae (I-II) to (I-IV) and (I-a).

In preferred embodiments, compounds of formula (I) which do not contain at least one -L-TBM group are disclaimed. This disclaimer is, however, preferably not applicable to any claims relating to the medical or second medical use of compounds of formula (I). Accordingly, the disclaimer preferably also does not apply to methods of treatment as set out herein.

In the compound of formula (I), Ring a is optionally substituted with -L-TBM, wherein L is a linker moiety and TBM is a moiety binding to a target protein. It is to be understood that -L-TBM may be attached at any available position of Ring a. By available position, any one of the four positions of ring a which can potentially bear a hydrogen is meant. In other words -L-TBM may be present at the position of $R^3$ as shown in formula (I), as $R^3$ in A, as $R^2$ as shown in formula (I), or as $R^3$ in E. This is illustrated by the following formulae:

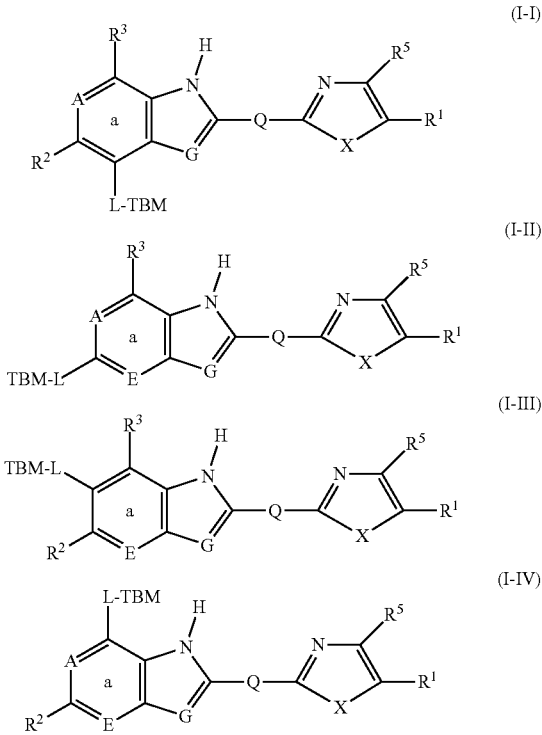

Among these, preferred are formulae (I-II) and (I-III). Even more preferred is formula (I-II). -L-TBM is preferably present at only one position of the ring a. It is preferred that -L-TBM is present at the position where $R^2$ is shown in formula (I). In such a case, $R^2$ would formally be regarded as —H, the —H being replaced by -L-TBM as the substituent. It is to be understood that the possible positions of -L-TBM are also applicable to any more specific definitions of the compound of formula (I).

It has been found that the compounds of the present invention can act as molecular glue even in the absence, or particularly well in the absence, of -L-TBM. It is therefore preferred that the compounds of the present invention do not contain -L-TBM, i.e. that -L-TBM in any formulae disclosed herein is replaced by —H.

A is C—$R^3$ or N. A is preferably C—$R^3$, more preferably C—H or C—F, even more preferably C—H.

E in formula (I) is C—$R^3$ or N. E is preferably C—$R^3$, more preferably C—H or C—F, even more preferably C—H.

G is C—$R^3$ or N. Preferably, G is N.

X in formula (I) is —$CR^5$=$CR^5$—, —S— or —O—, wherein each $R^5$ is independently selected from —H, —OH, —O—$C_{1-2}$ alkyl, -Hal, and $C_{1-2}$ alkyl which is optionally substituted with one or more F. X is preferably —$CR^5$=$CR^5$—, wherein each $R^5$ is independently selected from —H, —OH, —O—$C_{1-2}$ alkyl, -Hal, and $C_{1-2}$ alkyl which is optionally substituted with one or more F. More preferably, each $R^5$ is independently selected from —H, —OH, and $C_{1-2}$ alkyl which is optionally substituted with one or more F. Even more preferably each $R^5$ is —H. These preferred definitions of $R^5$ also apply as preferred definitions to the other $R^5$ in the ring containing X.

$R^1$ is selected from —F, —Cl, —Br, —I and $C_{1-2}$ alkyl which is optionally substituted with one or more F. $R^1$ is preferably selected from —Cl, —Br, —I and $C_{1-2}$ alkyl which is optionally substituted with one or more F. More preferably, $R^1$ is selected from —Cl, —Br and Me which is optionally substituted with one or more F, Even more preferably, $R^1$ is selected from —Cl and —Br.

$R^2$ is selected from hydrogen, halogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH ($C_{1-5}$ alkyl), —($C_{0-3}$ alkylene)-N($C_{1-5}$ alkyl)($C_{1-5}$ alkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH ($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH ($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), and —($C_{0-3}$ alkylene)-N($C_{1-5}$ alkyl)-SO$_2$—($C_{1-5}$ alkyl), wherein each alkylene and alkyl is optionally substituted with one or more halogen, preferably F.

$R^2$ is preferably selected from hydrogen, halogen, $C_{1-5}$ alkyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-NH$_2$, —($C_{0-3}$ alkylene)-NH ($C_{1-5}$ alkyl), —($C_{0-3}$ alkylene)-N($C_{1-5}$ alkyl)($C_{1-5}$ alkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH ($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), and —($C_{0-3}$ alkylene)-N($C_{1-5}$ alkyl)-CO—($C_{1-5}$ alkyl), wherein each alkylene and alkyl is optionally substituted with one or more halogen, preferably F.

More preferably, $R^2$ is selected from hydrogen, halogen, $C_{1-5}$ alkyl, and —($C_{0-3}$ alkylene)-O($C_{1-5}$ alkyl), wherein each alkylene and alkyl is optionally substituted with one or more F.

Even more preferably $R^2$ is hydrogen and -L-TBM is present at the position of $R^2$.

Each $R^3$ is selected from hydrogen, halogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH ($C_{1-5}$ alkyl), —($C_{0-3}$ alkylene)-N($C_{1-5}$ alkyl)($C_{1-5}$ alkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH ($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH ($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), and —($C_{0-3}$ alkylene)-N($C_{1-5}$ alkyl)-SO$_2$—($C_{1-5}$ alkyl), wherein each alkylene and alkyl is optionally substituted with one or more halogen, preferably F.

each $R^3$ is preferably selected from hydrogen, halogen, $C_{1-5}$ alkyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-NH$_2$, —($C_{0-3}$ alkylene)-NH ($C_{1-5}$ alkyl), —($C_{0-3}$ alkylene)-N($C_{1-5}$ alkyl)($C_{1-5}$ alkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH ($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), and —($C_{0-3}$ alkylene)-N($C_{1-5}$ alkyl)-CO—($C_{1-5}$ alkyl), wherein each alkylene and alkyl is optionally substituted with one or more halogen, preferably F.

More preferably, $R^3$ is selected from hydrogen, halogen, $C_{1-5}$ alkyl, and —($C_{0-3}$ alkylene)-O($C_{1-5}$ alkyl), wherein each alkylene and alkyl is optionally substituted with one or more F.

Even more preferably, each $R^3$ is independently —H or —F. Still more preferably each $R^3$ is —H.

Q is a linear $C_{4-5}$ alkylene group wherein one or more of the CH$_2$ units are replaced by any one independently selected from S, O and NH, wherein the linear $C_{4-5}$ alkylene group is optionally substituted with 1, 2, 3 or 4 substituents independently selected from =O, —OH, -Hal, and —$C_{1-6}$ alkyl which is optionally substituted with one or more halogen. It is to be understood that the 1, 2, 3 or 4 substituents may be present at any of the CH$_2$ units, NH units or S units and may thus, e.g., form units such as —C(H)(OH)—, —C(=O)—, —C(H)(Hal)-, —C(H)($C_{1-6}$ alkyl)-, —C(Hal)$_2$-, —C($C_{1-6}$ alkyl)$_2$-, —N($C_{1-6}$ alkyl)-, —N(OH)—, —S(O)— or —S(O)$_2$—.

Q is preferably represented by the following group:
-(α)$_n$-, wherein each a is independently selected from one or more groups selected from —N(R$^4$)—, —C(R$^4$)(R$^4$)—, —C(O)—, —O—, —S—, —S(O)— and —S(O)$_2$—, wherein each R$^4$ is independently selected from —H, -Hal and $C_{1-2}$ alkyl which is optionally substituted with one or more halogen; and n is 4 or 5, wherein two neighboring groups a are preferably not both —N(R$^4$)—, not both —C(O)—, not both —O—, not both —S—, not both —S(O)— and not both —S(O)$_2$— and preferably further two neighboring groups a do not form a direct bond between any of —O—, —S—, —S(O)— and —S(O)$_2$—.

More preferably, Q is represented by any one of the following groups, wherein preferably the left-hand side is bound to the five-membered ring containing G and the right-hand side is bound to the five-membered ring containing X:

—S—CH$_2$—C(=O)—NH—
—O—CH$_2$—C(=O)—NH—
—S—CH$_2$—S(=O)$_2$—NH—
—O—CH$_2$—S(=O)$_2$—NH—
—S—(CH$_2$)$_2$—C(=O)—NH—
—O—(CH$_2$)$_2$—C(=O)—NH—
—S—(CH$_2$)$_2$—S(=O)$_2$—NH—
—O—(CH$_2$)$_2$—S(=O)$_2$—NH—
—CH$_2$—S—CH$_2$—C(=O)—NH—

—CH$_2$—O—CH$_2$—C(=O)—NH—
—CH$_2$—S—CH$_2$—S(=O)$_2$—NH—
—CH$_2$—O—CH$_2$—S(=O)$_2$—NH—
—S—(CH$_2$)$_2$—NH—
—O—(CH$_2$)$_2$—NH—
—S—(CH$_2$)$_3$—NH—
—O—(CH$_2$)$_3$—NH—
—CH$_2$—S—CH$_2$—NH—
—CH$_2$—O—CH$_2$—NH—
—S—(CH$_2$)$_2$—O—
—O—(CH$_2$)$_2$—O—
—S—(CH$_2$)$_2$—S—
—O—(CH$_2$)$_2$—S—
—S—(CH$_2$)$_3$—O—
—O—(CH$_2$)$_3$—O—
—S—(CH$_2$)$_3$—S—
—O—(CH$_2$)$_3$—S—
—CH$_2$—S—CH$_2$—O—
—CH$_2$—O—CH$_2$—O—
—CH$_2$—S—(CH$_2$)$_2$—O— and
—CH$_2$—O—(CH$_2$)$_2$—O—.

Even more preferably, Q is represented by any one of the following groups:
—S—CH$_2$—C(=O)—NH— and
—O—CH$_2$—C(=O)—NH—.

Preferably, the compound of formula (I) is a compound of formula (Ia):

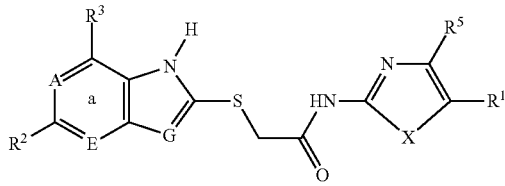

wherein the definitions of A, E, G, X, R$^1$, R$^2$, R$^3$ and R$^5$ set out above apply and Ring a is optionally substituted with -L-TBM, wherein L is a linker moiety and TBM is a moiety binding to a target protein,
or a stereoisomer, tautomer, pharmaceutically acceptable salt, solvate or prodrug thereof.

The compounds of the present invention are further preferably selected from compounds of the following formula (II):

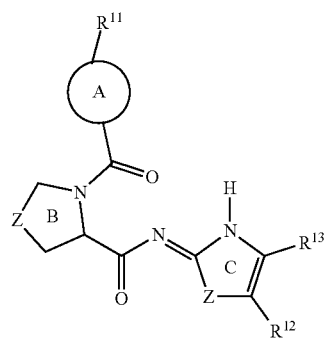

or a stereoisomer, tautomer, pharmaceutically acceptable salt, solvate or prodrug thereof.

The following two compounds are preferably disclaimed from the subject of matter claims, but not from the medical use claims:

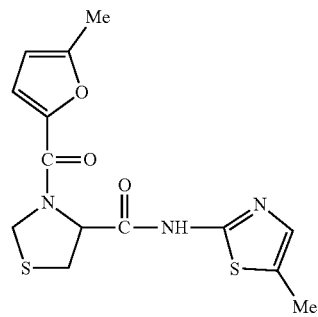

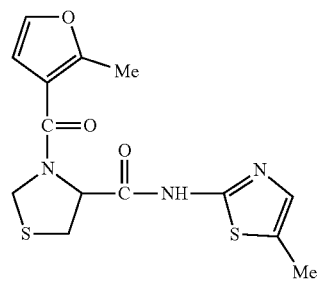

These may also be represented by their chemical names 3-[(5-methyl-2-furanyl) carbonyl]-N-(5-methyl-2-thiazolyl)-4-thiazolidinecarboxamide and 3-[(2-methyl-3-furanyl) carbonyl]-N-(5-methyl-2-thiazolyl)-4-thiazolidinecarboxamide.

It is to be understood that these compounds are preferably disclaimed only as such, i.e. their salts and solvates are preferably not disclaimed. Further preferably, these two compounds are disclosed from the scope of all claims.

If considered as falling under the present claims the following three compounds are preferably also disclaimed from the subject of matter claims, and optionally also from the medical use claims: 1-[(5-chloro-2-thienyl) carbonyl]-N-2-thiazolyl-2-pyrrolidinecarboxamide, 1-[(5-chloro-2-furanyl) carbonyl]-N-2-thiazolyl-2-pyrrolidinecarboxamide and 1-[(5-bromo-2-thienyl) carbonyl]-N-2-thiazolyl-2-pyrrolidinecarboxamide.

Any one of Rings A, B and C is optionally substituted with -L-TBM, wherein L is a linker moiety and TBM is a moiety binding to a target protein. The compounds of formula (II) preferably contain only one -L-TBM substituent. It is to be understood that -L-TBM may be attached at any available position of Rings A, B and C. In other words -L-TBM may replace an H in a C—H bond of one of Rings A, B and C. Alternatively, -L-TBM may replace one of R$^{12}$ and R$_{13}$ shown in formula (I). It is preferred that -L-TBM be present instead of R$^{12}$, such as in the following formula (II-I):

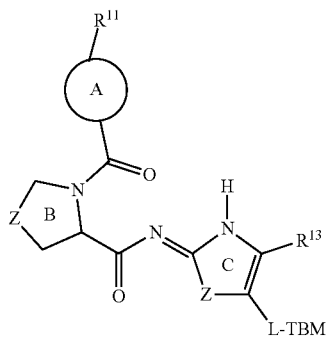

(II-I)

Ring A is a thiophen or furan ring, preferably a furan ring.

The compound of formula (II) is preferably a compound of formula (IIa) or formula (IIb):

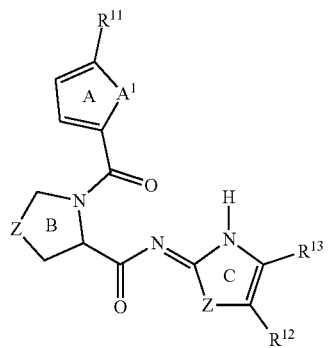

IIa

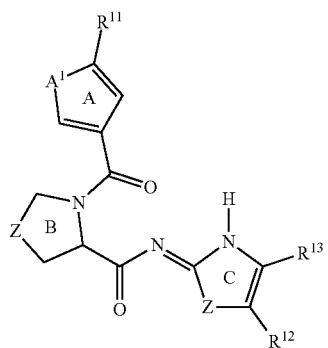

IIb

In these formulae, A1 is —S— or —O—. Preferably, $A^1$ is —O—.

Ring A is optionally further substituted with one or two selected from —F, —Cl, and —Br and $C_{1-2}$ alkyl which is optionally substituted with one or more F. The optional substituent of Ring A is preferably selected from —F. More preferably, the optional substituent of Ring A is absent.

Each Z is independently selected from —O— and —S—, preferably —S—.

$R^{11}$ is selected from —F, —Cl, —Br, —I and $C_{1-2}$ alkyl which is optionally substituted with one or more F. $R^{11}$ is preferably selected from —F, —Cl, —Br and methyl. More preferably, $R^{11}$ is selected from —Cl, —Br and methyl. Even more preferably, $R^{11}$ is methyl. Further preferably, $R^{11}$ and $R^{12}$ are methyl.

$R^{12}$ and $R_{13}$ are each independently selected from —H, —F, —Cl, —Br, —I, and $C_{1-2}$ alkyl which is optionally substituted with one or more F. Preferably $R^{13}$ is hydrogen and $R^{12}$ is selected from —H, —F, —Cl, —Br, —I, and $C_{1-2}$ alkyl which is optionally substituted with one or more F. Further preferably, $R^{13}$ is selected from —H, —F, —Cl, —Br, —I, and $C_{1-2}$ alkyl which is optionally substituted with one or more F, and $R^{12}$ is replaced by -L-TBM.

In the compounds of the present invention, L is preferably selected from a bond, $C_{1-20}$ alkylene, $C_{2-20}$ alkenylene, and $C_{2-20}$ alkynylene, wherein said alkylene, said alkenylene and said alkynylene are each optionally substituted with one or more groups independently selected from halogen, $C_{1-5}$ haloalkyl, —O($C_{1-5}$ haloalkyl), —CN, —$OR^{21}$, —$NR^{21}R^{21}$, —$NR^{21}OR^{21}$, —$COR^{21}$, —$COOR^{21}$, —$OCOR^{21}$, —$CONR^{21}R^{21}$, —$NR^{21}COR^{21}$, —$NR^{21}COOR^{21}$, —$OCONR^{21}R^{21}$, —$SR^{21}$, —$SOR^{21}$, —$SO_2R^{21}$, —$SO_2NR^{21}R^{21}$, —$NR^{21}SO_2R^{21}$, —$SO_3R^{21}$, and —$NO_2$, and further wherein one or more —$CH_2$-units comprised in said alkylene, said alkenylene or said alkynylene are each optionally replaced by a group independently selected from —O—, —$NR^{21}$—, —CO—, —S—, —SO—, and —$SO_2$—;

each $R^{21}$ is independently selected from hydrogen, $C_{1-5}$ alkyl, $C_{2-5}$ alkenyl, $C_{2-5}$ alkynyl, carbocyclyl, and heterocyclyl, wherein said alkyl, said alkenyl and said alkynyl are each optionally substituted with one or more groups $R^{Alk}$, and further wherein said carbocyclyl and said heterocyclyl are each optionally substituted with one or more groups $R^{Cyc}$; any two $R^{21}$ are optionally linked to for a ring;

each $R^{Alk}$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH ($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO($C_{1-5}$ alkyl), —CO—$NH_2$, —CO—NH ($C_{1-5}$ alkyl), —CO—N($C_{1-5}$ alkyl)($C_{1-5}$ alkyl), —NH—CO ($C_{1-5}$ alkyl), —N($C_{1-5}$ alkyl)-CO($C_{1-5}$ alkyl), —NH—COO ($C_{1-5}$ alkyl), —N($C_{1-5}$ alkyl)-COO($C_{1-5}$ alkyl), —O—CO—NH ($C_{1-5}$ alkyl), —O—CO—N($C_{1-5}$ alkyl)($C_{1-5}$ alkyl), —$SO_2$—$NH_2$, —$SO_2$—NH ($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH ($C_{1-5}$ alkyl), and —N($C_{1-5}$ alkyl)($C_{1-5}$ alkyl);

each $R^{Cyc}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH ($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO ($C_{1-5}$ alkyl), —CO—$NH_2$, —CO—NH ($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH ($C_{1-5}$ alkyl), —O—CO—N($C_{1-5}$ alkyl)($C_{1-5}$ alkyl), —$SO_2$—$NH_2$, —$SO_2$—NH ($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —NH$_2$, —NH ($C_{1-5}$ alkyl), and —N($C_{1-5}$ alkyl)($C_{1-5}$ alkyl).

The following compounds are particularly preferred among the compounds of formulae (I) and (II):

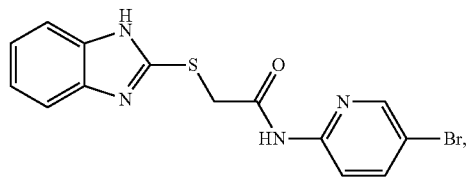

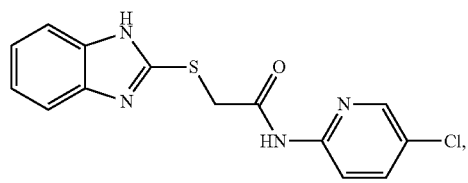

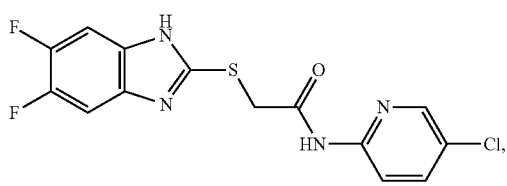

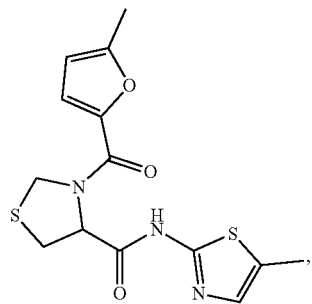

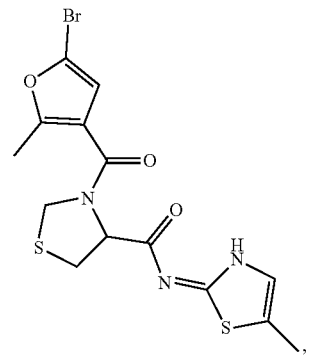

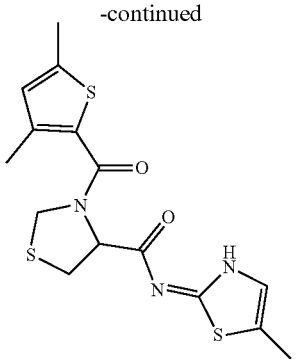

It is to be understood that these compounds are optionally substituted with one -L-TBM group as defined herein. Alternatively, the methyl group in the last three compounds is optionally replaced by an -L-TBM group as defined herein.

Accordingly, and disclosed herein, the compound may modify the function of the E3 ligase complex/cullin-RING ubiquitin ligase complex/CRL complex. This may occur for example by modifying posttranslational changes of a target protein as outlined above. The modified function of the E3 ligase complex/cullin-RING ubiquitin ligase complex/CRL complex comprises an enhanced activity of the E3 ligase complex/cullin-RING ubiquitin ligase complex/CRL complex. This enhanced activity of the E3 ligase complex/cullin-RING ubiquitin ligase complex/CRL complex may be determined by methods described herein above and herein below and as illustrated in the appended examples. As disclosed herein and as illustrated in the appended Examples, said enhanced activity of the E3 ligase complex/cullin-RING ubiquitin ligase complex/CRL complex may be determined by the measurement of the level/amount of target protein/target proteins in a cell expressing the target protein/target proteins in the presence of the compound and wherein the CRL activity is decreased in said cell compared to a control cell. Said control cell is preferably of the same cell type as the cell wherein the CRL activity is decreased. In the context of this invention, said control cell is also designated as "wild-type cell".

The terms "E3 ligase binding moiety" and "EBM" or are used interchangeably and means that the E3 ligase binding moiety/EBM is moiety modifying the function of the E3 ligase and/or binding to at least one regulator or member of the E3 ligase complex/cullin-RING ubiquitin ligase complex/CRL complex. "Modifying the function of the E3 ligase" as used in context of the invention means that the cullin-RING ubiquitin ligase activity/CRL activity is enhanced by the E3 ligase binding moiety/EBM, for example by binding of the E3 ligase binding moiety/EBM to the E3 ligase/cullin-RING ubiquitin ligase/CRL or by modifying the function of the E3 ligase complex/cullin-RING ubiquitin ligase complex/CRL complex.

The E3 ligase binding moiety/EBM may bind to or modify the function of the at least one member or regulator of the E3 ligase complex/cullin-RING ubiquitin ligase complex/CRL complex. Such at least one member of the E3 ligase complex/cullin-RING ubiquitin ligase complex/CRL complex may be CUL4B (NP_001073341.1); DDB1 (NP_001914.3); RBX1 (NP_055063.1); UBE2G1 (NP_003333.1); and CUL4A (NP_001008895.1 and all isoforms). For example, at least one member of the E3 ligase complex/cullin-RING ubiquitin ligase complex/CRL complex may be DDB1 (NP_001914.3).

Such at least one regulator of the E3 ligase complex/cullin-RING ubiquitin ligase complex/CRL complex may be UBE2M (NP_003960.1); UBA3 (NP_003959.3); UBE2F (NP_542409.1); NAE1 (NP_003896.1); COPS1 (NP_001308018.1), COPS2 (NP_004227.1), COPS3 (NP_003644.2),COPS4 (NP_057213.2),COPS5 (NP_006828.2), COPS6 (NP_006824.2), COPS7A (NP_001157566),COPS7B (NP_073567.1),COPS8 (NP_0067 01.1); DCUN1D1 (NP_065691.2); DCUN1D2 (NP_001014305.1); DCUN1D3 (NP_775746.1); DCUN1D4 (NP_001035492.1) and DCUN1D5 (NP_115675.1). Such at least one member of the E3 ligase complex as disclosed herein and in context of the invention may be identified by their respective accession numbers and/or sequences as provided, for example, by NCBI.

Particularly, such at least one member of the E3 ligase complex/cullin-RING ubiquitin ligase complex/CRL complex may be CUL4B or DDB1. More particular, such at least one member of the E3 ligase complex/cullin-RING ubiquitin ligase complex/CRL complex may be compounds of formula (I) and (II).

Binding of the E3 ligase binding moiety/EBM may to the E3 ligase complex/cullin-RING ubiquitin ligase complex/CRL complex, such as at least one member or regulator of said E3 ligase complex/cullin-RING ubiquitin ligase complex/CRL complex may be determined by methods known in the art, which are illustrated by the appended Examples, where the binding of the compound "JQ1" to the substrate receptor of the E3 ligase complex/cullin-RING ubiquitin ligase complex/CRL complex was shown; see Example 3. Further methods of how to determine Binding of the E3 ligase binding moiety/EBM may to the E3 ligase complex/cullin-RING ubiquitin ligase complex/CRL complex, such as at least one member or regulator of said E3 ligase complex/cullin-RING ubiquitin ligase complex/CRL complex are known in the art as outlined below. For example, means and methods known in the art of how to determine the E3 ligase binding moiety/EBM may to the E3 ligase complex/cullin-RING ubiquitin ligase complex/CRL complex comprise, inter alia, immunoassays (like Western blots, ELISA tests and the like) and/or reporter assay (like luciferase assays and the like).

In context of the invention, target proteins may include but are not limited to proteins associated with cancer, metabolic disorders, neurologic disorders or infectious diseases.

Non-limiting examples of the such target protein/target proteins associated with cancer may be transcription factors such as ESR1 (NP_000116.2), AR (NP_000035.2), MYB (NP_001123645.1), MYC (NP_002458.2); RNA binding proteins; scaffolding proteins; GTPases such as HRAS (NP_005334.1), NRAS (NP_002515.1), KRAS (NP_203524.1); solute carriers; kinases such as CDK4 (NP_000066.1), CDK6 (NP_001138778.1), CDK9 (NP_001252.1), EGFR (NP_005219.2), SRC (NP_938033.1), PDGFR (NP_002600.1), ABL1 (NP_005148.2), HER2 (NP_004439.2), HER3 (NP_001973.2), BCR-ABL (NP_009297.2), MEK1 (NP_002746.1), ARAF (NP_001645.1), BRAF (NP_004324.2), CRAF (NP_001341618.1), phosphatases, bromodomain- and chromodomain containing proteins such as BRD2 (NP_001106653.1), BRD3 (NP_031397.1), BRD4 (NP_490597.1), CBP (NP_004371.2), p300 (NP_001420.2), ATAD2 (NP_054828.2), SMARCA2 (NP_003061.3), SMARCA4 (NP_001122316.1), PBRM1 (NP_060783.3), G-protein coupled receptors; anti-apoptotic proteins like BCL2 (NP_000624.2) and MCL1 (NP_068779.1), phosphatases such as SHP2 (NP_002825.3), PTPN1 (NP_002818.1), PTPN12 (NP_002826.3); immune regulators such as PDL1 (NP_054862.1) and combinations thereof. Particular non-limiting examples of such target protein/target proteins associated with cancer may be BRD2, BRD3, BRD4, CBP, p300, ATAD2, SMARCA2, SMARCA4, PBRM1, CDK4, CDK6, CDK9, CDK12 (NP_057591.2) and/or CDK13 (NP_003709.3), EWS-FL1 (NP_002009.1), CDC6 (NP_001245.1), CENPE (NP_001804.2), EGFR, SRC, PDGFR, ABL1, HER2, HER3, BCR-ABL1, MEK1, ARAF, BRAF, CRAF, HRAS, NRAS, KRAS, BCL2, MCL1, SHP2, PTPN1, PTPN12, ESR1, AR, MYB, MYC, PDL1 and combinations thereof. More particular non-limiting examples of such target protein/target proteins associated with cancer may be KRAS, NRAS, MYC, MYB, ESR1, AR, EGFR, HER2, BCR-ABL and BRAF, even more particular KRAS, NRAS, MYC and MYB. Even more particular non-limiting examples of the one or more target protein/target proteins associated with cancer may be CDK12, CDK13 and/or CCNK, particularly CDK12 and/or CDK13.

Non-limiting examples of the one or more target protein/target proteins associated with metabolic disorders may be ARX (NP_620689.1), SUR (NP_001274103.1), DPP4 (NP_001926.2) and SGLT (NP_001243243.1). Non-limiting examples of the one or more target protein/target proteins associated with neurologic disorders may be Tau (NP_058519.3) and beta-amyloid (NP_000475.1). Non-limiting examples of the one or more target protein/target proteins associated with infectious diseases may be CCR5 (NP_000570.1) and PLA2G16 (NP_001121675.1).

Accordingly, the present invention relates to an in vivo method for identifying a compound having the ability to degrade one or more protein(s), the method comprising contacting a compound with a wild-type cell and with a mutated cell, wherein the mutation comprises a hypomorphic mutation or inactivation of at least one member or regulator of an E3 ubiquitin ligase complex; wherein the compound is determined to degrade one or more protein(s) if the level of the one or more protein(s) of the mutated cell is decreased compared to the wild-type cell.

The term "in vivo" is defined herein as not comprising humans and or animals and is to be restricted to isolated cells/isolated cellular systems and/or isolated tissues. In one very specific embodiment, the methods of the present invention may also comprise the testing of transgenic animals that are genetically modified to comprise cells/tissues wherein said cells/tissues comprise an decreased cullin-RING ubiquitin ligase (CRL) activity (as compared to animals/trasngenics that are not modified to comprise decreased cullin-RING ubiquitin ligase (CRL) activity. Means and methods to obtain "decreased cullin-RING ubiquitin ligase (CRL) activity" are amply provided herein for isolated cells/cellular systems. The same embodiments apply, mutatis mutantis, for the herein incorporated transgenic test animals. Similarly, the present invention may also comprise the use of xenograft and/or allograft (allotransplantation) models, for example the use of genetically modified tissues/cells that are manipulated to comprise decreased cullin-RING ubiquitin ligase (CRL) activity as defined above and that are transferred to living test animals. Such models are also comprised under the term "in vivo" as employed in context of the present invention.

The term "identifying a compound having the ability to degrade one or more protein(s)" means that identifying/ testing/obtaining a compound for its potential to induce and/or stimulate the ubiquitination of a target protein/target proteins. As evident from the appended Examples, the method for identifying a compound having the ability to degrade one or more protein(s) as provided herein comprises the determination of the level of the one or more protein(s) in a mutated cell and a corresponding wild-type cell. The decreased level of the one or more protein(s) in a mutated cell compared to the wild-type cell is indicative for the ability of the compound to degrade said one or more protein(s). In the mutated cell, the cullin-RING ubiquitin ligase activity/CRL activity is reduced or impaired compared to the cullin-RING ubiquitin ligase activity/CRL activity in the wild-type cell. Such a reduction or impairment of the cullin-RING ubiquitin ligase activity/CRL activity in the mutated cell is achieved by introducing a hypomorphic mutation or inactivation of at least one member or regulator of an E3 ubiquitin ligase complex of said mutated cell. Hence, in the mutated cell in context of the invention, the CRL activity is decreased by the hypomorphic mutation or inactivation of at least one member or regulator of an E3 ubiquitin ligase complex compared to the wild-type cell. It is of note that the term "wild-type cell" refers to a control cell which may be of the same cell type as the mutated cell. Such a wild-type cell also comprises an E3 ligase complex/cullin-RING ubiquitin ligase complex/CRL complex and also comprises the target protein/target proteins as described herein and used in context of the invention.

The term "contacting a compound with a wild-type cell and with a mutated cell" means that a compound suspected of stimulating/inducing ubiquitination of a target protein/target proteins is contacted to the wild-type cell and the mutated cell. A compound identified/tested/obtained by the method of the invention, i.e. a compound able to stimulate/induce ubiquitination of a target protein/target proteins, may stimulate/induce ubiquitination of a target protein/target proteins in the wild-type cell and ubiquitination of the target protein/target proteins in the mutant cell may be reduced compared to said wild-type cells. It is noted that a mutated cell comprises a decreased CRL activity which is induced by the hypomoprhic mutation or inactivation of the at least one member or regulator of the E3 ubiquitin ligase complex. Thus, a compound identified/tested/obtained to stimulate/induce ubiquitination of a target protein/target proteins via the ubiquitination system, i.e. degradation of a target protein/target proteins, is identified by the reduced or impaired ability to stimulate/induce ubiquitination of a target protein/target proteins via the ubiquitination system, i.e. degradation of a target protein/target protein, in said mutated cell, where the CRL activity is decreased, compared to a wild-type cell comprising CRL activity. In turn, a compound identified/tested/obtained to stimulate/induce ubiquitination of a target protein/target proteins via the ubiquitination system, i.e. degradation of a target protein/target proteins, is identified by the ability to stimulate/induce ubiquitination of a target protein/target proteins via the ubiquitination system, i.e. degradation of a target protein/target protein, in the wild-type cell comprising the CRL activity.

Such a stimulation/induction of ubiquitination of a target protein/target proteins may be indicated by the decreased level of the one or more protein(s) in the wild-type cell compared to the mutated cell. The level of the one or more protein(s) may be determined by methods known in the art and provided herein above and herein below. Hence, a compound which decreases the level of the one or more protein(s) in a wild-type cell compared to a mutant cell refers to a compound identified/tested/obtained to stimulate/induce ubiquitination of a target protein/target proteins refers to a compound. As disclosed herein and illustrated in the appended Examples, a corresponding read-out whether the compound to be identified in the methods of this invention is able and/or capable to stimulate/induce ubiquitination of a target protein/target proteins may be the measurement of the level of the target protein/target proteins. When said "level" of the target protein/target proteins determined in the wild-type cell is decreased compared to the "level" determined in the mutant cell, said compound is able to stimulate/induce the activity of the E3 ubiquitin ligase. In other words, the activity of the compound is measured in wild-type cells and mutant cells, i.e. cell that have a decreased CRL activity compared to a corresponding "wild-type" cell, i.e. a cell comprising CRL activity. Another read-out may comprise the test of viability of a wild-type cell compared to a mutant cell as illustrated in the appended Examples.

The cullin-RING ubiquitin ligase, its activity and means and methods for the detection and/or measurement of this activity are described in detail herein below and are also illustrated in the appended examples. The same applies, mutatis mutantis, for the E3 ligase complex and its members.

The term "hypomorphic mutation" refers to a mutation resulting in a reduction-in-function of the at least one member or regulator of an E3 ubiquitin ligase complex. In other words, the hypomorphic mutation results in a decreased activity of the E3 ubiquitin ligase complex compared to the activity of a E3 ubiqutin ligase complex in a corresponding wild-type cell. This decreased activity of the E3 ubiquitin ligase complex may be achieved by a lower expression level and/or level of activity of the at least one member of the E3 ubiquitin ligase complex relative to levels in the corresponding wild-type cell. For example, such a hypomorphic state can be caused by methods known in the art and described herein below. Non-limiting examples of hypomorphic mutations of the at least one member or regulator of the E3 ubiquitin ligase complex include, but are not limited to, Cas9/CRISPR, inhibitors, antibodies, monobodies and nanobodies, nucleic acid molecules including such as RNA and DNA for example antisense oligonucleotides, siRNA, shRNA or miRNA, or any combinations thereof. Accordingly, the inactivation of the at least one member or regulator of the E3 ubiquitin ligase complex refers to a complete or substantially complete loss of function of the at least one member of the E3 ubiquitin ligase complex, which results in decreased CRL activity. Means and methods of how to inactivate the at least one member or regulator of the E3 ubiquitin ligase complex are known in the art may be caused by a mutation in the at least one member or regulator of the E3 ubiquitin ligase complex or can be caused by various synthetic or natural agents or materials that can inhibit the at least one member or regulator of the E3 ubiquitin ligase complex. Such synthetic or natural agents or materials may include but are not limited to small molecules, proteins including antibodies and polypeptides, and nucleic acid molecules including such as RNA and DNA for example antisense oligonucleotides, siRNA, shRNA or miRNA, or any combinations thereof. For example, an inactivation by a mutation in the at least one member or regulator of the E3 ubiquitin ligase complex may be caused by a knock out. As illustrated in the appended Examples, such a knock out may be performed by Cas9/CRISPR (Clustered Regularly interspaced Short Palindromic Repeats). Particularly, a KBM-7 cell comprises a mutated UBE2M, wherein an 18 bp depletion of the UBE2M sequence has been introduced leading to a loss of 16 amino acids (SEQ ID NO.2: AGAC - - - - - - - - - - - - - - - - - - - GTTGGGGTGATAG). A comprising a wild-type UBE2M sequence (SEQ ID NO.1: AGACGTTGCCCTCGAGGT-CAATGTTGGGGTGATAG) is used as a control in the appended examples.

As provided herein and illustrated in the appended Examples, such at least one member of the E3 ubiquitin ligase complex which is mutated in the cell by hypomorphic mutation or inactivation resulting in decreased CRL activity may be CUL4B, DDB1, RBX1; UBE2G1 and CUL4A. Accordingly, such at least one regulator of the E3 ubiquitin ligase complex which is mutated in the cell by hypomorphic mutation or inactivation resulting in decreased CRL activity may be UBE2M, UBA3, UBE2F, NAE; COPS1, COPS2, COPS3, COPS5, COPS6, COPS7A, COPS7B, COPS8, DCUN1D2, DCUN1D3, DCUN1D4 and DCUN1D5. Particular examples of such at least one member or regulator of the E3 ubiquitin ligase may be CUL4B or DDB1.

In one embodiment, the compound preferably comprises a moiety binding to at least one member or regulator of the E3 ligase complex. For example, the at least one member or regulator of the E3 ligase complex to which the compound binds may be a substrate receptor, an adaptor protein or a cullin scaffold protein of the E3 ligase complex. Non-limiting examples of such a substrate receptor may be DCAF15, DCAF16, DCAF1, DCAF5, DCAF8, DET1, FBXO7, FBXO22, KDM2A, or KDM2B, particularly CRBN and DCAF15. Non-limiting examples of such an adaptor protein may be DDB1. Non-limiting examples of a such a cullin may be a cullin of the CRL4 complex, such as CUL4A and CUL4B. Thus, for example, a compound as disclosed herein and used in context of the invention comprises a moiety binding to at least one member of the E3 ligase complex, wherein the at least one member of the E3 ligase complex to which the compound binds may be an adaptor protein such as DDB1.

In another embodiment, the compound of formula (I) and (II) may comprise a moiety binding to the at least one member of the E3 ligase complex, wherein the ring of formula (I) containing X and ring A of formula (II) comprises the moiety binding to the at least one member of the E3 ligase complex. For example, the at least one member or regulator of the E3 ligase complex to which the compound binds may be a substrate receptor, an adaptor protein or a cullin scaffold protein of the E3 ligase complex. Non-limiting examples of such a substrate receptor may be CRBN and DCAF15. Non-limiting examples of such an adaptor protein may be DDB1. Thus, for example, the compound of formula (I) may comprise a moiety binding to at least one member of the E3 ligase complex, wherein the ring of formula (I) containing X comprises a moiety binding to at least one member of the E3 ligase complex, wherein the at least one member of the E3 ligase complex to which the compound bind may be an adaptor protein such as DDB1.

Non-limiting examples of a such a cullin may be a cullin of the CRL4 complex, such as CUL4A and CUL4B. Cullins may be found covalently conjugated with an ubiquitin-like molecule, NEDD8 (neural-precursor-cell-expressed developmentally down-regulated 8). As used herein, the term "NEDD8" refer to a protein that in humans is encoded by the NEDD8 gene. Nucleotide and amino acid sequences of NEDD8 proteins are known in the art. Non-limiting examples of NEDD8 sequences include *Homo sapiens* NEDD8, the nucleotide and amino acid sequences of which are set forth in GenBank Acc. Nos. NM_006156 and NP_006147, respectively; *Mus musculus* NEDD8, the nucleotide and amino acid sequences of which are set forth in GenBank Acc. Nos. NM_008683 and NP_032709, respectively (Kamitani et al. (1997) *J Biol Chem* 272:28557-28562; Kumar et al. (1992) *Biochem Biophys Res Comm* 185:1155-1161); and *Saccharomyces cerevisiae* Rub1, the nucleotide and amino acid sequences of which are set forth in GenBank Acc. Nos. Y16890 and CAA76516, respectively.

As is evident from the appended Examples, the compound of the present invention may bind a target protein/target proteins via the target binding moiety/TBM of the compound and bind or modify the function of the E3 ligase complex/cullin-RING ubiquitin ligase complex/CRL complex, for example by recruiting the target protein/target proteins bound to the target binding moiety/TBM of the compound to the E3 ligase complex/cullin-RING ubiquitin ligase complex/CRL complex. For example, the compound may bind to at least one member of the E3 ligase complex/cullin-RING ubiquitin ligase complex/CRL complex and the target protein. As another example, the compound in context of the invention may alter the function of a target protein, for example by modifying posttranslational changes of a target protein. A posttranslational modification may include but is not limited to the phosphorylation status of a protein, e.g. a tyrosine kinase phosphorylating a protein. Thus, the compound may induce ubiquitination of a target protein, e.g., by modifying a target protein in that the target protein becomes accessible for a E3 ligase complex/cullin-RING ubiquitin ligase complex/CRL complex, thereby the compound may not associate with a target protein and/or E3 ligase complex/cullin-RING ubiquitin ligase complex/CRL complex.

In one embodiment, the target binding moiety/TBM of the compound as described herein and in context of the invention may be a moiety binding to one or more protein(s) to be degraded. Particularly, the target binding moiety/TBM of the compound as described herein and in context of the invention may be a moiety binding to one or more protein(s) to be degraded, wherein Ring a of formula I, or Ring C of formula II comprises a moiety binding to a protein to be degraded.

The TBM may be a moiety binding to a target protein. Such a TBM may be a moiety binding to a target protein associated with cancer, metabolic disorders, neurologic disorders or infectious diseases. Non-limiting examples of one or more protein(s) associated with cancer to which the TBM may bind include DNA-binding proteins including transcription factors such as ESR1, AR, MYB, MYC; RNA binding proteins; scaffolding proteins; GTPases such as HRAS, NRAS, KRAS; solute carriers; kinases such as CCNK, CDK4, CDK6, CDK9, EGFR, SRC, PDGFR, ABL1, HER2, HER3, BCR-ABL, MEK1, ARAF, BRAF, CRAF, particularly such as CDK4, CDK6, CDK9, EGFR, SRC, PDGFR, ABL1, HER2, HER3, BCR-ABL, MEK1, ARAF, BRAF, CRAF, phosphatases, bromodomain- and chromodomain containing proteins such as BRD2, BRD3, BRD4, CBP, p300, ATAD2, SMARCA2, SMARCA4, PBRM1, G-protein coupled receptors; anti-apoptotic proteins such as SHP2, PTPN1, PTPN12; immune regulators such as PDL1 and combinations thereof. Particular non-limiting examples of one or more protein(s) associated with cancer to which the TBM may bind include CDK13, CDK12, CDK9, CDK6, CDK4, CCNK, BRD2, BRD3, BRD4, CBP, p300, ATAD2, SMARCA2, SMARCA4, PBRM1, CDK4, CDK6, CDK9, EWS-FL1, CDC6, CENPE, EGFR, SRC, PDGFR, ABL1, HER2, HER3, BCR-ABL, MEK1, ARAF, BRAF, CRAF, HRAS, NRAS, KRAS, BCL2, MCL2, SHP2, PTPN1, PTPN12, ESR1, AR, MYB, MYC, PDL1 and combinations thereof. Non-limiting examples of one or more protein(s) associated with cancer to which the TBM may bind include BRD2, BRD3, BRD4, CBP, p300, ATAD2, SMARCA2, SMARCA4, PBRM1, CDK4, CDK6, CDK9, CDK12 and/or CDK13, EWS-FL1, CDC6, CENPE, EGFR, SRC, PDGFR, ABL1, HER2, HER3, BCR-ABL, MEK1, ARAF, BRAF, CRAF, HRAS, NRAS, KRAS, BCL2, MCL2, SHP2, PTPN1, PTPN12, ESR1, AR, MYB, MYC, PDL1 and combinations thereof. More particular non-limiting examples of one or more protein(s) associated with cancer to which the TBM may bind include KRAS, NRAS, MYC, MYB, ESR1, AR, EGFR, HER2, BCR-ABL and BRAF. Even more particular non-limiting examples of one or more protein(s) associated with cancer to which the TBM may bind include KRAS, NRAS, MYC and MYB. Non-limiting examples of one or more protein(s) associated with metabolic disorders to which the TBM may bind include ARX, SUR, DPP4 and SGLT. Non-limiting examples of one or more protein(s) associated with neurologic disorders to which the TBM may bind include Tau and beta-amyloid. Non-limiting examples of one or more protein(s) associated with infectious diseases are selected from the group consisting of CCR5 and PLA2G16. For example, a TBM as described herein and in context of the invention may be a moiety binding to one or more target protein(s) associated with cancer, wherein the one or more protein(s) associated with cancer may be CDK12, CDK13 and/or CCNK. As still another example, a TBM can be a moiety binding to one or more target protein(s) associated with cancer, wherein one or more protein(s) associated with cancer is CDK12 and/or CDK13.

Means and methods of how to determine the binding of the compound to the at least one member or regulator of the E3 ligase complex and/or binding of the target binding moiety/TBM to the target protein are known in the art, described herein above and herein below, and are also illustrated in the appended Examples. Such means and methods to determine the binding of a compound to the E3 ubiquitin ligase can be determined, for example, by immunoassays as for instance but not limited to radioimmunoassays, chemiluminescence- and fluorescence-immunoassays, Enzyme-linked immunoassays (ELISA), Luminex-based bead arrays, protein microarray assays, assays suitable for point-of-care testing and rapid test formats such as for instance immune-chromatographic strip tests. Suitable immunoassays may be selected from the group of immuno-precipitation, enzyme immunoassay (EIA)), enzyme-linked immunosorbenassays (ELISA), radioimmunoassay (RIA), fluorescent immunoassay, a chemiluminescent assay, an agglutination assay, nephelometric assay, turbidimetric assay, a Western Blot, a competitive immunoassay, a non-competitive immunoassay, a homogeneous immunoassay a heterogeneous immunoassay, a bioassay and a reporter assay such as a luciferase assay or Luminex® Assays. An immunoassay is a biochemical test that measures the presence or concentration of a macromolecule/polypeptide in a solution through the use of an antibody or immunoglobulin as a binding agent. According to the invention, the antibodies may be monoclonal as well as polyclonal antibodies. Thus, at least one antibody is a monoclonal or polyclonal antibody. In certain aspects, the level of the marker is determined by high performance liquid chromatography (HPLC). In certain aspects, the HPLC can be coupled to an immunoassay. For example, in a sandwich immunoassay, two antibodies are applied. In principle, all labeling techniques which can be applied in assays of said type can be used, such as labeling with radioisotopes, enzymes, fluorescence-, chemoluminescence- or bioluminescence labels and directly optically detectable color labels, such as gold atoms and dye particles.

Further, binding of a compound to the E3 ubiquitin ligase may be detected, for example, in a Western Blot. Western blotting involves application of a protein sample (lysate) onto a polyacrylamide gel, subsequent separation of said complex mixture by electrophoresis, and transferal or "electro-blotting" of separated proteins onto a second matrix, generally a nitrocellulose or polyvinylidene fluoride (PVDF) membrane. Following the transfer, the membrane is "blocked" to prevent nonspecific binding of antibodies to the membrane surface. Many antibody labeling or tagging strategies are known to those skilled in the art. In the simplest protocols, the transferred proteins are incubated or complexed with a primary enzyme-labeled antibody that serves as a probe. After blocking non-specific binding sites a suitable substrate is added to complex with the enzyme, and together they react to form chromogenic, chemiluminescent, or fluorogenic detectable products that allow for visual, chemiluminescence, or fluorescence detection, respectively. This procedure is described by Gordon et al., U.S. Pat. No. 4,452,901 issued Jun. 15, 1984.

The invention further relates to a method for identifying a compound having the ability to degrade one or more protein(s), the method comprising contacting a compound with a wild-type cell and with a mutated cell, wherein the mutation comprises a hypomorphic mutation or inactivation of at least one member or regulator of an E3 ubiquitin ligase complex; wherein the compound is determined to degrade one or more protein(s) if the level of the one or more protein(s) of the wild-type cell is decreased compared to the mutant cell.

The term "cullin RING ubiquitin E3 ligase" or "CRL" are used interchangeably and refer to an ubiquitin ligase in a complex in which the catalytic core consists of a member of the cullin family and a RING domain protein; the core is associated with one or more additional proteins that confer substrate specificity. The RING domain proteins of the CRL mediate the transfer of ubiquitin from the E2 to the E3-bound substrate. In particular, the cullin RING ubiquitin E3 ligase (CRL) are modular multi-subunit complexes that all contain a common core comprising a cullin subunit and a zinc-binding RING domain subunit. In particular, the cullin subunit folds into an extended structure that forms the backbone of CRLs. The C-terminal region of the cullin subunit forms a globular domain that wraps itself around the RING protein, which in turn recruits the E2 conjugating enzyme to form the enzymatic core. The N-terminal region of the cullin subunit, which resides at the opposite end of the elongated cullin structure, recruits substrate receptors via adapter proteins.

Cullin-based E3 ligases comprise a large family of ubiquitin ligases and are composed of several subunits, consisting of one of seven mammalian cullin homologs (CUL1, CUL2, CUL3, CUL4A/B, CUL5 or CUL7) that bind to the RING domain protein. The cullin N terminus mediates binding of cullin homolog-specific substrate recognition subunits. Binding of the substrate recognition subunits often but not always requires specific adaptor proteins that bridge the interaction with the cullin homologs. For instance, CUL1 is known to bind substrate recognition subunits containing a conserved F-box via the adaptor protein Skp1, thus forming SCF (Skp1-Cul1-F-box) E3 ligases, whereas CUL2 and CUL5 recruit substrate recognition subunits with a VHL or SOCS box, respectively, via the adaptor proteins Elongin B and C. In contrast, CUL3 is known to bind directly to substrate recognition subunits via their BTB domain (also known as POZ domain). CUL4A acts as an assembly factor that provides a scaffold for assembly of a RING-box domain protein (RBX1) and the adaptor protein Damaged DNA Binding Protein 1 (DDB1) (Angers et al., Nature, 2006. 443(7111):590-3). RBX1 is the docking site for the activated E2 protein, and DDB1 recruits substrate specificity receptors or DCAFs (DDB1-cullin4-associated-factors) to form the substrate-presenting side of the CUL4 complex (Angers et al., Nature, 2006. 443(7111):590-3; He et al., Genes Dev, 2006. 20(21):2949-54; Higa et al. Nat Cell Biol, 2006. 8(11): p. 1277-83). Cereblon (CRBN) interacts with damaged DNA binding protein 1 and forms an E3 ubiquitin ligase complex with CUL4 where it functions as a substrate receptor in which the proteins recognized by CRBN might be ubiquitinated and degraded by proteasomes. Cullins may be found covalently conjugated with an ubiquitin-like molecule, NEDD8 (neural-precursor-cell-expressed developmentally down-regulated 8). As used herein, the term "NEDD8" refer to a protein that in humans is encoded by the NEDD8 gene. Nucleotide and amino acid sequences of NEDD8 proteins are known in the art. Non-limiting examples of NEDD8 sequences include *Homo sapiens* NEDD8, the nucleotide and amino acid sequences of which are set forth in GenBank Ace. Nos. NM_006156 and NP_006147, respectively; *Mus musculus* NEDD8, the nucleotide and amino acid sequences of which are set forth in GenBank Acc. Nos. NM_008683 and NP_032709, respectively (Kamitani et al. (1997) *J Biol Chem* 272:28557-28562; Kumar et al. (1992) *Biochem Biophys Res Comm* 185:1155-1161); and *Saccharomyces cerevisiae* Rub1, the nucleotide and amino acid sequences of which are set forth in GenBank Acc. Nos. Y16890 and CAA76516, respectively. CRLs may be activated when CRLs are present in a neddylated state, i.e. upon neddylation. As used herein, the term "neddylation" refers to a type of protein modification process by which the ubiquitin-: like protein NEDD8 is conjugated to the CRL through E1 activating enzyme (NAE; a heterodimer of NAE1 and UBA3 subunit), E2 conjugating enzyme (Ubc12, UBE2M) and E3 ligase (Gong et al. J. Biol. Chem. 2013; 274:1203612042). This modification, termed neddylation, activates the E3 ligase activity of CRLs by promoting substrate ubiquitination. The neddylation system is similar to UPS (ubiquitin-proteasome system) in which ubiquitin activating enzyme E1, ubiquitin conjugating enzyme E2 (UBC) and ubiquitin-protein isopeptide ligase E3 are involved (Hershko, A. Cell Death Differ. 2005; 12:1191-1197). Thus, as used herein, the terms "NAE" or "NEDD8 activating enzyme," refer to a protein capable of catalyzing the transfer of NEDDS's C terminus to the catalytic cysteine of NEDD8 E2, forming a thiolester-linked E2-NEDD8 intermediate (Gong and Yeh (1999) *J Biol Chem* 274:12036-12042; and Liakopoulos et al. (1998) *EMBO J* 17:2208-2214; Osaka et al. (1998) *Genes Dev* 12:2263-2268). NEDD8 E1 enzymes described in the art include a heterodimer of NAE1 (also referred to as APPBP1; amyloid beta precursor protein binding protein 1; and NEDD8-activating enzyme E1 regulatory subunit). Nucleotide and amino acid sequences of NAE1 proteins are known in the art. Non-limiting examples of NAE1 sequences include *Homo sapiens* NAE1, the nucleotide and amino acid sequences of which are set forth in GenBank Ace. Nos. NM_001018159 and NP_001018169, respectively; and *Mus musculus* NAE1, the nucleotide and amino acid sequences of which are set forth in GenBank Ace, Nos. NM_144931 and NP_659180, respectively. NEDD8 E2 enzymes play central roles in the E1-E2-E3 NEDD8 conjugation cascade. As used herein, the terms "NEDD8 conjugating enzyme," and "NEDD8 E2 enzyme" refer to a protein capable of transiently binding a NEDD8 E1 enzyme for generation and interacting with a NEDD8 E3 ligase. The two known NEDD8 conjugating enzymes are UBC12, which is also known as UBE2M, and UBE2F. Nucleotide and amino acid sequences of UBE2M proteins are known in the art. Non-limiting examples of UBE2M sequences include *Homo sapiens* UBE2M, the nucleotide and amino acid sequences of which are set forth in GenBank Acc. Nos. NM_003969 and NP_003960, respectively; *Mus musculus* UBC12, the nucleotide and amino acid sequences of which are set forth in GenBank Ace. Nos. NM_145578 and NP_663553, respectively; and *Saccharomyces cerevisiae* UBC12, the nucleotide and amino acid sequences of which are set forth in GenBank Acc. Nos. NM_001182194 and NP_013409, respectively.

Neddylation may be reversed by the COP9 signalosome (CSN), which enzymatically removes NEDD8 from a cullin molecule. Thus, the CSN is a central component of the activation and remodeling cycle of cullin-RING E3 ubiquitin ligases (Schlierf et al., Nat. Commun. 7, 13166 (2016)). The human CSN consists of nine protein subunits (COPS1-7A, 7B, 8), of which COPS5 contains a metalloprotease motif that provides the catalytic centre to the complex COPS5 exhibits proper deneddylating activity only in the context of the holocomplex and only the fully assembled CSN is competent to specifically remove NEDD8 from CRLs.

In this context and in context of this invention, the term "in vivo" relates to a method to be applied on isolated cells and/or cell lines as further defined herein below. The term "in vivo" in context of the methods of this invention does not rely to a method to be practiced on humans, i.e. a living human individual. Accordingly, the method(s) provided herein is/are method that is based on method wherein preferably isolated cells/cell lines are used and employed and, therefore, the herein claimed methods can also be characterized as an in vitro method. This is also evident form the appended examples and the disclosure herein below. Accordingly, the present invention provides for (living) test cell systems/(living) cellular systems useful in methods for identifying, testing, obtaining and/or screening compounds/agents able to induce ubiquitination of proteins of interest/target proteins.

A compound which decreases the level of the one or more protein(s) in a wild-type cell compared to a mutant cell refers to a compound identified/tested/obtained to stimulate/induce ubiquitination of a target protein/target proteins refers to a compound. As disclosed herein and illustrated in the appended Examples, a corresponding read-out whether the compound to be identified in the methods of this invention is able and/or capable to stimulate/induce ubiquitination of a target protein/target proteins may be the measurement of the level of the target protein/target proteins. When said "level" of the target protein/target proteins determined in the wild-type cell is decreased compared to the "level" determined in the mutant cell, said compound is able to stimulate/induce the activity of the E3 ubiquitin ligase. In other words, the activity of the compound is measured in wild-type cells and mutant cells, i.e. cell that have a decreased CRL activity compared to a corresponding "wild-type" cell, i.e. a cell comprising CRL activity. Further, methods of how to determine neddylated and deneddylated CRLs in a cell are described below and are exemplified in the appended Examples. Furthermore, the skilled person in the art knows how to determine the levels by methods described below in detail. In other words, the skilled person is aware of method of how to determine the neddylation/deneddylation status in a given cell. The gist of the present invention is a provision of cellular systems wherein via recombinant and/or chemical modification the neddylation status of the cullins (CUL1, CUL2, CUL3, CUL4A/B, CUL5, CUL6 or CUL7 constituting the various [E3] cullin RING ligases (CRL)) in a cell is modified/manipulated so that the CRL is deneddylated. A skilled person considers a CRL to be deneddylated if neddylation in said modified/manipulated cell is decreased over a corresponding control cell. A control cell may be the same cell/cell line that has been modified/manipulated, but which did not undergo said modification/manipulation. The skilled person is readily in a position to measure, if desired, the neddylation status of a given CRL in a given cell. One example of such a measurement or determination is to perform an immunoblot analysis of said cullin in both the modified/modulated and the control cell and to quantify the ratio of neddylated versus non-neddylated cullin. For example, commercially available cullin antibodies might be employed for such an immunoblot analysis. Commercial antibodies to cullins are readily available to the skilled person and/or can be obtained and generated by the skilled person via routine methods. Examples of cullin antibodies that are commercially available comprise, inter alia, CUL4A Cell Signaling Technology #2699S; CUL2 Sigma-Aldrich SAB2501565; CUL4B Proteintech #12916-1-AP).

As evident from the appended Examples, the method for identifying a compound having the ability to degrade one or more protein(s) as provided herein may comprise the determination of the level of the one or more protein(s) in a mutated cell and a corresponding wild-type cell. Another read-out may comprise the test of viability of a wild-type cell compared to a mutant cell as illustrated in the appended Examples. For example, such viability may be determined by measuring the $LC_{50}$ value. Means and methods of how to determine a $LC_{50}$ value and further quantify the viability of a cell are well known in the art. As illustrated in the examples and described in context of the invention, the viability may be determined by measuring the $LC_{50}$ value in a wild-type cell and in a mutant cell, wherein a decreased viability of the wild-type cell compared to the mutant cell indicates the ability of the compound as described herein and used in context of the invention to stimulate/induce ubiquitination of a target protein/target proteins. Particularly, the viability of the wild-type cell may be decreased by at least 2 fold, preferably by at least 5 fold, more preferably by at least 10 fold compared to the mutated cell. More particularly, the ability to degrade one or more protein(s) comprises a decreased level of the one or more protein(s) by at least 2-fold, preferably by at least 3-fold, more preferably by at least 5-fold, compared to the level of the one or more protein(s) in the mutated cell.

The decreased level of the one or more protein(s) in a mutated cell compared to the wild-type cell is indicative for the ability of the compound to degrade said one or more protein(s). In the mutated cell, the cullin-RING ubiquitin ligase activity/CRL activity is reduced or impaired compared to the cullin-RING ubiquitin ligase activity/CRL activity in the wild-type cell. Such a reduction or impairment of the cullin-RING ubiquitin ligase activity/CRL activity in the mutant cell is achieved by introducing a hypomorphic mutation or inactivation of at least one member or regulator of an E3 ubiquitin ligase complex of said mutated cell. Hence, in the mutated cell in context of the invention, the CRL activity is decreased by the hypomorphic mutation or inactivation of at least one member or regulator of an E3 ubiquitin ligase complex compared to the wild-type cell. It is of note that the term "wild-type cell" refers to a control cell which may be of the same cell type as the mutated cell.

Such a wild-type cell also comprises an E3 ligase complex/cullin-RING ubiquitin ligase complex/CRL complex and also comprises the target protein/target proteins as described herein and used in context of the invention. Such cells are described herein and are illustrated in the appended Examples. Without being limited to the cells of the examples, such cells (i.e. "wildtype cells" that have decreased CRL activity) comprise cancer cells, such as lung cancer cells, gastric cancer cells, melanoma cells, sarcoma cells, leukemia cancer cells, colon cancer cells or neuroblastoma cells.

For example, the prediction whether a compound is able to degrade a target protein, in particular by inducing ubiquitination of a target protein can be assessed, e.g., by the determination of a fold change in target protein level. Hereby, the respective fold change value for identifying a compound to degrade a protein refers to measurements of the level of a target protein. Fold change values may be determined by previously described methods known in the art. For example, methods are known to a skilled person for using the Coefficient of variation in assessing variability of quantitative assays in order to establish fold change values (Reed et al., Clin Diagn Lab Immunol. 2002; 9(6):1235-1239).

The term "identifying a compound having the ability to degrade one or more protein(s)" means that identifying/testing/obtaining a compound for its potential to induce and/or stimulate the ubiquitination of a target protein/target proteins. In context of the method of the invention, the term "compound" also relates to a compound to be identified for its capability/ability to induce ubiquitination of a target protein. Said "compound" may be a compound that may induce the ubiquitination of a target protein directly or indirectly (for example without physically binding to the E3 ligase and the target protein at the same time). For example, a compound as described herein and in context of the invention may degrade a target protein via a direct and/or an indirect binding mechanism. This is, inter alia also illustrated in the appended examples: a compound may bind to a protein associated with a target protein to be degraded, thereby stabilizing an interaction between the associated target protein and one or more components of the E3 ligase complex. Particular examples of such target proteins are, but are not limited to, cell cycle modulators including kinases such as cyclin-dependent kinases and/or transcriptional kinases, like CDK13, CDK12, CDK9, CDK6, CDK4 and/or cyclins, like cyclin B, cyclin E, cyclin H or cyclin K and combinations thereof. As illustrated in the appended, yet non limiting examples, the target protein CCNK may be degraded by binding of a compound to CDK12/13 associated with CCNK, thereby leading to the ubiquitination and degradation of CCNK. As further illustrated in appended Example 5, proteins associated with cancer, metabolic disorders, neurologic disorders or infectious diseases are downregulated upon degradation of CCNK by the E3 ligase as shown by the proteomics profiling analysis.

As illustrated herein also in the experimental part and in the appended figures, proteins associated with neurological disorder such as HECTD1, MBP and FEM1A are downregulated upon the inventive degradation of cell cycle modulators, like cyclin-dependant kinases, e.g. CDK13, CDK12 and/or cyclins, like cyclin K (CCNK). Particularly HECTD1 is known to be involved in the development of the cranial neural folds and neural tube development; MBP is known to be involved in axon remyelination and RRM2 is known to be involved in amyotrophic lateral sclerosis (ALS) pathogenesis; see inter alia Zohn et al., *Dev Biol.*, 2007, 306(1):

208; Llufriu-Daben et al., *Neurobiol. Dis.*, 2018, 109 (PtA): 11; Tavella et al. Biophys J. 2018 Nov. 6; 115(9):1673-1680. doi:10.1016/j.bpj.2018.09.011. Epub 2018 Sep. 21. As another example, proteins associated with metabolic diseases such as HMMR, LMNA and TMPO are also down-regulated upon degradation of targets like CCNK. Particularly HMMR is known to be involved in regulation of adipogenesis; FEM1A is known to be involved in inflammatory signaling; LMNA is known to be involved in ageing-Hutchington-Gilford progeria and TMPO is known to be involved in zinc disorders and thymogenesis; see inter alia Bahrami et al., Integr Biol., 2017, 9(3):223; Cambier et al., FEBS Letters, 2009, 583(10):1625; Prasad et al., Clin Endocrinol Metab., 1985, 14(3):567. As still another example, proteins associated with infectious disease such as ICAM2, CALCOCO2 and CDC6 are downregulated upon degradation of targets like CCNK. For example, ICAM2 is known to be involved in lymphocyte regulation; CALCOCO2 is known to be involved in autophagy-mediated intracellular bacteria degradation, and CDC6 is known to be involved in HPV infection; see inter alia Hobden, DNA Cell Biol., 2003, 22(10):649; Xic et al., Autophagy, 2015, 11(10):1775; Bonds et al; Arch Pathol Lab Med. 2002 October; 126(10): 1164-8 doi: 10.1043/0003 9985 (2002) 126. As yet still another example, cancer associated proteins such as BUB1, BUB1B, MCM10, CDCA7 and CDC6 are also all downregulated upon degradation of CCNK. Particularly, BUB1 and BUB1B are known to be involved in cell division/mitotic spindle; MCM10 is known to be involved in replication initiation; CDCA7 is known to be involved in anchorage-independent growth and CDC6 is known to be involved in DNA replication control and cell division; see inter alia Siemeister et al., Clin Cancer Res., 2019, 25(4):1404; Ma, Oncology Reports, 2017, 38(6); Mahadevappa et al., Cancers, 2018, 10(9):282; Osthus et al., Cancer Res, 2005, 65(13):5620 and Mahadevappa et al., Sci. Rep., 2017, 7:985. Thus, proteins that are downregulated upon degradation of CCNK involve proteins associated with cancer, metabolic disorders, neurologic disorders or infectious diseases.

The "compound" or said compound to be identified by means and methods of this invention may also be assessed for its capacity to bring the E3 ligase in contact with the target protein, i.e. a protein to be degraded. The "chemical to be identified/determined to induce ubiquitination of the target protein" may be a test compound to be assessed for its capacity to augment the inter cellular ubiquitination system, in particular for its capacity to augment the degradation of a protein of interest/target protein via E3 ubiquitin ligase.

As mentioned above and as illustrated in the appended Examples, said "compound" may also be a compound that is capable of bringing the E3 ligase complex in close proximity to the target protein (i.e. the protein to be degraded via ubiquitination), whereby, also in context of this invention, such compounds or agents may be designated as "molecular glues". The "compounds to be tested and/or assessed" for their capacity to induce ubiquitination of a protein of interest may also comprise heterobifunctional degraders, like Proteolysis Targeting Chimeras (PROTAC®) or heterobifunctional compounds composed of a target protein-binding ligand and an E3 ubiquitin ligase ligand. Accordingly, "compounds" to be tested with the herein disclosed inventive methods may comprise but are not limited to PROTAC® compounds or molecular glues.

A compound identified/tested/obtained by the method of the invention, i.e. a compound able to stimulate/induce ubiquitination of a target protein/target proteins, may stimulate/induce ubiquitination of a target protein/target proteins in the wild-type cell and ubiquitination of the target protein/target proteins in the mutant cell may be reduced compared to said wild-type cells. The cell in context of the invention may be an eukaryotic cell. The term "eukaryotic cell" is used herein to mean any nucleated cell, i.e., a cell that possesses a nucleus surrounded by a nuclear membrane, as well as any cell that is derived by terminal differentiation from a nucleated cell, even though the derived cell is not nucleated. Non-limiting examples of cells that may be used in context of the invention are provided herein below and are illustrated by the appended examples.

It is noted that a mutant cell comprises a decreased CRL activity which is induced by the hypomoprhic mutation or inactivation of the at least one member or regulator of the E3 ubiqutin ligase complex. Thus, a compound identified/tested/obtained to stimulate/induce ubiquitination of a target protein/target proteins via the ubiquitination system, i.e. degradation of a target protein/target proteins, is identified by the reduced or impaired ability to stimulate/induce ubiquitination of a target protein/target proteins via the ubiquitination system, i.e. degradation of a target protein/target protein, in said mutated cell, where the CRL activity is decreased, compared to a wild-type cell comprising CRL activity. In turn, a compound identified/tested/obtained to stimulate/induce ubiquitination of a target protein/target proteins via the ubiquitination system, i.e. degradation of a target protein/target proteins, is identified by the ability to stimulate/induce ubiquitination of a target protein/target proteins via the ubiquitination system, i.e. degradation of a target protein/target protein, in the wild-type cell comprising the CRL activity.

The cullin-RING ubiquitin ligase, its activity and means and methods for the detection and/or measurement of this activity may be determined by methods known in the art. For example, such methods may include, but are not limited to FRET (Förster Resonance Energy Transfer) analysis. The theory of FRET (Förster Resonance Energy Transfer) defines a distance dependent, non-radiative transfer of energy from an excited donor (D) to an acceptor molecule (A). The relationship between easily accessible spectroscopic data and theoretical equations was the achievement of Theodor Forster, thereby enabling the possibility of many FRET applications in all kinds of natural sciences. FRET has been used in biochemical applications within the 1 to 10 nm scale (K. E. Sapsford et al., Angew. Chem. Int. Ed., 45, 4562, 2006) (e.g. protein-protein binding, protein folding, molecular interactions at and in cell membranes, DNA hybridization and sequencing, immunoreactions of antigens and antibodies). Details of the theory of FRET are well known. Further examples include protein complementation assay (PCA). Protein complementation assays (PCA) provide a means to detect the interaction of two biomolecules, e.g., polypeptides. PCA utilizes two fragments of the same protein, e.g., enzyme, that when brought into close proximity with each other can reconstitute into a functional, active protein. The NANOBIT® technology (Promega Corporation) may be used to detect molecular proximity by virtue of the reconstitution of a luminescent enzyme via the binding interaction of enzyme components or subunits. By design, the NanoBiT subunits (i.e., 1.3 kDa peptide, 18 kDa polypeptide) weakly associate so that their assembly into a luminescent complex is dictated by the interaction characteristics of the target proteins, such as the at least one member of the E3 ligase complex used herein, onto which they are appended. Details are described, inter alia, in Dixon et al., "NanoLuc Complementation Reporter Optimized for Accurate Measurement of Protein Interactions in Cells,"

ACS Chem. Biol., Publication Date (Web): Nov. 16, 2015. In some aspects, the Nano-Glo® HiBiT Detection System (Promega Corporation) may be used to quantify HiBiT-tagged proteins in cell lysates using a add-mix-read assay protocol. Alternatively, HiBiT-tagged proteins, such as ligase substrate receptors, e.g. DCAF15, may be ectopically expressed. As illustrated in the appended Examples, HiBit-DCAF15 fusion protein may be ectopically expressed via a viral vector. HiBiT is an 11-amino-acid peptide tag that is fused to the N or C terminus of the protein of interest or inserted into an accessible location within the protein structure. The amount of a HiBiT-tagged protein expressed in a cell may be determined by adding a lytic detection reagent containing the substrate furimazine and Large BiT (LgBiT), the large subunit used in NanoLuc® Binary Technology (NanoBiT®; 1). Alternatively, when the LgBit may be ectopically introduced, such as by but not limited to lentiviral expression, the HiBit level may be measured in living cells by adding luciferase substrate(s).

The term "cancer cell" as used herein means a tumor cell having an ability to proliferate depending on a particular oncogene expressed in the cancer cell. The cancer cell may include a primary cultured cell, a cell line, or a cancer stem cell. As used herein, the "dependence (depending)" concerning the proliferation of the cell refers to the state of the oncogene addiction or the addiction, where the cell proliferates depending on the particular oncogene. Whether or not the cell proliferates depending on the particular oncogene can be confirmed by treating the cell with an inhibitor of the particular oncogene and then evaluating a proliferation ability of the treated cell. For example, the cell as used in context of the method of the invention may be a cancer cell. Particularly, such as cancer cell may be a KBM-7, a Mv4-11 or a Jurkat cell; a pancreatic cancer cell, particularly a AsPC-1 cell; a lung cancer cell, particularly a NCI-H446 cell; a gastric cancer cell; a melanoma cell; a sarcoma cell; a colon cell, particularly a HCT116 or RKO cell; or a neuroblastoma cell, particularly a Be (2) C cell; more particularly the cancer cell may be a KBM-7 cell.

The proliferation ability can be evaluated by, for example, an MTT assay or an MTS assay. It is known that cell death due to apoptosis can be induced, when the cell in the oncogene addiction for the particular oncogene is treated with the inhibitor of such an oncogene. Therefore, the oncogene addiction in the cell for the particular oncogene may be confirmed by evaluating whether or not the apoptosis can be induced by inhibition of the oncogene. The induction of the apoptosis can be evaluated by, for example, a TUNEL assay, detection of active caspase, or detection of annexin V. The cancer cell can be derived from any tissues. Examples of such a tissue may include respiratory tissues (e.g., lung, trachea, bronchi, pharynx, nasal cavity, paranasal cavity), gastrointestinal tissues (e.g., stomach, small intestine, large intestine, rectum), pancreas, kidney, liver, thymus, spleen, heart, thyroid, adrenal, prostate, ovary, uterus, brain, skin, and a blood tissue (e.g., bone marrow, peripheral blood). In another viewpoint, the cancer cell can be an adherent cell or a non-adherent cell (i.e., a blood cell). In still another viewpoint, the cancer cell can be a cell present in the above tissues or tissues other than the above tissues. Examples of such a cell may include a gland cell (e.g., gland cell (adenocyte) in lung, mammary gland cell), an epithelial cell, an endothelial cell, an epidermal cell, an interstitial cell, a fibroblast, an adipocyte, a pancreatic P cell, a nerve cell, a glia cell, and a blood cell.

As used herein, the cancer cell of the method of the present invention comprises a hypomorphic mutation or inactivation of at least one member of the E3 ligase complex. Thus, a hypomorphic mutation or inactivation of at least one member of the E3 ligase complex may be induced in a cancer cell, e.g., a host cancer cell. The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. The transformed cell includes transiently or stably transformed cell. Progeny may not be completely identical in nucleic acid content to a parent cell, but may contain mutations. Mutant progeny that have the same function or biological activity as screened or selected for in the originally transformed cell are included herein. In some aspects, the host cell is transiently transfected with the exogenous nucleic acid. In another aspects, the host cell is stably transfected with the exogenous nucleic acid. An "isolated" fusion protein is one that has been separated from the environment of a host cell that recombinantly produces the fusion protein. In some aspects, the fusion protein of the present invention is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of purity, see, e.g., Flatman et al., *J. Chromatogr. B* 848:79-87 (2007).

As evident from the appended examples, the method for identifying a compound able to induce degradation of one or more protein(s) associated with cancer as provided herein comprises the determination of the viability of a cancer cell compared to a mutant cancer cell, wherein the mutation of said mutant cell comprises a hypomorphic mutation or inactivation of at least one member of the E3 ligase complex. As provided in one aspect of the present invention, the mutated at least one member of the E3 ligase complex results in an impaired activity of the E3 ligase complex, e.g. impaired neddylation of the E3 ligase complex due to the mutation of the at least one member of the E3 ligase complex.

As provided herein, the at least one member of the E3 ligase complex refers to any protein that may be associated, directly or indirectly, with the E3 ligase complex. As used herein, the "at least one member of the E3 ligase complex" refers to a polypeptide comprising an amino acid of which the skilled person in the art is aware of. For examples, the at least one member of the E3 ligase complex as used in accordance with the method of the present invention is at least one member which is in molecular proximity of the CRL, is able to be ubiquitinated by the CRL and is degradable by the CRL.

For example, the mutated at least one member of the E3 ligase complex may be UBE2M. As another example, the mutated at least one member of the E3 ligase complex may be a cullin of the E3 ligase complex. As still another example, the mutated at least one member of the E3 ligase complex may be an adaptor protein of the E3 ligase complex, such as DDB1. As yet still another example, the mutated at least one member of the E3 ligase complex may be a substrate receptor, such as cereblon (CRBN) or DCAF15. The term "cereblon" refers to polypeptides ("polypeptides," "peptides" and "proteins" are used interchangeably herein) comprising the amino acid sequence any CRBN, such as a human CRBN protein (e.g., human CRBN isoform 1, GenBank Accession No. NP-057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants); splice variants; fragments; derivatives; substitution, deletion, and insertion variants; fusion polypeptides; and interspecies homologs, which, in certain aspects, retain CRBN activity and/or are sufficient to generate an anti —CRBN immune response. In another example, the substrate receptor may be DCAF15.

The person skilled in the art knows that also proteins implicated in the pathway of E3 ligase ubiquitination are encompassed by the mutated at least one member of the E3 ligase complex of the invention as long as they result in an impairment in the activity of the E3 ligase complex. In this context, the skilled person is able to identify such proteins implicated in the E3 ligase ubiquitination pathway. These proteins include but are not limited to, e.g. NAE1. It can also be understood that at least one member of the E3 ligase complex can be inactivated by means other than by mutation, such as by the addition compounds inhibiting at least one member of the E3 ligase complex, such as antibodies or shRNA. Thus, the term inactivation as provided herein also encompasses the use of inhibitory molecules that are able to reduce the activity of the E3 ligase complex by inhibiting at least one member of the E3 ligase complex.

Further, the skilled person is aware of the fact that the CRL activity of a cell may depend on the type of cell used. CRLs may be activated when dissociated from Cullin-associated NEDD8-dissociated protein 1 (CAND1) and/or Cullin-associated NEDD8-dissociated protein 2 (CAND2). The CAND1 gene encodes an essential regulator of Cullin-RING ubiquitin ligases, which are in involved in ubiquitinylation of proteins degraded by the ubiquitin proteasome system. The encoded CAND1 binds to unneddylated cullin-RING box protein complexes and acts as an inhibitor of cullin neddylation and of Skp1, cullin, and F box ubiquitin ligase complex assembly and activity (Liu et al., (2018) Molecular Cell 69, 773-786).

The ubiquitination of these proteins is mediated by a cascade of enzymatic activity. As used herein, "ubiquitin" refers to a polypeptide which is ligated to another polypeptide by ubiquitin ligase enzymes. The ubiquitin can be from any species of organism, preferably a eukaryotic species. Preferably, the ubiquitin is mammalian. More preferably, the ubiquitin is human ubiquitin. In a preferred embodiment, when ubiquitin is ligated to a target protein of interest, that protein is targeted for degradation by the 26S proteasome. Also encompassed by "ubiquitin" are naturally occurring alleles. Ubiquitin is first activated in an ATP-dependent manner by an ubiquitin activating enzyme (E1). The C-terminus of an ubiquitin forms a high energy thiolester bond with E1. The ubiquitin is then passed to an ubiquitin conjugating enzyme (E2; also called ubiquitin carrier protein), also linked to this second enzyme via a thiolester bond. The ubiquitin is finally linked to its target protein to form a terminal isopeptide bond under the guidance of an ubiquitin ligase (E3). In this process, chains of ubiquitin are formed on the target protein, each covalently ligated to the next through the activity of E3. Thus, as used herein, the term "ubiquitination" refers to the covalent attachment of ubiquitin to a protein through the activity of ubiquitination enzymes. E3 enzymes contain two separate activities: an ubiquitin ligase activity to conjugate ubiquitin to target proteins and form ubiquitin chains via isopeptide bonds, and a targeting activity to physically bring the ligase and target protein together. The specificity of the process is controlled by the E3 enzyme, which recognizes and interacts with the target protein to be degraded. Thus, as used herein, the term "ubiquitin ligase", "ubiquitin E3 ligase" or "E3 ligase" are used interchangeably and refer to an ubiquitination enzyme capable of catalyzing the covalent binding of an ubiquitin to another protein. As used in context of the present invention, it is to be understood that ubiquitination of a target protein such as a protein associated with cancer may be induced if the target protein is in molecular proximity to a CRL. The term "molecular proximity" refers to the physical distance between two molecules that results in a biological event if the molecules are in close proximity to each other. It often but not always involves some chemical bonding, for example non-covalent bonds or covalent bonds.

In one aspect, the present invention relates to a compound for use in medicine. The term "medicine" as used herein is intended to be a generic term inclusive of prescription and non-prescription medications. The compound for use in medicine should be understood as being useful in maintaining health or promoting recovery from a disease, preferably cancer. Further, the term "medicine" includes medicine in any form, including, without limitation, e.g., pills, salves, creams, powders, ointments, capsules, injectable medications, drops, vitamins and suppositories. The scope of this invention is not limited by the type, form or dosage of the medicine. The compounds as described herein and in the context of the present invention, may be for use in treating or preventing cancer, metabolic disorders, neurologic disorders or infectious diseases. In this regard, the compounds as described herein and in the context of the present invention may degrade proteins associated with cancer, metabolic disorders, neurologic disorders or infectious diseases directly or indirectly via the E3 ligase as described herein. For example, as illustrated in appended Example 5, proteins associated with cancer, metabolic disorders, neurologic disorders or infectious diseases may be downregulated upon degradation of CCNK by the E3 ligase as shown by the proteomics profiling analysis.

Particularly, proteins associated with neurological disorder such as HECTD1, MBP and FEM1A are downregulated upon degradation of CCNK. As another example, proteins associated with metabolic diseases such as HMMR, LMNA and TMPO are also downregulated upon degradation of CCNK. As still another example, proteins associated with infectious disease such as ICAM2, CALCOCO2 and CDC6 are downregulated upon degradation of CCNK. As yet still another example, cancer associated proteins such as BUB1, BUB1B, MCM10, CDCA7 and CDC6 are also all downregulated upon degradation of CCNK. Thus, proteins that are downregulated upon degradation of CCNK involve proteins associated with cancer, metabolic disorders, neurologic disorders or infectious diseases.

In one aspect of the present invention, the chemical compound or agent is for use in the treatment of cancer. A "disorder," a "disease," or a "condition," as used interchangeably herein, is any condition that would benefit from treatment with a composition (e.g., a pharmaceutical composition) described herein, e.g., a composition (e.g., a pharmaceutical composition) that includes the fusion protein of the present invention. This includes chronic and acute disorders or diseases including those pathological conditions which predispose the mammal to the disorder in question.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

The term "pharmaceutically acceptable", as used in connection with compositions of the invention, refers to molecular entities and other ingredients of such compositions that are physiologically tolerable and do not typically produce untoward reactions when administered to a mammal (e.g., human). The term "pharmaceutically acceptable" may also mean approved by a regulatory ageney of the Federal or a state government or listed in the U.S. Pharmacopeia or other generally recognized pharmacopeia for use in mammals, and more particularly in humans. A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative. Such pharmaceutically acceptable carriers may be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by A. R. Gennaro, 20th Edition.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. "Alleviation," "alleviating," or equivalents thereof, refer to both therapeutic treatment and prophylactic or preventative measures, wherein the object is to ameliorate, prevent, slow down (lessen), decrease or inhibit a disease or condition, e.g., the formation of atherosclerotic plaques. Those in need of treatment include those already with the disease or condition as well as those prone to having the disease or condition or those in whom the disease or condition is to be prevented.

The term "cancer" as used herein refers to any malignant tumor in the aforementioned tissue and cell type. Examples of the cancer may include a cancer which can be caused by an abnormal adherent cell, or a cancer which can be caused by an abnormal blood cell (e.g., leukemia, lymphoma, multiple myeloma). Specifically, examples of the cancer which can be caused by the abnormal adherent cell may include a lung cancer (e.g. squamous cell carcinoma, non-small cell carcinoma such as adenocarcinoma and large cell carcinoma, and small cell carcinoma), a gastrointestinal cancer (e.g., stomach cancer, small intestine cancer, large intestine cancer, rectal cancer), a pancreatic cancer, a renal cancer, a hepatic cancer, a thymic cancer, a spleen cancer, a thyroid cancer, an adrenal cancer, a prostate cancer, an urinary bladder cancer, an ovarian cancer, an uterus cancer (e.g., endometrial carcinoma, cervical cancer), a bone cancer, a skin cancer, a brain tumor, a sarcoma, a melanoma, a blastoma (e.g., neuroblastoma), an adenocarcinoma, a planocellular cancer, a solid cancer, an epithelial cancer, and a mesothelioma. Particularly, the cancer may be leukemia, particularly acute myeloid leukemia (AML) and B-cell acute lymphoblastic leukemia (B-ALL) a chronic leukemia, such as chronic myeloid leukemia; adenoid cystic carcinoma; osteosarcoma; ovarian cancer; Ewings sarcoma; lung adenocarcinoma and prostate cancer; lymphoma, neuroblastoma, gastrointestinal cancers, endometrial cancers, medulloblastoma, prostate cancers, esophagus cancer, breast cancer, thyroid cancer, meningioma, liver cancer, colorectal cancer, pancreatic cancer, chondrosarcoma, osteosarcoma, kidney cancer, preferably the cancer is leukemia.

As also discussed above, a cancer to be treated in accordance with the present invention and by the means and methods provided herein may be cancer associated with cell cycle modulators, like cyclin-dependant kinases or transcriptional kinases, like e.g. CDK12, CDK13 and/or cyclins, like CCNK. As used herein a "cancer associated with CDK12, CDK13 and/or CCNK" also includes a cancer associated with a complex of CDK12/13 and CCNK. The same applies, mutatis mutantis, for other disorders discussed herein, like neurological disorders/diseases, metabolic disorders/diseases, and/or infectious diseases. Also these disease may be, in cotext of this invention, associated with cell cycle modulators, like cyclin-dependant kinases or transcriptional kinases, like e.g. CDK12, CDK13 and/or cyclins, like CCNK.

Degradation of CCNK has been described to induce genomic instability of cancer, such as of prostate cancer (see Wu et al 2018, *Cell*. 2018 Jun. 14; 173(7):1770-1782.e14. doi: 10.1016/j.cell.2018.04.034) and has been suggested to be effective in cancers associated with mutations in DNA damage response genes such as those described in Table 1 of Lord et al 2016, *Nat Rev Cancer*. 2016 February; 16(2):110-20. doi: 10.1038/nrc.2015.21. Epub 2016 Jan. 18. Further, CCNK degradation has been described to be particularly effective in cancers associated with increased levels of cyclin E1. Thus, as described herein, a cancer associated with cell-cycle modulators, like CDK12, CDK13 and/or CCNK includes, but is not limited, to cancer with an overexpression of cyclin E1 such as breast cancer, ovarian cancer, melanoma, bladder cancer, gastric cancer, stomach adenocarcinoma, lung squamous cancer, lung adenocarcinoma, glioblastoma multiforme and colorectal cancer; see Lei et al.; *Nat Commun*. 2018 May 14; 9(1):1876.

The "cancer" in cancer-related terms such as terms "cancer cell" and "cancer gene (oncogene)" can also mean the same meaning. The cancer cell can be derived from any mammalian species. Such a mammalian species may include, for example, humans, monkeys, cattle, swines, mice, rats, guinea pigs, hamsters, and rabbits. The mammalian species is preferably the human in terms of clinical application. Therefore, the cancer cell may be a cancer cell isolated from a patient with cancer or a cancer cell derived therefrom. The cancer cell may be a cell not infected with virus or a cell infected with virus. Examples of a carcinogenic virus capable of infecting the cell may include Epstein Barr virus, hepatitis virus, human papilloma virus, human T cell leukemia virus, and Kaposi sarcoma-associated herpes virus. The cancer cell may also be a cancer cell derived from an embryonic stem cell, a somatic stem cell, or an artificial stem cell (e.g., iPS cell) produced from a normal cell. The cancer cell from which the artificial cell of the present invention is derived can express an inherent oncogene. As used herein, the term "inherent oncogene" means an oncogene responsible for proliferation of the cancer cell, which is expressed by the cancer cell that can be used as a material in the establishment of the artificial cell of the present invention. The oncogene can be a gene that is overexpressed in the cancer cell (e.g., overexpression due to increase of copy number of the gene) and transmits a signal for proliferation excessively, or a gene that a mutation occurs which continuously transmit a proliferation signal in the cancer cell. Examples of the mutation may include point mutation (e.g., substitution), deletion, addition, insertion, and mutation causing a fusion (e.g., inversion, translocation). As used herein, the term "gene" may intend to be a mutated gene. Examples of the inherent oncogene may include genes for kinase such as tyrosine kinase (receptor type, and non-receptor type) and serine/threonine kinase, small G-proteins, and transcription factors. Examples of the tyrosine kinase which can play a role in proliferation of the cancer cell may include molecules belonging to an epidermal growth factor receptor (EGFR) family (e.g., EGFR, HER2, HER3, HER4), molecules belonging to platelet derived growth factor receptor (PDGFR) family (e.g., PDGFRα, PDGFRβ), an anaplastic lymphoma kinase (ALK), a hepatocyte growth factor receptor (c-MET), and a stem cell factor receptor (c-KIT). As another example, of kinases which can play a role in proliferation of the cancer may include CDK12, CDK13 and/or CCNK. For example, CDK12, CDK13 and/or CCNK can play a role in proliferation of cancer including but not limited to breast cancer, ovarian cancer, melanoma, bladder cancer, gastric cancer, stomach adenocarcinoma, lung squamous cancer, lung adenocarcinoma, glioblastoma multiforme and colorectal cancer.

In one aspect, the present invention further relates to a method treating cancer comprising administering the chemical compound or agent to a patient having cancer. For example, the compound may be a compound binding to one or more protein(s) to be degraded, wherein the one or more protein(s) are proteins associated with cancer and may be a kinase such as a kinase selected from the group consisting of cyclin-dependent kinases and/or transcriptional kinases, like CDK12, CDK13 and/or cyclins, like CCNK. In this context, the invention may relate to a method for treating cancer comprising administering the chemical compound or agent to a patient having cancer, wherein the compound may be a compound binding to one or more protein(s) selected from the group consisting of CDK12, CDK13 and/or CCNK. For example, said chemical compound or agent is used for the treatment of cancer, wherein said cancer may be selected from breast cancer, ovarian cancer, melanoma, bladder cancer, gastric cancer, stomach adenocarcinoma, lung squamous cancer, lung adenocarcinoma, glioblastoma multiforme and colorectal cancer.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the patient, individual, or subject is a human. In one embodiment, the patient may be a "cancer patient," i.e. one who is suffering or at risk for suffering from one or more symptoms of cancer.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy.

The term "hydrocarbon group" refers to a group consisting of carbon atoms and hydrogen atoms.

The term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_{1-4}$ alkyl, more preferably to methyl or ethyl, and even more preferably to methyl.

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_{2-4}$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-5}$ alkynyl" denotes an alkynyl group having 2 to 5 carbon atoms. Preferred exemplary alkynyl groups are ethynyl, propynyl (e.g., propargyl), or butynyl. Unless defined otherwise, the term "alkynyl" preferably refers to $C_{2-4}$ alkynyl.

As used herein, the term "alkylene" refers to an alkanediyl group, i.e. a divalent saturated acyclic hydrocarbon group which may be linear or branched. A "$C_{1-5}$ alkylene" denotes an alkylene group having 1 to 5 carbon atoms, and the term "$C_{0-3}$ alkylene" indicates that a covalent bond (corresponding to the option "$C_0$ alkylene") or a $C_{1-3}$ alkylene is present. Preferred exemplary alkylene groups are methylene (—$CH_2$—), ethylene (e.g., —$CH_2$—$CH_2$— or —CH(—$CH_3$)—), propylene (e.g., —$CH_2$—$CH_2$—$CH_2$—, —CH(—$CH_2$—$CH_3$)—, —$CH_2$—CH(—$CH_3$)—, or —CH(—$CH_3$)—$CH_2$—), or butylene (e.g., —$CH_2$—$CH_2$—$CH_2$—$CH_2$—). Unless defined otherwise, the term "alkylene" preferably refers to $C_{1-4}$ alkylene (including, in particular, linear $C_{1-4}$ alkylene), more preferably to methylene or ethylene, and even more preferably to methylene.

As used herein, the term "alkoxy" refers to an —O-alkyl group, wherein the alkyl moiety comprised in this group is as defined above.

As used herein, the term "carbocyclyl" refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. Unless defined otherwise, "carbocyclyl" preferably refers to aryl, cycloalkyl or cycloalkenyl.

As used herein, the term "heterocyclyl" refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. Unless defined otherwise, "heterocyclyl" preferably refers to heteroaryl, heterocycloalkyl or heterocycloalkenyl.

As used herein, the term "cyclyl" refers to a carbocyclyl or a heterocyclyl, as defined herein above.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7] phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-11}$ cycloalkyl, and more preferably refers to a $C_{3-7}$ cycloalkyl. A particularly preferred "cycloalkyl" is a monocyclic saturated hydrocarbon ring having 3 to 7 ring members. Moreover, unless defined otherwise, the term "cycloalkyl" even more preferably refers to cyclohexyl or cyclopropyl, and yet even more preferably refers to cyclohexyl.

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{3-11}$ cycloalkenyl, and more preferably refers to a $C_{3-7}$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), dihydropyridinyl (e.g., 1,2-dihydropyridinyl or 2,3-dihydropyridinyl), pyranyl (e.g., 2H-pyranyl or 4H-pyranyl), thiopyranyl (e.g., 2H-thiopyranyl or 4H-thiopyranyl), dihydropyranyl, dihydrofuranyl, dihydropyrazolyl, dihydropyrazinyl, dihydroisoindolyl, octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I)

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to —$CF_3$, —$CHF_2$, —$CH_2F$, —$CF_2$—$CH_3$, —$CH_2$—$CF_3$, —$CH_2$—$CHF_2$, —$CH_2$—$CF_2$—$CH_3$, —$CH_2$—$CF_2$—$CF_3$, or —$CH(CF_3)_2$. A particularly preferred "haloalkyl" group is —$CF_3$.

As used herein, terms such as "binding to at least one member of the E3 ligase complex" do not necessarily imply that the binding has to be directly to a moiety of the E3 ligase. Rather the compound may bind to a protein being part of the E3 ligase complex or a protein which interacts (before or after binding of the compound to the protein, optionally as part of a complex of proteins) with the E3 ligase complex.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

A skilled person will appreciate that the substituent groups comprised in the compounds of formulae (I) and (II) may be attached to the remainder of the respective compound via a number of different positions of the corresponding specific substituent group. Unless defined otherwise, the preferred attachment positions for the various specific substituent groups are as illustrated in the examples.

As used herein, unless explicitly indicated otherwise or contradicted by context, the terms "a", "an" and "the" are used interchangeably with "one or more" and "at least one". Thus, for example, a composition comprising "a" compound of formulae (I) and (II) can be interpreted as referring to a composition comprising "one or more" compounds of formulae (I) and (II).

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

Moreover, unless indicated otherwise, any reference to an industry standard, a pharmacopeia, or a manufacturer's manual refers to the corresponding latest version that was available at the priority date (i.e., at the earliest filing date) of the present specification.

The scope of the invention embraces all pharmaceutically acceptable salt forms of the compounds provided herein, particularly the compounds of formulae (I) and (II), which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogenearbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts.

Moreover, the scope of the invention embraces the compounds provided herein, particularly the compounds of formulae (I) and (II), in any solvated form, including, e.g., solvates with water (i.e., as a hydrate) or solvates with organic solvents such as, e.g., methanol, ethanol or acetonitrile (i.e., as a methanolate, ethanolate or acetonitrilate), or in any crystalline form (i.e., as any polymorph), or in amorphous form. It is to be understood that such solvates of the compounds provided herein, particularly the compounds of formulae (I) and (II), also include solvates of pharmaceutically acceptable salts of the corresponding compounds.

Furthermore, the compounds provided herein, particularly the compounds of formulae (I) and (II), may exist in the form of different isomers, in particular stereoisomers (including, e.g., geometric isomers (or cis/trans isomers), enantiomers and diastereomers) or tautomers. All such isomers of the compounds provided herein are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the compounds provided herein.

The scope of the invention also embraces the compounds provided herein, particularly the compounds of formulae (I) and (II), in which one or more atoms are replaced by a specific isotope of the corresponding atom. For example, the invention encompasses compounds of formulae (I) and (II), in which one or more hydrogen atoms (or, e.g., all hydrogen atoms) are replaced by deuterium atoms (i.e., $^2$H; also referred to as "D"). Accordingly, the invention also embraces compounds of formulae (I) and (II) which are enriched in deuterium. Naturally occurring hydrogen is an isotopic mixture comprising about 99.98 mol-% hydrogen-1 ($^1$H) and about 0.0156 mol-% deuterium (2H or D). The content of deuterium in one or more hydrogen positions in the compounds of formulae (I) and (II) can be increased using deuteration techniques known in the art. For example, a compound of formulae (I) and (II) or a reactant or precursor to be used in the synthesis of the compound of formulae (I) and (II) can be subjected to an H/D exchange reaction using, e.g., heavy water (D$_2$O). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; or Modvig A et al., *J Org Chem*, 79, 5861-5868, 2014. The content of deuterium can be determined, e.g., using mass spectrometry or NMR spectroscopy. Unless specifically indicated otherwise, it is preferred that the compound of formulae (I) and (II) is not enriched in deuterium. Accordingly, the presence of naturally occurring hydrogen atoms or $^1$H hydrogen atoms in the compounds of formulae (I) and (II) is preferred.

The present invention also embraces the compounds provided herein, particularly the compounds of formulae (I) and (II), in which one or more atoms are replaced by a positron-emitting isotope of the corresponding atom, such as, e.g., $^{18}$F, $^{11}$C, $^{13}$N, $^{15}$O, $^{76}$Br, $^{77}$Br, $^{120}$I and/or $^{124}$I. Such compounds can be used as tracers or imaging probes in positron emission tomography (PET). The invention thus includes (i) compounds of formulae (I) and (II), in which one or more fluorine atoms (or, e.g., all fluorine atoms) are replaced by $^{18}$F atoms, (ii) compounds of formulae (I) and (II), in which one or more carbon atoms (or, e.g., all carbon atoms) are replaced by $^{11}$C atoms, (iii) compounds of formulae (I) and (II), in which one or more nitrogen atoms (or, e.g., all nitrogen atoms) are replaced by $^{13}$N atoms, (iv) compounds of formulae (I) and (II), in which one or more oxygen atoms (or, e.g., all oxygen atoms) are replaced by $^{15}$O atoms, (v) compounds of formulae (I) and (II), in which one or more bromine atoms (or, e.g., all bromine atoms) are replaced by $^{16}$Br atoms, (vi) compounds of formulae (I) and (II), in which one or more bromine atoms (or, e.g., all bromine atoms) are replaced by $^{77}$Br atoms, (vii) compounds of formulae (I) and (II), in which one or more iodine atoms (or, e.g., all iodine atoms) are replaced by $^{120}$I atoms, and (viii) compounds of formulae (I) and (II), in which one or more iodine atoms (or, e.g., all iodine atoms) are replaced by $^{124}$I atoms. In general, it is preferred that none of the atoms in the compounds of formulae (I) and (II) are replaced by specific isotopes.

Pharmaceutically acceptable prodrugs of the compounds provided herein, particularly the compounds of formulae (I) and (II), are derivatives which have chemically or metabolically cleavable groups and become, by solvolysis or under physiological conditions, the compounds of the invention which are pharmaceutically active in vivo. Prodrugs of the compounds according to the present invention may be formed in a conventional manner with a functional group of the compounds such as, e.g., with an amino, hydroxy or carboxy group. The prodrug form often offers advantages in terms of solubility, tissue compatibility or delayed release in a mammalian organism (see, Bundgaard, H., Design of Prodrugs, pp. 7-9, 21-24, Elsevier, Amsterdam 1985). Prodrugs include acid derivatives, such as, e.g., esters prepared by reaction of the parent acidic compound with a suitable alcohol, or amides prepared by reaction of the parent acid compound with a suitable amine. If a compound of the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. If a compound of the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(═O)—CH$_3$, —OC(═O)—C$_2$H$_5$, —OC(═O)-(tert-Bu), —OC(═O)—C$_{15}$H$_{31}$, —OC(═O)-(m-COONa-Ph), —OC(═O)—CH$_2$CH$_2$COONa, —O(C═O)—CH(NH$_2$) CH$_3$ or —OC(═O)—CH$_2$—N(CH$_3$)$_2$. If a compound of the present invention has an amino group, an amide derivative prepared by reacting the amino group with a suitable acid halide or a suitable mixed anhydride is exemplified as a prodrug. An especially preferred amide derivative as a prodrug is —NHC(═O)—(CH$_2$)$_2$OCH$_3$ or —NHC(═O)—CH(NH$_2$) CH$_3$.

The compounds provided herein, including in particular the compounds of formulae (I) and (II), may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers.

The pharmaceutical compositions may comprise one or more solubility enhancers, such as, e.g., poly(ethylene glycol), including poly(ethylene glycol) having a molecular weight in the range of about 200 to about 5,000 Da (e.g., PEG 200, PEG 300, PEG 400, or PEG 600), ethylene glycol, propylene glycol, glycerol, a non-ionic surfactant, tyloxapol, polysorbate 80, macrogol-15-hydroxystearate (e.g., Kolliphor® HS 15, CAS 70142-34-6), a phospholipid, lecithin, dimyristoyl phosphatidylcholine, dipalmitoyl phosphatidylcholine, distearoyl phosphatidylcholine, a cyclodextrin, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, a carboxyalkyl thioether, hydroxypropyl methylcellulose, hydroxypropylcellulose, polyvinylpyrrolidone, a vinyl acetate copolymer, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in "Remington: The Science and Practice of Pharmacy", Pharmaceutical Press, 22$^{nd}$ edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds provided herein, particularly the compounds of formulae (I) and (II), or the above described pharmaceutical compositions comprising such a compound may be administered to a subject by any convenient route of administration, whether systemically/peripherally or at the site of desired action, including but not limited to one or more of: oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, or vaginal administration.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (see, e.g., U.S. Pat. No. 3,773,919), copolymers of L-glutamic acid and gamma-ethyl -L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; JP 83-118008; U.S. Pat. Nos. 4,485,045; 4,544,545; and EP0102324.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the compounds provided herein, particularly the compounds of formulae (I) and (II), for pulmonary administration, particularly inhalation. Such dry powders may be prepared by spray drying under conditions which result in a substantially amorphous glassy or a substantially crystalline bioactive powder. Accordingly, dry powders of the compounds of the present invention can be made according to the emulsification/spray drying process disclosed in WO 99/16419 or WO 01/85136. Spray drying of solution formulations of the compounds of the invention can be carried out, e.g., as described generally in the "Spray Drying Handbook", 5th ed., K. Masters, John Wiley & Sons, Inc., NY (1991), in WO 97/41833, or in WO 03/053411.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

The present invention thus relates to the compounds or the pharmaceutical compositions provided herein, wherein the corresponding compound or pharmaceutical composition is to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route. Particularly preferred routes of administration are oral administration or parenteral administration.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds according to the invention for oral administration to a human (of approximately 70 kg body weight) may be 0.05 to 8000 mg, preferably 0.1 mg to 4000 mg, of the active ingredient per unit dose. The unit dose may be administered, e.g., 1 to 3 times per day. The unit dose may also be administered 1 to 7 times per week, e.g., with not more than one administration per day. A further exemplary dose of the compounds of formulae (I) and (II) for oral administration to a human is 50 to 200 mg/kg bodyweight/day, particularly 100 mg/kg/day. It will be appreciated that it may be necessary to make routine variations to the dosage depending on the age and weight of the patient/subject as well as the severity of the condition to be treated. The precise dose and also the route of administration will ultimately be at the discretion of the attendant physician or veterinarian.

The compounds provided herein, particularly the compound of formulae (I) and (II), or a pharmaceutical composition comprising such a compound can be administered in monotherapy (e.g., without concomitantly administering any further therapeutic agents, or without concomitantly administering any further therapeutic agents against the same disease that is to be treated or prevented with the compound of formulae (I) and (II)). However, the compound of formulae (I) and (II) or a pharmaceutical composition comprising the compound of formulae (I) and (II) can also be administered in combination with one or more further therapeutic agents. If the compound of formulae (I) and (II) is used in combination with a second therapeutic agent active against the same disease or condition, the dose of each compound may differ from that when the corresponding compound is used alone, in particular, a lower dose of each compound may be used. The combination of the compound of formulae (I) and (II) with one or more further therapeutic agents (such as, e.g., a BRD4 inhibitor, preferably a direct BRD4 inhibitor) may comprise the simultaneous/concomitant administration of the compound of formulae (I) and (II) and the further therapeutic agent(s) (either in a single pharmaceutical formulation or in separate pharmaceutical formulations), or the sequential/separate administration of the compound of formulae (I) and (II) and the further therapeutic agent(s). If administration is sequential, either the compound of formulae (I) and (II) according to the invention or the one or more further therapeutic agents may be administered first. If administration is simultaneous, the one or more further therapeutic agents may be included in the same pharmaceutical formulation as the compound of formulae (I) and (II), or they may be administered in one or more different (separate) pharmaceutical formulations.

Preferably, the one or more further therapeutic agents to be administered in combination with a compound of the present invention are anticancer drugs. The anticancer drug(s) to be administered in combination with a compound of formulae (I) and (II) according to the invention may, e.g., be selected from: a tumor angiogenesis inhibitor (e.g., a protease inhibitor, an epidermal growth factor receptor kinase inhibitor, or a vascular endothelial growth factor receptor kinase inhibitor); a cytotoxic drug (e.g., an antimetabolite, such as purine and pyrimidine analog antimetabolites); an antimitotic agent (e.g., a microtubule stabilizing drug or an antimitotic alkaloid); a platinum coordination complex; an anti-tumor antibiotic; an alkylating agent (e.g., a nitrogen mustard or a nitrosourea); an endocrine agent (e.g., an adrenocorticosteroid, an androgen, an anti-androgen, an estrogen, an anti-estrogen, an aromatase inhibitor, a gonadotropin-releasing hormone agonist, or a somatostatin analog); or a compound that targets an enzyme or receptor that is overexpressed and/or otherwise involved in a specific metabolic pathway that is misregulated in the tumor cell (e.g., ATP and GTP phosphodiesterase inhibitors, histone deacetylase inhibitors, protein kinase inhibitors (such as serine, threonine and tyrosine kinase inhibitors, e.g., Abelson protein tyrosine kinase inhibitors) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (e.g., cyclooxygenase-1 or cyclooxygenase-2 inhibitors), topoisomerase inhibitors (e.g., topoisomerase I inhibitors or topoisomerase II inhibitors), poly ADP ribose polymerase inhibitors (PARP inhibitors), and epidermal growth factor receptor (EGFR) inhibitors/antagonists.

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazine (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, tesetaxel, or nab-paclitaxel (e.g., Abraxane®)), a *Vinca* alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, axitinib, nintedanib, ponatinib, or vandetanib.

A topoisomerase inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

A PARP inhibitor which can be used as an anticancer drug in combination with a compound of the present invention may be, for example, BMN-673, olaparib, rucaparib, veliparib, CEP 9722, MK 4827, BGB-290, or 3-aminobenzamide.

An EGFR inhibitor/antagonist which can be used as an anticancer drug in combination with a compound of the present invention may be, for example, gefitinib, erlotinib, lapatinib, afatinib, neratinib, ABT-414, dacomitinib, AV-412, PD 153035, vandetanib, PKI-166, pelitinib, canertinib, icotinib, poziotinib, BMS-690514, CUDC-101, AP26113, XL647, cetuximab, panitumumab, zalutumumab, nimotuzumab, or matuzumab.

Further anticancer drugs may also be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, vorinostat, or iniparib.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in cotherapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP1071752) and anti-TNF antibodies (see, e.g., Taylor P C. Antibody therapy for rheumatoid arthritis. Curr Opin Pharmacol. 2003. 3(3):323-328). Further antibodies, antibody fragments, antibody constructs and/or modified antibodies to be used in cotherapy approaches with the compounds of the invention can be found, e.g., in: Taylor P C. Curr Opin Pharmacol. 2003. 3(3):323-328; or Roxana A. Maedica. 2006. 1(1):63-65.

An anticancer drug which can be used in combination with a compound of the present invention may, in particular, be an immunooncology therapeutic (such as an antibody (e.g., a monoclonal antibody or a polyclonal antibody), an antibody fragment, an antibody construct (e.g., a single-chain construct), or a modified antibody (e.g., a CDR-grafted antibody, a humanized antibody, or a "full humanized" antibody) targeting any one of CTLA-4, PD-1/PD-L1, TIM3, LAG3, OX4, CSF1R, IDO, or CD40. Such immunooncology therapeutics include, e.g., an anti-CTLA-4 antibody (particularly an antagonistic or pathway-blocking anti-CTLA-4 antibody; e.g., ipilimumab or tremelimumab), an anti-PD-1 antibody (particularly an antagonistic or pathway-blocking anti-PD-1 antibody; e.g., nivolumab (BMS-936558), pembrolizumab (MK-3475), pidilizumab (CT-011), AMP-224, or APE02058), an anti-PD-L1 antibody (particularly a pathway-blocking anti-PD-L1 antibody; e.g., BMS-936559, MEDI4736, MPDL3280A (RG7446), MDX-1105, or MEDI6469), an anti-TIM3 antibody (particularly a pathway-blocking anti-TIM3 antibody), an anti-LAG3 antibody (particularly an antagonistic or pathway-blocking anti-LAG3 antibody; e.g., BMS-986016, IMP701, or IMP731), an anti-OX4 antibody (particularly an agonistic anti-OX4 antibody; e.g., MEDI0562), an anti-CSF1R antibody (particularly a pathway-blocking anti-CSF1R antibody; e.g., IMC-CS4 or RG7155), an anti-IDO antibody (particularly a pathway-blocking anti-IDO antibody), or an anti-CD40 antibody (particularly an agonistic anti-CD40 antibody; e.g., CP-870,893 or Chi Lob 7/4). Further immunooncology therapeutics are known in the art and are described, e.g., in: Kyi C et al., FEBS Lett, 2014, 588(2):368-76; Intlekofer A M et al., J Leukoc Biol, 2013, 94(1):25-39; Callahan M K et al., J Leukoc Biol, 2013, 94(1):41-53; Ngiow S F et al., Cancer Res, 2011, 71(21):6567-71; and Blattman J N et al., Science, 2004, 305(5681):200-5.

A BRD4 inhibitor (preferably a direct BRD4 inhibitor), such as CeMMEC2, may also be used as a further therapeutic agent in combination with the compound of formulae (I) and (II).

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (particularly the compound of formulae (I) and (II) or a pharmaceutically acceptable salt, solvate or prodrug thereof) or the further therapeutic agent(s) may be administered first. When administration is simultaneous, the combination may be administered either in the same pharmaceutical composition or in different pharmaceutical compositions. When combined in the same formulation, it will be appreciated that the two or more compounds must be stable and compatible with each other and the other components of the formulation. When formulated separately, they may be provided in any convenient formulation.

The compounds provided herein, particularly the compounds of formulae (I) and (II), can also be administered in combination with physical therapy, such as radiotherapy. Radiotherapy may commence before, after, or simultaneously with administration of the compounds of the invention. For example, radiotherapy may commence 1-10 minutes, 1-10 hours or 24-72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a compound of formulae (I) and (II) or a pharmaceutically acceptable salt, solvate, or prodrug thereof, or a pharmaceutical composition comprising any of the aforementioned entities in combination with a pharmaceutically acceptable excipient, for use in the treatment or prevention of cancer, wherein the compound or the pharmaceutical composition is to be administered in combination with one or more anticancer drugs and/or in combination with radiotherapy.

Yet, the compounds of formulae (I) and (II) can also be used in monotherapy, particularly in the monotherapeutic treatment or prevention of cancer (i.e., without administering any other anticancer agents until the treatment with the compound(s) of formulae (I) and (II) is terminated). Accordingly, the invention also relates to a compound of formulae (I) and (II) or a pharmaceutically acceptable salt, solvate, or prodrug thereof, or a pharmaceutical composition comprising any of the aforementioned entities in combination with a pharmaceutically acceptable excipient, for use in the monotherapeutic treatment or prevention of cancer.

The subject or patient to be treated in accordance with the present invention may be an animal (e.g., a non-human animal), a vertebrate animal, a mammal, a rodent (e.g., a guinea pig, a hamster, a rat, or a mouse), a canine (e.g., a dog), a feline (e.g., a cat), a porcine (e.g., a pig), an equine (e.g., a horse), a primate or a simian (e.g., a monkey or an ape, such as a marmoset, a baboon, a gorilla, a chimpanzee, an orangutan, or a gibbon), or a human. In accordance with the present invention, it is envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal. More preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig). Most preferably, the subject/patient is a human.

The term "prevention" of a disorder or disease as used herein (e.g., "prevention" of cancer) is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of a compound of the present invention before any clinical and/or pathological symptoms are diagnosed or determined or can be diagnosed or determined by the attending physician.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formulae (I) and (II).

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention relates in particular to the following items:

1. A compound of the following formula (I):

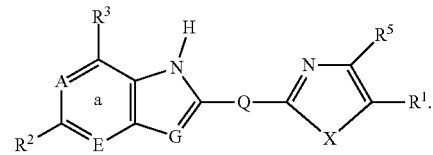

wherein
Ring a is optionally substituted with -L-TBM, wherein L is a linker moiety and TBM is a moiety binding to a target protein;
A is C—$R^3$ or N;
E is C—$R^3$ or N;
G is C—$R^3$ or N;
X is —$CR^5$=$CR^5$—, —S— or —O—;
Q is a linear $C_{4-5}$ alkylene group wherein one or more of the $CH_2$ units are replaced by any one independently selected from S, O and NH, wherein the linear $C_{4-5}$ alkylene group is optionally substituted with 1, 2, 3 or 4 substituents independently selected from =O, —OH, -Hal, and —C$_{1-6}$ alkyl which is optionally substituted with one or more halogen;

R$^1$ is selected from —F, —Cl, —Br, —I and C$_{1-2}$ alkyl which is optionally substituted with one or more F;

R$^2$ is selected from hydrogen, halogen, C$_{1-5}$ alkyl, C$_{2-5}$ alkenyl, C$_{2-5}$ alkynyl, —(C$_{0-3}$ alkylene)-OH, —(C$_{0-3}$ alkylene)-O(C$_{1-5}$ alkyl), —(C$_{0-3}$ alkylene)-O(C$_{1-5}$ alkylene)-OH, —(C$_{0-3}$ alkylene)-O(C$_{1-5}$ alkylene)-O (C$_{1-5}$ alkyl), —(C$_{0-3}$ alkylene)-SH, —(C$_{0-3}$ alkylene)-S(C$_{1-5}$ alkyl), —(C$_{0-3}$ alkylene)-NH$_2$, —(C$_{0-3}$ alkylene)-NH (C$_{1-5}$ alkyl), —(C$_{0-3}$ alkylene)-N(C$_{1-5}$ alkyl)(C$_{1-5}$ alkyl), —(C$_{0-3}$ alkylene)-CF$_3$, —(C$_{0-3}$ alkylene)-CN, —(C$_{0-3}$ alkylene)-NO$_2$, —(C$_{0-3}$ alkylene)-CHO, —(C$_{0-3}$ alkylene)-CO—(C$_{1-5}$ alkyl), —(C$_{0-3}$ alkylene)-COOH, —(C$_{0-3}$ alkylene)-CO—O—(C$_{1-5}$ alkyl), —(C$_{0-3}$ alkylene)-O—CO—(C$_{1-5}$ alkyl), —(C$_{0-3}$ alkylene)-CO—NH$_2$, —(C$_{0-3}$ alkylene)-CO—NH (C$_{1-5}$ alkyl), —(C$_{0-3}$ alkylene)-CO—N(C$_{1-5}$ alkyl) (C$_{1-5}$ alkyl), —(C$_{0-3}$ alkylene)-NH—CO—(C$_{1-5}$ alkyl), —(C$_{0-3}$ alkylene)-N(C$_{1-5}$ alkyl)-CO—(C$_{1-5}$ alkyl), —(C$_{0-3}$ alkylene)-SO$_2$—NH$_2$, —(CO-3 alkylene)-SO$_2$—NH (C$_{1-5}$ alkyl), —(C$_{0-3}$ alkylene)-SO$_2$—N(C$_{1-5}$ alkyl)(C$_{1-5}$ alkyl), —(C$_{0-3}$ alkylene)-NH—SO$_2$—(C$_{1-5}$ alkyl), and —(C$_{0-3}$ alkylene)-N(C$_{1-5}$ alkyl)-SO$_2$—(C$_{1-5}$ alkyl), wherein each alkylene and alkyl is optionally substituted with one or more halogen, preferably F;

each R$^3$ is preferably selected from hydrogen, halogen, C$_{1-5}$ alkyl, —(C$_{0-3}$ alkylene)-OH, —(C$_{0-3}$ alkylene)-O (C$_{1-5}$ alkyl), —(C$_{0-3}$ alkylene)-O(C$_{1-5}$ alkylene)-OH, —(C$_{0-3}$ alkylene)-O(C$_{1-5}$ alkylene)-O(C$_{1-5}$ alkyl), —(C$_{0-3}$ alkylene)-NH$_2$, —(C$_{0-3}$ alkylene)-NH (C$_{1-5}$ alkyl), —(C$_{0-3}$ alkylene)-N(C$_{1-5}$ alkyl)(C$_{1-5}$ alkyl), —(C$_{0-3}$ alkylene)-CF$_3$, —(C$_{0-3}$ alkylene)-CN, —(C$_{0-3}$ alkylene)-NO$_2$, —(C$_{0-3}$ alkylene)-CHO, —(C$_{0-3}$ alkylene)-CO—(C$_{1-5}$ alkyl), —(C$_{0-3}$ alkylene)-COOH, —(C$_{0-3}$ alkylene)-CO—O—(C$_{1-5}$ alkyl), —(C$_{0-3}$ alkylene)-O—CO—(C$_{1-5}$ alkyl), —(C$_{0-3}$ alkylene)-CO—NH$_2$, —(C$_{0-3}$ alkylene)-CO—NH (C$_{1-5}$ alkyl), —(C$_{0-3}$ alkylene)-CO—N(C$_{1-5}$ alkyl)(C$_{1-5}$ alkyl), —(C$_{0-3}$ alkylene)-NH—CO—(C$_{1-5}$ alkyl), —(C$_{0-3}$ alkylene)-N(C$_{1-5}$ alkyl)-CO—(C$_{1-5}$ alkyl) and, wherein each alkylene and alkyl is optionally substituted with one or more halogen, preferably F;

R$^5$ is selected from —H, —OH, —O—C$_{1-2}$ alkyl, -Hal, and C$_{1-2}$ alkyl which is optionally substituted with one or more F;

or a stereoisomer, tautomer, pharmaceutically acceptable salt, solvate or prodrug thereof.

2. The compound of item 1, wherein

Ring a is optionally substituted with -L-TBM, wherein L is a linker moiety and TBM is a moiety binding to a target protein;

A is C—R$^3$ or N;
E is C—R$^3$ or N;
G is C—R$^3$ or N;
X is —CR$^5$=CR$^5$—, —S— or —O—;
Q is a linear C$_{4-5}$ alkylene group wherein one or more of the CH$_2$ units are replaced by any one independently selected from S, O and NH, wherein the linear C$_{4-5}$ alkylene group is optionally substituted with 1, 2, 3 or 4 substituents independently selected from =O, —OH, -Hal, —C$_{1-6}$ alkyl which is optionally substituted with one or more F;

R$^1$ is selected from —F, —Cl, —Br, —I and C$_{1-2}$ alkyl which is optionally substituted with one or more F;

R$^2$ is selected from R$^3$;

each R$^3$ and R$^5$ are each independently selected from —H, -Hal, and C$_{1-2}$ alkyl which is optionally substituted with one or more F;

or a stereoisomer, tautomer, pharmaceutically acceptable salt, solvate or prodrug thereof.

3. The compound of item 1, wherein Q is represented by the following group:

-(α)$_n$-, wherein each a is independently selected from one or more groups selected from —N(R$^4$)—, —C(R$^4$)(R$^4$)—, —C(O)—, —O—, —S—, —S(O)— and —S(O)$_2$—, wherein each R$^4$ is independently selected from —H, -Hal and C$_{1-2}$ alkyl which is optionally substituted with one or more halogen; and n is 4 or 5, wherein two neighboring groups a are preferably not both —N(R$^4$)—, not both —C(O)—, not both —O—, not both —S—, not both —S(O)— and not both —S(O)$_2$— and preferably further two neighboring groups a do not form a direct bond between any of —O—, —S—, —S(O)— and —S(O)$_2$—.

4. The compound of any one of items 1 to 3, wherein the compound of formula (I) is a compound of formula (Ia):

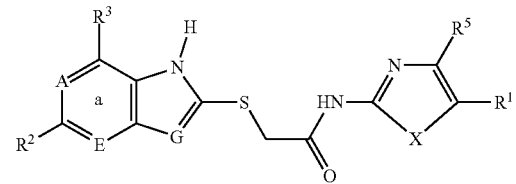

wherein the definitions of A, E, G, X, R$^1$, R$^2$, R$^3$ and R$^5$ set out in item 1 apply and Ring a is optionally substituted with -L-TBM, wherein L is a linker moiety and TBM is a moiety binding to a target protein, or a stereoisomer, tautomer, pharmaceutically acceptable salt, solvate or prodrug thereof.

5. A compound of the following formula (II):

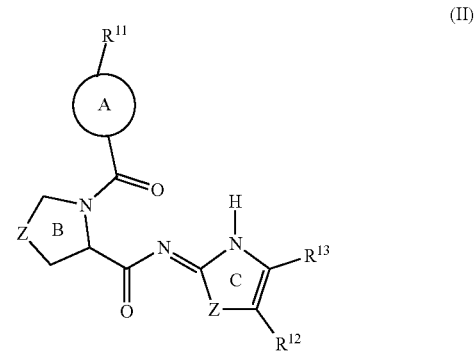

wherein
any one of Rings A, B and C is optionally substituted with -L-TBM, wherein L is a linker moiety and TBM is a moiety binding to a target protein;

Ring A is a thiophen or furan ring;
wherein Ring A is optionally further substituted with one or two selected from —F, —Cl, and —Br and C$_{1-2}$ alkyl which is optionally substituted with one or more F;

each Z is independently selected from —O— and —S—, preferably —S—;

$R^{11}$ is selected from —F, —Cl, —Br, —I and $C_{1-2}$ alkyl which is optionally substituted with one or more F;

$R^{12}$ and $R_{13}$ are each independently selected from —H, —F, —Cl, —Br, —I, and $C_{1-2}$ alkyl which is optionally substituted with one or more F, or a stereoisomer, tautomer, pharmaceutically acceptable salt, solvate or prodrug thereof.

6. The compound of item 5, wherein the compound of formula (II) is a compound of formula (IIa) or formula (IIb):

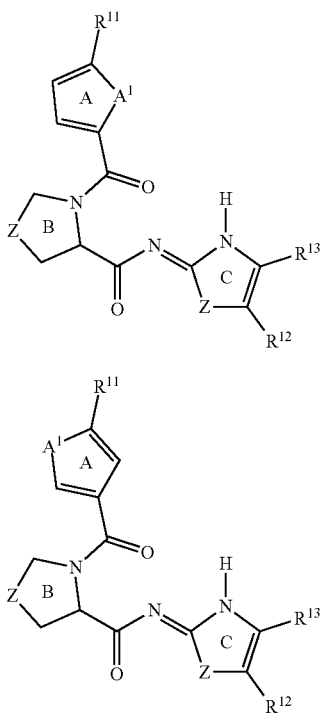

wherein the definitions relating to Z, $R^{11}$, $R^{12}$, $R^{13}$ and the substituents of ring A set out in item 5 apply and any one of Rings A, B and C is optionally substituted with -L-TBM, wherein L is a linker moiety, and TBM is a moiety binding to a target protein, and each A1 is independently selected from —O— and —S—, or a stereoisomer, tautomer, pharmaceutically acceptable salt, solvate or prodrug thereof.

7. The compound of any one of the previous items, wherein L is selected from a bond, $C_{1-20}$ alkylene, $C_{2-20}$ alkenylene, and $C_{2-20}$ alkynylene, wherein said alkylene, said alkenylene and said alkynylene are each optionally substituted with one or more groups independently selected from halogen, $C_{1-5}$ haloalkyl, —O($C_{1-5}$ haloalkyl), —CN, —$OR^{21}$, —$NR^{21}R^{21}$, —$NR^{21}OR^{21}$, —$COR^{21}$, —$COOR^{21}$, —$OCOR^{21}$, —$CONR^{21}R^{21}$, —$NR^{21}COR^{21}$, —$NR^{21}COOR^{21}$, —$OCONR^{21}R^{21}$, —$SR^{21}$, —$SOR^{21}$, —$SO_2R^{21}$, —$SO_2NR^{21}R^{21}$, —$NR^{21}SO_2R^{21}$, —$SO_3R^{21}$, and —$NO_2$, and further wherein one or more —$CH_2$-units comprised in said alkylene, said alkenylene or said alkynylene are each optionally replaced by a group independently selected from —O—, —$NR^{21}$—, —CO—, —S—, —SO—, and —$SO_2$—;

each $R^{21}$ is independently selected from hydrogen, $C_{1-5}$ alkyl, $C_{2-5}$ alkenyl, $C_{2-5}$ alkynyl, carbocyclyl, and heterocyclyl, wherein said alkyl, said alkenyl and said alkynyl are each optionally substituted with one or more groups $R^{AlK}$, and further wherein said carbocyclyl and said heterocyclyl are each optionally substituted with one or more groups $R^{Cyc}$;

any two $R^{21}$ are optionally linked to form a ring;

each $R^{AlK}$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH ($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO($C_{1-5}$ alkyl), —CO—$NH_2$, —CO—NH ($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH ($C_{1-5}$ alkyl), —O—CO—N($C_{1-5}$ alkyl)($C_{1-5}$ alkyl), —$SO_2$—$NH_2$, —$SO_2$—NH ($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH ($C_{1-5}$ alkyl), and —N($C_{1-5}$ alkyl)($C_{1-5}$ alkyl);

each $R^{Cyc}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH ($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO ($C_{1-5}$ alkyl), —CO—$NH_2$, —CO—NH ($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH ($C_{1-5}$ alkyl), —O—CO—N($C_{1-5}$ alkyl)($C_{1-5}$ alkyl), —$SO_2$—$NH_2$, —$SO_2$—NH ($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH ($C_{1-5}$ alkyl), and —N($C_{1-5}$ alkyl)($C_{1-5}$ alkyl).

8. A composition comprising a compound of any of items 1 to 7.

9. The compound of any of items 1 to 7 or the composition of item 8 further comprising a pharmaceutically acceptable diluent, excipient or carrier.

10. The compound of any of items 1 to 9 or the composition of item 8 or 9 for use as a medicament.

11. The compound of any of items 1 to 10 or composition of any of items 8 to 10 for use in treating or preventing cancer, metabolic disorders, neurologic disorders or infectious diseases.

12. The compound or composition of item 11 for use in treating or preventing cancer.

13. An in vivo method for identifying a compound having the ability to degrade one or more protein(s), the method comprising contacting a compound with a wild-type cell and with a mutated cell, wherein the mutation comprises a hypomorphic mutation or inactivation of at least one member or regulator of an E3 ubiquitin ligase complex;

wherein the compound is determined to degrade one or more protein(s) if the level of the one or more protein(s) of the wild-type cell is decreased compared to the mutated cell.

14. The compound of any of items 8 to 12 wherein the TBM is a moiety binding to one or more protein(s) to be degraded, the composition of any of items 8 to 12, or the method of item 13, wherein the one or more protein(s) is one or more protein(s) associated with cancer, metabolic disorders, neurologic disorders or infectious diseases.

15. The method, compound or composition of item 14, wherein the one or more protein(s) associated with cancer are selected from the group consisting of CDK13, CDK12, CDK9, CDK6, CDK4, CCNK, BRD2, BRD3, BRD4, CBP, p300, ATAD2, SMARCA2, SMARCA4, PRBM1, EWS-FL1, CDC6, CENPE, EGFR, SRC, PDGFR, ABL1, HER2, HER3, BCR-ABL1, MEK1, ARAF, BRAF, CRAF, HRAS, NRAS, KRAS, BCL2, MCL2, SHP2, PTPN1, PTPN12, ESR1, AR, MYB, MYC, PDL1 and combinations thereof.

The Figures show

Figure 1:
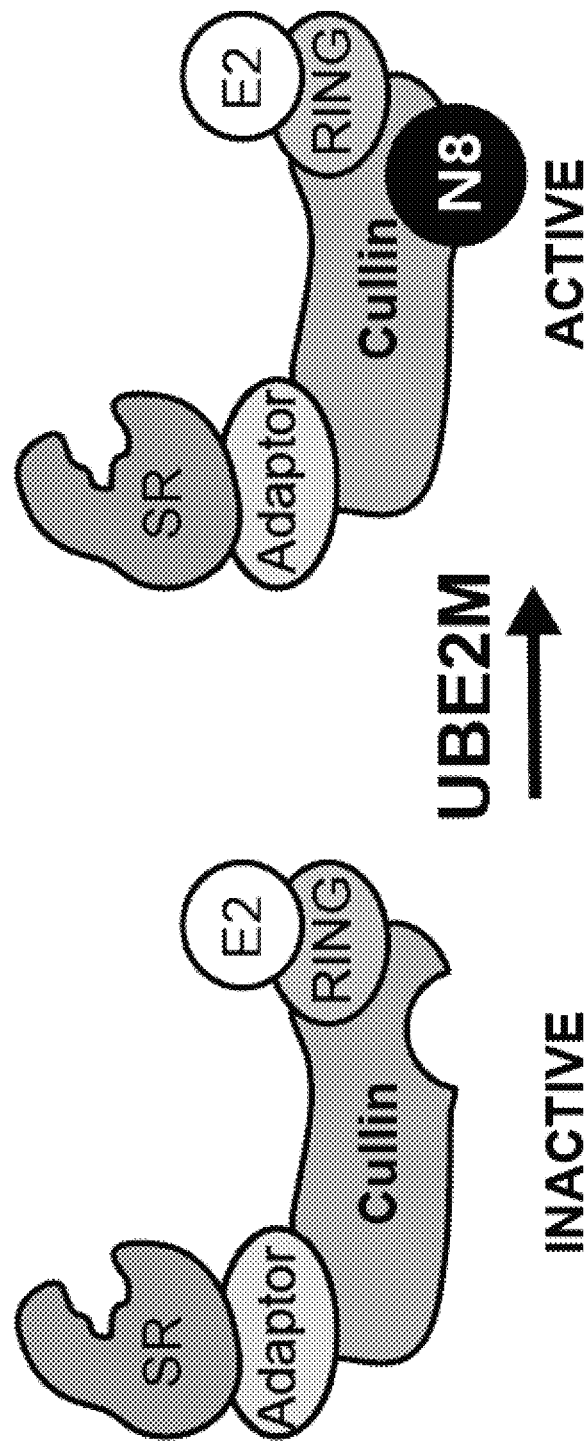

FIG. 1. Architecture of cullin RING ubiquitin ligases (CRLs). CRLs are modular protein assemblies formed by a cullin scaffold that mediates contacts between an E2 enzyme (via a RING protein) and the target (via a substrate receptor and an adaptor). CLR activity requires the attachment of NEDD8 to the cullin. UBE2M is an essential component of the neddylation enzymatic cascade.

Figure 2:
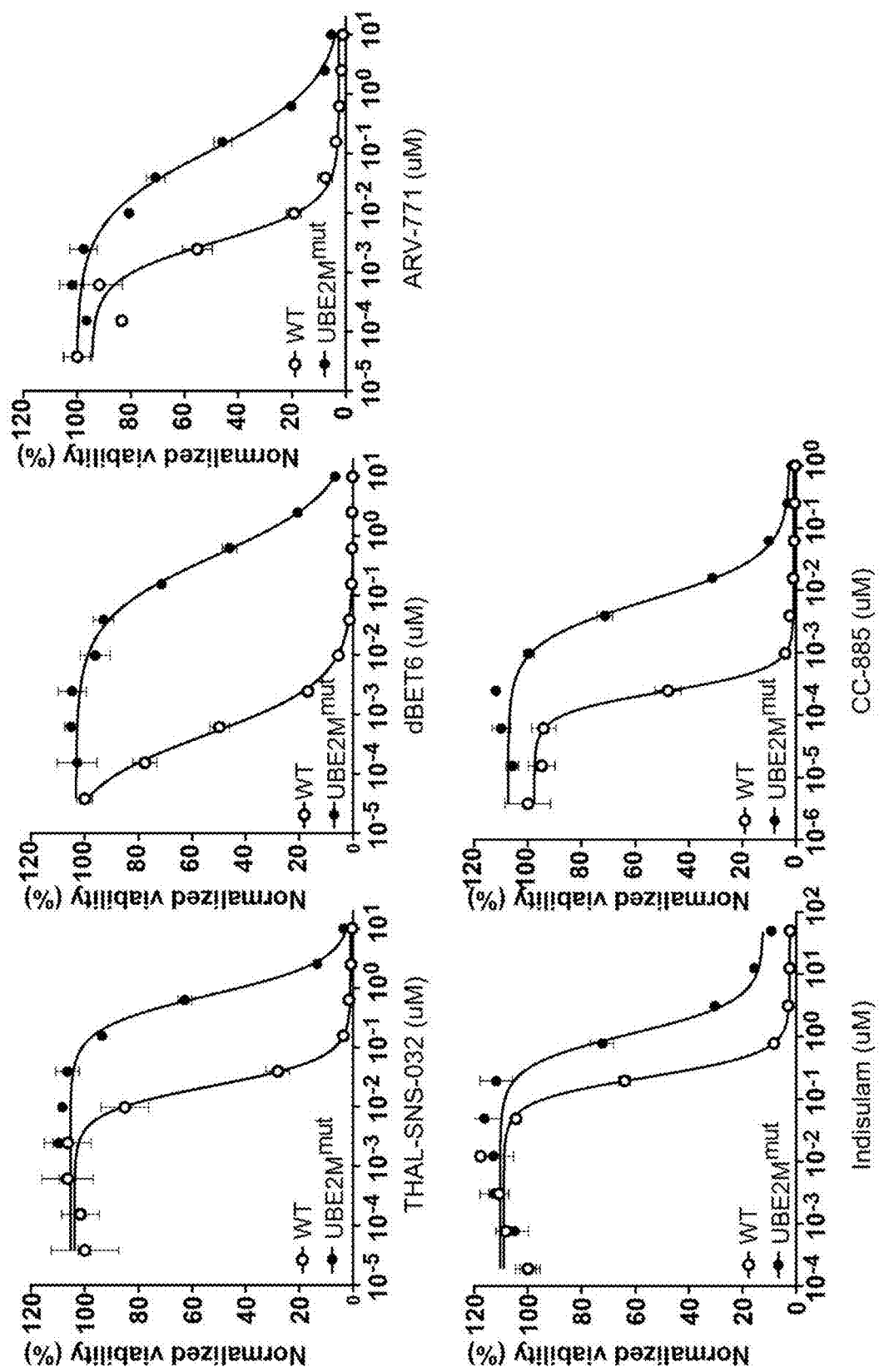

FIG. 2. Dose-ranging viability assays of known degraders in WT or UBE2M mutant cells. DMSO-normalized cellular viability after 3-day degrader treatment. A set of five degraders recruiting different CRLs was used: dBET6, THAL-SNS-032 and CC-885 (that hijack $CRL4^{CRBN}$ to degrade BRD2/3/4, CDK9 and GSPT1 respectively), indisulam (that recruits $CRL4^{DCAF15}$ and promotes RBM39 degradation) and ARV-771 (that recruits $CRL2^{VHL}$ and degrades BRD2/3/4).

FIG. 3. Results of the phenotypic screen based on differential viability. (A) Primary screening data comparing cellular viability of WT and UBE2M mutant KBM7 cells treated with a structurally diverse compound library composed by 2000 cytotoxic molecules. Doses tested were 10 µM and 500 nM. Cell viability was measured after 3 days of treatment. (B) Chemical structure of the best validated small-molecule hits.

Figure 4:
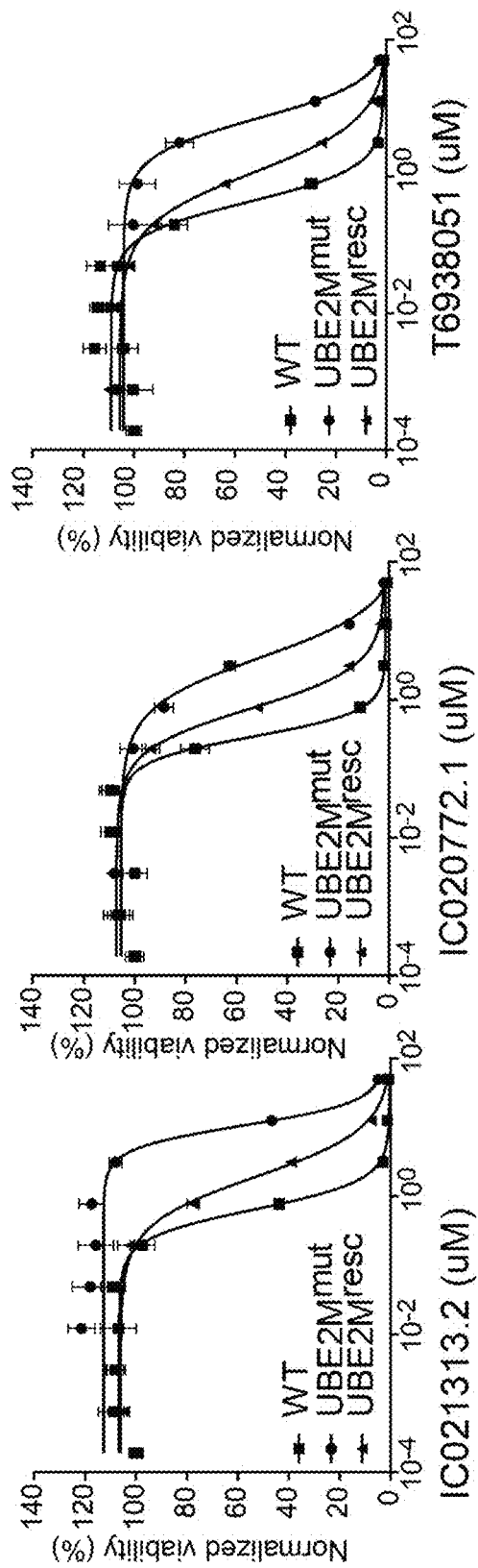

FIG. 4. Dose-ranging viability data of selected small-molecule hits in different isogenic backgrounds. DMSO-normalized cellular viability after 3-day hit treatment in $KBM7^{WT}$, $UBE2M^{mut}$ and $UBE2M^{resc}$ cells.

Figure 5:
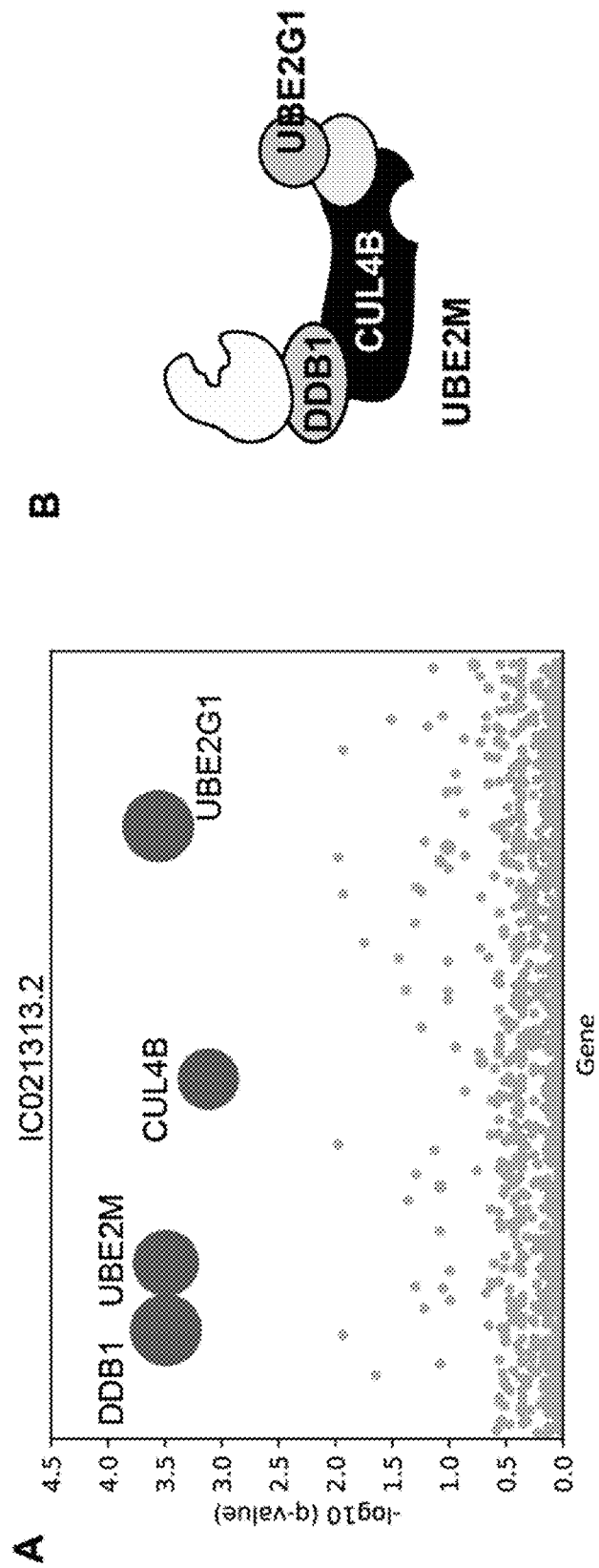

FIG. 5. Genome-scale CRISPR/Cas9 resistance screens link the anti-proliferative mechanism of our small-molecule hits to CRL4B. (A) Results of genome-wide CRISPR/Cas9 screen geared to identify genes required for the anti-proliferative consequences of IC021313.2. Y-axis position corresponds to significance, circle size to measured enrichment over vehicle treated control. (B) Schematic depiction of how screening hits are all required for the formation of a functional CRL4B complex.

Figure 6:
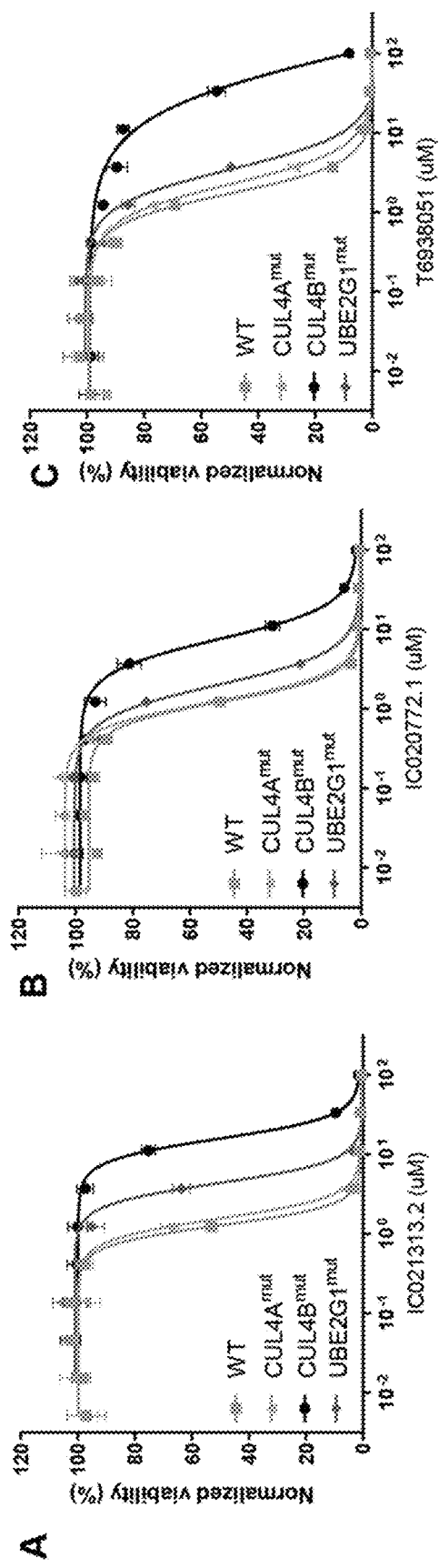

FIG. 6. Dose-ranging viability data of selected compounds in the indicated genetic backgrounds. DMSO-normalized cellular viability after 3-day hit treatment in $KBM7^{WT}$, $CUL4A^{mut}$, $CUL4B^{mut}$ and $UBE2G1^{mut}$ cells.

Note the differential effect of mutating CUL4A and CUL4B, thus validating the screening hits.

Figure 7:
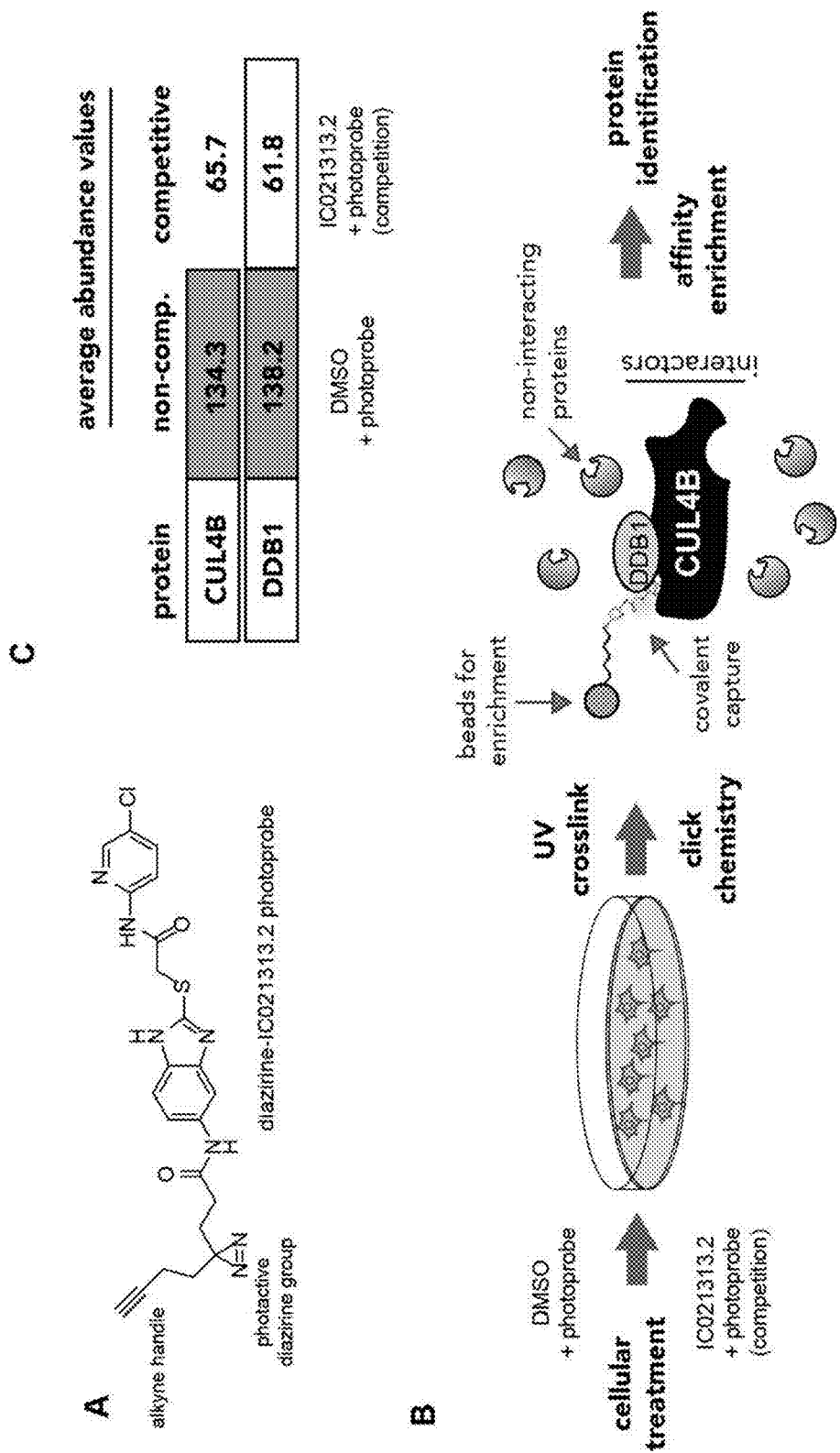

FIG. 7. Chemoproteomics shows that IC021313.2 physically engages with a CRL4B complex. (A) Chemical structure of the functionalized IC021313.2 analog ("photoprobe"), derivatized via conjugation to a constant side chain consisting of a photoreactive diazirine group and an alkyne handle. (B) Schematic depiction of the workflow. Cells are pretreated with DMSO or the parental hit, and then treated with the photoprobe. Target proteins are covalently linked to the probe via photo-crosslinking and extracted. The alkyne handle of the probe is conjugated to biotin, which allows enrichment of target proteins via streptavidin-pulldown. Resulting eluates of biotinylated proteins are subjected to mass spectrometry analysis. (C) Abundance value table of identified interactors CUL4B and DDB1 found to bind to the photoprobe in a competitive manner.

Figure 8:
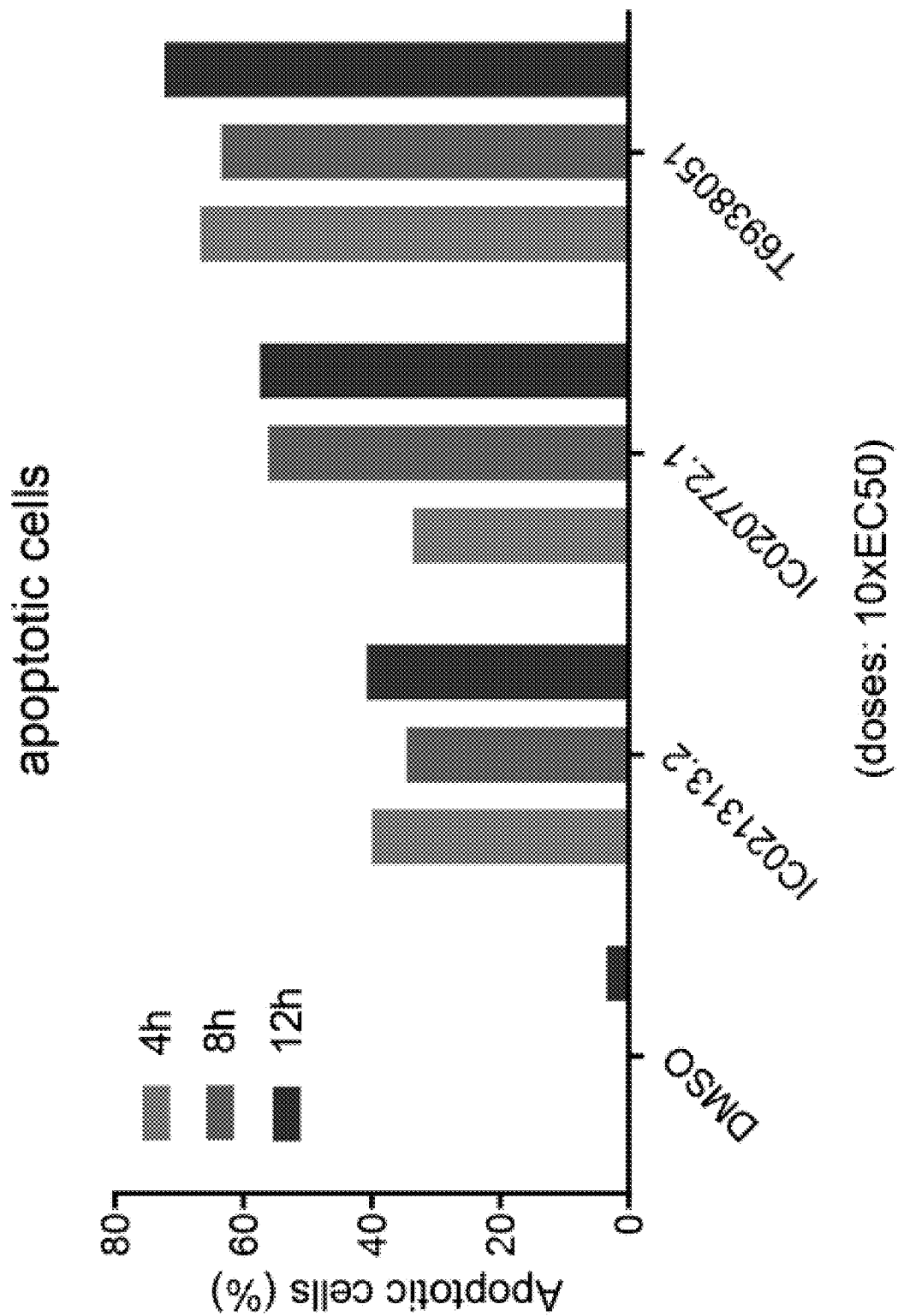

FIG. 8. Induction of apoptosis after treatment with selected compounds. $KBM7^{WT}$ cells were treated with DMSO or drug at a 10× EC50 dose, for the indicated time-points. After the treatments, apoptosis induction was assessed by flow cytometry after staining with AnnexinV/PI.

Figure 9:
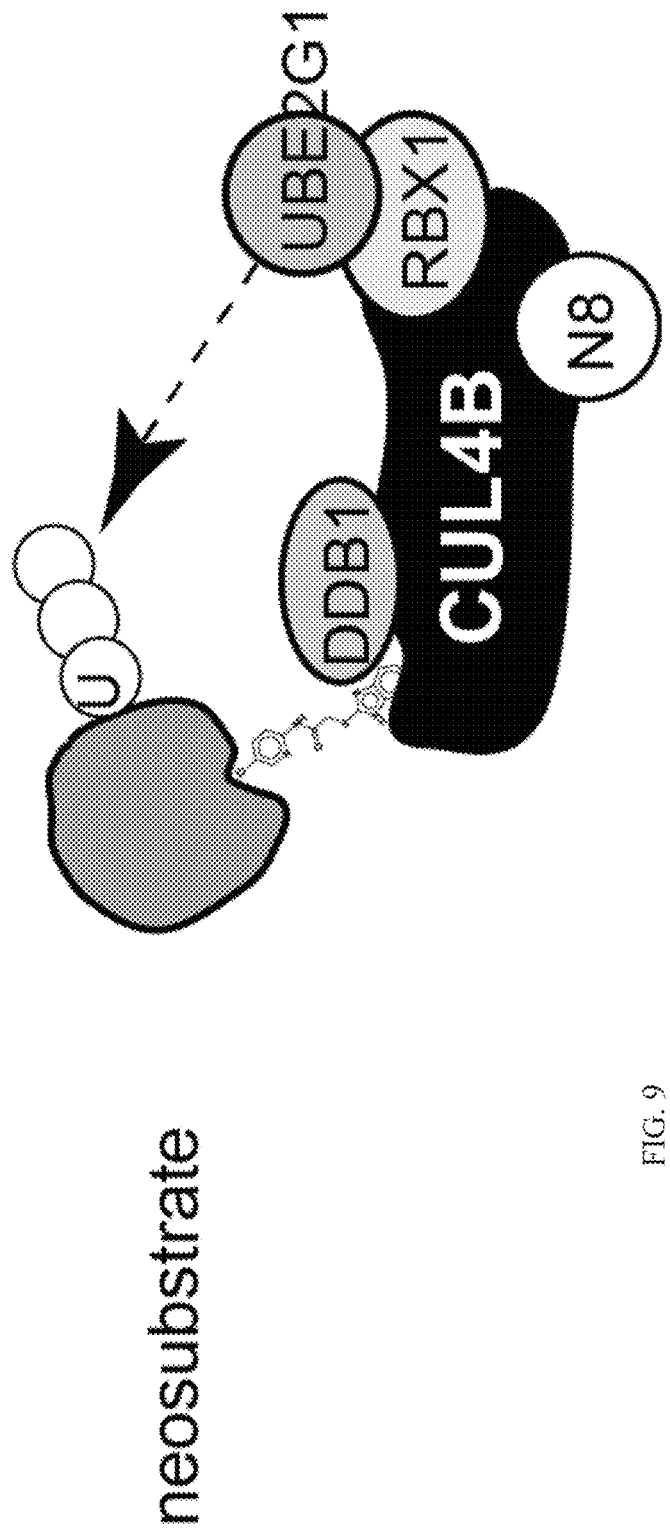

FIG. 9. Schematic depiction of a possible drug mechanism of action. Drug binding to the CUL4B scaffold and/or DDB1 recruits a neo-substrate directly to the cullin backbone/adaptor, without the mediation a of substrate receptor. An alternative/complementary option is that drug binding stabilizes CLR4B function, promoting functionally competent CUL4B complex formation and, therefore, neo-substrate degradation. Both predicted mechanisms of action would result in functionally altered CRL4B complexes and neo-substrate degradation.

Figure 10A:
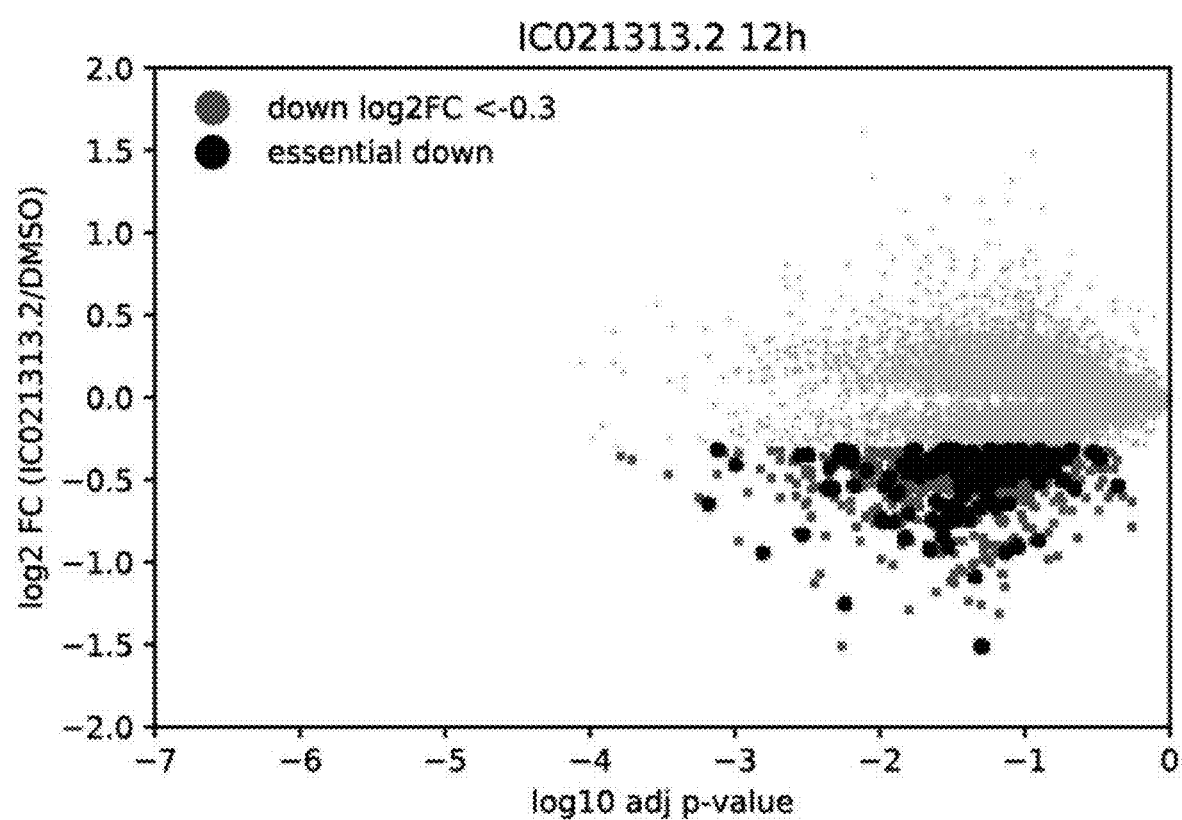
Figure 10B:
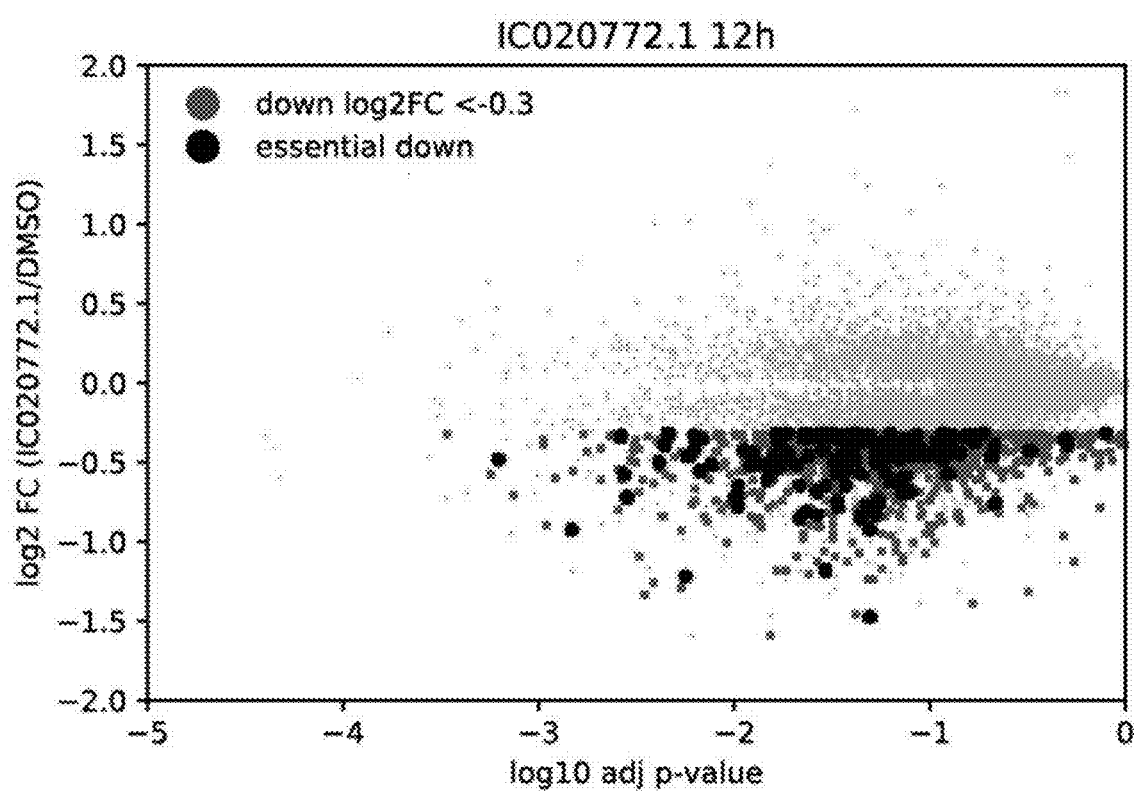
Figure 10C:
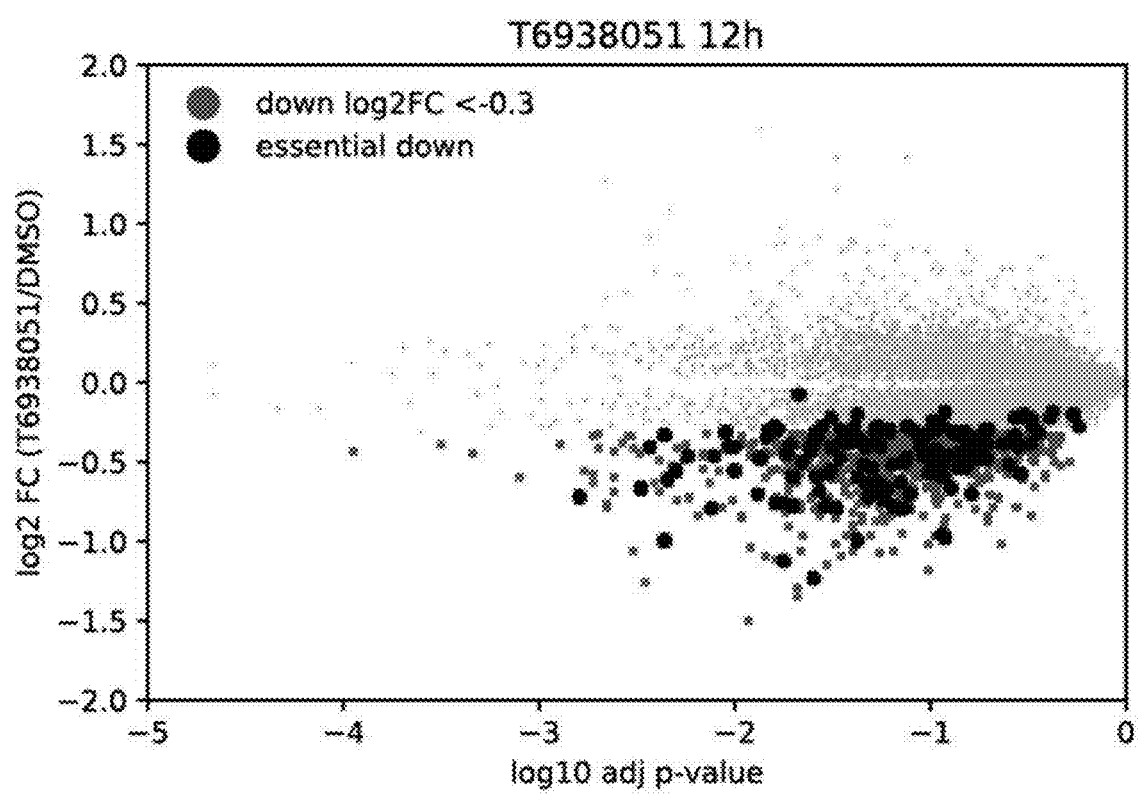

FIG. 10. Expression protcomics analysis. $KBM7^{WT}$ cells were treated with DMSO or drug at a 10×EC50 dose, for 12h. Differential protein levels are displayed as log 2FC in protein abundance vs-log 10 (p-value). Proteins that are significantly downregulated (log 2FC <−0.3) are indicated in blue. Proteins that are significantly downregulated and are known to be essential for proliferation of KBM7 leukemia cells are highlighted in black. Non-destabilized proteins are marked in gray.

FIG. 11. Derivatization of substrate receptor-independent PROTACs. (A) Chemical structure of PROTAC molecule series based on IC021313.2 as CLR4-ligand, linked to a binder of the "protein of interest" (in this case, the BRD4 inhibitor JQ1). The linker can vary in length (for instance 2-40 atoms) and composition (aliphatic or PEG-based). (B) Depiction of the possible mechanism of action of substrate receptor-independent PROTACs. Binding of the putative PROTAC to the CUL4B scaffold and/or DDB1 recruits BRD4 as a neo-substrate, without the mediation of a substrate receptor. BRD4 is ubiquitinated and therefore marked for proteasomal degradation.

Figure 12:
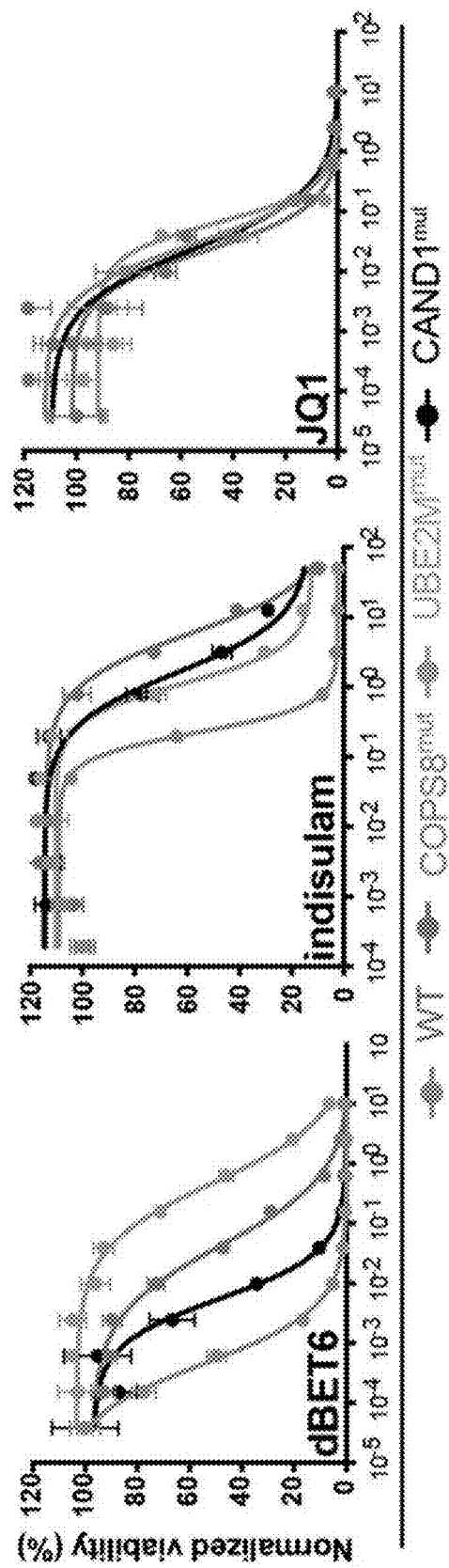

FIG. 12. Dose-ranging cellular viability assays in isogenic human leukemia cells (KBM7) with truncations or focal deletions in CAND1, COPS8 or UBE2M. Compared are the CRBN-based PROTAC dBET6, the DCAF1-based MG indisulam and the BET inhibitor JQ1.

Figure 13:
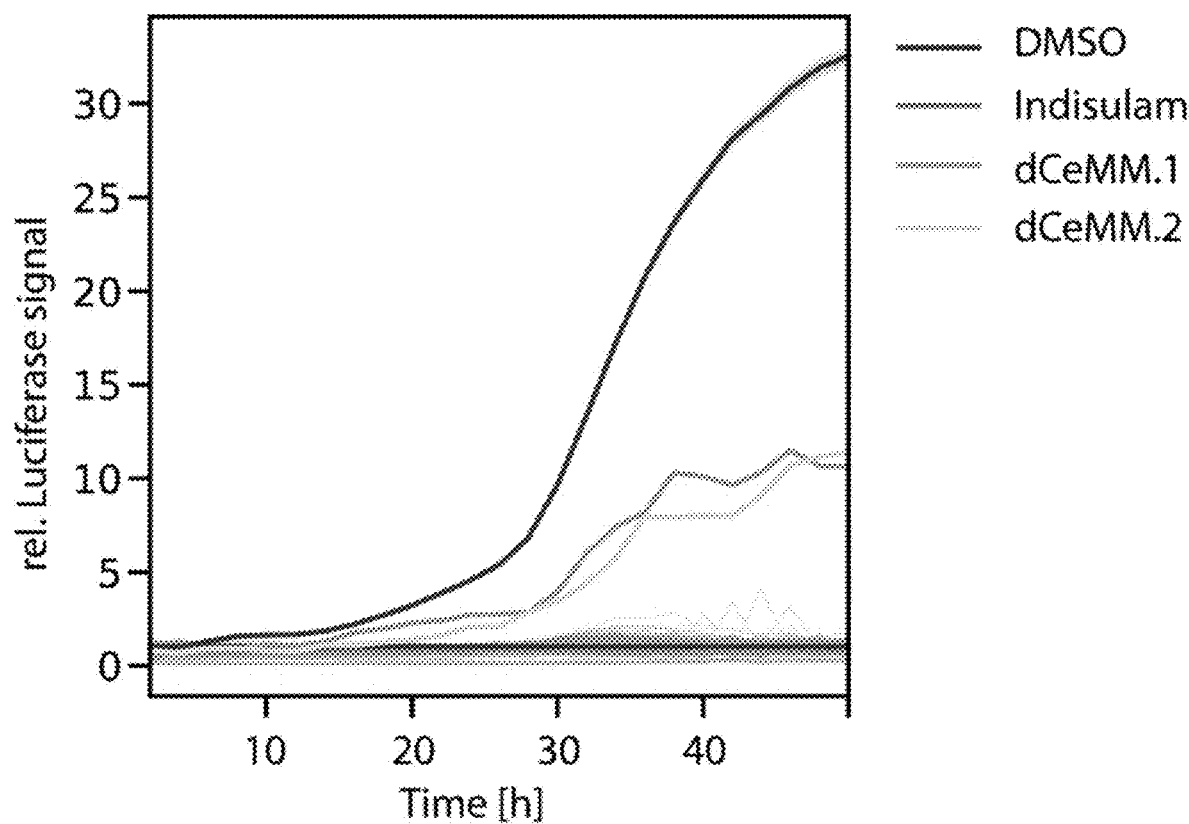

FIG. 13. Results of the high-throughput screen. The curves show the relative luciferase signal (approximating DCAF15 levels) after individual drug treatments at 10 µM as a function of time. As expected, a significant stabilization of DCAF15 over time after cellular treatment with the known DCAF15-based molecular glue indisulam was observed. While the vast majority of tested compounds did not yield a measurable DCAF15 stabilization (>200 inactive compounds displayed, all in light gray), a significant stabilization with two test compounds here named "dCeMM.1" and "dCeMM.2" was observed.

Figure 14:
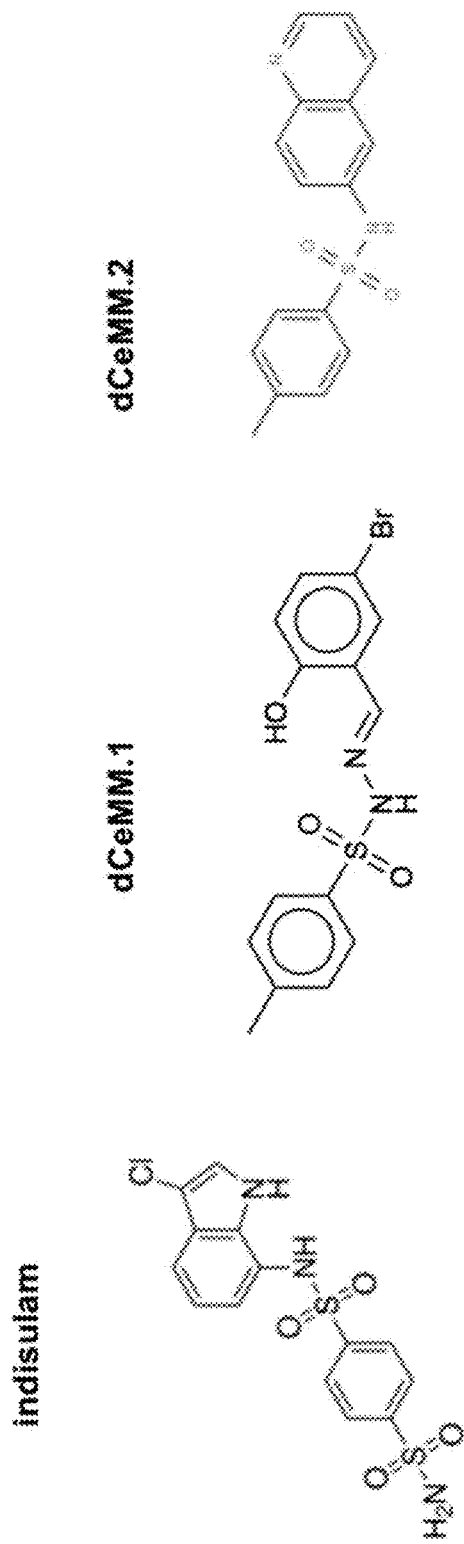

FIG. 14. Chemical structure of indisulam and the two identified hits.

Figure 15:
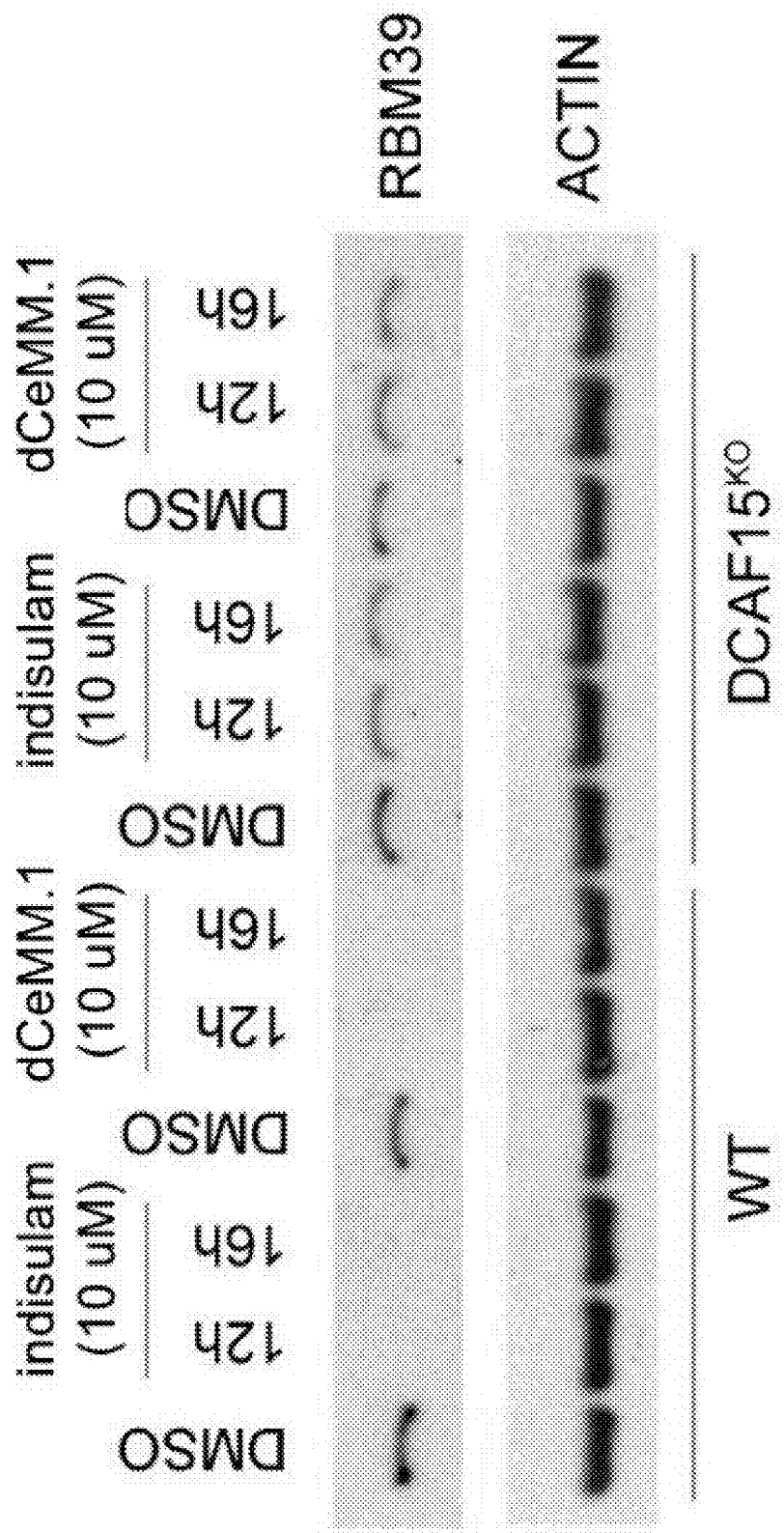

FIG. 15. Western Blot analysis of RBM39- and actin loading control levels after 12 or 16 h treatment of KBM7 wildtype cells ("WT") that have not been engineered to carry additional mutations, or after treatment with KBM7 cells that were engineered to be deficient for DCAF15 via CRISPR/Cas9 technology. dCeMM-1 led to a significant destabilization of RBM39 levels that was comparable to destabilization achieved with indisulam. As predicted from a glue-type molecule, compound effects are dependent on DCAF15 expression.

Figure 16:
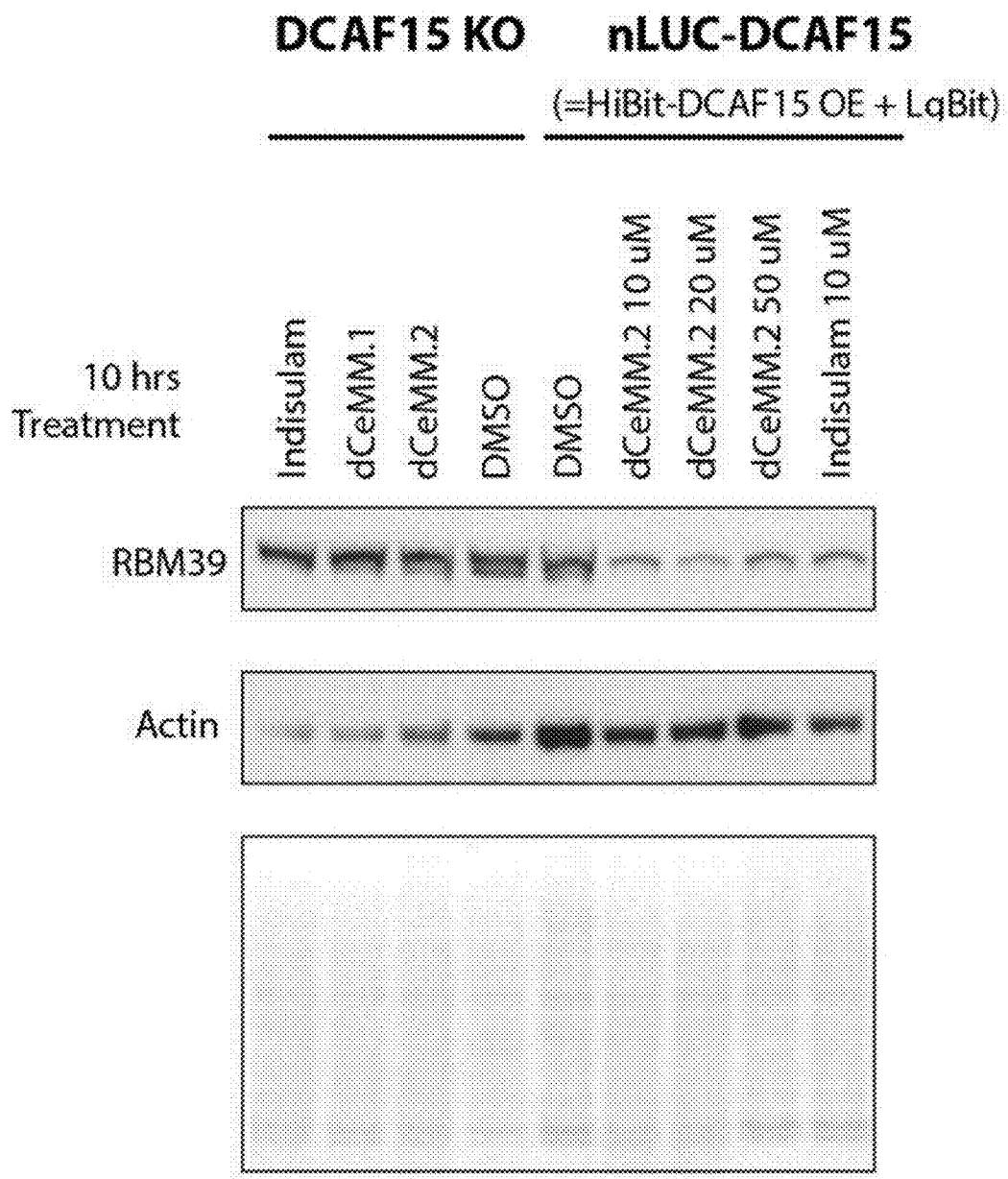

FIG. 16. Western Blot analysis of RBM39- and actin loading control levels after 10 h treatment of 293T cells that are deficient for DCAF15 ("DCAF15 KO"), or after treatment of cells that have been reconstituted to express nLUC-tagged DCAF15 (the same cells that have been used for the initial screen as outlined in FIG. 13). dCeMM-2 led to a significant destabilization of RBM39 levels that was comparable to destabilization achieved with indisulam. As predicted from a glue-type molecule, compound effects are dependent on DCAF15 expression.

Figure 17:
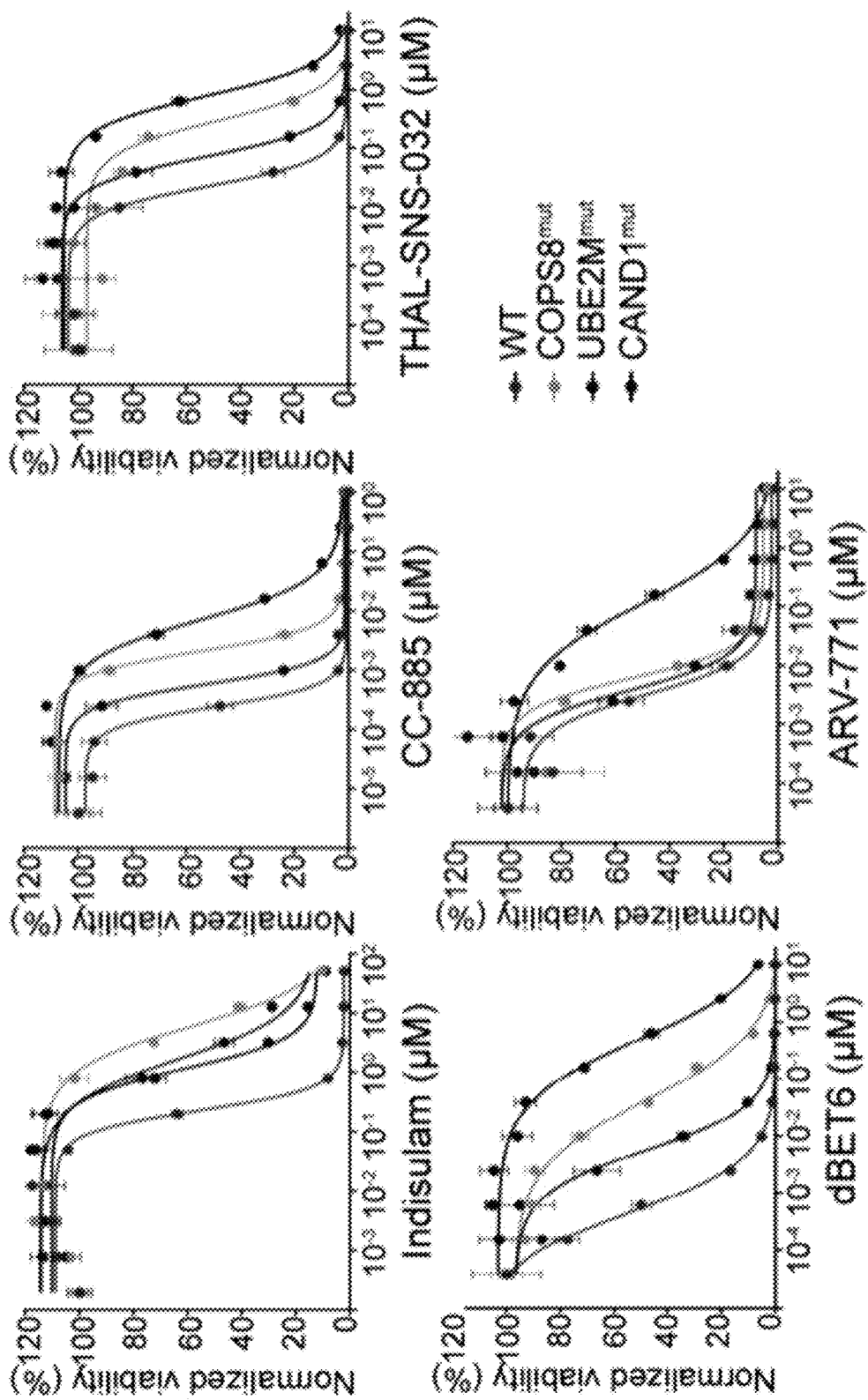

FIG. 17. Five known degraders all depend on the enzyme UBE2M for their cytotoxic activity in the leukemic cell line KBM7.

Figure 18:
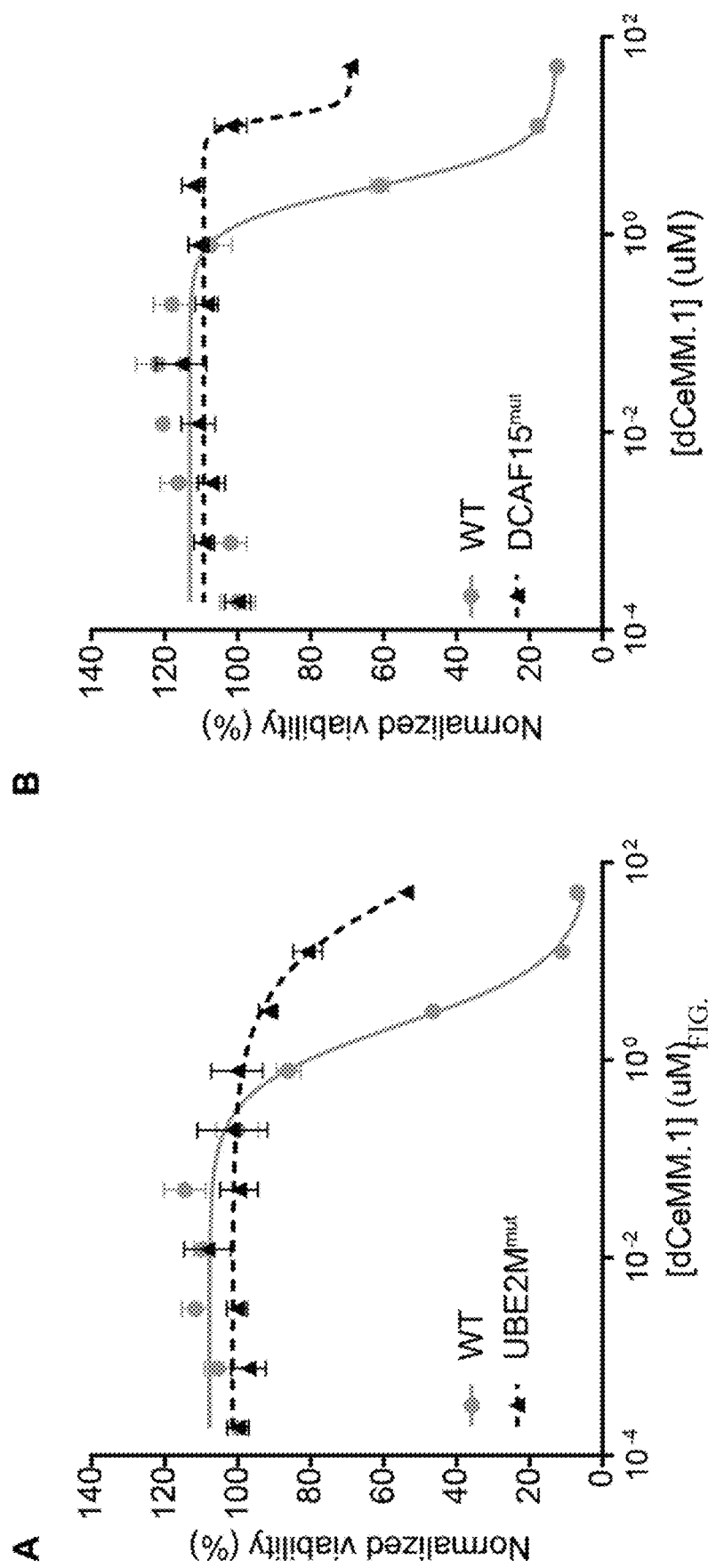

FIG. 18. (A) Cellular viability of KBM7 cells (WT or UBE2M mutant) after treatment with dCeMM.1. (72 hour treatment) (B) cellular viability of KBM7 cells (WT or DCAF15 knockout) after dose-ranging treatment with dCeMM.1 (72 hour treatment).

FIG. 19. IC020772.1; IC021313.2 and T6938051 are novel and structurally different CCNK degraders. a, DMSO-normalized expression proteomics after 5h IC020772.1; IC021313.2 and T6938051 treatment (2.5 µM, 7 µM, 3.5 µM) in KBM7 cells. b, DMSO-normalized expression proteomics after 12h IC020772.1; IC021313.2 and T6938051 treatment (2.5 µM, 7 µM, 3.5 µM) in KBM7 cells. c CCNK levels upon IC020772.1; IC021313.2 and T6938051 treatment in KBM7 cells. d, IC020772.1 (2.5 µM, 5h) destabilizes CCNK. 30 min pretreatment with 1 µM carfilzomib, 1 µM MLN4924, 10 µM TAK-243 or 1 µM THZ531 rescues CCNK destabilization. e, Protein-protein interaction analysis (STRING) with downregulated proteins among the top100 differentially expressed proteins. Functional enrichments in the network are as indicated.

FIG. 20. IC020772.1; IC021313.2 and T6938051 induce proximity between CUL4B: DDB1 and CDK12/13:CCNK. a, IC021313.2$^{NH2}$ chemical structure (IC021313.2 tethered analog). b, Drug affinity chromatography strategy based on probe-coupled agarose beads pulldowns after DMSO or THZ531 (competition) pretreatment in lysates. c, CCNK and DDB1 enrichment in IC021313.2$^{NH2}$-based pulldowns. For quantification, eluted protein was normalized to protein available (input panels). THZ531-competed (100 µM, 1h) ratios were set to 1. d, Chemical structure of IC021313.2$^{PAP}$ (PAP: photo-affinity probe). e, Drug-target enrichment strategy based on cellular IC021313.2$^{PAP}$ co-treatment with DMSO or THZ531 (100 µM, competition) after Carfilzomib pretreatment (10 µM, 30 min). f, CCNK and DDB1 enrichment in IC021313.2$^{PAP}$-based pulldowns. For quantification, eluted protein was normalized to protein available (input panels). THZ531-competed (100 µM, 1h) ratios were set to 1. g, Proximity labeling strategy to assess drug-induced dimerization in intact cells based on the biotin ligase miniTurbo (mTurbo). h, Biotin-labeled CDK12 and DDB1 enrichment following 1h DMSO or IC020772.1 treatment in the presence of carfilzomib (10u M) in HEKs transfected with DDB1- or CDK12-m Turbo fusions.

Figure 21D:
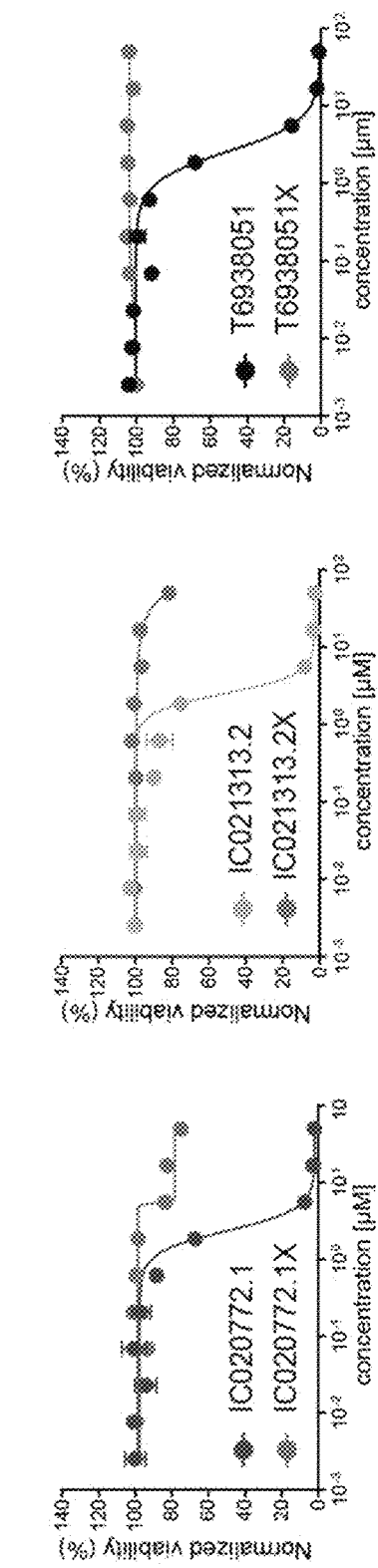

FIG. 21. IC020772.1; IC021313.2 and T6938051 selectively induce acute CCNK destabilization and milder CDK12/13 destabilization. a, CCNK and CDK12 degradation upon exposure to IC020772.1 (2.5 µM), IC021313.2 (7 µM) and T6938051 (3.5 µM) for 20h in WT and UBE2M$^{mut}$ KBM7 cells. b, Chemical structures of the inactive analogs of IC020772.1; IC021313.2 and T6938051. c, CCNK destabilization upon exposure to IC020772.1/X (2.5 µM), IC021313.2/X (6 µM) and T6938051/X (3.5 µM) for 3h in WT KBM7 cells. d, DMSO-normalized viability in WT KBM7 cells after 3-day IC020772.1X/IC021313.2X/T6938051X treatment. Mean±SEM; n=3.

FIG. 22. CRL-focused CRISPR screens show that IC020772.1; IC021313.2 and T6938051 mechanism of action is mediated via a CRL4B ligase complex in a SR-independent manner. a, CRL-focused CRISPR screens of IC020772.1; IC021313.2 and T6938051 resistance in KBM7 cells with constitutive (upper panel) or inducible (lower panel) Cas9 expression. Results shown are the median of 2 independent screens per drug. Top: bubble plot displaying median enrichment over DMSO for each gene, bubble size indicates significance. Bottom: enrichment of sgRNAs targeting indicated genes, background indicates distribution of all sgRNAs in the screen. b, Growth curves of the KBM7 mutant CLR-focused libraries (top) treated with DMSO or IC020772.1; IC021313.2 and T6938051 in duplicates. Growth curves of the KBM7 mutant genome-scale library (bottom) treated with DMSO or dCeMM2/3/4 for 15 days. c, Depiction of the relevant hits found in the IC020772.1; IC021313.2 and T6938051 CRISPR screens. Note the absence of a dedicated SR.

FIG. 23. Induced CCNK degradation is mediated via a CRL4B ligase complex in a SR-independent manner. a, Genome-wide CRISPR IC020772.1; IC021313.2 and T6938051 resistance screens. Top: bubble plot displaying median sgRNA enrichment over DMSO, bubble size indicates significance. Bottom: sgRNA enrichment targeting indicated genes, background indicates distribution of all sgRNAs. b-c, IC020772.1-induced CCNK degradation (2.5 µM) is rescued in UBE2M-, CUL4B-(b) and UBE2G1-(c) deficient cells.

EXAMPLES
TABLE 3
Structure-Activity Relationship of compounds tested in AsPC1 pancreatic cancer cells (WT or UBE2Mmut), MV4;11 and Jurkat leukemia cells, Be(2)C neuroblastoma cells, and NCI-H446 lung cancer cells.
| Compound Name | | KBM7_ WT | KBM7_ UBE2M_ mut | KBM7_ CUL4B_ mut | KBM7_ UBE2G1_ mut | HCT116_ WT | HCT116_ UBE2M_ mut |
|---|---|---|---|---|---|---|---|
| Z201181756 | 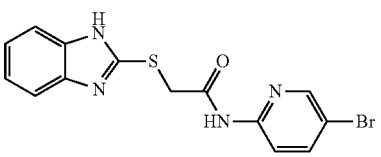 [SMILES: O=C(CSc1nc2ccccc2[nH]1)Nc1ccc(Br)cn1] | 1.41 | 34.7 | 12.6 | 6.17 | 33.3 | 35.0 |
| Z54609541 | 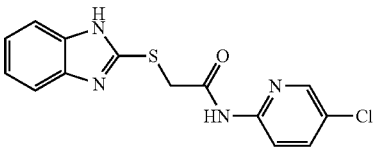 [SMILES: O=C(CSc1nc2ccccc2[nH]1)Nc1ccc(Cl)cn1] | 2.41 | 24.4 | 11.9 | 7.60 | 26.6 | 34.6 |
| Z278182910 | 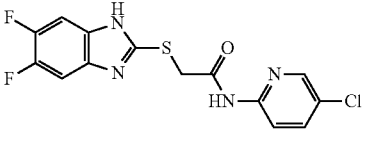 [SMILES: O=C(CSc1nc2cc(F)c(F)cc2[nH]1)Nc1ccc(Cl)cn1] | 1.66 | 18.7 | 9.35 | 4.48 | 36.6 | 31.9 |
| Z19221914 | 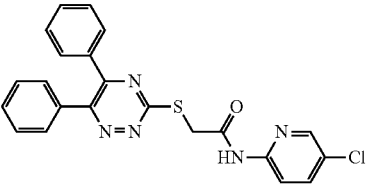 [SMILES: O=C(CSc1nnc(-c2ccccc2)c(-c2ccccc2)n1)Nc1ccc(Cl)cn1] | >60 | >60 | | | >60 | >60 |
| PV-001867336262 | 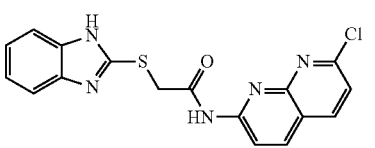 [SMILES: O=C(CSc1nc2ccccc2[nH]1)Nc1ccc2ccc(Cl)nc2n1] | >60 | >60 | | | >60 | >60 |
| Z19650610 | 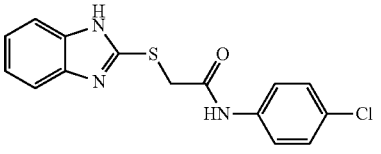 [SMILES: O=C(CSc1nc2ccccc2[nH]1)Nc1ccc(Cl)cc1] | 38.6 | 38.7 | 41.2 | 38.2 | 40.7 | 95.1 |
| Z1126858802 | 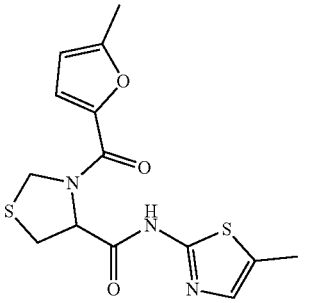 [SMILES: Cc1ccc(C(=O)N2CSCC2C(=O)Nc2ncc(C)s2)o1] | 12.5 | >108 | 79.4 | 47.1 | >108 | >108 |

TABLE 3-continued
Structure-Activity Relationship of compounds tested in AsPC1 pancreatic cancer cells (WT or UBE2Mmut), MV4;11 and Jurkat leukemia cells, Be(2)C neuroblastoma cells, and NCI-H446 lung cancer cells.
| Compound | Structure | | | | | |
|---|---|---|---|---|---|---|
| PV-001830246512 | 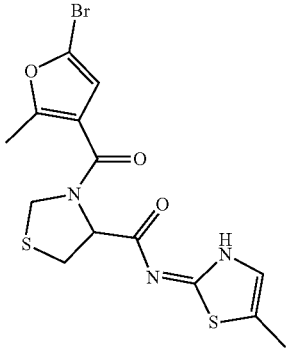 | 1.22 | 11.4 | 4.88 | 2.97 | 38.4 | 23.9 |
| PV-001830247701 | 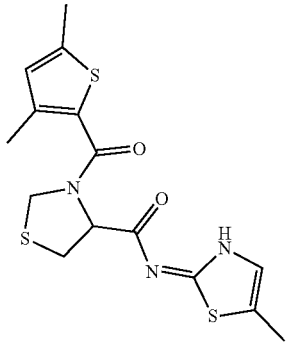 | 4.01 | 38.9 | 12.5 | 11.6 | 84.2 | 102.0 |
| Z1167275502 | 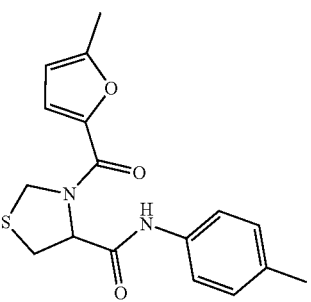 [SMILES: Cc1ccc(NC(=O)C2CSCN2C(=O)c2ccc(C)o2)cc1] | >60 | >60 | | >60 | >60 |
| Z1068813390 | 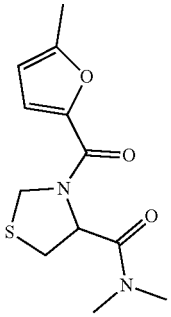 [SMILES: Cc1ccc(C(=O)N2CSCC2C(=O)N(C)C)o1] | >7.5 | >7.5 | | >7.5 | >7.5 |

TABLE 3-continued

Structure-Activity Relationship of compounds tested in AsPC1 pancreatic cancer cells (WT or UBE2Mmut), MV4;11 and Jurkat leukemia cells, Be(2)C neuroblastoma cells, and NCI-H446 lung cancer cells.

| | | | | | | | |
|---|---|---|---|---|---|---|---|
| PV-001830245440 | | >60 | >60 | | >60 | | >60 |

| Compound Name | AsPC1_WT | AsPC1_UBE2M_mut | RKO | NCI-H446 | Be(2)C | Mv4_11 | Jurkat |
|---|---|---|---|---|---|---|---|
| Z201181756 | 31.1 | 34.7 | <60 | 9.25 | 12.0 | 6.72 | 7.51 |
| Z54609541 | ~12 | 34.3 | <60 | 12.0 | 11.3 | 11.0 | 7.97 |
| Z278182910 | 12.1 | 38.9 | <60 | 9.65 | 6.60 | 4.36 | 6.76 |
| Z19221914 | >60 | >60 | >60 | >60 | >60 | >60 | |
| PV-001867336262 | >60 | >60 | >60 | >60 | >60 | >60 | |
| Z19650610 | ~80 | 105.4 | >60 | 37.6 | 42.7 | 37.1 | 37.2 |
| Z1126858802 | >108 | >108 | >7.5 | >108 | >108 | 47.4 | 49.8 |
| PV-001830246512 | 15.2 | 51.5 | <60 | 6.61 | 6.13 | 3.07 | 3.44 |
| PV-001830247701 | 39.2 | 106.2 | <60 | 19.7 | 12.9 | 12.2 | 11.9 |
| Z1167275502 | >60 | >60 | >60 | >60 | >60 | >60 | |
| Z1068813390 | >7.5 | >7.5 | >7.5 | >7.5 | >7.5 | >7.5 | |
| PV-001830245440 | >60 | >60 | >60 | >60 | >60 | >60 | |

Example 1

All synthesis was carried out at Enamine Ltd (Kyiv, Ukraine) from commercially available building blocks.

General Procedure for Compounds Following Formula I N-(5-chloropyridin-2-yl)-2-((5,6-difluoro-1H-benzo[d]imidazol-2-yl)thio)acetamide (Z278182910)

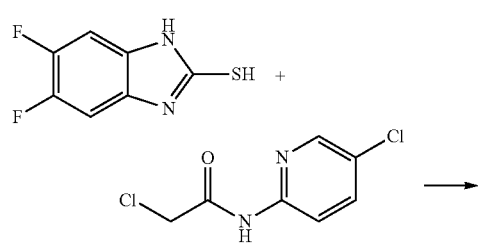

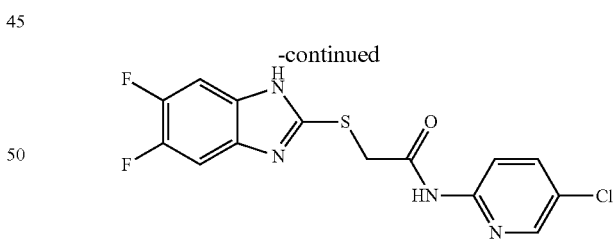

To a stirred solution containing 55 mg (0.295 mmol, 1 eq.) 5,6-difluoro-1H-benzo[d]imidazole-2-thiol, DIPEA (1.2 eq.), and potassium iodide (0.1 eq.) in 1 mL of DMF, 61 mg (0.295 mmol, 1 eq.) 2-chloro-N-(5-chloropyridin-2-yl) acetamide was added. The reaction mixture was allowed to stir on a boiling water bath for ca. 5 min. Upon a complete dissolution of the reagents the stirred reaction mixture was heated on the boiled water bath for 4 h. The reaction mixture was triturated with an excess of deionized water and sonicated until a crystalline precipitate was formed. The precipitate was filtered, washed twice with methanol, and dried. The crude product was purified by chromatography using Agilent 1260 Infinity systems equipped with DAD and mass-detector. Waters Sunfire C18 OBD Prep Column, 100 A, 5 μm, 19 mm×100 mm with SunFire C18 Prep Guard Cartridge, 100 A, 10 μm, 19 mm×10 mm was used. Yield 23%. Exact mass 354.02; mass found [MH+] 354.9

2-((1H-benzo[d]imidazol-2-yl)thio)-N-(5-bromopyridin-2-yl) acetamide (Z201181756)

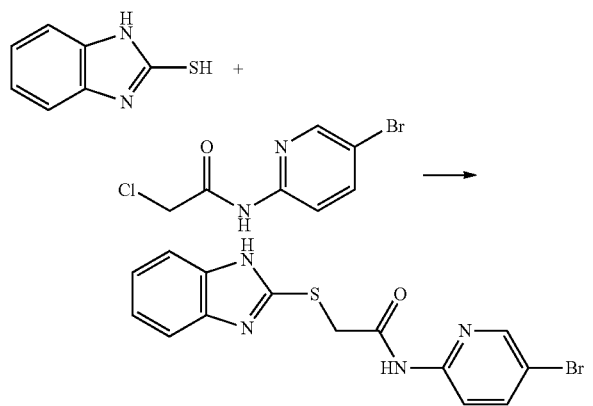

To a stirred solution containing 83 mf (0.551 mmol, 1 eq.) 1H-benzo[d]imidazole-2-thiol, DIPEA (1.2 eq.), and potassium iodide (0.1 eq.) in 1 mL of DMF, 137 mg (0.551 mmol, 1 eq.) N-(5-bromopyridin-2-yl)-2-chloroacetamide was added. The reaction mixture was allowed to stir on a boiling water bath for ca. 5 min. Upon a complete dissolution of the reagents the stirred reaction mixture was heated on the boiled water bath for 4 h. The reaction mixture was triturated with an excess of deionized water and sonicated until a crystalline precipitate was formed. The precipitate was filtered, washed twice with methanol, and dried. The crude product was purified by chromatography using Agilent 1260 Infinity systems equipped with DAD and mass-detector. Waters Sunfire C18 OBD Prep Column, 100 A, 5 μm, 19 mm×100 mm with SunFire C18 Prep Guard Cartridge, 100 A, 10 μm, 19 mm×10 mm was used. Yield 40%. Exact mass 361.98; mass found [MH+] 363.0.

2-((1H-benzo[d]imidazol-2-yl)thio)-N-(5-chloropyridin-2-yl) acetamide (Z54609541)

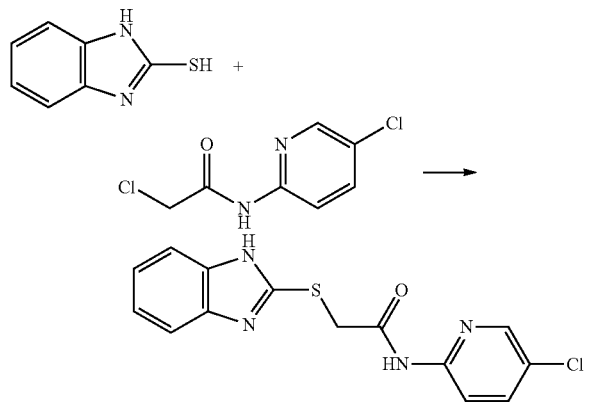

To a stirred solution containing 94 mg (0.627 mmol, 1 eq.) 1H-benzo[d]imidazole-2-thiol, DIPEA (1.2 eq.), and potassium iodide (0.1 eq.) in 1 mL of DMF, 129 mg (0.627 mmol, 1 eq.) 2-chloro-N-(5-chloropyridin-2-yl) acetamide was added. The reaction mixture was allowed to stir on a boiling water bath for ca. 5 min. Upon a complete dissolution of the reagents the stirred reaction mixture was heated on the boiled water bath for 4 h. The reaction mixture was triturated with an excess of deionized water and sonicated until a crystalline precipitate was formed. The precipitate was filtered, washed twice with methanol, and dried. The crude product was purified by chromatography using Agilent 1260 Infinity systems equipped with DAD and mass-detector. Waters Sunfire C18 OBD Prep Column, 100 A, 5 μm, 19 mm×100 mm with SunFire C18 Prep Guard Cartridge, 100 A, 10 μm, 19 mm×10 mm was used. Yield 32%. Exact mass 318.03; mass found [MH+] 319.0.

N-(5-chloropyridin-2-yl)-2-((5-methyl-1H-benzo[d]imidazol-2-yl)thio) acetamide (Z18442615)

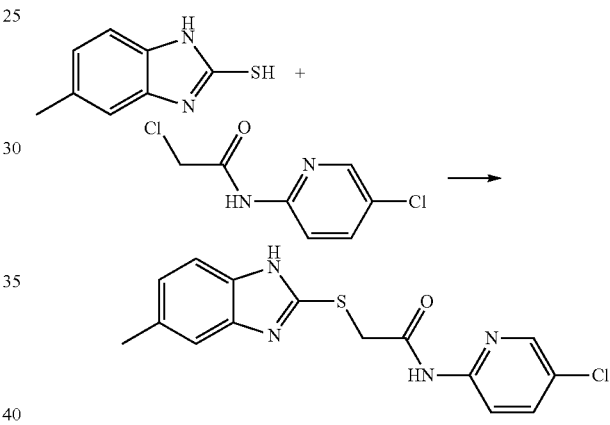

To a stirred solution containing 1 eq. 5-methyl-1H-benzo[d]imidazole-2-thiol, DIPEA (1.2 eq.), and potassium iodide (0.1 eq.) in 1 mL of DMF, 2-chloro-N-(5-chloropyridin-2-yl) acetamide (1 eq.) was added. The reaction mixture was allowed to stir on a boiling water bath for ca. 5 min. Upon a complete dissolution of the reagents the stirred reaction mixture was heated on the boiled water bath for 4 h. The reaction mixture was triturated with an excess of deionized water and sonicated until a crystalline precipitate was formed. The precipitate was filtered, washed twice with methanol, and dried. The crude product was purified by chromatography using Agilent 1260 Infinity systems equipped with DAD and mass-detector. Waters Sunfire C18 OBD Prep Column, 100 A, 5 μm, 19 mm×100 mm with SunFire C18 Prep Guard Cartridge, 100 A, 10 μm, 19 mm×10 mm was used. $^1$H NMR (DMSO-$d_6$+CCl$_4$, 400 MHZ): Delta 2.4 (s, 3H), 4.2 (s, 2H), 6.9 (dd, 1H), 7.3 (bd, 2H), 7.7 (dd, 1H), 8.1 (dd, 1H), 8.2 (dd, 1H), Literature for synthesis: Mahmoud, A. M.; El-Sherief, H. A.; Abdel-Rahman, A. E. European Journal of Medicinal Chemistry 1981, 16(4), 383-4.

General Procedure for Compounds Following Formula II 3-(5-bromo-2-methylfuran-3-carbonyl)-N-(5-methylthiazol-2-yl) thiazolidine-4-carboxamide (PV-001830246512)

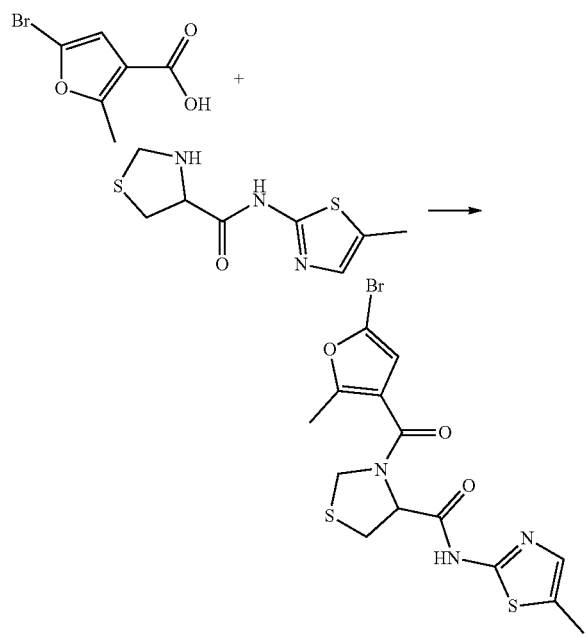

5-bromo-2-promo-2-methylturan-3-carboxylic acid (1.1 mmol) and a solution of N-hydroxybenzotriazole in DMSO (100 g/L, 2 mL, 1.5 mmol) were placed in a vial, and N-(5-methylthiazol-2-yl) thiazolidine-4-carboxamide (1 mmol) was added. The reaction mixture was stirred for 30 min in a shaker, and EDC (1.2 mmol) was added. After all the reagents were loaded, the vial was sealed and stirred in a shaker for 1 h. If clear solution was formed, the vial was left at it for 24 h. Otherwise, the reaction mixture was kept in a sonication bath for 24h (strong heating should be avoided). If strong thickening of the reaction mixture was observed so that stirring was not effective, 0.2 mL of DMSO might be added in one portion. The crude reaction mixture was analyzed by LC-MS and then subjected to chromatographic purification*. *The purification was performed using Agilent 1260 Infinity systems equipped with DAD and mass-detector. Waters Sunfire $C_{18}$ OBD Prep Column, 100 A, 5 μm, 19 mm×100 mm with SunFire $C_{18}$ Prep Guard Cartridge, 100 A, 10 μm, 19 mm×10 mm was used. Deionized Water (phase A) and HPLC-grade Methanol (phase B) were used as an eluent. In some cases, ammonia or TFA was used as an additive to improve the separation of the products. In these cases, free bases and TFA salts of the products were formed respectively. Exact mass 414.97; mass found: [MH+] 416.0.

3-(5-methylfuran-2-carbonyl)-N-(5-methylthiazol-2-yl) thiazolidine-4-carboxamide (Z1126858802)

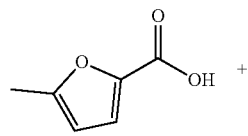

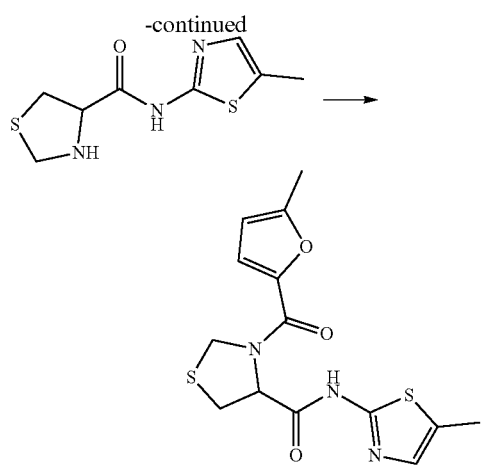

243 mg 5-methylfuran-2-carboxylic acid (1.926 mmol, 1.3 eq.) and a solution of N-hydroxybenzotriazole in DMSO (100 g/L, 2 mL, 1.5 eq.) were placed in a vial, and 340 mg N-(5-methylthiazol-2-yl) thiazolidine-4-carboxamide (1.482 mmol, 1 eq.) was added. The reaction mixture was stirred for 30 min in a shaker, and EDC (1.2 mmol) was added. After all the reagents were loaded, the vial was scaled and stirred in a shaker for 1 h. The reaction mixture was kept in a sonication bath for 24h (strong heating should be avoided). The crude reaction mixture was analyzed by LC-MS and then subjected to chromatographic purification. The purification was performed using Agilent 1260 Infinity systems equipped with DAD and mass-detector. Waters Sunfire C18 OBD Prep Column, 100 A, 5 μm, 19 mm×100 mm with SunFire C18 Prep Guard Cartridge, 100 A, 10 μm, 19 mm×10 mm was used. Deionized Water (phase A) and HPLC-grade Methanol (phase B) were used as an eluent. In some cases, ammonia or TFA was used as an additive to improve the separation of the products. In these cases, free bases and TFA salts of the products were formed respectively. Yield 79%. $^1$H NMR (DMSO-$d_6$+CCl$_4$, 400 MHZ): Delta 2.4 (s, 6H), 3.2 (bs, 1H), 3.5 (bs, 1H), 5.1 (m, 3H), 6.2 (s, 1H), 7.0 (d, 2H)

3-(3,5-dimethylthiophene-2-carbonyl)-N-(5-methylthiazol-2-yl) thiazolidine-4-carboxamide (PV-001830247701)

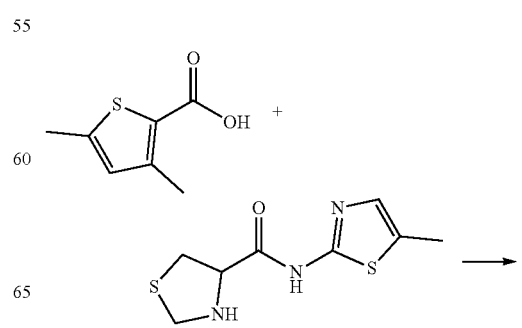

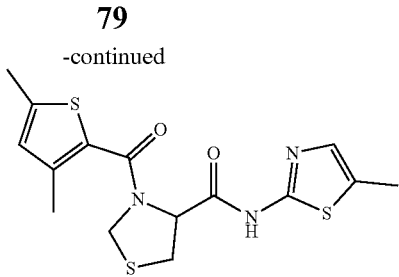

53 mg 3,5-dimethylthiophene-2-carboxylic acid (0.339 mmol, 1.1 eq.) and a solution of N-hydroxybenzotriazole in DMSO (100 g/L, 2 mL, 1.5 eq.) were placed in a vial, and 71 mg N-(5-methylthiazol-2-yl) thiazolidine-4-carboxamide (0.308 mmol, 1 eq.) was added. The reaction mixture was stirred for 30 min in a shaker, and EDC (1.2 eq.) was added. After all the reagents were loaded, the vial was sealed and stirred in a shaker for 1 h. The reaction mixture was kept in a sonication bath for 24h (strong heating should be avoided). The crude reaction mixture was analyzed by LC-MS and then subjected to chromatographic purification. The purification was performed using Agilent 1260 Infinity systems equipped with DAD and mass-detector. Waters Sunfire C18 OBD Prep Column, 100 A, 5 µm, 19 mm×100 mm with SunFire C18 Prep Guard Cartridge, 100 A, 10 µm, 19 mm×10 mm was used. Deionized Water (phase A) and HPLC-grade Methanol (phase B) were used as an eluent. In some cases, ammonia or TFA was used as an additive to improve the separation of the products. In these cases, free bases and TFA salts of the products were formed respectively. Yield 42%. Exact mass 367.05; mass found [MH+] 368.0.

General Methods

Cell Lines

KBM7 cells with the specified genetic backgrounds were grown in IMDM supplemented with 10% FBS and 1% penicillin/streptomycin (pen/strep). AsPC1, HCT116, NCI-H446 and 293T cells were grown in DMEM 10% FBS and 1% pen/strep. MV4; 11, Jurkat and Be (2) C cells were grown in RPMI 10% FBS 1% pen/strep. KBM7, AsPC1 and HCT116 cells expressing Cas9 were generated using the plasmid Lenti_Cas9_Blasti (Addgene #52962). The lentiviral plasmid lentiGuide-Puro (Addgene #52963) was used to express sgRNAs against the genes UBE2M (in KBM7-Cas9, AsPC1-Cas9 and HCT116-Cas9 cells), UBE2G1 (in KBM7-Cas9 cells) and CUL4B (in KBM7-Cas9 cells). The lentiviral plasmid lentiGuide-Puro-IRES-mCherry (modified from Addgene #52963) was used to express sgRNAs against CUL4A (in KBM7-Cas9 cells). The lentiviral plasmid pLenti-PGK-Hygro-DEST-UBE2M was generated by Gateway cloning (empty destination vector Addgene #19066), and used to generate UBE2M$^{resc}$ KBM7 cells.

| sgRNA name | sequence |
| --- | --- |
| sgUBE2M (SEQ ID NO. 3) | TCACCCCAACATTGACCTCG |
| sgUBE2G1 (SEQ ID NO. 4) | ATGACAATGATCTCTACCGA |
| sgCUL4A (SEQ ID NO. 5) | AGTTCTGCAGCACATAGGTG |
| sgCUL4B (SEQ ID NO. 6) | AGCATGTGGTACTTACTGGG |

Example 2: Discovery and Characterization of Cullin RING Ubiquitin Ligase Modulators 1.1 Study Design All known small molecule degraders (heterobifunctional PROTACs as well as molecular glues) require the activity of the pan CRL regulator UBE2M. In other words: cancer cells where UBE2M has been mutated via CRISPR/Cas9 technology are insensitive to the anti-cancer properties of these degraders (FIG. 2).

Methods of Cell Viability Assay as Shown in FIG. 2

KBM7$^{WT}$ and UBE2M mutant KBM7 clones (UBE2M$^{mut}$) were seeded at a cell density of 50,000 cells/mL in 96-well with DMSO or degraders in triplicates. The small-molecule degraders used were: ARV-771 (MedChemExpress, HY-100972), CC-885 (AxonMedChem, 2645), indisulam (Sigma-Aldrich, SML1225), dBET6 and THAL-SNS-032. Cells were treated for 3 days, after which a cell viability assay was performed (CellTiter Glo, Promega), according to manufacturer's protocol. Survival curves and EC50 values were calculated by best-fit analysis of the log 10 drug concentration to fold change of drug-treated cells over DMSO-treated cells. All survival assays included technical triplicates per sample, per experiment.

Following this observation, it was rationalized that novel small molecule degraders can be identified in an unbiased manner, simply by searching for compounds that lose activity in the absence of UBE2M. 2000 small molecules, mostly of unknown function/target, were tested for their antiproliferative effects in human leukemia cells (KBM7). These cells were either transduced with a control sgRNA (KBM7WT), or with an sgRNA targeting UBE2M, leading to a hypomorph (deletion of six amino acids) with a functional impairment (UBE2Mmut). Thus, a putative novel degrader would potently inhibit the proliferation of KBM7WT cells, while sparing UBE2Mmut isogenic counterparts.

Methods of Cell Viability Assay as Shown in FIG. 3:

KBM7$^{WT}$ and UBE2M$^{mut}$ cells were treated with a compound library (2000 cytotoxic diverse small-molecules, mostly of unknown function/target). Briefly, the screening was divided in three parts 1) primary screening, 2) follow up and 3) validation. During the primary screening, cells were treated with 10 µM and 500 nM of every compound. DMSO was used as a negative control, YM155 1 µM was used as a cytotoxic positive control (it kills both cell lines), and the degrader ARV-771 was used as a differential viability positive controls at 50 nM and 250 nM (as shown in FIG. 2. ARV-771 efficacy is significantly abrogated in UBE2M mutant clones). After 3 days of treatment, cell viability was measured (CellTiter Glo, Promega). The screen was perform in 384-well plates (Corning 3712) and the reagent/compound dispensing system used was: Echo 520 Liquid Handler, Multidrop™ Combi Reagent Dispenser. Control compounds were included in several wells, in all the plates. Method for validation of IC021313.2, IC020822.1, IC020772.1, T6938051 as described above in (i).

Indeed, >20 compounds were identified that fulfilled this criteria. Among those, four compounds (IC021313.2, IC020822.1, IC020772.1, T6938051) stood out in terms of fold-change significance, as well as structural similarity (FIG. 3). The initial screening assay was conducted at two concentrations (10 µM and 500 nM). The dose ranging differential effect of these four hits was assessed/validated, comparing their activity in KBM7WT vs UBE2MMUT cells. In line with the previous screening results, all assayed compounds showed a pronounced shift in their anti-proliferative effects upon mutation of UBE2M, as observed by a shift in their half maximal effector concentration (LC50). A genetic rescue experiment, where UBE2M cDNA was re-introduced into the UBE2Mmut clone (UBE2Mresc), did (at least partically) reconstitute the initial sensitivity to the assessed compounds (FIG. 4, Table 1).

TABLE 1

LC50 values of data depicted in FIG. 4

| Compound name | $LC_{50}$ WT | $LC_{50}$ UBE2Mmut | $LC_{50}$ UBE2Mresc |
|---|---|---|---|
| IC021313.2 | 0.65 | 10.66 | 1.94 |
| IC020772.1 | 0.29 | 4.15 | 0.75 |
| T6938051 | 0.42 | 7.04 | 1.15 |

The dependency on the NEDD8-conjugating E2 enzyme UBE2M (also called UBC12) suggested that the assayed compounds convey their anti-proliferative effects in KBM7 human leukemia cells via a mechanism that is dependent on a cullin RING E3 ubiquitin ligase (CRL). To validate this hypothesis, and to uncover a potentially ligase complex, a genome-scale CRISPR/Cas9 positive selection screens were conducted.

Methods for Genome-Wide CRISPR/Cas9 Screens

Lentivirus Production 293T cells seeded on 15 cm culture plates 16h before were transfected with 5 µg Brunello pooled library (Addgene #73178; 2-vector system), 2.5 µg pMD2.G (Addgene #12259), and 3.75 µg psPAX2 (Addgene #12260) using PolyFect (Qiagen) according to the manufacturer's protocol. Viral supernatant was harvested 72h after transfection and concentrated using Lenti—X-concentrator (Takara), according to the manufacturer's protocol. Concentrated viral supernatant was stored in aliquots at −80° C. and titrated to achieve a MOI of 0.2-0.3.

Pooled Library Screens 250 million KBM7-Cas9 cells were transduced at MOI 0.23, yielding a calculated library representation of 668 cells/sgRNA (library representation=50 million cells). For transduction, 20 µL of concentrated viral supernatant was added to 5 million cells in 1.5 mL IMDM and 8 µg/mL polybrene in 6-well plates. Plates were centrifuged at 2000 rpm for 1 h at 30° C. in a benchtop centrifuge, 0.5 mL IMDM were added and then incubated at 37° C. overnight. The next day, transduced cells were pooled and diluted. Pools were selected with 1 µg/mL puromycin for 5 days. Three independent resistance screens were performed with the library using drugs at starting concentrations of $4 \times EC_{50}$. Selective drug treatment was performed on 50 million cells/drug at a seeding density of 500,000 cells/mL. Every 5 days, cells were pooled, counted and re-seeded to 50 million cells in 100 mL, applying fresh drug. Drug resistant pools were harvested after 15 days of treatment, snap-frozen in liquid nitrogen and stored at −80° C.

Library Preparation for Next Generation Sequencing

Genomic DNA (gDNA) was extracted from 50 million cell frozen pellets using DNeasy Blood & Tissue mini kits (Qiagen), according to the manufacturer's protocol. PCR on the genomic DNA templates was performed to amplify sgRNA sequences. The isolated gDNA was processed in parallel to yield 10 µg gDNA per 100 µL reaction. One PCR reaction contained 1.5 µL of ExTaq polymerase (Clontech), 10 µL 10× buffer, 8 µL of dNTP mix, 0.5 µL of 100 µM P5 forward primer mix, 10 µL of 5 µM condition-specific P7 barcoded primer, and water to reach 100 µL. DNA oligo primers were ordered PAGE purified from Sigma Aldrich. Target amplification was achieved by using: 1 minute at 95° C. initial denaturation; 30 seconds at 95° C., 30 seconds at 53° C., 30 seconds at 72° C., for 26-27 cycles; 10 minutes at 72° C. final elongation. Specific amplification of the 360 bp target was confirmed by agarose gel electrophoresis. All PCR reactions of a respective condition were pooled and 100 µL were purified using AMPure XP beads in a 1:1 ratio, following standard protocols. Purified amplicon was eluted using 50 µL TE buffer. Final sequencing libraries were pooled in equimolar amounts and sequenced on a HiSeq 3000/4000.

Next Generation Sequencing Data Analysis

De-multiplexed raw reads were processed to count sgRNA spacer abundance using a custom script. The first 20 bp of the trimmed reads were collected and aligned against the Brunello spacer index using Bowtie2. Spacers were counted using cut-f 3|sort|uniq -c on the aligned SAM files. A count table with all drug conditions was then assembled and normalized to counts-per-million. Log 2 fold changes of drug treatment vs DMSO were calculated from normalized counts, omitting spacers with no reads in the DMSO condition. The enrichment rank of each spacer sequence was expressed as a fraction of the total number of spacers, so that the most enriched spacer is assigned a perturbation strength of 1, in accordance with the STARS algorithm. Gene hits were called using the STARS v1.3 algorithm with options --dir P --thr 10 --use-first-pert N, testing against a null hypothesis of 5,000 permutations. Hits with a q-value lower than 0.1 were deemed significant.

In brief, 250 million Cas9 expression KBM7 cells were mutagenized with a genome-wide sgRNA library, and subjected to selective pressure via continuous drug treatment. This setup thus selects for predominantly inactivating mutations in genes that are functionally required for the anti-proliferative mechanism of action of the employed small-molecule drugs. Genome-wide screens were conducted both for IC021313.2, IC020772.1 and T6938051. In the three cases, analysis of drug-tolerant populations that survived after two weeks of continuous drug treatment revealed a striking enrichment in only four genes (FIG. 5).

Validating the previous results, a strong enrichment for cells transduced with UBE2Mtargeting sgRNAs was detected. Interestingly, these screens also revealed enrichment for mutations in DDB1, CUL4B, and UBE2G1. All of these proteins form a functional CRL complex where DDB1 acts as the adaptor protein that binds to the CUL4 scaffold and thus connects the cullin backbone to a substrate receptor. UBE2G1 is an E2 ligase known to associate with CRL4 ligases. Other components that are part of this complex were found in ensuing, focused experiments using inducible Cas9. Examples are for instance RBX1, the protein connecting UBE2G1 to CUL4B (data not shown). The fact that Rbx1 was not detected in the initial experiment is likely explained by the fact that prolonged loss of RBX1 function is detrimental to cellular fitness. Noteworthy, the screen functionally segregated CUL4B from CUL4A, even though both genes are often treated interchangeably with largely overlapping functions. To understand if the tested compounds were uniquely dependent on CUL4B over CUL4A, a differential drug efficacy was assessed in dose ranging viability assays in KBM7 WT cells and isogenic clones deficient in either CUL4A, CUL4B, and UBE2G1. In accordance with data from the genome-wide screen, sensitivity of WT cells to the tested drugs was unaffected by mutation of CUL4A. In contrast, clones deficient for CUL4B and UBE2G1 showed a pronounced resistance against all drugs (FIG. 6, Table T2).

TABLE 2

LC50 values of data depicted in FIG. 6

| Compound name | LC50 WT | LC50 CUL4Amut | LC50 CUL4Bmut | LC50 UBE2G1mut |
|---|---|---|---|---|
| IC021313.2 | 1.27 | 1.56 | 15.74 | 4.34 |
| IC020772.1 | 1.25 | 1.22 | 7.53 | 2 |
| T6938051 | 1.72 | 2.26 | 109.9 | 3.47 |

In summary, genome-scale functional interrogation of the identified compounds has linked their antiproliferative mechanism to the availability of a functional CRL4B E3 ligase complex. Of note, known molecular glues/CRL modulators, such as the IMiDs or indisulam, all operate by physically binding to an CRL substrate receptor ("SR", such as CRBN or DCAF15). Given that rescue of drug efficacy with mutations in individual SRs was not observed, several explanations appeared plausible. (1) it could be that the putative SRs were highly essential. However, screens and follow-up experiments did reveal the relevance of highly essential CRL components such as DDB1 (the adaptor of all CRL4-based SRs) and RBX1, both of which are known as classical pan-essential genes. It thus appears unlikely that an individual substrate receptor remained undetected based on impaired cellular fitness of the loss of function clones.

Another explanation would be (2) functional redundancy, where our identified small-molecules modulate more than one SR in an interchangeable manner (either directly or indirectly). Lastly (3), it could be that the tested molecules endow a neomorphic function of the CRL4B complex by binding to a non-SR component. In order to disentangle these hypotheses, and to test if the assayed molecules would directly bind to/physically engage the CRL4B complex, IC021313.2 was derivatized with a moiety consisting of a photoactive diazirine group and an alkyl handle (FIG. 7). The ensuing functionalized molecule was used to purify proteins physically binding to the compound ("interactors"). In order to gain increased confidence, a competitive setup was chosen where cells were initially treated with the parental, non-modified compound or vehicle control. Compound treatment (1h) at excess concentrations of 100 μM was expected to saturate binding sites. Subsequently, cells (both vehicle- and compound-treated) were treated with the functionalized probe for 1 h at 10 μM, followed by UV-crosslinking. Next, cells were lysed and a biotin-azide linker was attached via click chemistry, and interacting proteins ("interactors") were purified via biotin enrichment over a Streptavidin column and subjected to unbiased detection via label-free proteomics analysis.

Methods for Chemoproteomics Experiment
Sample Preparation for Chemo-Proteomics (Competitive Setup)

20 million KBM7$^{WT}$ cells per condition (duplicates) were pre-treated with either DMSO(non-competing condition) or IC021313.2 (100 μM, competition condition) for 1h in serum-free IMDM medium (3 ml/20 million cells/10 cm dish). Then, cells were treated with the IC021313.2-photoaffinity probe (10 μM) for 1h. Target proteins were covalently linked to the probe via photo-crosslinking using an UV crosslinker at 4° C. (365 nm wavelength for 10 min). Cell pellets were collected, PBS-washed and snap-frozen in liquid $N_2$. For protein extraction, thawed pellets were resuspended in 500 μl lysis buffer (NP-40 0.8%, HEPES pH 7.5 50 mM, Glycerol 5%, NaCl 150 mM, $Mg_2Cl$ 1.5 mM, SDS 1%, protease inhibitor and benzonase) and incubated on ice for 30 min. Click reaction to conjugate azide-PEG3-biotin to the photoprobe was performed using 900 μg of protein per sample (1 mL total volume): 20 μl of 5 mM Azide-PEG3-biotin (Sigma-Aldrich, 762024-25 MG) was added to each sample followed by a mix of 60 μl 1.7 mM TBTA, 20 μl 50 mM $CuSO_4$ and 20 μl 50 mM TCEP (=100 μl per sample), and left at room temperature for 2h. SpinOUT™ G-600 columns (G-Biosciences, 786-1621) were used to purify protein samples after the click reaction, according to manufacturer's protocol. 500 μg per sample were used for the pulldowns. Enrichment of target proteins was done using Pierce™ High Capacity NeutrAvidin™ Agarose beads (Thermo Scientific, 29202), according to manufacturer's protocol. After last washing step, beads were resuspended in 100 μl elution Buffer (HEPES pH 8 50 mM, NaCl 150 mM, EDTA 5 mM, SDS 4%), incubated at 75° C. for 30 min and eluted by centrifuging at full speed for 3 min. Eluates were subjected to single-pot solid-phase-enhanced sample preparation (Hughes et. al. *Mol Syst Biol,* 2014) and solid-phase extraction. Peptides were cleaned up by acidifying the samples to a final concentration of 1% TFA prior to immobilizing the beads on the magnetic rack to perform solid phase extraction of the recovered supernatant using C18 SPE columns (SUM SS18V, NEST group, USA) according to the manufacturer. Peptides were eluted using two times 50 μl 90% Acetonitrile, 0.4% formic acid, dried in a vacuum concentrator before reconstitution in 26 μl of 5% formic acid (Suprapur, MERCK KgaA, Germany).

LC-MS

Liquid chromatography mass spectrometry was performed on a Q Exactive™ Hybrid Quadrupole-Orbitrap (ThermoFisher Scientific, Waltham, MA) coupled to a Dionex U3000 RSLC nano system (Thermo Fisher Scientific, San Jose, CA) via nanoflex source interface. Tryptic peptides were loaded onto a trap column (Acclaim™ PepMap™ 100 C18, 3 μm, 5×0.3 mm, Fisher Scientific, San Jose, CA) at a flow rate of 10 μL/min using 5% acetonitrile in 0.1% TFA as loading buffer. After loading, the trap column was switched in-line with a 30 cm, 75 μm inner diameter analytical column (packed in-house with ReproSil-Pur 120 C18-AQ, 3 μm, Dr. Maisch, Ammerbuch-Entringen, Germany). Mobile-phase A consisted of 0.4% formic acid in water and mobile-phase B of 0.4% formic acid in a mix of 90% acetonitrile and 10% water. The flow rate was set to 230 nL/min and a 90 min gradient used (4 to 24% solvent B within 82 min, 24 to 36% solvent B within 8 min and, 36 to 100% solvent B within 1 min, 100% solvent B for 6 min before re-equilibrating at 4% solvent B for 18 min).

For the MS/MS experiment, the Q Exactive™ MS was operated in a top 10 data-dependent acquisition mode with a MS1 scan range of 375 to 1,650 m/z at a resolution of 70,000 (at 200 m/z). Automatic gain control (AGC) was set to a target of 1×10$^6$ and a maximum injection time of 55 ms. MS2-scans were acquired at a resolution of 15,000 (at 200 m/z) with AGC settings of 1×10$^5$ and a maximum injection time of 110 ms. Precursor isolation width was set to 1.6 Da and the HCD normalized collision energy to 28%. The threshold for selecting precursor ions for MS2 switching from MS1 to MS2 was set to ~2,000. Dynamic exclusion for selected ions was 60 s. A single lock mass at m/z 445.120024 was employed (2). All samples were analysed in duplicates, back-to-back replicates. XCalibur version 4.1.31.9 and Tune 2.9.2926 were used to operate the instrument.

MS Data Analysis

Acquired raw data files were processed using the Proteome Discoverer 2.2.0.388 platform, utilising the database search engine Sequest HT. Percolator V3.0 was used to remove false positives with a false discovery rate (FDR) of 1% on peptide and protein level under strict conditions. Searches were performed with full tryptic digestion against the human SwissProt database v2017.06 (20,456 sequences and appended known contaminants) with up to two miscleavage sites. Oxidation (+15.9949 Da) of methionine and acetylation (+42.010565 Da) of protein N-terminus were set as variable modification, whilst carbamidomethylation (+57.0214 Da) of cysteine residues was set as fixed modifications. Data was searched with mass tolerances of ±10 ppm and 0.02 Da on the precursor and fragment ions, respectively. Results were filtered to include peptide spectrum matches (PSMs) with Sequest HT cross-correlation factor (Xcorr) scores of ≥1 and proteins including ≥2 unique peptides. For calculation of protein areas Minora Feature Detector node and Precursor Ions Quantifier node, both integrated in Thermo Protcome Discoverer were used. Automated chromatographic alignment and feature linking mapping were enabled. Precursor abundance was calculated using intensity of peptide features including only unique peptide groups. To equalize total abundance between different runs, protein abundance values were normalized using the total peptide amount approach. No computational missing value imputation was applied to fill gaps. For statistical analysis a non-nested (un-paired) approach was applied using pairwise ratio calculation and background-based ANOVA statistical testing. Peptide abundance values are calculated as median abundancies of all technical replicates. The application then calculates the peptide group ratios as the geometric median of all combinations of ratios from all the replicates for the two defined study groups of DMSO treated versus drug treated. The subsequent protein ratio is calculated as the geometric median of the peptide group ratios. Pairwise ratio calculation was chosen to make the analysis less sensitive towards missing values. Background-based ANOVA uses the background population of ratios for all peptides and proteins in order to determine whether any given single peptide or protein is significantly changing relative to that background (as stated in the manual of Proteome Discoverer 2.2, Thermo Fisher Scientific, Waltham, MA). Adjusted p-values are calculated using the Benjamini-Hochberg method. High-confidence interactors are expected to be enriched in the non-competing condition, while their enrichment should be abrogated upon competition with the parental compound.

Given the competitive experimental setup, high-confidence interaction partners were expected to be enriched in the non-competing (DMSO-pretreated) conditions, while their enrichment should be abrogated upon pretreatment/ competition with the parental compound. Interestingly, among a small fraction of competitively binding protein targets, CUL4B and DDB1 (FIG. 7c) were identified, indicating that the assayed compound directly and physically engages with CRLB4 ligase complex. The specificity for CUL4B over CUL4A in both genetics and proteomics experiments was a striking observation given the high sequence conservation of both proteins (83%).

It was suggested that the identified compound might bind the N-terminal region of CUL4B, which is absent in CUL4A. Given that CUL4B knockout rescues drug effect, it was posited that the molecules do not inhibit CUL4B/ CRL4B function, but rather modulate its function in a way that is detrimental to the cellular fitness of KBM7 human leukemia cells. To better characterize the anticancer activity of the assayed molecules, Annexin V/PI staining in KBM7 at various timepoints was conducted (FIG. 8).

Methods for Apoptosis Measurements:

KBM7WT cells were treated with DMSO or drug (~10× EC50) for 4 h, 8 h and 12h. To asses apoptosis induction we used AnnexinV/PI (BD Bioscience #556547). 5×105 cells were collected, pelleted by centrifugation, washed with PBS and resuspended in 1× binding buffer at a concentration of ~1×10$^6$ cells/mL, preparing a sufficient volume to have 100 µL per sample. 5 µl of staining solution was added per sample and incubated for 20 min at room temperature in the dark. 400 µl of 1× binding buffer was added and cells were analyzed (within 1h) by flow cytometry.

The mechanism by which the assayed molecules reprogram a functional CRL4B complex based on the data shown could be that drug binding to CUL4B recruits a neo-substrate directly to the cullin backbone. Alternatively, drug binding could stabilize CUL4B function to boost time intervals where a functionally competent CUL4B complexes can be formed. Here, the word "functional" implies that the CUL4B backbone of this complex needs to be neddylated, and a CUL4B associated E2 ubiquitin-conjugating enzyme (UBE2G1) needs to be bound. FIG. 9 outlines one possible mechanism. Both predicted mechanisms of action would result in a functionally altered CRL4B complex, and thus an altered stability of drug-induced (neo-) substrates. In order to identify target proteins with a decreased abundance or, in other words, target proteins that become degraded by CRL4B after drug treatment, global proteome composition was measured using quantitative expression proteomics (TMT-labeling). In brief, KBM7 cells were drug treated for 12 hours, lysed, and subjected to isobaric tagging. Ensuing proteomics analysis quantified a total of 7,903 proteins at a minimum spectral count of 2. At this relatively late timepoint, the following numbers of proteins were found to be significantly downregulated (log 2FC <−0.3) for IC021313.2 (839 destabilized proteins; Table 4), IC020772.1 (869 destabilized proteins; Table 5) and T6938051 (793 destabilized proteins; Table 6). Of these proteins, a total of 183 proteins downregulated by IC021313.2 are known to be implicated in KBM7 proliferation (=are essential for KBM7 viability) (Table 4). Similarly, 147 proteins downregulated by IC020772.1 are known to be implicated in KBM7 proliferation (Table 5), and 142 proteins downregulated by T6938051 (Table 6) are known to be implicated in KBM7 proliferation (FIG. 10). Data on essentiality are taken from Hart et al., G3, August 2017 (PMID: 28655737).

Finally, a total of structurally similar analogs was tested to unravel structure-activity relationship of the identified molecules. To that end, their anti-cancer activity was assayed in WT cells, as well as KBM7 cells deficient in genes identified in the genome-wide CRISPR screens (UBE2M, CUL4B, UBE2G1). Moreover, the compounds were also tested in AsPC1 pancreatic cancer cells (WT or UBE2Mmut), MV4; 11 and Jurkat leukemia cells, Be (2) C neuroblastoma cells, and NCI-H446 lung cancer cells (Table 3 at the end of this document)

Methods for Expression Proteomics:

We compared overall proteome-wide changes in KBM7$^{WT}$ cells treated with DMSO or drug (~10×EC50, 12h), using quantitative proteomics based on isobaric tagging.

Sample preparation

50×10$^6$ KBM7$^{WT}$ cells per condition were collected, washed four times with ice-cold PBS, the supernatant aspirated and pellets snap-frozen in liquid N$_2$. Each washed cell pellet was lysed separately in 40 µL of freshly prepared lysis buffer as previously described (see Mayor-Ruiz et al., Mol Cell 2019)

Offline Fractionation via RP-HPLC at high pH and 2D-RP/RP Liquid Chromatography Mass Spectrometry were performed as previously described (see Mayor-Ruiz et al., *Mol Cell* 2019).

Data Analysis

Acquired raw data files were processed using the Proteome Discoverer 2.2.0 platform, utilizing the Sequest HT database search engine and Percolator validation software node (V3.04) to remove false positives with a false discovery rate (FDR) of 1% on peptide and protein level under strict conditions. Searches were performed with full tryptic digestion against the human SwissProt database v2017.06 with up to two allowed miscleavage sites. Oxidation (+15.9949 Da) of methionine was set as variable modification, whilst carbamidomethylation (+57.0214 Da) of cysteine residues and TMT 6-plex labelling of peptide N-termini and lysine residues were set as fixed modifications. Data was searched with mass tolerances of ±10 ppm and ±0.02 Da on the precursor and fragment ions, respectively. Results were filtered to include peptide spectrum matches (PSMs) with Sequest HT cross-correlation factor (Xcorr) scores of 21 and high peptide confidence assigned by Percolator. $MS^2$ signal-to-noise values (S/N) values of TMT reporter ions were used to estimate peptide/protein abundance changes. PSMs with precursor isolation interference values of ≥ 50% and average TMT-reporter ion S/N≤10 were excluded from quantitation. Only unique peptides were used for TMT quantitation as well as for TOP3 label-free quantitation. Isotopic impurity correction and TMT channel-normalization based on total peptide amount were applied. For statistical analysis and p-value calculation, the integrated ANOVA hypothesis test was used. TMT ratios with p-values below 0.01 were considered as significant. Only proteins with >1 peptide detected and >1 unique peptide detected were considered for further analysis. For the calling of destabilized proteins, a log 2 fold change threshold (drug/DMSO) of −0.3 was applied. (Tables of significantly downregulated proteins as well as information on either essentiality status can be found in associated Table 4 to 6)

Example 3: Derivatization for PROTAC Development

Heterobifunctional degraders typically feature a tripartite design where two ligands are connected via a flexible linker (FIG. 11). This design thus allows simultaneous binding to the protein of interest (the protein to be degraded) and the E3 ligase. In most cases, the "E3 ligase ligand" binds to the interchangeable substrate receptors of a cullin RING ligase, such as CRBN or VHL. In the case of CRBN, the first evidence that this substrate receptor (and thus the entire $CRL4^{CRBN}$ complex) could be harnessed for targeted protein degradation came from a chemoproteomics approach (Ito et al. "Identification of a primary target of thalidomide teratogenicity. Science 2010 Mar. 12; 327(5971):1345-50. doi: 10.1126/science.1177319). Ito and colleagues have used a tethered analog of thalidomide as an affinity resin to enrich for cellular binding proteins. This led to the identification of CRBN as the direct cellular binding partner of thalidomide.

While existing PROTACs hijack CRL complexes by binding to the interchangeable substrate receptors, the present approach allows for the first PROTAC that actually engages a non-substrate receptor protein of a CRL complex (such as CRL4B or DDB1). Given the predominant nuclear localization of CRL4B, such CUL4B-based PROTACs are particularly suited for nuclear targets. FIG. 11 below outlines the structure of a putative PROTAC molecule series based on the chemical matter discovered here (FIG. 11A) as well as a schematic depiction of a possible mechanism of action (FIG. 11B). In this example, the putative PROTAC consists of the novel chemical matter that serves as recruitment element binding to CRL4B. Moreover it consists of a flexible linker that can be of varying length (2-40 atoms) and composition (aliphatic or PEG-based). Many examples for successful linker designs are available in the scientific literature, exemplified via CRBN- or VHL-based degraders. Finally, the putative PROTAC consists of a targeting ligand that binds to the "protein of interest" that is to be degraded. For the example below, a targeting ligand is chosen that is inspired by the competitive BET-bromodomain ligand JQ1 (Nature, 2010: PMID 20871596) which is known to bind to BRD4 and the closely related BRD2, BRD3 and BRDT. It is therefore derived that the designed CRL4B-based PROTACs can induce the degradation of a variety of other proteins. A prerequisite here is the identification of a sufficiently potent (likely below 10 µM) small-molecule ligand that directly binds to a putative protein of interest. Even though CUL4B predominantly localizes to the nucleus, it cannot be ruled out that also cytoplasmic proteins, or transmembrane proteins can be degraded via a CRL4B-based PROTAC. Examples of possible degradable protein classes include, but are not limited to, the following:

bromodomain containing proteins (such as BRD2, BRD3, BRD4, CBP, p300, ATAD2, SMARCA2, SMARCA4, PBRM1, and others) o kinases, pseudo-kinases and disease-relevant mutations/fusions thereof (such as CDK4, CDK6, CDK9, EGFR, SRC, PDGFR, ABL1, HER2, HER3, BCR-ABL, MEK1, ARAF, BRAF, CRAF . . . )

GTPases and disease-relevant mutations thereof (such as HRAS, NRAS, KRAS)

anti-apoptotic proteins (such as BCL2, MCL1)

phosphatases (such as SHP2, PTPN1, PTPN12)

transcription factors and disease-relevant mutations/fusions thereof (such as ESR1, AR, MYB, MYC)

immune regulators (such as PDL1)

scaffolding proteins, G-protein coupled receptors, metabolic enzymes

Example 4

Genetic screens were conducted and identified that known degraders (monovalent glues and PROTACs) depend on the enzyme UBE2M for their activity (FIG. 15). Next, 2000 compounds were screened in a comparative set up. The PROTAC ARV-771 was taken as positive control. Of 18 identified hits (FIG. 16), 12 of these compounds validated in dose response curves. Out of these 12 compounds, three had a known primary function: the anti-folates Methotrexate, Raltitrexed an Pralatrexate and 9 were without annotated function. Notably, one of the hits (dCeMM.1) has an arylsulfonamide structure and is thus related to the structure to the known degrade indisulam, which redirects the ligase DCAF 15 to degrade the splicing factor RBM39. dCeMM.1 could be validated as novel DCAF 15-dependent degrader that induced the degradation of RBM39, but also of three related proteins denoted as SRSF5, RBM5 and RBM38 (FIG. 17). Three out of the 9 hits without annotated function followed an apparent structure-activity relationship (FIG. 16). For 8 of the compounds without annotated function including dCcMM.1 as shown in FIG. 17, global expression protcomics was performed. After 12 hours >100 proteins were destabilized.

Subsequently, in this context, the E3 ligase substrate receptor (SR) stabilization approach was employed in order to identify novel chemical matter that can bind and chemically re-program the substrate receptor DCAF15. To be able to screen a collection of around 8000 small-molecules, a cellular system was developed that enabled monitoring of DCAF15 levels in live cells in multi-well format. To that end, DCAF15 was first knocked out in 293T cells via CRISPR/Cas9 technology. Then, DCAF15 was stably expressed as a HiBit® fusion protein in these cells. After further transducing these cells with LgBit, this allowed live-cell tracing of DCAF15 levels in 384 well format by measuring bioluminescence (FIG. 13).

In brief, cells were seeded at a concentration of 250'000 cells/ml in DMEM+10% FCS+25 mM Hepes. The luciferase substrate Endurazine was added at concentrations recommended by the manufacturer. Small-molecules were added at a concentration of 10 µM, and their effect on DCAF15 levels was assayed by continuous bioluminescent imaging (measurements were taken every 120 minutes). In total, 8000 compounds were tested.

In total, 8000 compounds were tested (FIG. 13 only shows only a subset of the 8000 tested molecules. In detail, 200 negative controls=compounds that did not appear to cause DCAF15 stabilization are displayed). The known DCAF15 molecular glue indisulam was used as a positive control. In brief, indisulam is known to act as a DCAF15-dependent molecular glue that binds DCAF15 and induced proximity between DCAF15 and RBM39, leading to the degradation of the latter. As predicted, treatment with indisulam led to a pronounced stabilization of DCAF15 over time. Of note, two additional molecules (dCeMM.1 and dCeMM.2) were also identified to prompt significant DCAF15 stabilization. The chemical structure of dCeMM.1 and dCeMM.2 alongside indisulam are shown in FIG. 14. Interestingly, both test compounds feature an aryl sulfonamide structure similar to indisulam. Given the structural similarity to indisulam, it was assayed if the two new test compounds would similarly lead to the degradation of RBM39 in a DCAF15-dependent manner. Towards that end, their effect on RBM39 levels in wildype cells as well as cells deficient for DCAF15 levels was tested. KBM7 (WT or knockout, FIG. 15) as well as 293T cells (DCAF15-HiBit overexpression vs knockout, see FIG. 16) were tested in various conditions of dCEMM.1 and/or dCEMM.2, comparing their effect to indisulam.

In sum, in a screening of multiple compounds for their ability to redirect the ligase DCAF15, a known positive control (such as indisulam) as well as compounds with unknown annotated function, e.g. the compounds denoted as dCeMM.1 and dCcMM.2, have been identified as positive hits, i.e. compounds that act in a DCAF15-dependent manner binding to DCAF15 and inducing proximity between DCAF15 and (a) target protein(s) such as RBM39, leading to the degradation of the target protein(s).

In another experiment, 2000 compounds were screened in a set up comparing their anti-proliferative effect in KBM7 cells modified in the UBE2M gene to wildtype KBM7 cells (FIG. 3). The PROTAC® ARV-771 was taken as positive control. Of note, among the identified hits was also dCeMM.1, which was similarly identified via the aforementioned DCAF15 restabilization assay. FIG. 21 shows that dCeMM.1 loses anti-proliferative activity in KBM7 cells mutant for UBE2M as compared to KBM7 WT cells (19A). To further ascertain that the shift in viability is dependent on DCAF15, we also showed that inactivitation of DCAF15 in KBM7 cells lead to a pronounced resistance to dCeMM.1 as compared to KBM7 WT cells.

Example 5

5.1 Identification of Novel, Structurally Distinct Cyclin K Degraders

Figure 19A:
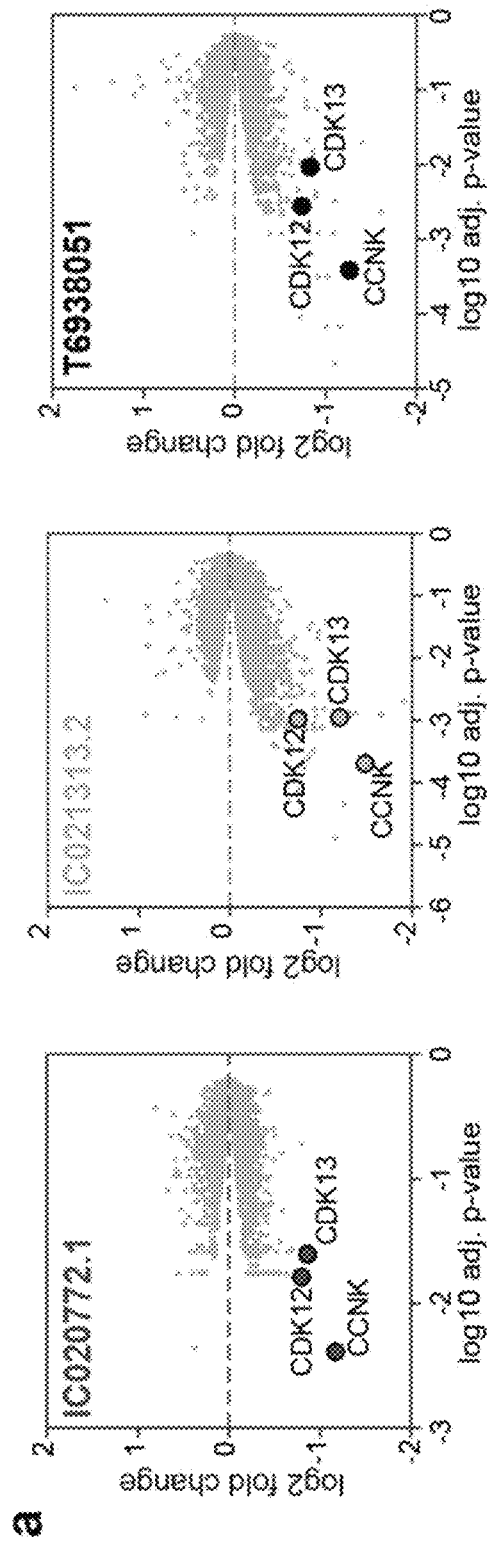
Figure 19B:
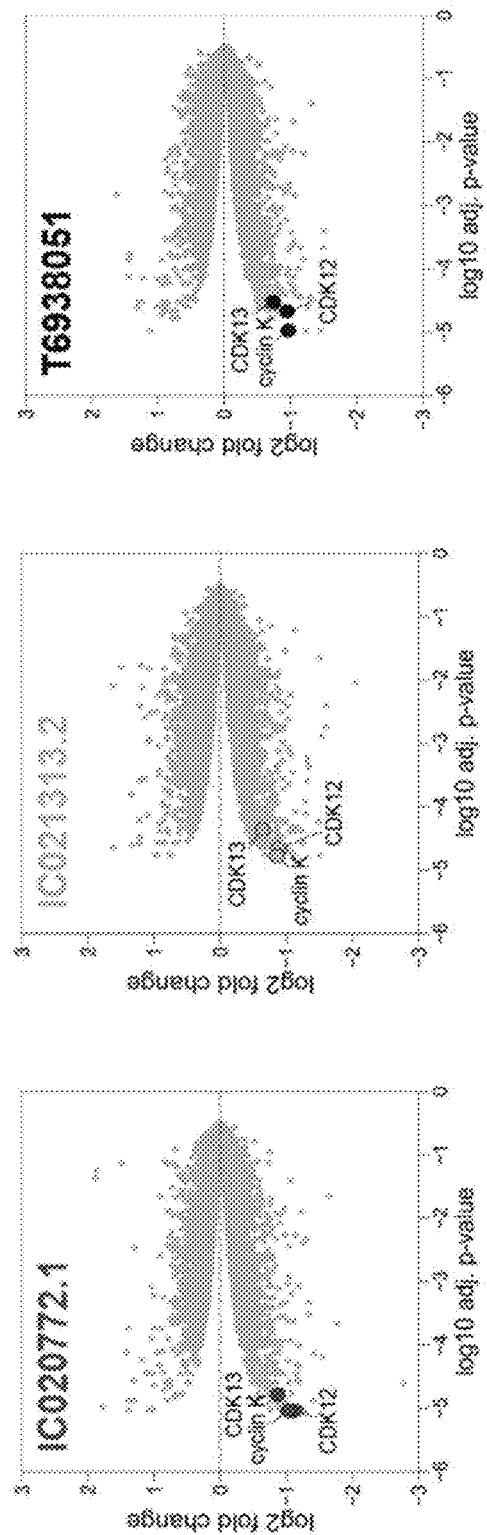
Figure 19E:
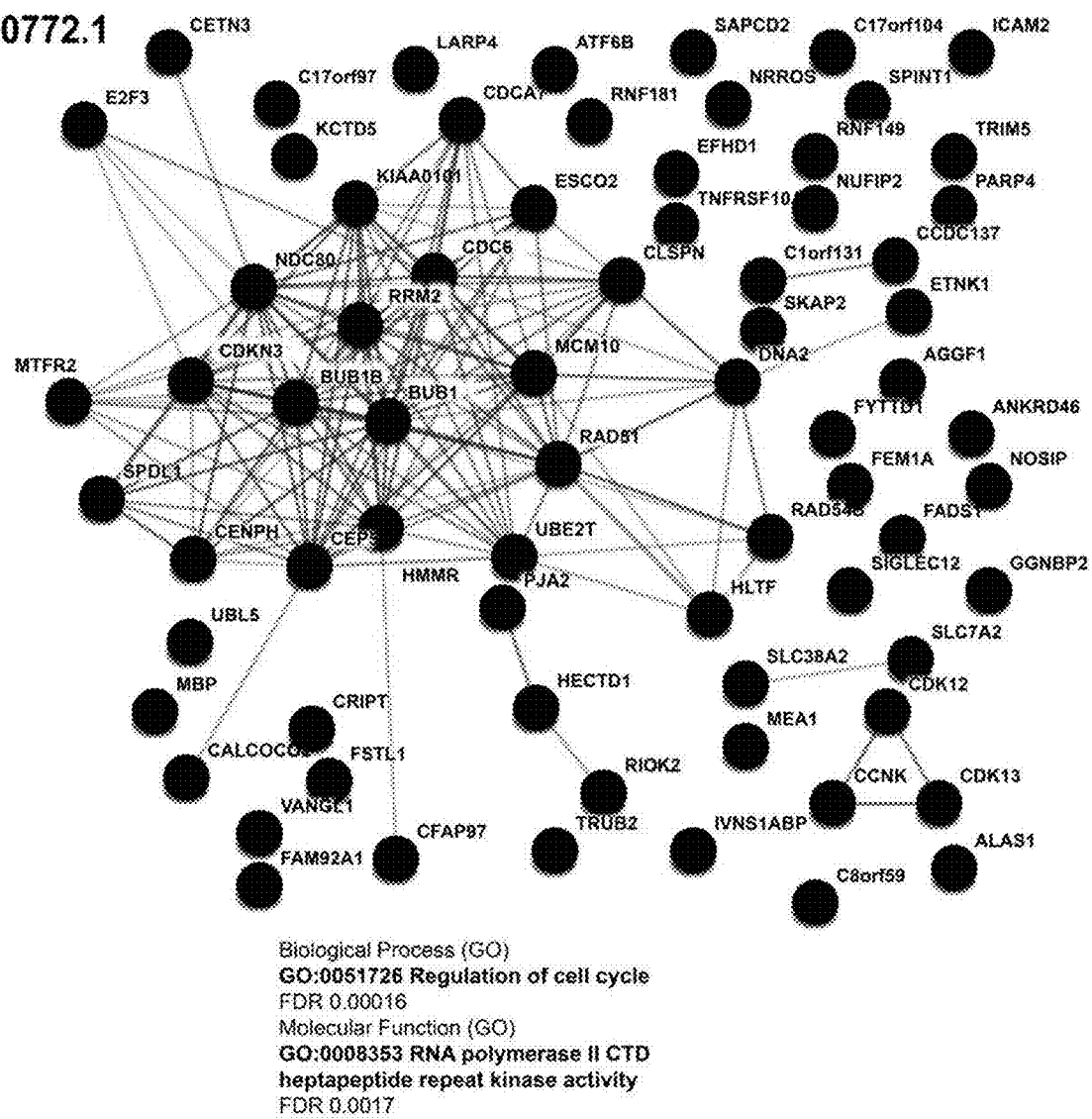
Figure 19F:
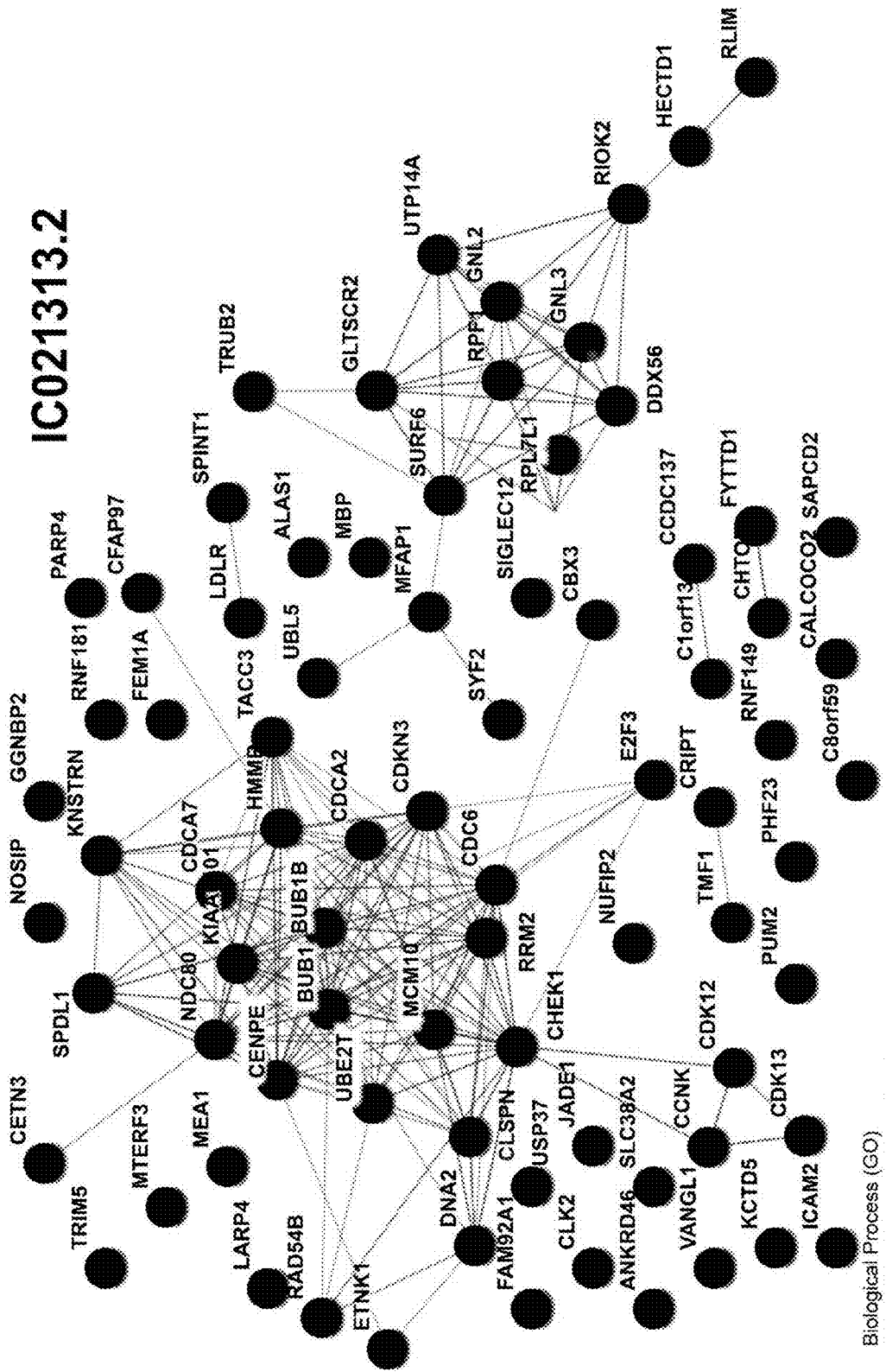
Figure 19G:
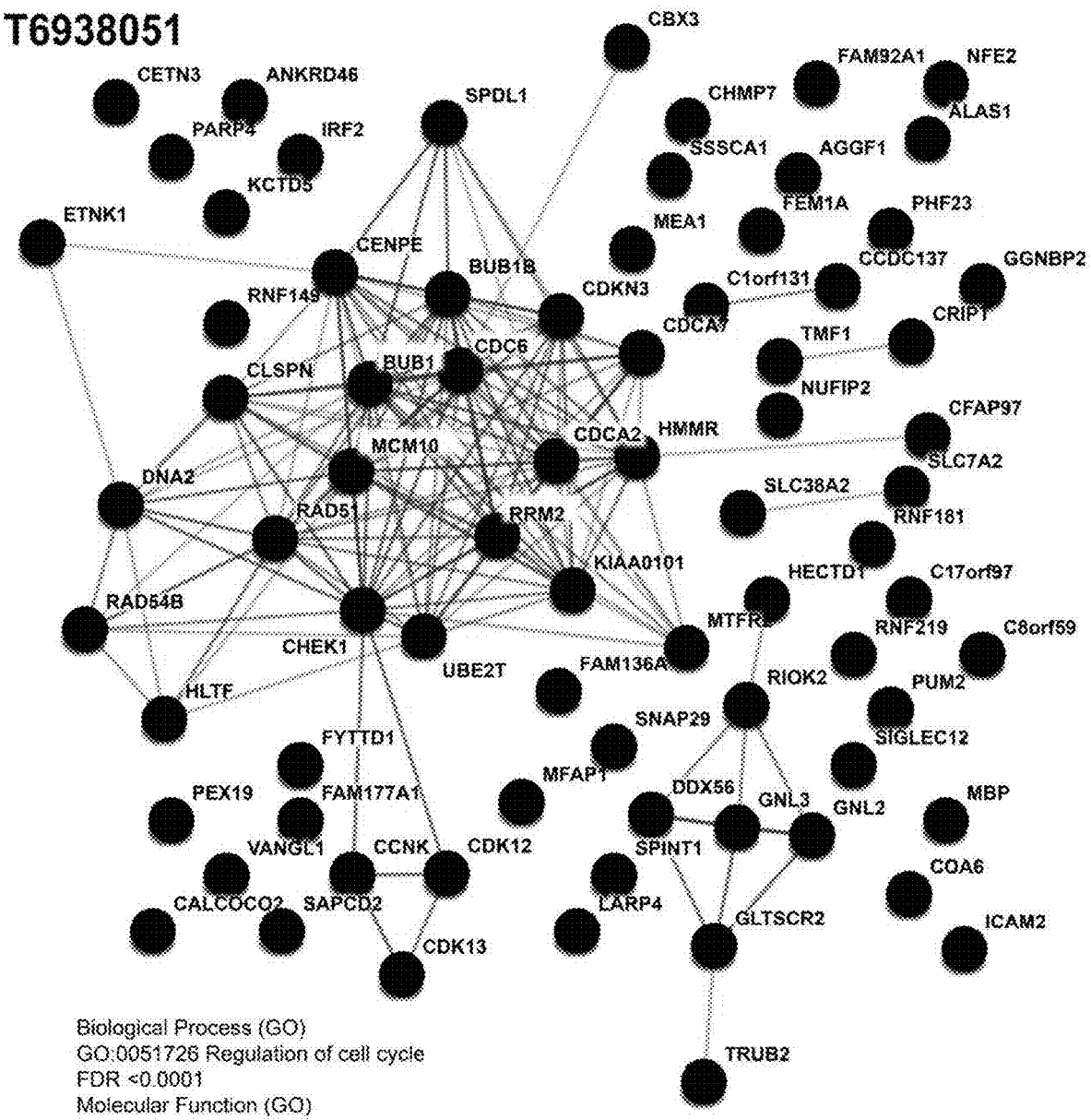

The hypomorphic phenotype of the mutated UBE2M allele in KBM7 cells (KBM7 UBE2M$^{mut}$ cells) was assessed. In this regard, CRISPR/Cas9-induced mutation of UBE2M inactivated CRL activity including CRL4$^{CRBN}$ and CRL2$^{VHL}$. Cellular treatment of the mutated cells with three compounds shown in FIG. 3b and denoted as IC020772.1; IC021313.2 and T6938051 in comparison with wild-type KBM7 cells revealed that these compounds led to a destabilization of cyclin K (CCNK) and of both associated kinases CDK12 and CDK13 in wild-type KBM7 cells (FIGS. 19a and b). Additionally, CCNK destabilization by all three compounds was validated via time-resolved immunoblots wherein CCNK degradation was evident after two hours (FIG. 19c).

Subsequently, a total of 53 structurally related analogue compounds in dose-ranging viability assays in KBM7 wild-type- and UBE2M$^{mut}$ cells was tested to develop a structure-activity relationship for the assayed compounds. This informed on sites amenable for derivatization of analogs (FIG. 20a), and also to the identification of structurally similar small molecules with no measurable activity that are thus suited negative controls. Inactive analogs dCeMM IC020772.1X/IC021313.2X/T6938051X failed to induce pronounced CCNK destabilization and did not affect KBM7 cells in dose-ranging viability assays (FIG. 21a-d). CRL activity-dependent degradation of CCNK could be rescued by pharmacologic NAE inhibition and by blocking the ubiquitin activating enzyme UBA1, particularly by pretreating the cells with 1 µM carfilzomib (Selleckchem, S2853), 1 µM MLN4924 (Selleckchem, S7109), 10 µM TAK-243 (MedChemExpress, HY-100487) or 1 µM THZ531 (MedChemExpress HY-103618) (FIG. 19d). Furthermore, treatment with the selective covalent CDK12/13 inhibitor THZ531, which binds to the ATP binding pocket of CDK12/13, rescued CCNK degradation (FIG. 19d) indicating the role of the active site of CDK12/13 for CRL activity-dependent CCNK degradation by the identified compounds (FIG. 19d).

Proteomics profiling enabled functional enrichment analysis of the differentially expressed protein-protein interaction networks prompted by cyclin K degradation. Thereby, "Regulation of cell cycle" and "RNA polymerase II CTD heptapeptide repeat kinase activity" were the major Gene Ontology biological processes/molecular functions affected (FIG. 19 e, f, and g). Specifically, as shown in FIG. 19 e, f and g, cellular treatment with all three compounds IC020772.1 (FIG. 19 e), IC021313.2 (FIGS. 19 f) and T6938051 (FIG. 19 g) degraded CCNK and downregulated additional disease-associated proteins as a consequence of the degradation of CCNK. For example, proteins as shown in FIG. 19 e to f comprise those proteins regulated downstream from the pathway involving CCNK or complexes comprising CCNK, such as CDK12:CCNK or CDK13:CCNK. As outlined above in connection with the down-regulated proteins shown in FIGS. 19 c to g, these proteins are also known to be involved in Gene Ontology biological processes/molecular functions of "Regulation of cell cycle" and "RNA polymerase II CTD heptapeptide repeat kinase activity" and thus in functions of gene disease-associated transcription processes.

Specifically, as shown in FIG. 19 e to g, proteins associated with neurological disorder such as HECTD1, MBP and FEM1A are downregulated upon degradation of CCNK. Further, proteins associated with metabolic diseases such as HMMR, LMNA and TMPO are also downregulated upon degradation of CCNK. Furthermore, proteins associated with infectious disease such as ICAM2, CALCOCO2 and CDC6 are downregulated upon degradation of CCNK. Cancer associated proteins such as BUB1, BUB1B, MCM10, CDCA7 and CDC6 are also all downregulated upon degradation of CCNK. Thus, proteins that are downregulated upon degradation of CCNK involve proteins associated with cancer, metabolic disorders, neurologic disorders or infectious diseases.

Materials and Methods
Cell Viability Assays

KBM7$^{WT}$, mutant KBM7 clones (UBE2M$^{mut}$, UBE2M$^{resc}$, UBE2G1$^{mut}$ CUL4A$^{mut}$, CUL4B$^{mut}$), and 3-day doxycycline pretreated KBM7$^{iCas9}$_sgDDB1 cells were seeded at a cell density of 50,000 cells/mL in 96-well plates with DMSO or drug, in triplicates. Drugs used: IC020772.1/IC020772.1X, IC021313.2/IC021313.2X, T6938051/T6938051X or THZ531. Cells were treated for 3 days, after which cell viability was assessed according to manufacturer's protocol (CellTiter Glo, Promega G7570). Survival curves and EC$_{50}$ values were calculated by best-fit analysis of the log 10 drug concentration to fold change of drug-treated cells over DMSO-treated cells. All survival assays included technical triplicates per sample, per experiment.

Western Blot Analysis

PBS-washed cell pellets were lysed in 50 mM Tris pH 7.9, 8M Urea and 1% CHAPS and incubated with shaking at 4° C. for at least 30 min. 20 µg of supernatants were run and transferred for detection. Antibodies used: CUL1 (Santa Cruz Biotechnology, sc-1276), CUL2 (Sigma-Aldrich, SAB2501565-100), CUL3 (Cell Signaling Technology, 2759), CUL4A (Cell Signaling Technology, 2699S), CUL4B (Proteintech, 12916-1-AP), CUL5 (Santa Cruz Biotechnology, sc-373822), UBE2M (Santa Cruz Biotechnology, sc-390064), DDB1 (Cell Signaling Technology, 5428S), CCNK (Bethyl, A301-939A), CDK12 (Cell Signaling Technology, 11973S), CDK13 (Bethyl, A301-458A), RBM39 (1:500, Santa Cruz Biotechnology sc-376531), V5 (Cell Signaling Technology, 13202), Ubiquityl-Histone H2A (K119) (Cell Signaling, 8240-20). ACTIN (Sigma-Aldrich, A5441), VINCULIN (Santa Cruz Biotechnology, sc-25336). Secondary antibodies anti-mouse/rabbit/goat (Jackson ImmunoResearch 115-035-003, 111-035-003 and 705-035-003).

Expression Proteomics

Comparison of overall proteome-wide changes in KBM7 cells treated with IC020772.1 (2.5 µM), IC021313.2 (7 µM) or T6938051 (3.5 µM) for 5 h and 12h, using quantitative proteomics based on isobaric tagging.

5.2 Drug-Induced CCNK Degradation is Mediated Via a CRL4B Ligase Complex

The molecular mechanism of drug induced CCNK destabilization and degradation was assessed, thereby identifying the components of the ubiquitin ligase interacting with the one or more target protein(s) to be degraded. For this purpose, KBM7 cells were subjected to CRISPR/Cas9-induced mutagenesis using a sgRNA library as described herein, e.g. as outlined in Example 2. Mutagenized cell pools were selected via exposure to IC020772.1; IC021313.2 and T6938051 to identify loss of function (LOF) mutations that allow clonal outgrowth, and thus highlighting genes that are functionally required for the anti-proliferative effects of the assayed compounds. In line with the initial chemical profiling in hypo-neddylated cells illustrated in the appended Examples above, UBE2M was identified as hit in all tested conditions.

Figure 22A:
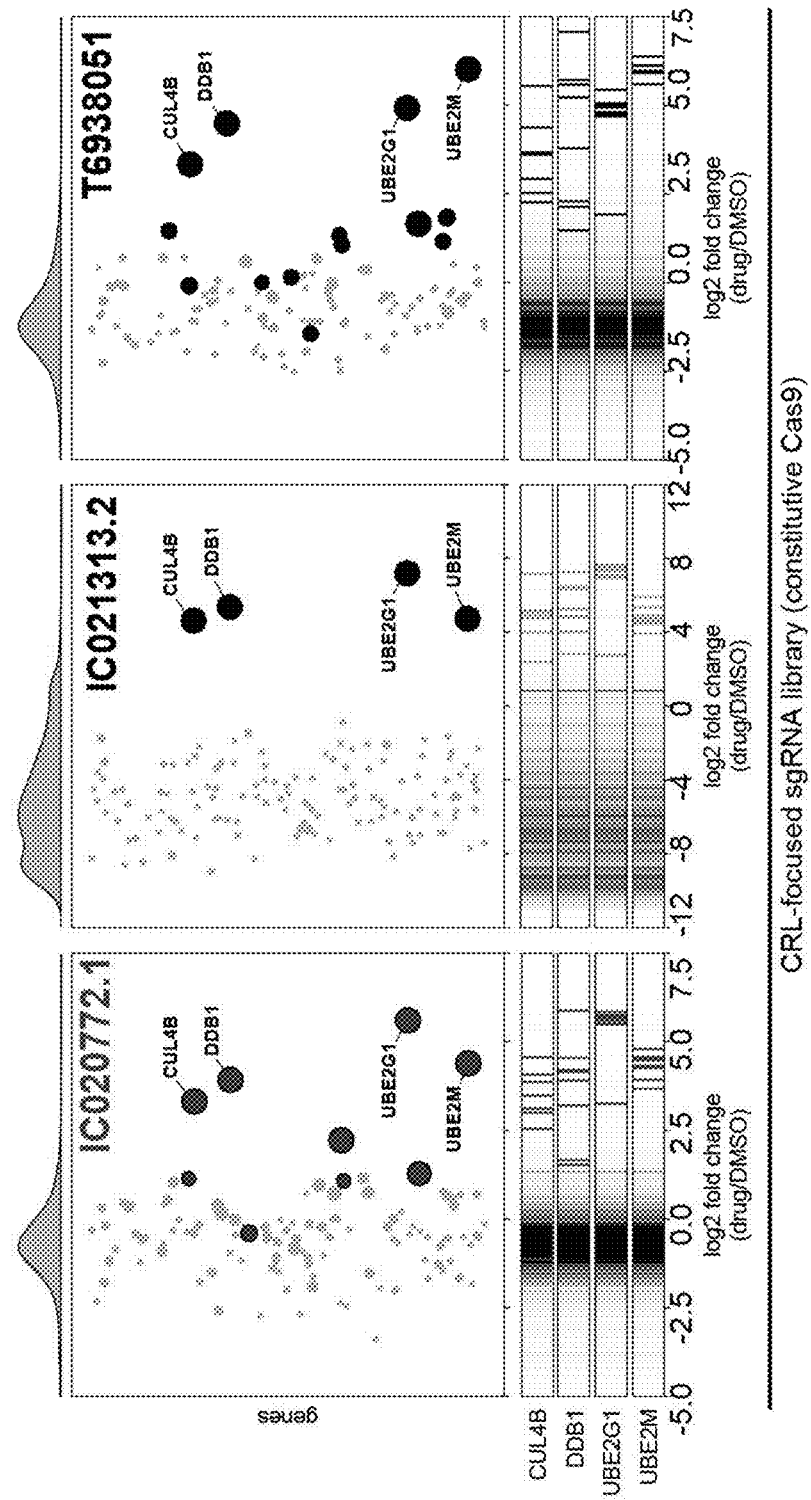
Figure 22A:
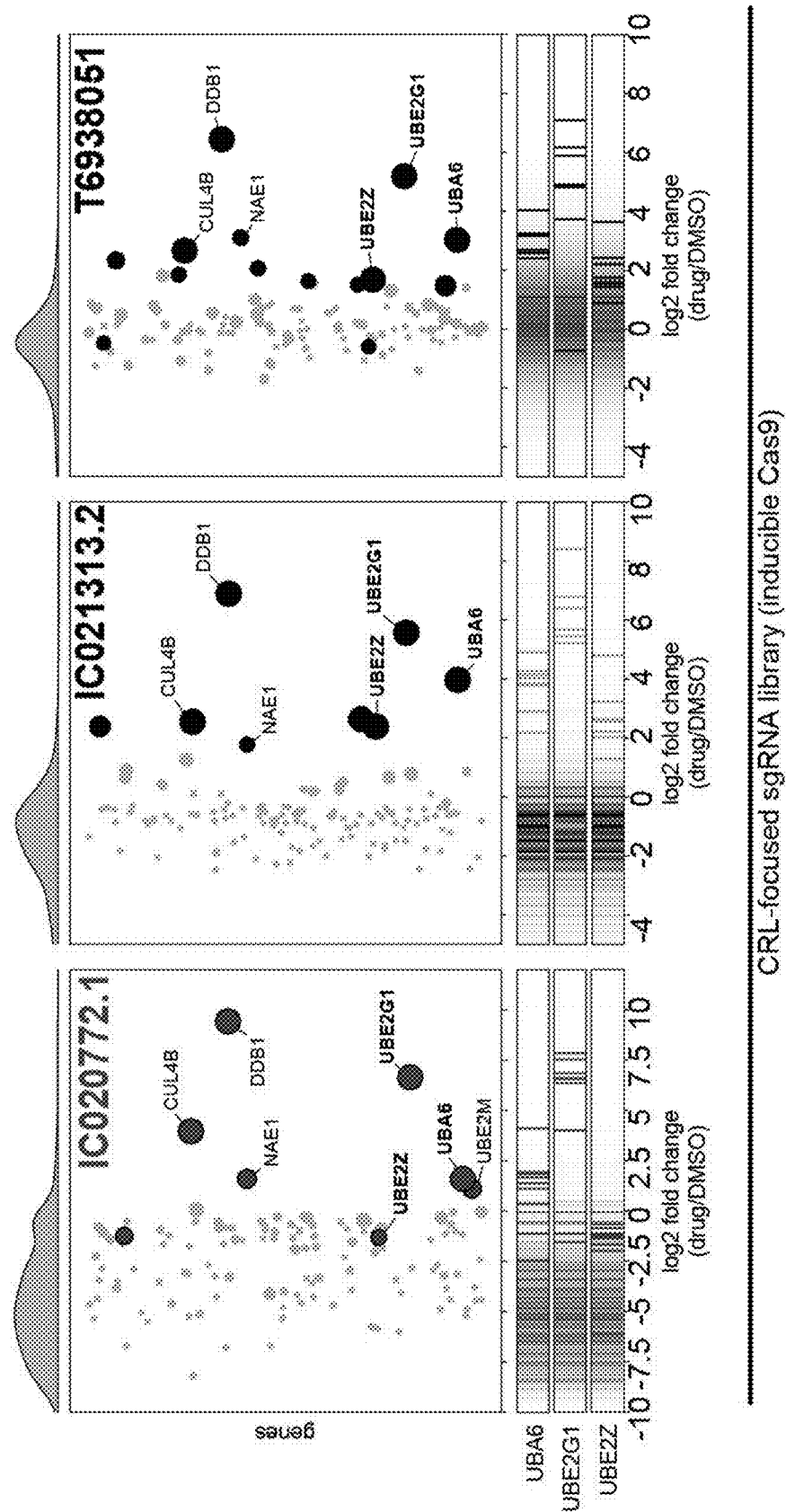
Figure 22B:
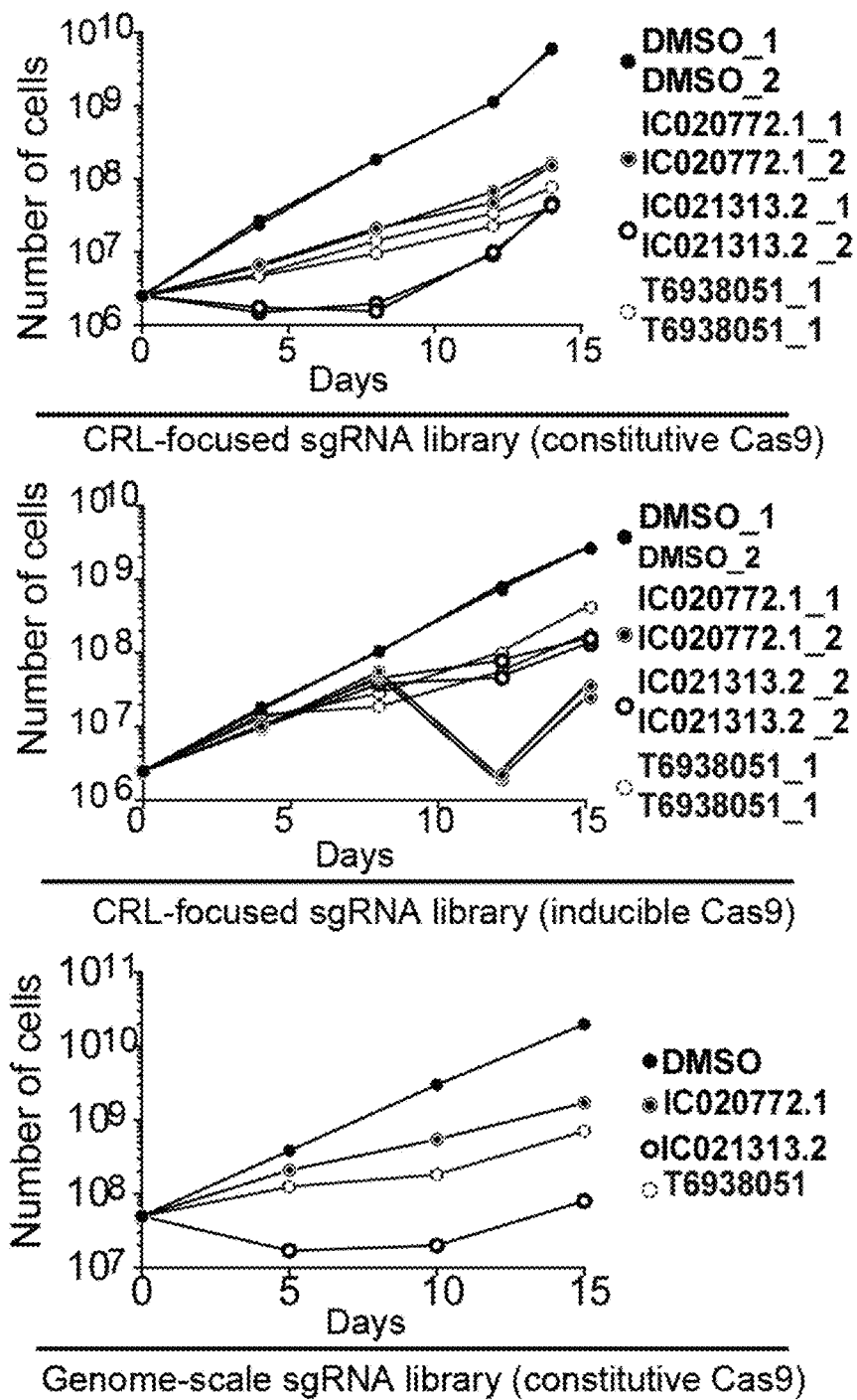
Figure 22C:
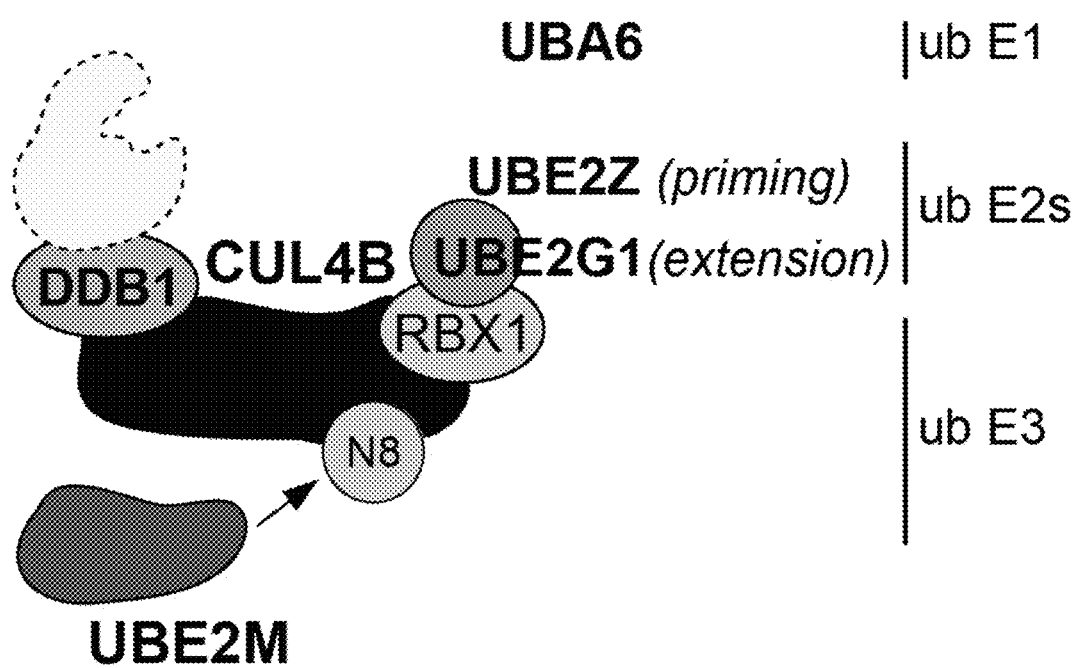

Moreover, three additional genes were identified that, inter alia, constitute a CRL complex: the cullin scaffold CUL4B, the adaptor protein DDB1, and the E2 ubiquitin-conjugating enzyme UBE2G1. In addition to UBE2G1, known to extend ubiquitin chains, also UBE2Z was identified, an E2 conjugating enzyme known to prime ubiquitin chains, alongside the E1 ubiquitin-activating enzyme UBA6 (FIG. 22a-c). Each of these screens failed to identify a consensus CRL SR (substrate receptor). To exclude involvement of an orphan SR, genome-scale CRISPR/Cas9 screens using a previously reported library was performed (Doench, J. G. et al., Nat Biotechnol 34, 184-191, doi:10.1038/nbt.3437 (2016)). Again, a pronounced enrichment of the top four genes of the CRL-focused sgRNA library (DDB1, CUL4B, UBE2M and UBE2G1) was found (FIG. 23a-c and FIG. 22a-c). No similarly enriched genes were identified that would indicate the involvement of a hitherto orphan SR. Hence, these results point to a SR independent type of mechanism by these molecular degraders.

Validating the pooled screening approach, targeted CRISPR-induced inactivation of CUL4B and UBE2G1 strongly abrogated drug-induced CCNK degradation. Inactivation of DDB1, UBE2G1 and UBE2M also abrogated drug-induced CCNK degradation induced by IC020772.1; IC021313.2 and T6938051, however inhibition of CCNK by THZ531 was not affected by inactivation of DDB1, UBE2G1 and UBE2M. This further corroborates the CRL activity-dependent CCNK degradation mechanism of action by the tested compounds.

Material and Methods -CRISPR/Cas9 Resistance Screens (CLR-Focused sgRNA Library and Genome-Scale Brunello sgRNA Library)

Lentivirus Production 293T cells seeded on 15 cm culture plates 16h before were transfected with 5 µg Brunello pooled library (Addgene 73178; 2-vector system), 2.5 µg pMD2.G (Addgene 12259), and 3.75 µg psPAX2 (Brunello sgRNA library, Addgene 12260) or CLR sgRNA library, using PEI (Polysciences, 24765-1). Viral supernatant was harvested 72h after transfection and concentrated using Lenti-X-concentrator (Takara). Concentrated viral supernatant was stored in aliquots at −80° C. and titrated following a standard protocol[26] to achieve a MOI of 0.2-0.3.

CLR sgRNA Library Screens 12 million KBM7$^{Cas9}$ or KBM7$^{iCas9}$ cells were transduced at MOI 0.3, yielding a calculated library representation of 635 cells/sgRNA (library representation=2.5 million cells). For transduction, 100 µL of concentrated viral supernatant was added to 3 million cells in 3 mL IMDM and 8 µg/mL polybrene in a 12-well plate. Plate was centrifuged at 2000 rpm for 1 h at 30° C. in a benchtop centrifuge and then incubated at 37° C. overnight. Transduction efficiency was titrated following a standard protocol (Doench, J. G. et al. Nat Biotechnol 34, 184-191, doi:10.1038/nbt.3437 (2016)). Pools were selected with 1 µg/mL puromycin for 5 days (KBM7Cas9) or 500 µg/mL neomycin for 8 days (iCas9 cells, followed by 5 days of cas9 expression by doxycycline 0.5 µg/mL). Independent resistance screens were performed with both mutant libraries in duplicates, using drugs at starting concentrations of 4×EC$_{50}$: IC020772.1 0.9 µM, IC021313.2 2.8 µM and T6938051 1.25 µM and a respective DMSO control. Every 4 days, cells were counted and re-seeded to 2.5 million cells in 5 mL, applying fresh drug. Drug concentrations were dynamically adjusted to the growth curves to yield a consistent impact on cell proliferation. Drug resistant pools were harvested after 14 days of treatment, snap-frozen in liquid nitrogen and stored at −80° C.

Brunello Pooled Library Screens 250 million KBM7-Cas9 cells or were transduced at MOI 0.23, yielding a calculated library representation of 668 cells/sgRNA (library representation=50 million cells). For transduction, 20 µL of concentrated viral supernatant was added to 5 million cells in 1.5 mL IMDM and 8 µg/mL polybrene in 6-well plates. Plates were centrifuged at 2000 rpm for 1 h at 30° C. in a benchtop centrifuge, 0.5 mL IMDM were added and then incubated at 37° C. overnight. The next day, transduced cells were pooled and diluted. Pools were selected with 1 µg/mL puromycin for 5 days. Independent resistance screens were performed with the library using drugs at starting concentrations of 4×EC50: IC020772.1 0.9 µM, IC021313.2 2.8 µM and T6938051 1.25 µM. Selective drug treatment was performed on 50 million cells/drug at a seeding density of 500,000 cells/mL. Every 5 days, cells were pooled, counted and re-seeded to 50 million cells in 100 mL, applying fresh drug. Drug concentrations were dynamically adjusted to the growth curves to yield a consistent impact on cell proliferation. Drug resistant pools were harvested after 15 days of treatment, snap-frozen in liquid nitrogen and stored at −80° C.

5.3 Drug-Induced Dimerization Between CUL4B: DDB1 and CDK12/13:CCNK

To validate if the drug-induced degradation of CCNK via the CRL4B: DDB1 complex is mediated via direct or indirect drug engagement, a drug affinity chromatography using tethered analogs of IC021313.2 was performed. Two complementary strategies were performed in this regard.

Regarding the first strategy, a variant of IC021313.2 associated with a free amine and named IC021313.2$^{NH2}$ allowed immobilizing IC021313.2$^{NH2}$ on sepharose beads, and purification of interacting proteins out of whole cell lysates (FIG. 20 a, b). Coupling IC021313.2$^{NH2}$ pulldowns with immunoblotting revealed both CCNK and DDB1 as interacting proteins (FIG. 20c). Treating lysates with THZ531 and thus covalently blocking the active sites on CDK12/13 prevented DDB1 and CCNK enrichment via the IC021313.2$^{NH2}$ resin. This is in line with the fact that cellular co-treatment with THZ531 was able to abrogate drug-induced CCNK degradation (FIG. 19 d).

Regarding the second strategy, an alternative method for drug-target enrichment that is based on cellular treatment with IC021313.2$^{PAP}$, a functionalized analog of IC021313.2 containing a photoactive diazirine moiety and an alkyne handle was performed (FIG. 20 d). Following cellular treatment with IC021313.2$^{PAP}$, cells were UV crosslinked, lysed and the alkyne handle in IC021313.2$^{PAP}$ was biotinylated for subsequent immobilization on streptavidin beads and identification of drug-interacting proteins via immunoblots. Again, DDB1 and CCNK were enriched in the eluates, indicating that target engagement also occurs in intact cells and that this interaction is independent of post-lysis artifacts (FIG. 20 e, f). Also in this setup, covalently saturating the CDK12/13 binding site with THZ-531 competed with IC021313.2$^{PAP}$ enrichment (FIG. 20 e, f). Collectively, both strategies indicate simultaneous engagement of the destabilized CCNK and the CRL4 adaptor protein DDB1 in a CDK12/13-dependent manner.

The direct, drug-induced association of CDK12:CCNK and DDB1:CUL4B was further assessed in a cellular assay based on enzyme-catalyzed proximity labeling via the efficient biotin ligase miniTurbo (mTurbo) (Branon, T. C. et al. Efficient proximity labeling in living cells and organisms with TurboID. Nat Biotechnol 36, 880-887, doi:10.1038/nbt.4201 (2018)) was performed. This assay enables recording dynamic changes in molecular proximity of an mTurbo-tagged bait protein by streptavidin purification of covalently biotinylated, proximal proteins. For this purpose, c-terminally tagged DDB1, or CDK12 mTurbo-fusions were transiently expressed in HEK cells. Cells were treated for one hour with C020772.1 or vehicle (DMSO) control, including a 30 minute biotin labeling pulse (FIG. 20 g, h). In line with a drug-induced molecular proximity, CDK12 interactions with DDB1 were exclusively identified in the presence of IC020772.1. Vice-versa, DDB1 was only identified as CDK12 interactor after drug treatment, but was not purified after vehicle-control treatment (FIG. 20 h). Collectively, three independent experimental strategies showed IC020772.1/IC021313.2/T6938051—dependent induction proximity between CDK12:CCNK and DDB1:CUL4B.

Collectively, this outlines that comparative drug profiling in hypo-neddylated cellular models enables the identification of novel molecular glue degraders.

Materials and Methods-Synthesis of dCeMM3$^{NH2}$ and Pulldown

Coupling of dCeMM3$^{NH2}$ to NHS-Sepharose Beads

100 µL NHS-Activated Sepharose 4 Fast Flow (GE Life Sciences, 17090601) per condition were washed with 500 µL DMSO 3 times (3 min 800 rpm centrifugation at RT). Beads were resuspended in 50 µL DMSO and 2.5 µL IC021313.2$^{NH2}$ 10 mM and 0.75 µL TEA (Sigma-Aldrich, T0886) were added. After 16-24h of incubation on roto-shaker at RT, the remaining free amino groups on beads were blocked by adding 2.5 µL ethanolamine (Sigma-Aldrich, 11016-7) and incubating on a roto-shaker for at least 8h at RT. Beads were centrifuged and 500 µL-DMSO washed twice before proceeding with drug pulldown.

Preparation of Cell Lysates 200 million KBM7 cells were resuspended in 2 mL lysis buffer (50 nM Tris pH 7.5, 0.2% NP-40, 5% glycerol, 1.5 mM MgCl$_2$, 100 mM NaCl, 1 mM EDTA) supplemented with protease inhibitors (Thermo Scientific, 78437) and benzonase (Merck, US170746-370746) and incubated on ice for 30 min. After centrifugation (full-speed, 4° C., 30 min) supernatant was transferred to a new tube and extracted protein measured with BCA (Fisher Scientific, 23225). 3 mg of protein lysate were pretreated with DMSO or THZ531 100 µM for 1h on a roto-shaker at 4° C.

Protein Affinity Purification and Elution

Drug-coupled beads were washed with 1x lysis buffer by centrifugation 3 times. Washed drug-coupled beads were gently resuspended in the pretreated cell lysates for 2h on a roto-shaker at 4° C. After incubation, beads were centrifuged, supernatant removed and washed with lysis buffer at 4° C. Beads were transferred to unplugged mini Bio-Spin Chromatography Columns (BioRad, 732-6207 in washing buffer (50 mM pH8 HEPES, 150 mM NaCl and 5 mM EDTA) and washed 3 times with 1 ml buffer II (all steps performed at 4° C.). Columns were transferred to RT, plugged and beads incubated with 4% SDS buffer II for 15 min. Unplugged columns were placed in 1.5 mL Eppendorf tubes and centrifuged for 1min at RT to let eluates enter into the tubes. Eluates were analyzed by WB. Quantification was performed with ImageJ.

Synthesis of IC021313.2-Photoaffinity Probe (IC021313.2$^{PAP}$) and Pulldown

IC021313.2$^{NH2}$ was conjugated to a constant side chain consisting of a photosensitive diazirine group and an alkyne handle.

20 million KBM7$^{WT}$ cells per condition were pre-treated with either DMSO or 100 μM THZ531 (competition condition) for 1h in the presence of 10 μM carfilzomib (Sell-eckchem, S2853) in serum-free IMDM medium (3 ml/20 million cells/10 cm dish). Then, cells were treated with 10 μM IC020772.1$^{PAP}$ for 1h. Target proteins were covalently linked to the probe via photo-crosslinking using an UV crosslinker at 4° C. (365 nm wavelength for 10 min). Cell pellets were collected, PBS-washed and snap-frozen in liquid nitrogen. For protein extraction, thawed pellets were resuspended in 500 μl lysis buffer (NP-40 0.8%, HEPES pH 7.5 50 mM, Glycerol 5%, NaCl 150 mM, Mg$_2$Cl 1.5 mM, SDS 1%, protease inhibitors and benzonase) and incubated on ice for 30 min. Click reaction to conjugate azide-PEG3-biotin to the photoprobe was performed using 1000 μg of protein per sample (1 mL total volume): 20 μl of 5 mM Azide PEG3-biotin (Sigma-Aldrich, 762024-25 MG) was added to each sample followed by a mix of 60 μl 1.7 mM TBTA, 20 μl 50 mM CuSO$_4$ and 20 μl 50 mM TCEP (=100 μl per sample), and left at room temperature for 2h. Spin-OUT™ G-600 columns (G-Biosciences, 786-1621) were used to purify protein samples after the click reaction, according to manufacturer's protocol. 700 μg per sample were used for the pulldowns. Enrichment of target proteins was done using Pierce™ High Capacity NeutrAvidin™ Agarose beads (Thermo Scientific, 29202). After the last washing step beads were resuspended in 100 μl elution Buffer (HEPES pH8 50 mM, NaCl 150 mM, EDTA 5 mM, SDS 4%), incubated at 75° C. for 30 min and eluted by centrifuging at full speed for 3 min. Eluates were analyzed by WB. Quantification was performed with ImageJ.

Materials and Methods-Biotin Proximity Labeling with miniTurbo in Live Cells

Biotin Proximity Labeling with miniTurbo in Live Cells: Cloning of DDB1-miniTurbo-V5 and CDK12-miniTurbo-V5 attB1-MCS-mCherry-MCS-miniTurbo-MCS-V5-attB2 was synthesized as a gBlock (IDTDNA) and cloned into a Gateway-compatible donor vector (pDONR221) using BP clonase (Invitrogen, 11789-020) to generate pENTR221_MCS_mCherry_miniTurbo_V5 (mini Turbo sequence obtained from Addgene, 107170). DDB1 and CDK12 were cloned by Gibson assembly (NEB, E5510S) into NdeI+XbaI digested pENTR221_MCS_mCherry_miniTurbo_V5.

pcDNA3-FLAG-DDB1 (Addgene, 19918) and pHAGE-CDK12 (Addgene, 116723) were used as a template. Resulting plasmids were pENTR221_DDB1_miniTurbo_V5 and pENTR221_CDK12_miniTurbo_V5. Both miniTurbo fusions were cloned into a Gateway compatible destination vector (Addgene, 19066) using LR clonase (Thermo Fisher Scientific, 11-791-020) to generate pLenti_DDB1_miniTurbo_V5 and pLenti_CDK12_miniTurbo_V5.

Biotin Labeling in Live Cells and Pulldown

One 10-cm culture plate of 293T cells (70%-80% confluent) was transfected with 2 μg of pLenti_DDB1_miniTurbo_V5 or pLenti_CDK12_miniTurbo_V5 using Lipofectamine 2000 (Invitrogen, 11668019). On the next day, each plate was expanded to 2x 10-cm plates. 48h after transfection, cells were pretreated with 10 μM Carfilzomib for 30 min, then treated with either DMSO or 20 μM IC020772.1 for 1.5h, adding 500 μM biotin during the last 30 min. Labeling was stopped by transferring the cells to ice and washing 5 times with ice-cold PBS. Cells were collected and lysed in 600 μL of lysis buffer (50 mM Tris-HCl PH 7.5, 125 mM NaCl, 5% glycerol, 0.2% NP-40, 1.5 mM MgCl2 and protease inhibitors). After 15 min incubation at RT, lysates were clarified by centrifuging at 15,000g for 10 min. For streptavidin pull-down of the biotinylated proteins, 500 μg of protein per condition were incubated with 50 μL of lysis buffer-washed streptavidin magnetic beads (Thermo Fisher Scientific, 11205D) for 1 h at RT on a rotator. Beads were pelleted using a magnetic rack and each bead sample was washed 3 times with lysis buffer. To elute biotinylated proteins, beads were resuspended in 65 μl elution Buffer (HEPES pH8 50 mM, NaCl 150 mM, EDTA 5 mM, SDS 4%) and incubated at 75° C. for 30 min. Beads were pelleted on a magnetic rack and eluate (60 μl) was collected. Eluates were analyzed by WB. Quantification was performed with ImageJ.

The protein names in Table 4, Table 5 and Table 6 refer to the protein names as provided by HUGO Gene Nomenclature Committee (HGNC) database. The accession numbers in Table 4, Table 5 and Table 6 refer to the accession numbers as provided by the uniprot database (https://www.uniprot.org).

TABLE 4

IC021313.2: 839 proteins
log2FC < −0.3 (183 essential proteins)

| Accession | Protein Name | logFC (IC021313.2/ DMSO) | essential |
|---|---|---|---|
| Q96QD9-1 | FYTTD1 | −1.51046 | false |
| Q53H80 | AKIRIN2 | −1.50226 | true |
| Q9H7X3 | ZNF696 | −1.30045 | false |
| O95864-1 | FADS2 | −1.28279 | false |
| Q99741 | CDC6 | −1.24127 | true |
| Q9BV29-2 | CCDC32 | −1.23786 | false |
| Q8N0T1-1 | C8orf59 | −1.23447 | false |
| Q9Y448-1 | KNSTRN | −1.16488 | false |
| Q9NWQ9 | C14orf119 | −1.13606 | false |
| Q9BWT1-1 | CDCA7 | −1.12029 | false |
| Q6IE81-1 | JADE1 | −1.11716 | false |
| Q8IWD4-1 | CCDC117 | −1.1016 | true |
| O75683 | SURF6 | −1.08009 | true |
| O95159 | ZFPL1 | −1.06794 | false |
| Q8TAA9-1 | VANGL1 | −1.05589 | false |
| Q15004-1 | PCLAF | −1.05289 | false |
| P17025-1 | ZNF182 | −1.04692 | false |
| Q9NPA8-1 | ENY2 | −1.02621 | true |
| Q9Y6H1 | CHCHD2 | −1.0145 | false |
| Q16621 | NFE2 | −1.00578 | false |
| Q9BSK4 | FEM1A | −0.98564 | false |
| Q6PK04 | CCDC137 | −0.98279 | false |
| Q6P589 | TNFAIP8L2 | −0.97426 | false |
| Q6ZWK4 | C1orf186 | −0.96578 | false |
| Q9UBZ4 | APEX2 | −0.96297 | false |
| P57086 | SCAND1 | −0.95736 | false |
| P34910-2 | EVI2B | −0.95456 | false |
| Q15043-1 | SLC39A14 | −0.84425 | false |
| Q8TF61 | FBXO41 | −0.84166 | false |
| Q9NPD8 | UBE2T | −0.83908 | false |
| P46013-2 | MKI67 | −0.83393 | false |
| Q9NY93-1 | DDX56 | −0.83393 | true |
| Q96GA3 | LTV1 | −0.83136 | true |
| Q9HAW4-1 | CLSPN | −0.82623 | true |
| Q9BRT6 | LLPH | −0.82623 | false |
| Q96PQ1-1 | SIGLEC12 | −0.82113 | false |
| Q13137-4 | CALCOCO2 | −0.81858 | false |
| Q15011-1 | HERPUD1 | −0.80844 | false |
| Q96DU3-1 | SLAMF6 | −0.79586 | false |
| Q6PU6-1 | FBXO38 | −0.78836 | false |
| Q9P2D6-1 | FAM135A | −0.77596 | false |
| Q86U06-1 | RBM23 | −0.77349 | false |

TABLE 4-continued

IC021313.2: 839 proteins
log2FC < −0.3 (183 essential proteins)

| Accession | Protein Name | logFC (IC021313.2/ DMSO) | essential |
|---|---|---|---|
| P55081 | MFAP1 | −0.77103 | true |
| Q8N5D6-1 | GBGT1 | −0.77103 | false |
| Q86WX3 | RPS19BP1 | −0.76611 | false |
| P13598 | ICAM2 | −0.75633 | false |
| O43683-1 | BUB1 | −0.7539 | false |
| Q96AH0-1 | NABP1 | −0.7539 | false |
| Q6DKI1-1 | RPL7L1 | −0.75147 | true |
| Q96QD8-1 | SLC38A2 | −0.75147 | false |
| Q6GTX8-1 | LAIR1 | −0.74662 | true |
| Q86UD0 | SAPCD2 | −0.7442 | false |
| Q9UMX1-1 | SUFU | −0.7442 | false |
| O75794 | CDC123 | −0.74178 | true |
| Q9BVS4-1 | RIOK2 | −0.74178 | true |
| P31350-2 | RRM2 | −0.73937 | true |
| O95926-1 | SYF2 | −0.73697 | true |
| Q5T6F0 | DCAF12 | −0.73456 | false |
| Q8WXI2-1 | CNKSR2 | −0.73456 | false |
| E9PRG8 | C11orf98 | −0.72738 | false |
| O60566-3 | BUB1B | −0.72738 | true |
| Q9BSR8 | YIPF4 | −0.72499 | false |
| O60828-1 | PQBP1 | −0.72499 | false |
| O00488 | ZNF593 | −0.72261 | false |
| P13196-1 | ALAS1 | −0.72261 | true |
| Q92624 | APPBP2 | −0.72261 | false |
| Q9P2B7-1 | CFAP97 | −0.72023 | false |
| Q8TB72-1 | PUM2 | −0.71786 | false |
| Q6PGQ7-1 | BORA | −0.71549 | false |
| Q8NDD1-1 | C1orf131 | −0.71312 | false |
| Q9UKK3 | PARP4 | −0.7084 | false |
| Q9H9Y2 | RPF1 | −0.7084 | true |
| Q96GE4-1 | CEP95 | −0.70134 | false |
| Q9BSF8-2 | BTBD10 | −0.63263 | false |
| O75563 | SKAP2 | −0.62816 | false |
| Q96SZ6-3 | CDK5RAP1 | −0.62816 | false |
| Q8IUX1-1 | TMEM126B | −0.62593 | false |
| O43324-1 | EEF1E1 | −0.62593 | false |
| Q5T3F8-1 | TMEM63B | −0.62371 | false |
| A2VDJ0-5 | TMEM131L | −0.62371 | false |
| Q9BVP2-1 | GNL3 | −0.62371 | true |
| Q68D85 | NCR3LG1 | −0.62371 | false |
| Q9Y2G9-1 | SBNO2 | −0.62149 | false |
| Q8NC42 | RNF149 | −0.61927 | false |
| P84101-1 | SERF2 | −0.61927 | false |
| Q6ZQX7-4 | LIAT1 | −0.61927 | false |
| Q9BSI4-1 | TINF2 | −0.61485 | false |
| Q9C0D0-1 | PHACTR1 | −0.61485 | false |
| Q5W0B1 | RNF219 | −0.61264 | false |
| Q96EA4-1 | SPDL1 | −0.61264 | false |
| Q66K64 | DCAF15 | −0.60823 | false |
| Q96BH1 | RNF25 | −0.60823 | false |
| Q7Z417-1 | NUFIP2 | −0.60823 | false |
| Q15119-1 | PDK2 | −0.60823 | false |
| Q8ND25-1 | ZNRF1 | −0.60603 | false |
| O60927 | PPP1R11 | −0.60603 | false |
| Q96EC8-1 | YIPF6 | −0.60603 | false |
| Q9NYJ1-2 | COA4 | −0.60603 | false |
| P02538 | KRT6A | −0.60603 | false |
| Q9BUB5-1 | MKNK1 | −0.60603 | false |
| Q9NSI2-1 | FAM207A | −0.60165 | false |
| O00716-1 | E2F3 | −0.59946 | false |
| Q9BRS2 | RIOK1 | −0.59728 | false |
| Q8WVZ9 | KBTBD7 | −0.59728 | false |
| P01130-1 | LDLR | −0.5951 | false |
| Q9Y620-1 | RAD54B | −0.59292 | false |
| Q6PCD5 | RFWD3 | −0.59074 | false |
| Q9H446-1 | RWDD1 | −0.58857 | false |
| Q15056-1 | EIF4H | −0.58857 | false |
| P17544-6 | ATF7 | −0.58641 | false |
| Q00765-1 | REEP5 | −0.58641 | false |
| Q02224-1 | CENPE | −0.58424 | true |
| Q99607 | ELF4 | −0.58424 | false |
| Q8NDZ2-1 | SIMC1 | −0.58208 | false |
| Q8WUD4 | CCDC12 | −0.57992 | false |
| O43257 | ZNHIT1 | −0.57992 | false |
| Q06609-1 | RAD51 | −0.57992 | true |
| Q02742 | GCNT1 | −0.57777 | false |
| Q9H5Z6-1 | FAM124B | −0.57777 | false |
| P82094-1 | TMF1 | −0.53742 | false |
| Q9Y314 | NOSIP | −0.53533 | false |
| Q8NFZ0-2 | FBXO18 | −0.53533 | false |
| Q6NW34-1 | NEPRO | −0.53324 | false |
| O43766-1 | LIAS | −0.53324 | true |
| A4D1E9-1 | GTPBP10 | −0.53116 | false |
| O95721 | SNAP29 | −0.53116 | false |
| Q8WVX3-2 | C4orf3 | −0.53116 | false |
| Q9UKL3 | CASP8AP2 | −0.53116 | false |
| P35527 | KRT9 | −0.52907 | false |
| Q96BD8-1 | SKA1 | −0.52907 | true |
| P41440-1 | SLC19A1 | −0.52907 | true |
| P62491-1 | RAB11A | −0.52907 | false |
| Q9NRD1 | FBXO6 | −0.52907 | false |
| P47224 | RABIF | −0.52699 | false |
| O75506 | HSBP1 | −0.52699 | false |
| Q9BZL1 | UBL5 | −0.52699 | true |
| P61024 | CKS1B | −0.52699 | false |
| Q9BVJ6-1 | UTP14A | −0.52699 | false |
| Q99618 | CDCA3 | −0.52492 | false |
| Q3B7T1-1 | EDRF1 | −0.52492 | false |
| Q9C035-1 | TRIM5 | −0.52492 | false |
| Q99704-1 | DOK1 | −0.52492 | false |
| Q69YH5-1 | CDCA2 | −0.52492 | false |
| Q8IXZ2-1 | ZC3H3 | −0.52492 | true |
| P0CG12-1 | CHTF8 | −0.52284 | true |
| Q9BY77-1 | POLDIP3 | −0.52077 | false |
| Q8NAV1-1 | PRPF38A | −0.52077 | true |
| Q7Z7L9-1 | ZSCAN2 | −0.5187 | true |
| P10242-4 | MYB | −0.5187 | true |
| Q7Z7K0 | CMC1 | −0.5187 | false |
| P27544-1 | CERS1 | −0.51664 | false |
| O14777 | NDC80 | −0.51664 | true |
| Q53EP0-1 | FNDC3B | −0.51664 | false |
| Q9NSI8-1 | SAMSN1 | −0.51664 | false |
| Q9BU40-4 | CHRDL1 | −0.51457 | false |
| P48509 | CD151 | −0.51457 | false |
| P16150 | SPN | −0.51457 | false |
| P28749-1 | RBL1 | −0.51457 | false |
| P10721-1 | KIT | −0.51251 | false |
| Q2KHR2-1 | RFX7 | −0.51251 | false |
| Q7L7V1-1 | DHX32 | −0.51251 | false |
| Q9NRA0-5 | SPHK2 | −0.51046 | false |
| P81274 | GPSM2 | −0.51046 | false |
| Q9BQD3 | KXD1 | −0.51046 | false |
| Q8WUH1-1 | CHURC1 | −0.51046 | false |
| Q5JUQ0 | FAM78A | −0.47995 | false |
| A2RUB1-4 | MEIOC | −0.47794 | false |
| Q86Y91-2 | KIF18B | −0.47794 | false |
| P09234 | SNRPC | −0.47794 | false |
| Q9BWG6-1 | SCNM1 | −0.47594 | false |
| O95229-1 | ZWINT | −0.47594 | true |
| Q9BS16 | CENPK | −0.47594 | false |
| Q15796-1 | SMAD2 | −0.47594 | false |
| Q8WXS3-1 | BAALC | −0.47193 | false |
| Q6ZUT1-2 | NKAPD1 | −0.47193 | false |
| O00429-4 | DNM1L | −0.47193 | true |
| Q9Y6V7-1 | DDX49 | −0.46993 | true |
| Q8N567 | ZCCHC9 | −0.46993 | false |
| Q8N128-2 | FAM177A1 | −0.46993 | false |
| P35790-1 | CHKA | −0.46993 | true |
| Q13740-1 | ALCAM | −0.46993 | false |
| Q9HD26-1 | GOPC | −0.46993 | false |
| Q14164-1 | IKBKE | −0.46993 | false |
| Q86V81 | ALYREF | −0.46793 | true |
| P37268-1 | FDFT1 | −0.46793 | false |
| P62891 | RPL39 | −0.46793 | false |
| Q6NSJ2-1 | PHLDB3 | −0.46793 | false |
| Q8TD30-1 | GPT2 | −0.46594 | false |

TABLE 4-continued

IC021313.2: 839 proteins
log2FC < −0.3 (183 essential proteins)

| Accession | Protein Name | logFC (IC021313.2/ DMSO) | essential |
|---|---|---|---|
| Q6IQ49-1 | SDE2 | −0.46594 | true |
| P09496-2 | CLTA | −0.46594 | false |
| Q4KWH8-1 | PLCH1 | −0.46395 | false |
| Q9H300-1 | PARL | −0.46395 | false |
| Q96CM3-1 | RPUSD4 | −0.46395 | true |
| Q9Y6Y0 | IVNS1ABP | −0.46196 | false |
| Q9BQE9-1 | BCL7B | −0.46196 | false |
| Q96AT1 | KIAA1143 | −0.46196 | false |
| Q8IZT6-1 | ASPM | −0.46196 | false |
| O14965 | AURKA | −0.46196 | true |
| Q9Y4B6-1 | DCAF1 | −0.46196 | false |
| Q96R06 | SPAG5 | −0.45997 | true |
| P00973-3 | OAS1 | −0.45997 | false |
| Q9NUL7 | DDX28 | −0.45997 | true |
| P67809 | YBX1 | −0.45799 | false |
| Q99941-1 | ATF6B | −0.45799 | false |
| Q7Z7F0-1 | KIAA0907 | −0.45799 | false |
| O75575-1 | CRCP | −0.45601 | false |
| Q96HE9 | PRR11 | −0.45601 | false |
| PODPB5-1 | POLRID | −0.45601 | false |
| Q8N2K1-3 | UBE2J2 | −0.45601 | true |
| Q9UBX1 | CTSF | −0.45601 | false |
| P49459-1 | UBE2A | −0.45601 | false |
| Q96CS2-1 | HAUS1 | −0.43051 | true |
| P62166-1 | NCS1 | −0.43051 | false |
| O14628-1 | ZNF195 | −0.43051 | false |
| Q3SXY8-1 | ARL13B | −0.42857 | false |
| P52815 | MRPL12 | −0.42857 | true |
| P17813-1 | ENG | −0.42857 | false |
| P29084 | GTF2E2 | −0.42857 | false |
| Q9NS18-2 | GLRX2 | −0.42857 | false |
| P18850 | ATF6 | −0.42663 | false |
| O60869-1 | EDF1 | −0.42469 | false |
| P04035-3 | HMGCR | −0.42469 | true |
| Q06413-1 | MEF2C | −0.42469 | false |
| O75319-1 | DUSP11 | −0.42275 | false |
| Q9BVC3 | DSCC1 | −0.42275 | true |
| Q9Y2R4 | DDX52 | −0.42275 | true |
| Q96LR5 | UBE2E2 | −0.42275 | false |
| Q8TBR7-2 | FAM57A | −0.42275 | false |
| O75925-2 | PIAS1 | −0.42082 | false |
| Q9BWT6 | MND1 | −0.42082 | false |
| O60232 | SSSCA1 | −0.42082 | false |
| Q8TCZ2-1 | CD99L2 | −0.42082 | false |
| Q14527-1 | HLTF | −0.41889 | false |
| Q9NY27-1 | PPP4R2 | −0.41889 | false |
| P78324-1 | SIRPA | −0.41696 | false |
| Q53R41-1 | FASTKD1 | −0.41696 | false |
| Q9UBE8 | NLK | −0.41504 | false |
| P13612-1 | ITGA4 | −0.41504 | false |
| P62277 | RPS13 | −0.41504 | true |
| O43791 | SPOP | −0.41504 | true |
| Q7Z7C8-2 | TAF8 | −0.41504 | true |
| Q4J6C6-1 | PREPL | −0.41504 | false |
| O95243-1 | MBD4 | −0.41312 | false |
| Q7L273 | KCTD9 | −0.41312 | false |
| Q56A73 | SPIN4 | −0.41312 | false |
| Q9NRX1 | PNO1 | −0.41312 | false |
| Q9UBR2 | CTSZ | −0.41312 | false |
| Q86XK2-5 | FBXO11 | −0.41312 | false |
| Q96EZ8-2 | MCRS1 | −0.4112 | false |
| P48200-1 | IREB2 | −0.4112 | true |
| O95391 | SLU7 | −0.4112 | true |
| O15392-1 | BIRC5 | −0.4112 | true |
| Q8NDV7-1 | TNRC6A | −0.4112 | false |
| Q6Y7W6-1 | GIGYF2 | −0.40928 | true |
| Q5TFE4-1 | NT5DC1 | −0.40928 | false |
| Q8NEF9 | SRFBP1 | −0.40928 | false |
| Q9NUN5-1 | LMBRD1 | −0.40928 | false |
| P59923 | ZNF445 | −0.39025 | false |
| Q13442 | PDAP1 | −0.38836 | true |
| O60353-1 | FZD6 | −0.38836 | false |
| Q15223-1 | NECTIN1 | −0.38836 | false |
| Q9BUW7 | C9orf16 | −0.38647 | false |
| Q49B96 | COX19 | −0.38647 | false |
| Q8IVQ6 | ZDHHC21 | −0.38647 | false |
| P30520 | ADSS | −0.38647 | true |
| Q5SVS4-1 | SLC25A30 | −0.38647 | false |
| P31785-1 | IL2RG | −0.38458 | false |
| Q9BQE5 | APOL2 | −0.38458 | false |
| Q5THK1-1 | PRR14L | −0.38458 | false |
| O00220 | TNFRSF10A | −0.38458 | false |
| O43399-7 | TPD52L2 | −0.38458 | false |
| O75127 | PTCD1 | −0.38458 | true |
| Q96B01-1 | RAD51AP1 | −0.3827 | false |
| O60603 | TLR2 | −0.3827 | false |
| Q6ULP2-1 | AFTPH | −0.3827 | false |
| Q9NZN8-1 | CNOT2 | −0.3827 | false |
| Q15050 | RRS1 | −0.3827 | true |
| Q99871-2 | HAUS7 | −0.3827 | true |
| P08195-3 | SLC3A2 | −0.3827 | true |
| Q9Y3C1-1 | NOP16 | −0.3827 | true |
| Q9P013 | CWC15 | −0.38082 | false |
| Q93096 | PTP4A1 | −0.37894 | false |
| Q6ZW76-1 | ANKS3 | −0.37894 | false |
| Q15291-1 | RBBP5 | −0.37894 | true |
| Q10589-1 | BST2 | −0.37894 | false |
| O94964-2 | SOGA1 | −0.37894 | false |
| Q9P007 | CCDC59 | −0.37894 | true |
| Q53HL2 | CDCA8 | −0.37707 | true |
| Q9HDC5 | JPH1 | −0.3752 | false |
| Q9NPA3 | MID1IP1 | −0.3752 | false |
| P43007-1 | SLC1A4 | −0.3752 | false |
| O60858-3 | TRIM13 | −0.37333 | false |
| Q9NVR7-1 | TBCCD1 | −0.37333 | false |
| Q9BX70-1 | BTBD2 | −0.37333 | false |
| Q9NZZ3-1 | CHMP5 | −0.37333 | true |
| Q9NQW6-1 | ANLN | −0.37333 | true |
| Q9NYF3 | FAM53C | −0.37333 | false |
| P52569-3 | SLC7A2 | −0.37333 | false |
| Q9H9L3 | ISG20L2 | −0.37333 | true |
| Q9Y605 | MRFAP1 | −0.37333 | false |
| Q9H7B2 | RPF2 | −0.37146 | true |
| P62273-2 | RPS29 | −0.37146 | true |
| Q9NUQ3-1 | TXLNG | −0.37146 | false |
| Q9NWS6-1 | FAM118A | −0.3603 | false |
| Q49AN0-1 | CRY2 | −0.3603 | false |
| Q92686 | NRGN | −0.35845 | false |
| Q99707-1 | MTR | −0.35661 | false |
| Q4AC94-5 | C2CD3 | −0.35661 | false |
| P48552 | NRIP1 | −0.35661 | false |
| Q96MW1-1 | CCDC43 | −0.35661 | false |
| P47974 | ZFP36L2 | −0.35661 | true |
| Q8WXD5 | GEMIN6 | −0.35661 | false |
| Q9H649 | NSUN3 | −0.35476 | false |
| P63272 | SUPT4H1 | −0.35476 | false |
| O15145 | ARPC3 | −0.35476 | false |
| P10644-1 | PRKAR1A | −0.35476 | false |
| O43617-1 | TRAPPC3 | −0.35476 | false |
| P53365-1 | ARFIP2 | −0.35476 | false |
| Q9BZE4-1 | GTPBP4 | −0.35476 | false |
| O95235-1 | KIF20A | −0.35476 | true |
| Q9H501 | ESF1 | −0.35476 | false |
| P62913-1 | RPL11 | −0.35292 | true |
| Q53FT3 | HIKESHI | −0.35292 | false |
| Q92854-1 | SEMA4D | −0.35292 | false |
| Q6PL18-1 | ATAD2 | −0.35292 | false |
| Q9HCU4 | CELSR2 | −0.35292 | false |
| Q9UG63-2 | ABCF2 | −0.35292 | false |
| P51948-1 | MNAT1 | −0.35292 | true |
| Q6UWY0 | ARSK | −0.35107 | false |
| Q5EBL8-2 | PDZD11 | −0.35107 | false |
| O60291-2 | MGRN1 | −0.35107 | false |
| Q8WTV0-2 | SCARB1 | −0.35107 | false |
| Q92600-2 | CNOT9 | −0.35107 | false |
| Q9Y597-1 | KCTD3 | −0.35107 | false |

TABLE 4-continued

IC021313.2: 839 proteins
log2FC < −0.3 (183 essential proteins)

| Accession | Protein Name | logFC (IC021313.2/ DMSO) | essential |
|---|---|---|---|
| O15530-1 | PDPK1 | −0.35107 | false |
| P12081-1 | HARS | −0.34924 | true |
| Q7Z5L9-1 | IRF2BP2 | −0.34924 | true |
| Q8TF40-3 | FNIP1 | −0.34924 | false |
| Q9Y3A4 | RRP7A | −0.34924 | false |
| P61956-1 | SUMO2 | −0.34924 | false |
| Q16342-1 | PDCD2 | −0.34924 | true |
| Q6PII3 | CCDC174 | −0.34924 | false |
| Q9NWZ8 | GEMIN8 | −0.34924 | false |
| Q8NBR6-1 | MINDY2 | −0.34924 | false |
| Q16254 | E2F4 | −0.3474 | false |
| Q8NG11-1 | TSPAN14 | −0.3474 | false |
| Q8NFH4 | NUP37 | −0.3474 | false |
| Q9H0K1 | SIK2 | −0.3474 | false |
| Q9NY97-1 | B3GNT2 | −0.3474 | true |
| Q8TEL6-1 | TRPC4AP | −0.33097 | false |
| Q9Y5N6 | ORC6 | −0.33097 | true |
| Q96Q89-3 | KIF20B | −0.33097 | false |
| Q7Z7A4-1 | PXK | −0.32916 | false |
| Q8WUX2 | CHAC2 | −0.32916 | false |
| Q9GZU8 | FAM192A | −0.32916 | false |
| Q9Y3B9 | RRP15 | −0.32916 | false |
| Q96SN8-1 | CDK5RAP2 | −0.32916 | true |
| O75410-1 | TACC1 | −0.32916 | false |
| Q8IY81 | FTSJ3 | −0.32916 | true |
| Q9BVC5-1 | C2orf49 | −0.32916 | false |
| O14737-1 | PDCD5 | −0.32916 | false |
| Q8N490-2 | PNKD | −0.32735 | false |
| P07108-5 | DBI | −0.32735 | false |
| Q9UL46 | PSME2 | −0.32735 | false |
| Q92734-1 | TFG | −0.32735 | false |
| Q8NG68 | TTL | −0.32735 | false |
| P62701 | RPS4X | −0.32554 | true |
| Q8NEJ9-1 | NGDN | −0.32554 | true |
| Q969P6-1 | TOP1MT | −0.32554 | false |
| Q13268-2 | DHRS2 | −0.32554 | false |
| Q9H6T3-1 | RPAP3 | −0.32554 | false |
| A5PLN9-5 | TRAPPC13 | −0.32554 | false |
| Q5T8D3-3 | ACBD5 | −0.32373 | false |
| Q8ND83-1 | SLAIN1 | −0.32373 | false |
| Q969Q0 | RPL36AL | −0.32373 | false |
| Q9H6R4-1 | NOL6 | −0.32373 | true |
| P63146 | UBE2B | −0.32373 | false |
| P04183 | TK1 | −0.32373 | false |
| Q13813-1 | SPTAN1 | −0.32373 | false |
| P60484-2 | PTEN | −0.32373 | false |
| P18077 | RPL35A | −0.32373 | true |
| Q9BXS4 | TMEM59 | −0.32193 | false |
| LOR8F8-1 | MIEF1 | −0.32193 | false |
| Q13287 | NMI | −0.32193 | false |
| Q8IWZ8-1 | SUGP1 | −0.32193 | false |
| Q9NY35-1 | CLDND1 | −0.32193 | false |
| Q7L4I2-1 | RSRC2 | −0.32193 | true |
| P25774-1 | CTSS | −0.32193 | false |
| P10619-1 | CTSA | −0.32193 | false |
| Q96HR3-1 | MED30 | −0.32013 | true |
| Q13614-1 | MTMR2 | −0.32013 | false |
| O75665-1 | OFD1 | −0.32013 | false |
| P33981-1 | TTK | −0.32013 | false |
| Q13686 | ALKBH1 | −0.32013 | false |
| P40222 | TXLNA | −0.32013 | false |
| Q86Y82 | STX12 | −0.30936 | false |
| P25942-1 | CD40 | −0.30936 | false |
| O95789-3 | ZMYM6 | −0.30757 | false |
| Q56P03 | EAPP | −0.30757 | false |
| Q9NXR1-1 | NDE1 | −0.30757 | false |
| Q8N543-1 | OGFOD1 | −0.30757 | false |
| Q4VC31 | CCDC58 | −0.30757 | false |
| Q96AP0-1 | ACD | −0.30757 | false |
| P51784 | USP11 | −0.30757 | false |
| Q68CQ7-1 | GLT8D1 | −0.30579 | false |
| Q92830-1 | KAT2A | −0.30579 | true |
| O60315-1 | ZEB2 | −0.30579 | false |
| Q99717 | SMAD5 | −0.30579 | false |
| P25208 | NFYB | −0.30579 | false |
| Q8TCB7-1 | METTL6 | −0.30579 | false |
| Q5JUR7-1 | TEX30 | −0.30579 | false |
| Q07020-1 | RPL18 | −0.30579 | true |
| P30307-1 | CDC25C | −0.30579 | false |
| Q9NQV6-6 | PRDM10 | −0.30401 | false |
| P49642 | PRIM1 | −0.30401 | true |
| P30419-1 | NMT1 | −0.30401 | true |
| Q8N9V3-1 | WDSUB1 | −0.30401 | false |
| P49366-1 | DHPS | −0.30401 | true |
| Q92985-4 | IRF7 | −0.30401 | false |
| P62328 | TMSB4X | −0.94342 | false |
| Q86WW8 | COA5 | −0.94064 | true |
| O95478 | NSA2 | −0.93788 | true |
| P02686-1 | MBP | −0.93512 | false |
| Q99808-2 | SLC29A1 | −0.93512 | false |
| P19438-1 | TNFRSF1A | −0.93236 | false |
| Q9Y3Y2-3 | CHTOP | −0.93236 | false |
| Q86T82-1 | USP37 | −0.9105 | true |
| Q9NRP4 | SDHAF3 | −0.90779 | false |
| Q9P021 | CRIPT | −0.90239 | false |
| O43278-1 | SPINT1 | −0.8997 | false |
| Q9NYV4-1 | CDK12 | −0.89701 | true |
| Q9H3H5-1 | DPAGT1 | −0.89432 | true |
| P17707-1 | AMD1 | −0.88364 | false |
| Q6FIF0-1 | ZFAND6 | −0.88098 | false |
| Q9P0P0 | RNF181 | −0.88098 | false |
| Q9NZM5 | NOP53 | −0.87567 | false |
| O75330-3 | HMMR | −0.87567 | false |
| O75909-3 | CCNK | −0.87303 | false |
| Q9H3S4-1 | TPK1 | −0.86775 | false |
| Q13445 | TMED1 | −0.86512 | false |
| Q9BR77-1 | CCDC77 | −0.86512 | false |
| P51530-1 | DNA2 | −0.85988 | false |
| Q9Y5X0-1 | SNX10 | −0.85726 | false |
| Q16667-1 | CDKN3 | −0.85726 | false |
| Q9Y255-1 | PRELID1 | −0.85726 | true |
| Q9C0F1-2 | CEP44 | −0.85465 | false |
| Q96T88-2 | UHRF1 | −0.85465 | false |
| Q9H3C7-1 | GGNBP2 | −0.85465 | false |
| Q9UIB8-1 | CD84 | −0.84684 | false |
| Q6NYC1-3 | JMJD6 | −0.69432 | true |
| O43164-1 | PJA2 | −0.68966 | false |
| P28908-1 | TNFRSF8 | −0.68733 | false |
| Q9UGY1 | NOL12 | −0.68733 | true |
| P14209-1 | CD99 | −0.68501 | false |
| Q16626 | MEA1 | −0.68501 | false |
| Q9Y421-1 | FAM32A | −0.68501 | false |
| O95249-1 | GOSR1 | −0.6827 | false |
| Q96FX2-1 | DPH3 | −0.6827 | true |
| Q7L590-1 | MCM10 | −0.68038 | false |
| Q96A00-1 | PPP1R14A | −0.67807 | false |
| O75054-2 | IGSF3 | −0.67116 | false |
| Q9HC44 | GPBP1L1 | −0.66887 | false |
| P09326-1 | CD48 | −0.66887 | false |
| P14635-1 | CCNB1 | −0.66658 | false |
| O95707 | POP4 | −0.66658 | true |
| Q14162-1 | SCARF1 | −0.66658 | false |
| Q9Y6D0 | SELENOK | −0.66658 | false |
| Q9Y2U9-1 | KLHDC2 | −0.66429 | false |
| Q9Y6A5 | TACC3 | −0.66429 | true |
| Q9BZD4 | NUF2 | −0.662 | true |
| Q86W74-1 | ANKRD46 | −0.65972 | false |
| Q6SJ93-1 | FAM111B | −0.65972 | false |
| Q15468-2 | STIL | −0.65745 | true |
| O15287 | FANCG | −0.65745 | true |
| Q14004-2 | CDK13 | −0.65745 | true |
| Q96K31-1 | C8orf76 | −0.65745 | false |
| Q96BK5-1 | PINX1 | −0.65745 | false |
| Q56NI9-1 | ESCO2 | −0.65517 | false |
| Q96E29-1 | MTERF3 | −0.6529 | false |
| Q9HBU6-1 | ETNK1 | −0.64837 | false |

TABLE 4-continued

IC021313.2: 839 proteins
log2FC < −0.3 (183 essential proteins)

| Accession | Protein Name | logFC (IC021313.2/ DMSO) | essential |
|---|---|---|---|
| Q9Y2Y1 | POLR3K | −0.64611 | true |
| Q8NCY6 | MSANTD4 | −0.64386 | false |
| PO2533 | KRT14 | −0.64386 | false |
| Q14980-2 | NUMA1 | −0.64386 | false |
| Q13823 | GNL2 | −0.6416 | true |
| O00311-1 | CDC7 | −0.6416 | true |
| P24864-1 | CCNE1 | −0.63935 | false |
| Q9NVW2-1 | RLIM | −0.63711 | false |
| Q8N5I9 | C12orf45 | −0.63711 | true |
| P78330 | PSPH | −0.63711 | false |
| Q14CS0 | UBXN2B | −0.63711 | false |
| Q9NXV2 | KCTD5 | −0.63487 | false |
| A1XBS5-1 | FAM92A | −0.63487 | false |
| Q6P444-1 | MTFR2 | −0.63487 | false |
| P98179 | RBM3 | −0.63263 | false |
| Q99755-3 | PIP5K1A | −0.57562 | false |
| O95900-1 | TRUB2 | −0.57562 | true |
| P78395 | PRAME | −0.57347 | false |
| Q9NQC1-1 | JADE2 | −0.57347 | false |
| Q9BUL5-1 | PHF23 | −0.57347 | false |
| Q9NYS0 | NKIRAS1 | −0.57132 | false |
| O94900 | TOX | −0.56918 | false |
| O15182 | CETN3 | −0.56918 | false |
| O15116 | LSM1 | −0.56704 | false |
| Q9ULT8 | HECTD1 | −0.56704 | false |
| Q9NZ71-2 | RTEL1 | −0.56704 | true |
| Q8NBI5-2 | SLC43A3 | −0.56704 | false |
| Q9BT23 | LIMD2 | −0.5649 | false |
| P04264 | KRT1 | −0.5649 | false |
| Q9NRY2-1 | INIP | −0.56277 | false |
| P57076 | C21orf59 | −0.56064 | true |
| Q8N302-1 | AGGF1 | −0.56064 | false |
| Q9Y6R9-1 | CCDC61 | −0.56064 | false |
| P61966-1 | AP1S1 | −0.55852 | false |
| Q8TCG1-1 | KIAA1524 | −0.55639 | false |
| Q96BR5 | COA7 | −0.55639 | false |
| Q86YC3 | NRROS | −0.55639 | false |
| O14757-1 | CHEK1 | −0.55427 | true |
| Q14135-4 | VGLL4 | −0.55216 | false |
| Q9BZM4 | ULBP3 | −0.55004 | false |
| P20336 | RAB3A | −0.55004 | false |
| Q9BWF2 | TRAIP | −0.55004 | true |
| Q9NUJ7 | PLCXD1 | −0.54793 | false |
| Q99519 | NEU1 | −0.54793 | false |
| P42081-1 | CD86 | −0.54582 | false |
| Q8N9M1-1 | C19orf47 | −0.54582 | false |
| P14316-1 | IRF2 | −0.54582 | false |
| Q6P4F7-1 | ARHGAP11A | −0.54582 | false |
| Q8N5L8 | RPP25L | −0.54372 | false |
| Q9H3U5-6 | MFSD1 | −0.54372 | false |
| O43699-1 | SIGLEC6 | −0.54372 | false |
| O95297-1 | MPZL1 | −0.54372 | false |
| P04114 | APOB | −0.54162 | false |
| Q01581 | HMGCS1 | −0.54162 | true |
| Q9BRT3 | MIEN1 | −0.54162 | false |
| Q8N2W9 | PIAS4 | −0.53952 | false |
| Q71RC2-4 | LARP4 | −0.53952 | false |
| Q9NYZ3 | GTSE1 | −0.53952 | true |
| Q9NPB0-1 | SAYSD1 | −0.53952 | false |
| P49760-1 | CLK2 | −0.53742 | false |
| P40855-1 | PEX19 | −0.51046 | false |
| Q6P6B1-1 | ERICH5 | −0.5084 | false |
| Q155Q3-1 | DIXDC1 | −0.5084 | false |
| Q9Y5A9-1 | YTHDF2 | −0.5084 | false |
| Q86WP2-2 | GPBP1 | −0.5084 | false |
| Q6P5R6 | RPL22L1 | −0.50635 | false |
| Q6PGN9-1 | PSRC1 | −0.50635 | false |
| P62487 | POLR2G | −0.50635 | true |
| Q96CX6 | LRRC58 | −0.5043 | false |
| Q14444-1 | CAPRIN1 | −0.5043 | false |
| Q96EU6-1 | RRP36 | −0.50226 | false |
| P42892-1 | ECE1 | −0.50226 | false |
| Q9HA38-1 | ZMAT3 | −0.50226 | false |
| Q9Y3B1-1 | PRELID3B | −0.50022 | false |
| Q6P3S6 | FBXO42 | −0.50022 | false |
| Q9BWL3-1 | C1orf43 | −0.50022 | false |
| P36404-1 | ARL2 | −0.50022 | true |
| Q15049-1 | MLC1 | −0.49818 | false |
| Q5JTJ3-2 | COA6 | −0.49614 | false |
| P06280 | GLA | −0.49614 | false |
| Q96L50-1 | LRR1 | −0.49411 | true |
| P49207 | RPL34 | −0.49208 | true |
| Q7Z7L7 | ZER1 | −0.49208 | false |
| Q9NWH2 | TMEM242 | −0.49208 | false |
| Q86TS9-1 | MRPL52 | −0.49208 | true |
| Q9UBT7-1 | CTNNAL1 | −0.49005 | false |
| Q9BXS6-1 | NUSAP1 | −0.49005 | false |
| O94842-1 | TOX4 | −0.48803 | false |
| Q06787-5 | FMR1 | −0.48803 | false |
| Q12841-1 | FSTL1 | −0.48803 | false |
| P61244-1 | MAX | −0.48803 | false |
| Q53EZ4-1 | CEP55 | −0.486 | false |
| O75414-1 | NME6 | −0.486 | false |
| Q9Y2H0-2 | DLGAP4 | −0.486 | false |
| P30281-1 | CCND3 | −0.48398 | false |
| P08779 | KRT16 | −0.48398 | false |
| O15504-1 | NUPL2 | −0.48398 | false |
| Q8IXQ3 | C9orf40 | −0.48398 | false |
| Q8WUX9-1 | CHMP7 | −0.48398 | false |
| Q15036-1 | SNX17 | −0.48398 | false |
| PO8174-7 | CD55 | −0.48197 | false |
| Q96C01 | FAM136A | −0.48197 | false |
| Q5VUG0 | SFMBT2 | −0.48197 | false |
| Q8IYL2-1 | TRMT44 | −0.48197 | false |
| Q9UMY1-1 | NOL7 | −0.47995 | true |
| P52756-1 | RBM5 | −0.47995 | true |
| Q03933-1 | HSF2 | −0.45403 | false |
| Q96L73-1 | NSD1 | −0.45403 | false |
| Q5MIZ7-1 | PPP4R3B | −0.45403 | false |
| P04921-1 | GYPC | −0.45403 | false |
| Q9H3R5 | CENPH | −0.45206 | false |
| P83881 | RPL36A | −0.45206 | false |
| Q96F44-1 | TRIM11 | −0.45206 | false |
| Q6PI26-1 | SHQ1 | −0.45206 | true |
| P61163 | ACTR1A | −0.45206 | false |
| P13693-1 | TPT1 | −0.45008 | true |
| Q96A49 | SYAP1 | −0.45008 | false |
| O95343 | SIX3 | −0.45008 | false |
| Q9Y3A2-1 | UTP11 | −0.45008 | false |
| P17535 | JUND | −0.44811 | false |
| Q96BZ8 | LENG1 | −0.44811 | false |
| Q9BZM6 | ULBP1 | −0.44811 | false |
| P58335-4 | ANTXR2 | −0.44811 | false |
| O94782 | USP1 | −0.44615 | false |
| Q9H8U3 | ZFAND3 | −0.44615 | false |
| Q14240-2 | EIF4A2 | −0.44615 | false |
| O95456-1 | PSMG1 | −0.44615 | true |
| Q14651 | PLSI | −0.44615 | false |
| Q9NVF7-1 | FBXO28 | −0.44615 | false |
| Q9ULF5-1 | SLC39A10 | −0.44418 | false |
| O00192-1 | ARVCF | −0.44418 | false |
| P13984 | GTF2F2 | −0.44418 | false |
| Q9NPE3 | NOP10 | −0.44418 | true |
| Q9HBM1 | SPC25 | −0.44222 | true |
| Q7Z3K6-2 | MIER3 | −0.44222 | false |
| Q5T310-3 | GPATCH4 | −0.44222 | false |
| Q16828-1 | DUSP6 | −0.44222 | false |
| Q9H1X3-1 | DNAJC25 | −0.44222 | false |
| Q9NW13-1 | RBM28 | −0.44026 | true |
| Q9NW81-4 | DMAC2 | −0.44026 | false |
| Q969Q4 | ARL11 | −0.44026 | false |
| Q14207 | NPAT | −0.43831 | true |
| Q9Y5J7 | TIMM9 | −0.43635 | false |
| Q86Y07-1 | VRK2 | −0.43635 | false |
| Q969Z4 | RELT | −0.4344 | false |
| Q9UGP4 | LIMD1 | −0.43245 | false |

TABLE 4-continued

IC021313.2: 839 proteins
log2FC < −0.3 (183 essential proteins)

| Accession | Protein Name | logFC (IC021313.2/DMSO) | essential |
|---|---|---|---|
| Q9BVW5 | TIPIN | −0.43245 | false |
| P48668 | KRT6C | −0.43245 | false |
| Q5T2R2-1 | PDSS1 | −0.43051 | true |
| Q9NXW2-1 | DNAJB12 | −0.43051 | false |
| Q1MSJ5-3 | CSPP1 | −0.43051 | false |
| Q8NC54 | KCT2 | −0.43051 | false |
| Q12899 | TRIM26 | −0.40928 | false |
| A6NHL2-1 | TUBAL3 | −0.40928 | false |
| Q96RT1-8 | ERBIN | −0.40928 | false |
| Q8N3Z6-1 | ZCCHC7 | −0.40928 | false |
| P00749-1 | PLAU | −0.40928 | false |
| P49773 | HINT1 | −0.40736 | false |
| Q08357 | SLC20A2 | −0.40736 | false |
| P49454 | CENPF | −0.40736 | false |
| Q9BW61 | DDA1 | −0.40736 | false |
| P62906 | RPL10A | −0.40736 | true |
| Q13573 | SNW1 | −0.40545 | true |
| Q8WXW3-1 | PIBF1 | −0.40545 | false |
| Q9UIM3 | FKBPL | −0.40545 | true |
| Q8WUX1-1 | SLC38A5 | −0.40545 | true |
| P62136-1 | PPPICA | −0.40545 | false |
| Q9Y2Y0-1 | ARL2BP | −0.40354 | false |
| P62987 | UBA52 | −0.40354 | true |
| P62253 | UBE2G1 | −0.40354 | false |
| Q9NU53 | GINM1 | −0.40354 | false |
| O43768-4 | ENSA | −0.40163 | false |
| O00559-2 | EBAG9 | −0.40163 | false |
| Q5VTB9-3 | RNF220 | −0.40163 | false |
| A6NDU8 | C5orf51 | −0.39973 | false |
| Q8TB03-1 | CXorf38 | −0.39973 | false |
| Q6FI81-1 | CIAPIN1 | −0.39973 | false |
| Q9Y5V0 | ZNF706 | −0.39973 | false |
| Q14542-1 | SLC29A2 | −0.39783 | false |
| Q2TAL8 | QRICH1 | −0.39783 | true |
| O75157-1 | TSC22D2 | −0.39783 | false |
| Q86XR8-1 | CEP57 | −0.39783 | true |
| P53350 | PLK1 | −0.39593 | true |
| Q13501-1 | SQSTM1 | −0.39593 | false |
| Q8IXS8 | FAM126B | −0.39593 | false |
| Q9NUG6 | PDRG1 | −0.39593 | true |
| Q969K3-2 | RNF34 | −0.39593 | false |
| Q15758-1 | SLC1A5 | −0.39593 | false |
| Q13123 | IK | −0.39593 | false |
| Q13158 | FADD | −0.39403 | false |
| O43566-7 | RGS14 | −0.39403 | false |
| Q14119 | VEZF1 | −0.39214 | false |
| Q8TAG9-1 | EXOC6 | −0.39214 | false |
| Q6UWB1 | IL27RA | −0.39214 | false |
| Q9UQB8-1 | BAIAP2 | −0.39025 | false |
| P50897-1 | PPT1 | −0.39025 | false |
| Q9Y4D8-5 | HECTD4 | −0.39025 | false |
| Q9H5V9-1 | CXorf56 | −0.39025 | false |
| P04818-1 | TYMS | −0.37146 | true |
| Q9NQZ5 | STARD7 | −0.37146 | false |
| Q9NQY0-1 | BIN3 | −0.36959 | false |
| Q9BTL3 | FAM103A1 | −0.36959 | false |
| Q8TDD1-2 | DDX54 | −0.36959 | true |
| Q9BUE6-2 | ISCA1 | −0.36959 | true |
| Q14692 | BMS1 | −0.36959 | true |
| Q5JS54-2 | PSMG4 | −0.36959 | true |
| Q86YQ8-1 | CPNE8 | −0.36959 | false |
| O43808 | SLC25A17 | −0.36959 | false |
| Q8TDN6 | BRIX1 | −0.36959 | true |
| Q01196-8 | RUNX1 | −0.36773 | true |
| Q6UVJ0 | SASS6 | −0.36773 | false |
| O43542 | XRCC3 | −0.36773 | true |
| Q8NB14-1 | USP38 | −0.36773 | false |
| Q8N0X7 | SPART | −0.36773 | false |
| P62875 | POLR2L | −0.36773 | true |
| Q76L83-1 | ASXL2 | −0.36587 | false |
| Q5JTH9-1 | RRP12 | −0.36587 | true |
| Q6GMV2 | SMYD5 | −0.36587 | false |
| P14317-1 | HCLS1 | −0.36587 | false |
| Q8WW33 | GTSF1 | −0.36587 | false |
| Q7L2H7-1 | EIF3M | −0.36587 | true |
| Q7L0Y3 | TRMT10C | −0.36587 | true |
| Q99569-1 | PKP4 | −0.36587 | false |
| Q9Y333 | LSM2 | −0.36587 | true |
| Q92625-1 | ANKSIA | −0.36401 | false |
| P53611 | RABGGTB | −0.36401 | true |
| Q9UHB6-1 | LIMA1 | −0.36401 | false |
| QO1826-2 | SATB1 | −0.36401 | false |
| Q9H4K7-1 | MTG2 | −0.36401 | true |
| Q9NR28-1 | DIABLO | −0.36401 | false |
| Q9P2N7-5 | KLHL13 | −0.36401 | false |
| Q8NC26-1 | ZNF114 | −0.36401 | false |
| Q16206-1 | ENOX2 | −0.36216 | false |
| Q15397 | PUM3 | −0.36216 | false |
| Q9UMR5-3 | PPT2 | −0.36216 | false |
| Q14690 | PDCD11 | −0.36216 | false |
| P07711 | CTSL | −0.36216 | false |
| P54760-1 | EPHB4 | −0.36216 | false |
| Q92917 | GPKOW | −0.36216 | true |
| P02786 | TFRC | −0.3603 | true |
| P53869-3 | AP2S1 | −0.3603 | true |
| Q13111-1 | CHAF1A | −0.3603 | true |
| Q9UI95 | MAD2L2 | −0.3603 | true |
| Q9NR82-6 | KCNQ5 | −0.3603 | false |
| Q9ULW3 | ABT1 | −0.3474 | true |
| Q9NXG0-2 | CNTLN | −0.34556 | false |
| Q8IYA6-1 | CKAP2L | −0.34556 | false |
| Q99684 | GFI1 | −0.34556 | true |
| Q9UH17-1 | APOBEC3B | −0.34556 | false |
| Q03112-3 | MECOM | −0.34556 | false |
| Q96DN5-1 | TBC1D31 | −0.34556 | false |
| O43716 | GATC | −0.34373 | true |
| Q15013-3 | MAD2L1BP | −0.3419 | true |
| P62244 | RPS15A | −0.3419 | true |
| Q9H4A5-1 | GOLPH3L | −0.3419 | false |
| O75528-1 | TADA3 | −0.3419 | true |
| Q9H0H5 | RACGAP1 | −0.3419 | true |
| Q7Z4L5-1 | TTC21B | −0.3419 | false |
| P25445-1 | FAS | −0.3419 | false |
| Q6P4H8-1 | FAM173B | −0.34008 | false |
| O43805 | SSNA1 | −0.34008 | false |
| P17947-2 | SPI1 | −0.34008 | true |
| P46976-1 | GYG1 | −0.34008 | false |
| Q7Z3T8-1 | ZFYVE16 | −0.33825 | false |
| P30626-1 | SRI | −0.33825 | false |
| Q9H078-2 | CLPB | −0.33825 | true |
| Q9P1U1-1 | ACTR3B | −0.33825 | false |
| Q969S3 | ZNF622 | −0.33825 | true |
| O95619 | YEATS4 | −0.33825 | false |
| Q9BT25-1 | HAUS8 | −0.33825 | true |
| Q96G01-1 | BICD1 | −0.33825 | false |
| Q6AI12 | ANKRD40 | −0.33825 | false |
| Q5SVZ6 | ZMYM1 | −0.33643 | false |
| Q92520 | FAM3C | −0.33643 | false |
| Q8IVD9 | NUDCD3 | −0.33643 | true |
| P08670 | VIM | −0.33643 | false |
| Q9H3J6-1 | C12orf65 | −0.33643 | false |
| O60749-1 | SNX2 | −0.33643 | false |
| Q9H6F5-1 | CCDC86 | −0.33643 | true |
| Q96GQ7 | DDX27 | −0.33643 | true |
| Q9NWT6 | HIF1AN | −0.33461 | false |
| P35637-1 | FUS | −0.33461 | false |
| Q9NZ72-1 | STMN3 | −0.33461 | false |
| Q96EY4 | TMA16 | −0.33461 | false |
| Q9H5U6-1 | ZCCHC4 | −0.33279 | false |
| Q2VPB7 | AP5B1 | −0.33279 | false |
| Q96NB1-1 | FOPNL | −0.33279 | false |
| Q9UPN9-1 | TRIM33 | −0.33097 | false |
| Q8N5M4-1 | TTC9C | −0.33097 | false |
| Q86WA8-1 | LONP2 | −0.33097 | false |
| Q49A88-1 | CCDC14 | −0.32013 | false |
| Q8NBJ4-1 | GOLM1 | −0.32013 | false |

TABLE 4-continued

IC021313.2: 839 proteins
log2FC < −0.3 (183 essential proteins)

| Accession | Protein Name | logFC (IC021313.2/ DMSO) | essential |
|---|---|---|---|
| Q08AG7 | MZT1 | −0.32013 | false |
| Q14249 | ENDOG | −0.32013 | false |
| Q9UL42 | PNMA2 | −0.31833 | false |
| Q9UHQ1-2 | NARF | −0.31833 | false |
| Q96SB4-2 | SRPK1 | −0.31833 | false |
| Q96EX3 | WDR34 | −0.31833 | false |
| Q7Z2Z1-1 | TICRR | −0.31833 | true |
| Q96ES7 | SGF29 | −0.31833 | false |
| Q8NHQ1-1 | CEP70 | −0.31833 | false |
| Q7Z6K3 | PTAR1 | −0.31833 | false |
| Q09328 | MGAT5 | −0.31833 | false |
| P98082-1 | DAB2 | −0.31653 | false |
| Q9Y6N7-2 | ROBO1 | −0.31653 | false |
| Q86UY6-1 | NAA40 | −0.31653 | false |
| Q9Y5J1 | UTP18 | −0.31653 | false |
| Q9NSK7-1 | C19orf12 | −0.31473 | false |
| Q9HA47-4 | UCK1 | −0.31473 | false |
| P05067-1 | APP | −0.31473 | false |
| Q9HD47-1 | RANGRF | −0.31473 | false |
| Q9NX18 | SDHAF2 | −0.31473 | false |
| P16220-1 | CREB1 | −0.31473 | false |
| O14578-4 | CIT | −0.31473 | false |
| O60427-1 | FADS1 | −0.31473 | false |
| P23588-1 | EIF4B | −0.31294 | false |
| Q9UHK0 | NUFIP1 | −0.31294 | true |
| P24863-1 | CCNC | −0.31294 | false |
| Q02108-1 | GUCY1A3 | −0.31294 | false |
| Q9H444 | CHMP4B | −0.31294 | true |
| Q96Q83-1 | ALKBH3 | −0.31294 | false |
| Q9HCD6-2 | TANC2 | −0.31294 | false |
| Q9H467 | CUEDC2 | −0.31294 | false |
| Q96DF8 | DGCR14 | −0.31294 | true |
| Q9NXW9-1 | ALKBH4 | −0.31115 | false |
| O15162-1 | PLSCR1 | −0.31115 | false |
| Q14126 | DSG2 | −0.31115 | false |
| Q13309-1 | SKP2 | −0.31115 | false |
| Q1RMZ1 | BMT2 | −0.31115 | false |
| Q9UGV2-1 | NDRG3 | −0.31115 | false |
| Q96GX2 | ATXN7L3B | −0.31115 | false |
| Q96EP9 | SLC10A4 | −0.31115 | false |
| Q99471-1 | PFDN5 | −0.31115 | false |
| Q01664 | TFAP4 | −0.30936 | true |
| P08708 | RPS17 | −0.30936 | true |
| Q15021 | NCAPD2 | −0.30936 | true |
| Q8NDX1-1 | PSD4 | −0.30223 | false |
| Q9UPP1-1 | PHF8 | −0.30223 | false |
| Q9H900-1 | ZWILCH | −0.30223 | false |
| Q8NBT0-1 | PO1A | −0.30223 | false |
| P32780-1 | GTF2H1 | −0.30223 | true |
| Q8WWW0-2 | RASSF5 | −0.30223 | false |
| Q9Y6I3-2 | EPN1 | −0.30223 | false |
| Q96E09 | FAM122A | −0.30223 | true |
| Q9BRP8-1 | PYM1 | −0.30223 | false |
| Q9NS87-1 | KIF15 | −0.30223 | false |
| Q9BZE2 | PUS3 | −0.30223 | false |
| Q9H8K7 | C10orf88 | −0.30045 | false |
| Q6IQ21 | ZNF770 | −0.30045 | false |
| O43463-2 | SUV39H1 | −0.30045 | false |
| P15151-1 | PVR | −0.30045 | false |
| Q92698 | RAD54L | −0.30045 | false |
| Q92564-3 | DCUN1D4 | −0.30045 | false |
| Q96BD0-1 | SLCO4A1 | −0.30045 | false |
| Q9H967 | WDR76 | −0.30045 | false |
| Q8WUA2 | PPIL4 | −0.30045 | false |
| Q9UKA4 | AKAP11 | −0.30045 | false |
| O75317 | USP12 | −0.30045 | false |
| O75354-1 | ENTPD6 | −0.30045 | false |

TABLE 5

IC020772.1: 869 proteins
log2FC < −0.3 (147 essential proteins)

| Accession | Protein | log2FC (IC020772.1/ DMSO) | essential |
|---|---|---|---|
| O95864-1 | FADS2 | −1.582079992 | false |
| Q53H80 | AKIRIN2 | −1.465938398 | true |
| Q8N0T1-1 | C8orf59 | −1.442222329 | false |
| P57086 | SCAND1 | −1.377069649 | false |
| Q9BWT1-1 | CDCA7 | −1.311148256 | false |
| Q14162-1 | SCARF1 | −1.2968993 | false |
| Q96QD9-1 | FYTTD1 | −1.279283757 | false |
| Q15004-1 | PCLAF | −1.248107862 | false |
| Q9UBZ4 | APEX2 | −1.224317298 | false |
| Q9BV9-2 | CCDC32 | −1.220950447 | false |
| Q99741 | CDC6 | −1.200912694 | true |
| Q9Y448-1 | KNSTRN | −1.184424571 | false |
| Q9NYV4-1 | CDK12 | −1.171368418 | true |
| Q9P2B7-1 | CFAP97 | −1.168122759 | false |
| Q92624 | APPBP2 | −1.164884385 | false |
| Q9BSK4 | FEM1A | −1.15521265 | false |
| Q9P021 | CRIPT | −0.962969269 | false |
| O75330-3 | HMMR | −0.951763814 | false |
| P17544-6 | ATF7 | −0.943416472 | false |
| P28908-1 | TNFRSF8 | −0.932361283 | false |
| Q6IE81-1 | JADE1 | −0.932361283 | false |
| Q9P0P0 | RNF181 | −0.926865295 | false |
| Q86U06-1 | RBM23 | −0.926865295 | false |
| P02686-1 | MBP | −0.924125133 | false |
| Q86WW8 | COA5 | −0.918660373 | true |
| Q14004-2 | CDK13 | −0.918660373 | true |
| A1XBS5-1 | FAM92A | −0.915935735 | false |
| Q56NI9-1 | ESCO2 | −0.905088353 | false |
| Q155Q3-1 | DIXDC1 | −0.902389203 | false |
| O43683-1 | BUB1 | −0.891642822 | false |
| O94900 | TOX | −0.883635243 | false |
| Q5T6F0 | DCAF12 | −0.880975897 | false |
| P00973-3 | OAS1 | −0.880975897 | false |
| Q9H3C7-1 | GGNBP2 | −0.878321443 | false |
| Q12841-1 | FSTL1 | −0.873027144 | false |
| Q9UMX1-1 | SUFU | −0.862496476 | false |
| Q96T88-2 | UHRF1 | −0.859975776 | false |
| Q9Y2U9-1 | KLHDC2 | −0.854648614 | false |
| Q15011-1 | HERPUD1 | −0.854648614 | false |
| Q6PGQ7-1 | BORA | −0.846843212 | false |
| Q86P82-1 | USP37 | −0.844250767 | true |
| Q86YC3 | NRROS | −0.844250767 | false |
| O75683 | SURF6 | −0.839079812 | true |
| O75794 | CDC123 | −0.831357964 | true |
| Q8N5D6-1 | GBGT1 | −0.831357964 | false |
| Q9NXV2 | KCTD5 | −0.828793173 | false |
| Q99808-2 | SLC29A1 | −0.828793173 | false |
| A2VDJ0-5 | TMEM131L | −0.826232932 | false |
| Q6P589 | TNFAIP8L2 | −0.826232932 | false |
| Q06609-1 | RAD51 | −0.821126042 | true |
| P17707-1 | AMD1 | −0.821126042 | false |
| Q9BU40-4 | CHRDL1 | −0.81857936 | false |
| O95159 | ZFPL1 | −0.81857936 | false |
| Q13137-4 | CALCOCO2 | −0.81857936 | false |
| Q6PU6-1 | FBXO38 | −0.813499442 | false |
| Q8NC54 | KCT2 | −0.810966176 | false |
| Q15049-1 | MLC1 | −0.810966176 | false |
| P81274 | GPSM2 | −0.805912948 | false |
| Q96PQ1-1 | SIGLEC12 | −0.805912948 | false |
| Q8WXI2-1 | CNKSR2 | −0.800877358 | false |
| P52569-3 | SLC7A2 | −0.800877358 | false |
| P31350-2 | RRM2 | −0.798366139 | true |
| Q9HAW4-1 | CLSPN | −0.713118852 | true |
| Q9NZM5 | NOP53 | −0.708396442 | false |
| O60566-3 | BUB1B | −0.708396442 | true |
| O94854-1 | KIAA0754 | −0.708396442 | false |
| Q99941-1 | ATF6B | −0.698997744 | false |
| Q96AH0-1 | NABP1 | −0.696657606 | false |
| Q96QD8-1 | SLC38A2 | −0.694321257 | false |
| Q15043-1 | SLC39A14 | −0.694321257 | false |
| Q9Y3Y2-3 | CHTOP | −0.689659879 | false |
| O00716-1 | E2F3 | −0.687334826 | false |
| O43699-1 | SIGLEC6 | −0.685013515 | false |

TABLE 5-continued

IC020772.1: 869 proteins
log2FC < −0.3 (147 essential proteins)

| Accession | Protein | log2FC (IC020772.1/ DMSO) | essential |
|---|---|---|---|
| Q99607 | ELF4 | −0.682695932 | false |
| Q8ND83-1 | SLAIN1 | −0.680382066 | false |
| Q969Q4 | ARL11 | −0.680382066 | false |
| Q3SXY8-1 | ARL13B | −0.678071905 | false |
| Q9Y620-1 | RAD54B | −0.675765438 | false |
| Q6PCD5 | RFWD3 | −0.675765438 | false |
| Q96L50-1 | LRR1 | −0.675765438 | true |
| Q53EZ4-1 | CEP55 | −0.673462652 | false |
| O15182 | CETN3 | −0.673462652 | false |
| O00192-1 | ARVCF | −0.671163536 | false |
| Q96GA3 | LTV1 | −0.668868078 | true |
| O95478 | NSA2 | −0.668868078 | true |
| Q8WUH1-1 | CHURC1 | −0.666576266 | false |
| Q8IXQ3 | C9orf40 | −0.66428809 | false |
| Q9Y6Y0 | IVNS1ABP | −0.662003536 | false |
| Q8N302-1 | AGGF1 | −0.662003536 | false |
| Q9NVF7-1 | FBXO28 | −0.662003536 | false |
| Q9NS18-2 | GLRX2 | −0.662003536 | false |
| Q9HC44 | GPBPIL1 | −0.659722595 | false |
| P17025-1 | ZNF182 | −0.652901329 | false |
| Q5W0B1 | RNF219 | −0.650634722 | false |
| Q9NRA0-5 | SPHK2 | −0.64385619 | false |
| Q14207 | NPAT | −0.64385619 | true |
| Q9BVS4-1 | RIOK2 | −0.639354798 | true |
| Q6P6B1-1 | ERICH5 | −0.637109357 | false |
| O95900-1 | TRUB2 | −0.637109357 | true |
| Q53EP0-1 | FNDC3B | −0.637109357 | false |
| Q9BSF8-2 | BTBD10 | −0.637109357 | false |
| Q9NRP4 | SDHAF3 | −0.634867407 | false |
| P41440-1 | SLC19A1 | −0.632628934 | true |
| E9PRG8 | C11orf98 | −0.63039393 | false |
| Q9BT23 | LIMD2 | −0.628162383 | false |
| P34910-2 | EVI2B | −0.628162383 | false |
| O95721 | SNAP29 | −0.628162383 | false |
| Q9BZD4 | NUF2 | −0.628162383 | true |
| Q14126 | DSG2 | −0.569179503 | false |
| Q9Y6R9-1 | CCDC61 | −0.567040593 | false |
| Q96AP0-1 | ACD | −0.567040593 | false |
| Q9H4D5-1 | NXF3 | −0.562772261 | false |
| Q9NXG0-2 | CNTLN | −0.55851652 | false |
| Q9BQE5 | APOL2 | −0.55851652 | false |
| Q01664 | TFAP4 | −0.55851652 | true |
| O14777 | NDC80 | −0.55851652 | true |
| Q16342-1 | PDCD2 | −0.55851652 | true |
| O00311-1 | CDC7 | −0.55851652 | true |
| Q8TB72-1 | PUM2 | −0.55851652 | false |
| Q13480-2 | GAB1 | −0.556393349 | false |
| Q9UBT7-1 | CTNNAL1 | −0.556393349 | false |
| Q8TD30-1 | GPT2 | −0.556393349 | false |
| Q96FX2-1 | DPH3 | −0.556393349 | true |
| Q9H8U3 | ZFAND3 | −0.554273297 | false |
| Q9H3S4-1 | TPK1 | −0.554273297 | false |
| Q14527-1 | HLTF | −0.554273297 | false |
| Q6NYC1-3 | JMJD6 | −0.552156356 | true |
| O14757-1 | CHEK1 | −0.552156356 | true |
| Q9BZL1 | UBL5 | −0.552156356 | true |
| Q8WTP8-2 | AEN | −0.552156356 | false |
| P58335-4 | ANTXR2 | −0.552156356 | false |
| Q8NC42 | RNF149 | −0.550042516 | false |
| Q8N2K1-3 | UBE2J2 | −0.550042516 | true |
| P30281-1 | CCND3 | −0.54793177 | false |
| Q99755-3 | PIP5K1A | −0.54793177 | false |
| Q8N5I9 | C12orf45 | −0.54793177 | true |
| Q96G01-1 | BICD1 | −0.54793177 | false |
| Q9NVW2-1 | RLIM | −0.545824107 | false |
| Q9NXW2-1 | DNAJB12 | −0.545824107 | false |
| Q5THK1-1 | PRR14L | −0.545824107 | false |
| Q6UWB1 | IL27RA | −0.545824107 | false |
| Q9NUL7 | DDX28 | −0.543719518 | true |
| P14635-1 | CCNB1 | −0.541617996 | false |
| Q8IZT6-1 | ASPM | −0.541617996 | false |
| Q8IYL2-1 | TRMT44 | −0.541617996 | false |
| P49760-1 | CLK2 | −0.53951953 | false |
| Q99707-1 | MTR | −0.53951953 | false |
| Q9NQC1-1 | JADE2 | −0.53951953 | false |
| Q13445 | TMED1 | −0.53951953 | false |
| Q9NZ71-2 | RTEL1 | −0.53951953 | true |
| Q8TBM8-1 | DNAJB14 | −0.537424112 | false |
| Q14CS0 | UBXN2B | −0.537424112 | false |
| Q9NYS0 | NKIRAS1 | −0.537424112 | false |
| Q8WVZ9 | KBTBD7 | −0.535331733 | false |
| Q6ZWJ1-1 | STXBP4 | −0.504304837 | false |
| Q96BD0-1 | SLCO4A1 | −0.504304837 | false |
| Q96CS2-1 | HAUS1 | −0.504304837 | true |
| P04114 | APOB | −0.50021788 | false |
| Q8WXW3-1 | PIBF1 | −0.50021788 | false |
| P13693-1 | TPT1 | −0.498178735 | true |
| Q9UBE8 | NLK | −0.498178735 | false |
| P30622-2 | CLIP1 | −0.498178735 | false |
| P00374-1 | DHFR | −0.496142467 | true |
| Q9UPP1-4 | PHF8 | −0.496142467 | false |
| Q1MSJ5-3 | CSPP1 | −0.496142467 | false |
| O95249-1 | GOSR1 | −0.496142467 | false |
| Q9H0K1 | SIK2 | −0.496142467 | false |
| Q8IUX1-1 | TMEM126B | −0.496142467 | false |
| Q8NB14-1 | USP38 | −0.49410907 | false |
| Q8NHQ1-1 | CEP70 | −0.49410907 | false |
| Q9NYZ3 | GTSE1 | −0.49410907 | true |
| P49459-1 | UBE2A | −0.492078535 | false |
| Q8N2W9 | PIAS4 | −0.490050854 | false |
| Q969Z4 | RELT | −0.490050854 | false |
| Q7Z4L5-1 | TTC21B | −0.490050854 | false |
| Q9UHQ1-2 | NARF | −0.488026018 | false |
| Q6ZUT1-2 | NKAPD1 | −0.488026018 | false |
| Q68D85 | NCR3LG1 | −0.488026018 | false |
| P40855-1 | PEX19 | −0.488026018 | false |
| Q6UWY0 | ARSK | −0.486004021 | false |
| Q16254 | E2F4 | −0.486004021 | false |
| Q8N128-2 | FAM177A1 | −0.486004021 | false |
| P14923 | JUP | −0.483984853 | false |
| Q86XK2-5 | FBXO11 | −0.483984853 | false |
| P11473-2 | VDR | −0.483984853 | false |
| P14316-1 | IRF2 | −0.483984853 | false |
| O60243-1 | HS6ST1 | −0.483984853 | false |
| Q14542-1 | SLC29A2 | −0.481968507 | false |
| P78330 | PSPH | −0.481968507 | false |
| A4D1E9-1 | GTPBP10 | −0.479954976 | false |
| Q7Z5Y7-1 | KCTD20 | −0.479954976 | false |
| P48509 | CD151 | −0.479954976 | false |
| O60353-1 | FZD6 | −0.479954976 | false |
| Q96PQ6-1 | ZNF317 | −0.479954976 | false |
| Q7L7V1-1 | DHX32 | −0.479954976 | false |
| Q14249 | ENDOG | −0.477944251 | false |
| Q9H6A9-1 | PCNX3 | −0.475936324 | false |
| Q9UJK0 | TSR3 | −0.475936324 | false |
| Q9Y597-1 | KCTD3 | −0.475936324 | false |
| P35790-1 | CHKA | −0.452056689 | true |
| Q96SN8-1 | CDK5RAP2 | −0.452056689 | true |
| P63146 | UBE2B | −0.452056689 | false |
| Q99871-2 | HAUS7 | −0.452056689 | true |
| Q13158 | FADD | −0.452056689 | false |
| Q96AT1 | KIAA1143 | −0.450084446 | false |
| Q8IUD6-1 | RNF135 | −0.450084446 | false |
| Q9HDC5 | JPH1 | −0.450084446 | false |
| Q96F44-1 | TRIM11 | −0.450084446 | false |
| O95343 | SIX3 | −0.450084446 | false |
| Q9NU53 | GINM1 | −0.450084446 | false |
| O75164-1 | KDM4A | −0.450084446 | false |
| Q9H9Y2 | RPF1 | −0.450084446 | true |
| Q9UPW6-1 | SATB2 | −0.448114897 | false |
| Q9NPF2-1 | CHST11 | −0.448114897 | false |
| O15116 | LSM1 | −0.446148032 | false |
| Q01826-2 | SATB1 | −0.446148032 | false |
| Q4AC94-5 | C2CD3 | −0.446148032 | false |
| Q6PL18-1 | ATAD2 | −0.446148032 | false |
| Q9NR82-6 | KCNQ5 | −0.446148032 | true |

TABLE 5-continued

IC020772.1: 869 proteins
log2FC < −0.3 (147 essential proteins)

| Accession | Protein | log2FC (IC020772.1/ DMSO) | essential |
|---|---|---|---|
| Q9H5Z6-1 | FAM124B | −0.446148032 | false |
| Q6ZW76-1 | ANKS3 | −0.444183845 | false |
| Q9NSA3 | CTNNBIP1 | −0.444183845 | false |
| Q8TCG1-1 | KIAA1524 | −0.444183845 | false |
| Q7Z7C8-2 | TAF8 | −0.444183845 | true |
| Q9NWT6 | HIF1AN | −0.442222329 | false |
| Q8ND25-1 | ZNRF1 | −0.442222329 | false |
| Q13686 | ALKBH1 | −0.442222329 | false |
| Q02742 | GCNT1 | −0.442222329 | false |
| Q9BXS4 | TMEM59 | −0.440263476 | false |
| Q17RS7 | GEN1 | −0.440263476 | false |
| Q96EC8-1 | YIPF6 | −0.440263476 | false |
| Q16625-1 | OCLN | −0.440263476 | false |
| Q9BVW5 | TIPIN | −0.440263476 | false |
| Q14651 | PLS1 | −0.440263476 | false |
| P04183 | TK1 | −0.440263476 | false |
| Q6AI12 | ANKRD40 | −0.440263476 | false |
| Q9Y5X0-1 | SNX10 | −0.438307279 | false |
| O75398-1 | DEAF1 | −0.438307279 | false |
| Q9NZN8-1 | CNOT2 | −0.438307279 | false |
| Q96T68-1 | SETDB2 | −0.438307279 | false |
| P38398-7 | BRCA1 | −0.438307279 | true |
| Q9ULF5-1 | SLC39A10 | −0.436353731 | false |
| Q6P4H8-1 | FAM173B | −0.436353731 | false |
| P13612-1 | ITGA4 | −0.436353731 | false |
| Q9Y5V0 | ZNF706 | −0.436353731 | false |
| Q9BYG5-1 | PARD6B | −0.415037499 | false |
| Q96C01 | FAM136A | −0.413115187 | false |
| Q9BRS2 | RIOK1 | −0.413115187 | false |
| O15318 | POLR3G | −0.413115187 | false |
| Q9UNY4-1 | TTF2 | −0.413115187 | false |
| Q13111-1 | CHAF1A | −0.413115187 | true |
| Q96GN5-1 | CDCA7L | −0.413115187 | false |
| P10242-4 | MYB | −0.411195433 | true |
| P48060-1 | GLIPR1 | −0.411195433 | false |
| Q9Y4B6-1 | DCAF1 | −0.411195433 | false |
| Q9UQB8-1 | BAIAP2 | −0.40927823 | false |
| Q02086-1 | SP2 | −0.40927823 | false |
| Q9NRZ9-1 | HELLS | −0.40927823 | false |
| Q96BR5 | COA7 | −0.40927823 | false |
| O14786-1 | NRP1 | −0.407363571 | false |
| P20336 | RAB3A | −0.407363571 | false |
| Q8WUX1-1 | SLC38A5 | −0.407363571 | true |
| Q9H0W8-1 | SMG9 | −0.40545145 | false |
| P15151-1 | PVR | −0.40545145 | false |
| A6NDU8 | C5orf51 | −0.40545145 | false |
| Q9H1X3-1 | DNAJC25 | −0.40545145 | false |
| O75467 | ZNF324 | −0.40354186 | false |
| Q9Y6N7-2 | ROBO1 | −0.40354186 | false |
| Q08AG7 | MZT1 | −0.40354186 | false |
| Q86Y91-2 | KIF18B | −0.40354186 | false |
| Q9NQY0-1 | BIN3 | −0.401634795 | false |
| Q9NW81-4 | DMAC2 | −0.401634795 | false |
| Q7Z3K6-2 | MIER3 | −0.401634795 | false |
| Q96ES7 | SGF29 | −0.401634795 | false |
| O00418 | EEF2K | −0.401634795 | false |
| P04818-1 | TYMS | −0.399730246 | true |
| P61956-1 | SUMO2 | −0.399730246 | false |
| Q8N3Z6-1 | ZCCHC7 | −0.399730246 | false |
| Q49AN0-1 | CRY2 | −0.399730246 | false |
| O43324-1 | EEF1E1 | −0.399730246 | false |
| Q56P03 | EAPP | −0.397828209 | false |
| Q9Y6M7-7 | SLC4A7 | −0.397828209 | false |
| Q49A88-1 | CCDC14 | −0.397828209 | false |
| Q06413-1 | MEF2C | −0.397828209 | false |
| P49715-4 | CEBPA | −0.397828209 | true |
| P53355-3 | DAPK1 | −0.395928676 | false |
| Q9H900-1 | ZWILCH | −0.395928676 | false |
| Q9NVN8 | GNL3L | −0.395928676 | true |
| Q5T3J3-1 | LRIF1 | −0.395928676 | false |
| Q9NPE3 | NOP10 | −0.395928676 | true |
| Q8TCB7-1 | METTL6 | −0.395928676 | false |
| Q14186-1 | TFDP1 | −0.378944497 | false |
| Q15119-1 | PDK2 | −0.378944497 | false |
| O60239-1 | SH3BP5 | −0.378944497 | false |
| Q8N339 | MTIM | −0.378944497 | false |
| Q9UPP1-1 | PHF8 | −0.377069649 | false |
| Q96HR3-1 | MED30 | −0.377069649 | true |
| Q00765-1 | REEP5 | −0.377069649 | false |
| O95977 | S1PR4 | −0.377069649 | false |
| Q9Y2Z2-6 | MTO1 | −0.377069649 | false |
| Q96AY4 | TTC28 | −0.377069649 | false |
| Q2TAL8 | QRICH1 | −0.375197235 | true |
| Q6P1Q9-1 | METTL2B | −0.375197235 | false |
| O15504-1 | NUPL2 | −0.375197235 | false |
| O00391-1 | QSOX1 | −0.375197235 | false |
| Q9BRT9-1 | GINS4 | −0.375197235 | true |
| Q8N3R9-1 | MPP5 | −0.375197235 | false |
| Q09328 | MGAT5 | −0.375197235 | false |
| Q9BVJ6-1 | UTP14A | −0.375197235 | false |
| Q99470 | SDF2 | −0.373327247 | false |
| O75925-2 | PIAS1 | −0.373327247 | false |
| Q9P0R6 | GSKIP | −0.373327247 | false |
| P61244-1 | MAX | −0.373327247 | false |
| Q08357 | SLC20A2 | −0.373327247 | false |
| Q9Y4D8-5 | HECTD4 | −0.373327247 | false |
| Q49B96 | COX19 | −0.373327247 | false |
| P36954 | POLR2I | −0.373327247 | true |
| P09496-2 | CLTA | −0.373327247 | false |
| P67809 | YBX1 | −0.371459681 | false |
| Q9P0K1-1 | ADAM22 | −0.371459681 | false |
| Q8IWZ8-1 | SUGP1 | −0.371459681 | false |
| Q8TCZ2-1 | CD99L2 | −0.371459681 | false |
| Q14980-2 | NUMA1 | −0.371459681 | false |
| Q8WVD5-1 | RNF141 | −0.369594529 | false |
| Q9H8E8-1 | KAT14 | −0.369594529 | false |
| Q13268-2 | DHRS2 | −0.369594529 | false |
| Q9BT17-1 | MTG1 | −0.369594529 | true |
| Q6FIF0-1 | ZFAND6 | −0.367731785 | false |
| P16220-1 | CREB1 | −0.367731785 | false |
| O75665-1 | OFD1 | −0.365871442 | false |
| Q8WUX2 | CHAC2 | −0.365871442 | false |
| P17535 | JUND | −0.365871442 | false |
| Q9UBH6-1 | XPR1 | −0.365871442 | false |
| Q8NCL4 | GALNT6 | −0.365871442 | false |
| Q9NXR1-1 | NDE1 | −0.364013496 | false |
| Q9C0F1-2 | CEP44 | −0.364013496 | false |
| Q9H981-1 | ACTR8 | −0.364013496 | true |
| Q6ZN06 | ZNF813 | −0.345564459 | false |
| P08174-7 | CD55 | −0.343732465 | false |
| P35556-1 | FBN2 | −0.343732465 | false |
| Q9HA47-4 | UCK1 | −0.343732465 | false |
| Q99551 | MTERF1 | −0.343732465 | false |
| Q92536 | SLC7A6 | −0.343732465 | false |
| P42768 | WAS | −0.343732465 | false |
| O14593-1 | RFXANK | −0.343732465 | false |
| Q674X7-1 | KAZN | −0.343732465 | false |
| Q92917 | GPKOW | −0.343732465 | true |
| O43291-1 | SPINT2 | −0.341902795 | false |
| Q9H4A5-1 | GOLPH3L | −0.341902795 | false |
| Q5JWR5 | DOPEY1 | −0.341902795 | false |
| Q96QC0 | PPP1R10 | −0.341902795 | true |
| Q86SQ9-2 | DHDDS | −0.341902795 | true |
| O75845 | SC5D | −0.340075442 | false |
| Q8TAP6-1 | CEP76 | −0.340075442 | false |
| Q2VPB7 | AP5B1 | −0.340075442 | false |
| Q9H5V9-1 | CXorf56 | −0.340075442 | false |
| Q16533 | SNAPC1 | −0.340075442 | true |
| Q96NB1-1 | FOPNL | −0.340075442 | false |
| Q53FT3 | HIKESHI | −0.3382504 | false |
| Q15056-1 | EIF4H | −0.3382504 | false |
| Q96PV7-1 | FAM193B | −0.3382504 | false |
| P11049-1 | CD37 | −0.3382504 | false |
| Q6PJP8 | DCLRE1A | −0.3382504 | false |
| P51784 | USP11 | −0.3382504 | false |
| Q9Y2F5 | ICE1 | −0.3382504 | false |

TABLE 5-continued

IC020772.1: 869 proteins
log2FC < −0.3 (147 essential proteins)

| Accession | Protein | log2FC (IC020772.1/ DMSO) | essential |
|---|---|---|---|
| Q92985-4 | IRF7 | −0.3382504 | false |
| O75478-1 | TADA2A | −0.336427665 | false |
| Q9H446-1 | RWDD1 | −0.336427665 | false |
| Q9UMY1-1 | NOL7 | −0.336427665 | true |
| Q96MN5-1 | TCEANC2 | −0.336427665 | false |
| Q6UB98-1 | ANKRD12 | −0.336427665 | false |
| Q53HC5 | KLHL26 | −0.336427665 | false |
| P56159-1 | GFRA1 | −0.336427665 | false |
| Q6UXT9 | ABHD15 | −0.336427665 | false |
| Q9NS28 | RGS18 | −0.334607229 | false |
| Q13136-1 | PPFIA1 | −0.334607229 | false |
| P53611 | RABGGTB | −0.334607229 | true |
| Q4VC05-1 | BCL7A | −0.334607229 | false |
| Q8TB03-1 | CXorf38 | −0.334607229 | false |
| Q12894-2 | IFRD2 | −0.334607229 | false |
| Q9H9V9-1 | JMJD4 | −0.334607229 | false |
| Q8NA72-1 | POC5 | −0.334607229 | false |
| Q8IY22-1 | CMIP | −0.334607229 | false |
| Q9Y2R2-1 | PTPN22 | −0.321928095 | false |
| Q14153-1 | FAM53B | −0.320125852 | false |
| Q8WU10-1 | PYROXD1 | −0.320125852 | true |
| Q9P1U1-1 | ACTR3B | −0.320125852 | false |
| O75387-2 | SLC43A1 | −0.320125852 | false |
| P62877 | RBX1 | −0.320125852 | true |
| Q7Z333-4 | SETX | −0.320125852 | false |
| P14317-1 | HCLS1 | −0.320125852 | false |
| Q9H967 | WDR76 | −0.320125852 | false |
| P78324-1 | SIRPA | −0.318325858 | false |
| Q14680-1 | MELK | −0.318325858 | false |
| Q9Y2Y0-1 | ARL2BP | −0.318325858 | false |
| O60779-1 | SLC19A2 | −0.318325858 | false |
| P41208 | CETN2 | −0.318325858 | false |
| Q16763 | UBE2S | −0.318325858 | false |
| P55082-1 | MFAP3 | −0.318325858 | false |
| Q8WYQ3 | CHCHD10 | −0.316528107 | false |
| Q5T6S3-1 | PHF19 | −0.316528107 | false |
| Q8TEV9-1 | SMCR8 | −0.316528107 | false |
| Q969X0 | RILPL2 | −0.316528107 | true |
| Q13740-1 | ALCAM | −0.316528107 | false |
| Q12815-1 | TROAP | −0.316528107 | false |
| P59923 | ZNF445 | −0.316528107 | false |
| Q8IWC1-1 | MAP7D3 | −0.316528107 | false |
| Q96CW6 | SLC7A6OS | −0.316528107 | true |
| Q13573 | SNW1 | −0.314732593 | true |
| Q8NG31-1 | KNL1 | −0.314732593 | false |
| Q96A19 | CCDC102A | −0.314732593 | false |
| Q9BRT2 | UQCC2 | −0.314732593 | false |
| O95801 | TTC4 | −0.314732593 | false |
| Q7RTN6-1 | STRADA | −0.314732593 | false |
| Q96DR7-1 | ARHGEF26 | −0.314732593 | false |
| P37268-1 | FDFT1 | −0.314732593 | false |
| Q13433-1 | SLC39A6 | −0.314732593 | false |
| Q9BZR9 | TRIM8 | −0.314732593 | false |
| Q9BRP8-1 | PYM1 | −0.314732593 | false |
| P30520 | ADSS | −0.314732593 | true |
| Q9NRN9 | METTL5 | −0.314732593 | false |
| P32519-1 | ELF1 | −0.312939312 | false |
| Q9NZZ3-1 | CHMP5 | −0.312939312 | true |
| Q9Y2G2-5 | CARD8 | −0.312939312 | false |
| Q10589-1 | BST2 | −0.312939312 | false |
| Q8ND24-1 | RNF214 | −0.312939312 | false |
| O95707 | POP4 | −0.312939312 | true |
| Q9NWZ8 | GEMIN8 | −0.312939312 | false |
| P46060 | RANGAP1 | −0.312939312 | true |
| Q9H501 | ESF1 | −0.304006187 | false |
| O75319-1 | DUSP11 | −0.30222618 | false |
| Q969E8 | TSR2 | −0.30222618 | true |
| Q8N5P1 | ZC3H8 | −0.30222618 | false |
| P19438-1 | TNFRSF1A | −1.123433941 | false |
| Q16667-1 | CDKN3 | −1.117161344 | false |
| Q9NWQ9 | C14orf119 | −1.110915901 | false |
| Q9P2D6-1 | FAM135A | −1.10780329 | false |
| O75909-3 | CCNK | −1.083141235 | false |
| P62328 | TMSB4X | −1.080087911 | false |
| Q9UKK3 | PARP4 | −1.080087911 | false |
| P51530-1 | DNA2 | −1.074000581 | false |
| Q9NYJ1-2 | COA4 | −1.064917477 | false |
| Q16621 | NFE2 | −1.061902439 | false |
| Q9NPD8 | UBE2T | −1.049904906 | false |
| Q9HBU6-1 | ETNK1 | −1.043943348 | false |
| Q6SJ93-1 | FAM111B | −1.035046947 | false |
| O75563 | SKAP2 | −0.997117491 | false |
| Q16626 | MEA1 | −0.991369695 | false |
| Q9H7X3 | ZNF696 | −0.988504361 | false |
| Q86UD0 | SAPCD2 | −0.985644707 | false |
| Q9UIB8-1 | CD84 | −0.985644707 | false |
| Q8TAA9-1 | VANGL1 | −0.974262439 | false |
| P18850 | ATF6 | −0.795859283 | false |
| Q9NUJ7 | PLCXD1 | −0.793356776 | false |
| O43278-1 | SPINT1 | −0.790858602 | false |
| P78395 | PRAME | −0.788364747 | false |
| Q6PK04 | CCDC137 | −0.788364747 | false |
| Q96DU3-1 | SLAMF6 | −0.788364747 | false |
| Q9NPA8-1 | ENY2 | −0.785875195 | true |
| Q6ZWK4 | C1orf186 | −0.785875195 | false |
| O43164-1 | PJA2 | −0.783389931 | false |
| P13598 | ICAM2 | −0.783389931 | false |
| Q9BSI4-1 | TINF2 | −0.783389931 | false |
| Q7L590-1 | MCM10 | −0.780908942 | false |
| O15055-1 | PER2 | −0.775959726 | false |
| O15287 | FANCG | −0.77349147 | true |
| P28749-1 | RBL1 | −0.77349147 | false |
| Q86W74-1 | ANKRD46 | −0.77102743 | false |
| Q03112-3 | MECOM | −0.77102743 | false |
| Q7Z7L7 | ZER1 | −0.768567592 | false |
| Q15468-2 | STIL | −0.76611194 | true |
| Q6GTX8-1 | LAIR1 | −0.758769964 | true |
| Q9C0D0-1 | PHACTR1 | −0.756330919 | false |
| Q8TF61 | FBXO41 | −0.75389599 | false |
| Q96GE4-1 | CEP95 | −0.75389599 | false |
| Q6PI26-1 | SHQ1 | −0.75389599 | true |
| Q9BWL3-1 | C1orf43 | −0.751465164 | false |
| O75054-2 | IGSF3 | −0.751465164 | false |
| Q9BR77-1 | CCDC77 | −0.751465164 | false |
| Q9BWF2 | TRAIP | −0.746615764 | true |
| Q9UKL3 | CASP8AP2 | −0.746615764 | false |
| P31785-1 | IL2RG | −0.744197163 | false |
| P14209-1 | CD99 | −0.744197163 | false |
| O95229-1 | ZWINT | −0.739372092 | true |
| Q9NPB0-1 | SAYSD1 | −0.739372092 | false |
| Q8NDZ2-1 | SIMC1 | −0.734563104 | false |
| Q9Y4C2-1 | TCAF1 | −0.732164608 | false |
| Q8IWD4-1 | CCDC117 | −0.732164608 | false |
| O43766-1 | LIAS | −0.727379545 | true |
| P13196-1 | ALAS1 | −0.727379545 | true |
| Q8NDD1-1 | C1orf131 | −0.727379545 | false |
| Q9Y2G9-1 | SBNO2 | −0.727379545 | false |
| Q6ZQX7-4 | LIAT1 | −0.724992953 | false |
| Q6P444-1 | MTFR2 | −0.722610301 | false |
| Q15036-1 | SNX17 | −0.722610301 | false |
| A2RUB1-4 | MEIOC | −0.720231578 | false |
| Q8NCY6 | MSANTD4 | −0.717856771 | false |
| Q99519 | NEU1 | −0.715485867 | false |
| O60427-1 | FADS1 | −0.628162383 | false |
| Q86Y07-1 | VRK2 | −0.625934282 | false |
| Q9BUP0-1 | EFHD1 | −0.61705613 | false |
| P10721-1 | KIT | −0.61705613 | false |
| Q9HD26-1 | GOPC | −0.61705613 | false |
| P17813-1 | ENG | −0.61705613 | false |
| Q9C035-1 | TRIM5 | −0.614845103 | false |
| Q15080-1 | NCF4 | −0.614845103 | false |
| Q96BH1 | RNF25 | −0.610433188 | false |
| Q9Y605 | MRFAP1 | −0.610433188 | false |
| Q5T3F8-1 | TMEM63B | −0.60823228 | false |
| Q71RC2-4 | LARP4 | −0.606034724 | false |
| Q9Y3B1-1 | PRELID3B | −0.603840511 | false |

TABLE 5-continued

IC020772.1: 869 proteins
log2FC < −0.3 (147 essential proteins)

| Accession | Protein | log2FC (IC020772.1/ DMSO) | essential |
|---|---|---|---|
| Q9NY93-1 | DDX56 | −0.603840511 | true |
| O43257 | ZNHIT1 | −0.603840511 | false |
| PODPB5-1 | POLR1D | −0.603840511 | false |
| Q9P2N7-5 | KLHL13 | −0.60164963 | false |
| Q96SZ6-3 | CDK5RAP1 | −0.60164963 | false |
| Q9H3R5 | CENPH | −0.59946207 | false |
| Q4KWH8-1 | PLCH1 | −0.597277823 | false |
| Q9BWG6-1 | SCNM1 | −0.597277823 | false |
| Q86XR8-1 | CEP57 | −0.597277823 | true |
| Q14164-1 | IKBKE | −0.597277823 | false |
| P42892-1 | ECE1 | −0.595096878 | false |
| Q16206-1 | ENOX2 | −0.590744853 | false |
| Q8TF40-3 | FNIP1 | −0.590744853 | false |
| Q9Y6D0 | SELENOK | −0.590744853 | false |
| Q9BX70-1 | BTBD2 | −0.588573754 | false |
| Q8WXS3-1 | BAALC | −0.588573754 | false |
| Q5JUQ0 | FAM78A | −0.588573754 | false |
| Q9BS16 | CENPK | −0.588573754 | false |
| O60828-1 | PQBP1 | −0.588573754 | false |
| Q8NFZ0-2 | FBXO18 | −0.586405918 | false |
| Q6P5R6 | RPL22L1 | −0.584241333 | false |
| Q6NUS6-1 | TCTN3 | −0.584241333 | false |
| Q9ULT8 | HECTD1 | −0.579921884 | false |
| O00220 | TNFRSF10A | −0.579921884 | false |
| Q96EA4-1 | SPDL1 | −0.579921884 | false |
| Q9Y2Y1 | POLR3K | −0.579921884 | true |
| Q7Z417-1 | NUFIP2 | −0.577766999 | false |
| Q8WVP5 | TNFAIP8L1 | −0.575615328 | false |
| Q9BSR8 | YIPF4 | −0.575615328 | false |
| Q9Y314 | NOSIP | −0.575615328 | false |
| P01130-1 | LDLR | −0.57132159 | false |
| Q96L73-1 | NSD1 | −0.57132159 | false |
| Q96K31-1 | C8orf76 | −0.57132159 | false |
| P47224 | RABIF | −0.535331733 | false |
| P82094-1 | TMF1 | −0.535331733 | false |
| Q12899 | TRIM26 | −0.535331733 | false |
| Q9BUB5-1 | MKNK1 | −0.535331733 | false |
| O94842-1 | TOX4 | −0.533242384 | false |
| Q96BZ8 | LENG1 | −0.533242384 | false |
| Q7Z7K0 | CMC1 | −0.533242384 | false |
| Q9H8K7 | C10orf88 | −0.529072743 | false |
| O60291-2 | MGRN1 | −0.529072743 | false |
| Q7Z591-1 | AKNA | −0.529072743 | false |
| Q5VUG0 | SFMBT2 | −0.529072743 | false |
| Q9NWH2 | TMEM242 | −0.529072743 | false |
| P05067-1 | APP | −0.526992432 | false |
| Q14135-4 | VGLL4 | −0.526992432 | false |
| Q86WX3 | RPS19BP1 | −0.526992432 | false |
| Q69YH5-1 | CDCA2 | −0.526992432 | false |
| P42081-1 | CD86 | −0.524915117 | false |
| P48200-1 | IREB2 | −0.524915117 | true |
| Q3B7T1-1 | EDRF1 | −0.522840789 | false |
| Q9H3U5-6 | MFSD1 | −0.522840789 | false |
| Q96DN5-1 | TBC1D31 | −0.522840789 | false |
| P16150 | SPN | −0.520769439 | false |
| P98179 | RBM3 | −0.518701058 | false |
| Q6DKI1-1 | RPL7L1 | −0.518701058 | true |
| P09326-1 | CD48 | −0.518701058 | false |
| Q99618 | CDCA3 | −0.514573173 | false |
| Q9BUL5-1 | PHF23 | −0.514573173 | false |
| Q8WZ82 | OVCA2 | −0.514573173 | false |
| O94964-2 | SOGA1 | −0.514573173 | false |
| Q6NSJ2-1 | PHLDB3 | −0.514573173 | false |
| P61024 | CKS1B | −0.514573173 | false |
| P84101-1 | SERF2 | −0.512513651 | false |
| Q02224-1 | CENPE | −0.512513651 | true |
| Q6PGN9-1 | PSRC1 | −0.512513651 | false |
| Q5T3I0-3 | GPATCH4 | −0.512513651 | false |
| P25774-1 | CTSS | −0.512513651 | false |
| Q96BK5-1 | PINX1 | −0.512513651 | false |
| Q6P3S6 | FBXO42 | −0.510457064 | false |
| Q9BQD3 | KXD1 | −0.510457064 | false |
| Q86YQ8-1 | CPNE8 | −0.510457064 | false |
| Q4J6C6-1 | PREPL | −0.510457064 | false |
| O60603 | TLR2 | −0.508403406 | false |
| P57076 | C21orf59 | −0.508403406 | true |
| Q5T2R2-1 | PDSS1 | −0.508403406 | true |
| Q9BUW7 | C9orf16 | −0.508403406 | false |
| O75354-1 | ENTPD6 | −0.508403406 | false |
| Q13823 | GNL2 | −0.475936324 | true |
| Q9BRT6 | LLPH | −0.475936324 | false |
| Q96NL6-1 | SCLT1 | −0.475936324 | false |
| O60232 | SSSCA1 | −0.473931188 | false |
| Q96CX6 | LRRC58 | −0.473931188 | false |
| Q9BX63-1 | BRIP1 | −0.473931188 | false |
| Q8WTV0-2 | SCARB1 | −0.471928835 | false |
| Q9UL42 | PNMA2 | −0.471928835 | false |
| O75506 | HSBP1 | −0.471928835 | false |
| O43768-4 | ENSA | −0.469929258 | false |
| Q8N0X7 | SPART | −0.469929258 | false |
| O75419-3 | CDC45 | −0.469929258 | true |
| O00429-4 | DNM1L | −0.469929258 | true |
| Q96CM3-1 | RPUSD4 | −0.469929258 | true |
| Q8IVU3-1 | HERC6 | −0.467932448 | false |
| Q96EX3 | WDR34 | −0.467932448 | false |
| Q86U28-1 | ISCA2 | −0.467932448 | true |
| O43566-7 | RGS14 | −0.467932448 | false |
| Q6Y7W6-1 | GIGYF2 | −0.465938398 | true |
| Q14443-1 | CAPRIN1 | −0.465938398 | false |
| Q8N9M1-1 | C19orf47 | −0.465938398 | false |
| O95297-1 | MPZL1 | −0.465938398 | false |
| Q8NC26-1 | ZNF114 | −0.465938398 | false |
| P55081 | MFAP1 | −0.4639471 | true |
| O95926-1 | SYF2 | −0.4639471 | true |
| P46013-2 | MKI67 | −0.461958547 | false |
| O60927 | PPP1R11 | −0.461958547 | false |
| P06280 | GLA | −0.461958547 | false |
| O43542 | XRCC3 | −0.459972731 | true |
| Q9BVP2-1 | GNL3 | −0.459972731 | true |
| Q9BRT3 | MIEN1 | −0.459972731 | false |
| Q8NBI5-2 | SLC43A3 | −0.459972731 | false |
| Q9NSI2-1 | FAM207A | −0.457989644 | false |
| Q96BD8-1 | SKA1 | −0.457989644 | true |
| Q96N96-6 | SPATA13 | −0.457989644 | false |
| O75081-1 | CBFA2T3 | −0.457989644 | false |
| Q7Z6K3 | PTAR1 | −0.457989644 | false |
| Q01196-8 | RUNX1 | −0.45600928 | true |
| Q9H4K7-1 | MTG2 | −0.45600928 | true |
| Q96E09 | FAM122A | −0.45600928 | true |
| Q2KHR2-1 | RFX7 | −0.45600928 | false |
| O00488 | ZNF593 | −0.454031631 | false |
| Q8IWK6-1 | ADGRA3 | −0.454031631 | false |
| Q9Y250-1 | LZTS1 | −0.454031631 | false |
| Q8NDV7-1 | TNRC6A | −0.454031631 | false |
| O43805 | SSNA1 | −0.452056689 | false |
| Q86UY6-1 | NAA40 | −0.436353731 | false |
| Q8N300 | SVBP | −0.434402824 | false |
| Q9HAW0-1 | BRF2 | −0.434402824 | true |
| Q9HCU4 | CELSR2 | −0.434402824 | false |
| Q9BZM6 | ULBP1 | −0.434402824 | false |
| Q9HBM1 | SPC25 | −0.432454552 | true |
| Q9Y255-1 | PRELID1 | −0.432454552 | true |
| Q9Y5A9-1 | YTHDF2 | −0.432454552 | false |
| Q96Q89-3 | KIF20B | −0.432454552 | false |
| O95789-3 | ZMYM6 | −0.430508908 | false |
| Q99684 | GFI1 | −0.430508908 | true |
| Q13362-4 | PPP2R5C | −0.428565884 | false |
| Q9H977 | WDR54 | −0.428565884 | false |
| Q96LB3-1 | IFT74 | −0.428565884 | false |
| Q86V81 | ALYREF | −0.426625474 | true |
| Q9BWT6 | MND1 | −0.426625474 | false |
| Q9Y6A5 | TACC3 | −0.426625474 | true |
| Q96DX7 | TRIM44 | −0.426625474 | false |
| P07108-5 | DB1 | −0.426625474 | false |
| Q96HE9 | PRR11 | −0.426625474 | false |
| Q1RMZ1 | BMT2 | −0.426625474 | false |

TABLE 5-continued

IC020772.1: 869 proteins
log2FC < −0.3 (147 essential proteins)

| Accession | Protein | log2FC (IC020772.1/ DMSO) | essential |
|---|---|---|---|
| Q8NBZ0-1 | INO80E | −0.426625474 | false |
| P57060 | RWDD2B | −0.426625474 | false |
| Q9Y289 | SLC5A6 | −0.424687669 | false |
| Q14674-1 | ESPL1 | −0.424687669 | true |
| Q99569-1 | PKP4 | −0.424687669 | false |
| Q15796-1 | SMAD2 | −0.424687669 | false |
| Q9UGY1 | NOL12 | −0.424687669 | true |
| Q53R41-1 | FASTKD1 | −0.422752464 | false |
| Q99704-1 | DOK1 | −0.422752464 | false |
| O60869-1 | EDF1 | −0.420819852 | false |
| Q9BZM4 | ULBP3 | −0.420819852 | false |
| O75386-2 | TULP3 | −0.420819852 | false |
| Q9Y287-1 | ITM2B | −0.420819852 | false |
| Q8N5L8 | RPP25L | −0.418889825 | false |
| Q9UL33-1 | TRAPPC2L | −0.418889825 | false |
| Q9NVR7-1 | TBCCD1 | −0.418889825 | false |
| Q9NZ72-1 | STMN3 | −0.418889825 | false |
| Q15758-1 | SLC1A5 | −0.418889825 | false |
| Q5MIZ7-1 | PPP4R3B | −0.418889825 | false |
| Q9NSI8-1 | SAMSN1 | −0.418889825 | false |
| Q92698 | RAD54L | −0.416962376 | false |
| Q8N543-1 | OGFOD1 | −0.416962376 | false |
| Q5JS54-2 | PSMG4 | −0.416962376 | true |
| P24864-1 | CCNE1 | −0.415037499 | false |
| Q8WW33 | GTSF1 | −0.415037499 | false |
| Q9UQ84-1 | EXO1 | −0.394031641 | false |
| Q92686 | NRGN | −0.394031641 | false |
| Q9H3H5-1 | DPAGT1 | −0.394031641 | true |
| Q460N5-6 | PARP14 | −0.394031641 | false |
| Q9UBX1 | CTSF | −0.394031641 | false |
| Q96EZ8-2 | MCRS1 | −0.392137097 | false |
| Q9NUQ3-1 | TXLNG | −0.392137097 | false |
| Q9NRY2-1 | INIP | −0.392137097 | false |
| Q9UKA4 | AKAP11 | −0.392137097 | false |
| Q96Q83-1 | ALKBH3 | −0.392137097 | false |
| Q8WUX9-1 | CHMP7 | −0.392137097 | false |
| Q96T21-1 | SECISBP2 | −0.392137097 | false |
| Q9BXS6-1 | NUSAP1 | −0.392137097 | false |
| Q9BQI3-1 | EIF2AK1 | −0.392137097 | false |
| Q9Y3A0-1 | COQ4 | −0.392137097 | true |
| Q9BVC3 | DSCC1 | −0.390245038 | true |
| Q9UBR2 | CTSZ | −0.390245038 | false |
| P53794 | SLC5A3 | −0.390245038 | true |
| Q9UGP4 | LIMD1 | −0.390245038 | false |
| Q5SVZ6 | ZMYM1 | −0.390245038 | false |
| Q5EBL8-2 | PDZD11 | −0.388355457 | false |
| P24863-1 | CCNC | −0.388355457 | false |
| Q14192-1 | FHL2 | −0.388355457 | false |
| Q06547-1 | GABPB1 | −0.388355457 | true |
| Q96B01-1 | RAD51AP1 | −0.386468347 | false |
| O43286 | B4GALT5 | −0.386468347 | false |
| O75147-3 | OBSL1 | −0.386468347 | false |
| Q9P2L0-1 | WDR35 | −0.386468347 | false |
| Q5VTB9-3 | RNF220 | −0.386468347 | false |
| Q86WP2-2 | GPBP1 | −0.386468347 | false |
| P62487 | POLR2G | −0.386468347 | true |
| Q86VI3 | IQGAP3 | −0.384583703 | false |
| O43900-1 | PRICKLE3 | −0.384583703 | false |
| Q9C099-1 | LRRCC1 | −0.382701517 | false |
| O43716 | GATC | −0.382701517 | true |
| P62891 | RPL39 | −0.382701517 | false |
| Q8IX90-1 | SKA3 | −0.382701517 | true |
| Q9UG63-2 | ABCF2 | −0.382701517 | false |
| P30307-1 | CDC25C | −0.382701517 | false |
| Q9H649 | NSUN3 | −0.380821784 | false |
| O43439-4 | CBFA2T2 | −0.380821784 | false |
| O75575-1 | CRCP | −0.380821784 | false |
| Q14687-1 | GSE1 | −0.380821784 | false |
| Q96EP9 | SLC10A4 | −0.380821784 | false |
| Q96R06 | SPAG5 | −0.378944497 | true |
| Q9H0I2-1 | ENKD1 | −0.378944497 | false |
| P52756-1 | RBM5 | −0.364013496 | true |
| Q02548-1 | PAX5 | −0.36215794 | false |
| P54760-1 | EPHB4 | −0.36215794 | false |
| Q32NC0-1 | C18orf21 | −0.36215794 | false |
| P13498 | CYBA | −0.360304767 | false |
| Q8IVQ6 | ZDHHC21 | −0.360304767 | false |
| Q9H467 | CUEDC2 | −0.360304767 | false |
| Q8NDX1-1 | PSD4 | −0.358453971 | false |
| Q7Z3T8-1 | ZFYVE16 | −0.358453971 | false |
| Q9NQZ6-1 | ZC4H2 | −0.358453971 | false |
| Q15050 | RRS1 | −0.358453971 | true |
| Q96GX2 | ATXN7L3B | −0.358453971 | false |
| Q86WA8-1 | LONP2 | −0.358453971 | false |
| O43617-1 | TRAPPC3 | −0.358453971 | false |
| Q9NVP2 | ASF1B | −0.356605547 | false |
| Q5TFE4-1 | NT5DC1 | −0.356605547 | false |
| Q9Y248 | GINS2 | −0.356605547 | true |
| Q53GT1-1 | KLHL22 | −0.356605547 | false |
| Q9GZU8 | FAM192A | −0.354759487 | false |
| P49642 | PRIM1 | −0.354759487 | true |
| Q9H6F5-1 | CCDC86 | −0.354759487 | true |
| P10646-1 | TFP1 | −0.352915787 | false |
| Q6FI81-1 | CIAPIN1 | −0.352915787 | false |
| Q9NVR5-1 | DNAAF2 | −0.352915787 | false |
| Q969K3-2 | RNF34 | −0.352915787 | false |
| P13984 | GTF2F2 | −0.352915787 | false |
| Q9HAU4 | SMURF2 | −0.352915787 | false |
| Q5H9F3-3 | BCORL1 | −0.352915787 | false |
| Q96DY7-1 | MTBP | −0.351074441 | false |
| P61966-1 | AP1S1 | −0.351074441 | false |
| O95273-1 | CCNDBP1 | −0.351074441 | false |
| Q8NAG6-2 | ANKLE1 | −0.351074441 | false |
| Q96E29-1 | MTERF3 | −0.349235441 | false |
| Q9NS87-1 | KIF15 | −0.349235441 | false |
| P48736 | PIK3CG | −0.349235441 | false |
| P26367-1 | PAX6 | −0.349235441 | false |
| O60674 | JAK2 | −0.347398782 | false |
| Q13287 | NMI | −0.347398782 | false |
| Q07866-6 | KLC1 | −0.347398782 | false |
| P54277-1 | PMS1 | −0.347398782 | false |
| Q9UH17-1 | APOBEC3B | −0.347398782 | false |
| P10619-1 | CTSA | −0.347398782 | false |
| P43007-1 | SLC1A4 | −0.347398782 | false |
| Q9NSD4-1 | ZNF275 | −0.347398782 | false |
| P98170 | XIAP | −0.347398782 | false |
| O14545-1 | TRAFD1 | −0.347398782 | false |
| O14578-4 | CIT | −0.334607229 | false |
| O95243-1 | MBD4 | −0.332789088 | false |
| Q8NFQ8-1 | TOR1AIP2 | −0.332789088 | false |
| Q13501-1 | SQSTM1 | −0.332789088 | false |
| O60315-1 | ZEB2 | −0.332789088 | false |
| Q01581 | HMGCS1 | −0.332789088 | true |
| Q96HC4-1 | PDLIM5 | −0.332789088 | false |
| O95391 | SLU7 | −0.332789088 | true |
| P12236 | SLC25A6 | −0.332789088 | false |
| Q13123 | IK | −0.332789088 | false |
| Q96GD4-5 | AURKB | −0.332789088 | true |
| Q9BT25-1 | HAUS8 | −0.332789088 | true |
| P13747 | HLA-E | −0.332789088 | false |
| Q8IVD9 | NUDCD3 | −0.330973234 | true |
| Q13888-1 | GTF2H2 | −0.330973234 | false |
| Q8NBJ4-1 | GOLM1 | −0.330973234 | false |
| P36404-1 | ARL2 | −0.329159664 | true |
| Q9Y2J4-4 | AMOTL2 | −0.329159664 | false |
| O95456-1 | PSMG1 | −0.329159664 | true |
| Q7L8J4-1 | SH3BP5L | −0.329159664 | false |
| Q53HL2 | CDCA8 | −0.329159664 | true |
| Q8NC60 | NOA1 | −0.329159664 | false |
| Q9H7B2 | RPF2 | −0.327348371 | true |
| Q6ULP2-1 | AFTPH | −0.327348371 | false |
| Q9P2W1-1 | PSMC3IP | −0.327348371 | false |
| P0CG12-1 | CHTF8 | −0.327348371 | true |
| Q9H7E9-2 | C8orf33 | −0.327348371 | true |
| Q9UBW8 | COPS7A | −0.327348371 | false |
| O94991-1 | SLITRK5 | −0.327348371 | false |

TABLE 5-continued

IC020772.1: 869 proteins
log2FC < −0.3 (147 essential proteins)

| Accession | Protein | log2FC (IC020772.1/ DMSO) | essential |
|---|---|---|---|
| P08195-1 | SLC3A2 | −0.327348371 | true |
| Q96EU6-1 | RRP36 | −0.325539348 | false |
| Q9NRX1 | PNO1 | −0.325539348 | false |
| P15907-1 | ST6GAL1 | −0.325539348 | false |
| Q9NY35-1 | CLDND1 | −0.325539348 | false |
| O43791 | SPOP | −0.325539348 | true |
| Q9HB58-7 | SP110 | −0.325539348 | false |
| Q9BX66-12 | SORBS1 | −0.323732592 | false |
| Q9H078-2 | CLPB | −0.323732592 | true |
| Q8NBT0-1 | POC1A | −0.323732592 | false |
| O75096 | LRP4 | −0.323732592 | false |
| Q9H3J6-1 | C12orf65 | −0.323732592 | false |
| P54132 | BLM | −0.321928095 | false |
| Q9BQA5-1 | HINFP | −0.321928095 | true |
| Q15527 | SURF2 | −0.321928095 | false |
| Q9HCM7 | FBRSL1 | −0.321928095 | false |
| O15392-1 | BIRC5 | −0.321928095 | true |
| Q9NWS6-1 | FAM118A | −0.312939312 | false |
| Q8NB16-1 | MLKL | −0.312939312 | false |
| Q9H6E5 | TUT1 | −0.312939312 | true |
| O60678-1 | PRMT3 | −0.312939312 | false |
| Q9Y6W3 | CAPN7 | −0.312939312 | false |
| Q14442 | PIGH | −0.311148256 | false |
| P15923-2 | TCF3 | −0.311148256 | false |
| Q8NFH4 | NUP37 | −0.311148256 | false |
| Q7L2H7-1 | EIF3M | −0.311148256 | false |
| O00308-1 | WWP2 | −0.311148256 | false |
| Q9BV40 | VAMP8 | −0.311148256 | false |
| Q53QZ3 | ARHGAP15 | −0.311148256 | false |
| O95684-1 | FGFR1OP | −0.309359421 | true |
| Q9NUX5-1 | POT1 | −0.309359421 | false |
| P32455 | GBP1 | −0.309359421 | false |
| Q969W8-2 | ZNF566 | −0.309359421 | false |
| Q9NW68-1 | BSDC1 | −0.309359421 | false |
| P49366-1 | DHPS | −0.309359421 | true |
| P29084 | GTF2E2 | −0.309359421 | false |
| Q9NXW9-1 | ALKBH4 | −0.307572802 | false |
| Q96A00-1 | PPP1R14A | −0.307572802 | false |
| Q9Y6I3-2 | EPN1 | −0.307572802 | false |
| Q9BVV6-3 | KIAA0586 | −0.307572802 | false |
| Q9C0B9-1 | ZCCHC2 | −0.307572802 | false |
| Q8WV92 | MITD1 | −0.305788392 | false |
| Q9Y6V7-1 | DDX49 | −0.305788392 | true |
| Q7Z6J8 | UBE3D | −0.305788392 | false |
| Q9UIV1-1 | CNOT7 | −0.305788392 | false |
| Q96Q45-3 | TMEM237 | −0.305788392 | false |
| P51811 | XK | −0.305788392 | false |
| Q9ULH7-5 | MKL2 | −0.305788392 | false |
| Q7Z7F0-1 | KIAA0907 | −0.305788392 | false |
| P53365-1 | ARFIP2 | −0.305788392 | false |
| Q96L34-1 | MARK4 | −0.305788392 | false |
| Q0VD83-4 | APOBR | −0.305788392 | false |
| Q9UMR5-3 | PPT2 | −0.305788392 | false |
| O14715 | RGPD8 | −0.304006187 | false |
| Q13309-1 | SKP2 | −0.304006187 | false |
| Q6P4I2 | WDR73 | −0.304006187 | false |
| Q8N4C6-7 | NIN | −0.304006187 | false |
| Q9NSV4-3 | DIAPH3 | −0.304006187 | false |
| Q5JTJ3-2 | COA6 | −0.304006187 | false |
| Q12980 | NPRL3 | −0.304006187 | false |
| Q9H2H9 | SLC38A1 | −0.304006187 | false |
| Q96RT1-8 | ERBIN | −0.304006187 | false |
| Q7Z7F7-2 | MRPL55 | −0.304006187 | false |
| Q9HBM6 | TAF9B | −0.30222618 | false |
| O43847-2 | NRDC | −0.30222618 | false |
| Q8N884-1 | MB21D1 | −0.300448367 | false |

TABLE 6

T6938051: 793 proteins
log2FC < −0.3 (142 essential proteins)

| Accession | Protein Name | log2FC (T6938051/ DMSO) | essential |
|---|---|---|---|
| Q96QD9-1 | FYTTD1 | −1.486 | false |
| Q9BV29-2 | CCDC32 | −1.32916 | false |
| Q8N0T1-1 | C8orf59 | −1.28983 | false |
| Q9BWT1-1 | CDCA7 | −1.25154 | false |
| Q53H80 | AKIRIN2 | −1.22769 | true |
| O95864-1 | FADS2 | −1.17137 | false |
| Q9NWQ9 | C14orf119 | −1.14242 | false |
| Q99741 | CDC6 | −1.12029 | true |
| Q16621 | NFE2 | −1.09542 | false |
| P02686-1 | MBP | −1.0862 | false |
| Q9Y448-1 | KNSTRN | −1.08314 | false |
| Q15004-1 | PCLAF | −1.0619 | false |
| Q6PK04 | CCDC137 | −1.0499 | false |
| Q9P2B7-1 | CFAP97 | −1.0499 | false |
| Q9H7X3 | ZNF696 | −1.03505 | false |
| Q92624 | APPBP2 | −1.03505 | false |
| Q6ZWK4 | C1orf186 | −1.01742 | false |
| Q9UBZ4 | APEX2 | −1.0145 | false |
| Q9UIB8-1 | CD84 | −1.00868 | false |
| O75909-3 | CCNK | −1.00578 | false |
| P81274 | GPSM2 | −1.00578 | false |
| Q9NYV4-1 | CDK12 | −0.98564 | true |
| O75683 | SURF6 | −0.98279 | true |
| Q86WW8 | COA5 | −0.97426 | true |
| P51530-1 | DNA2 | −0.95736 | false |
| O94900 | TOX | −0.95176 | false |
| Q9Y255-1 | PRELID1 | −0.94619 | true |
| Q9NPD8 | UBE2T | −0.94619 | false |
| Q9BSK4 | FEM1A | −0.94619 | false |
| P57086 | SCAND1 | −0.93788 | false |
| Q8TAA9-1 | VANGL1 | −0.90779 | false |
| Q9P0P0 | RNF181 | −0.90239 | false |
| Q6SJ93-1 | FAM111B | −0.88098 | false |
| Q6IE81-1 | JADE1 | −0.87303 | false |
| Q16667-1 | CDKN3 | −0.8625 | false |
| P19438-1 | TNFRSF1A | −0.85988 | false |
| Q8N5D6-1 | GBGT1 | −0.7539 | false |
| Q96AH0-1 | NABP1 | −0.7539 | false |
| P14209-1 | CD99 | −0.75147 | false |
| Q15043-1 | SLC39A14 | −0.75147 | false |
| O43278-1 | SPINT1 | −0.75147 | false |
| O95478 | NSA2 | −0.75147 | true |
| Q9NQC1-1 | JADE2 | −0.74904 | false |
| Q8WXS3-1 | BAALC | −0.74662 | false |
| Q8NCY6 | MSANTD4 | −0.7442 | false |
| O60566-3 | BUB1B | −0.7442 | true |
| P17707-1 | AMD1 | −0.7442 | false |
| Q9UMX1-1 | SUFU | −0.73456 | false |
| Q96GA3 | LTV1 | −0.73216 | true |
| Q16626 | MEA1 | −0.72977 | false |
| Q86UD0 | SAPCD2 | −0.72261 | false |
| P55081 | MFAP1 | −0.71786 | true |
| Q15011-1 | HERPUD1 | −0.71549 | false |
| O75054-2 | IGSF3 | −0.71312 | false |
| O95721 | SNAP29 | −0.71312 | false |
| Q9Y6R9-1 | CCDC61 | −0.71076 | false |
| Q9UGY1 | NOL12 | −0.7084 | true |
| Q9Y5X0-1 | SNX10 | −0.70604 | false |
| Q99618 | CDCA3 | −0.70604 | false |
| Q96T88-2 | UHRF1 | −0.70604 | false |
| Q7Z7L7 | ZER1 | −0.70604 | false |
| P14316-1 | IRF2 | −0.70604 | false |
| Q86T82-1 | USP37 | −0.70369 | true |
| Q7L590-1 | MCM10 | −0.70369 | false |
| P13196-1 | ALAS1 | −0.70134 | true |
| O43257 | ZNHIT1 | −0.70134 | false |
| Q6P5R6 | RPL22L1 | −0.699 | false |
| A2VDJ0-5 | TMEM131L | −0.69666 | false |
| P78395 | PRAME | −0.69432 | false |
| Q6P444-1 | MTFR2 | −0.69199 | false |
| Q96FX2-1 | DPH3 | −0.68733 | true |
| Q9BWF2 | TRAIP | −0.68733 | true |
| O43699-1 | SIGLEC6 | −0.68733 | false |

TABLE 6-continued

T6938051: 793 proteins
log2FC < −0.3 (142 essential proteins)

| Accession | Protein Name | log2FC (T6938051/ DMSO) | essential |
|---|---|---|---|
| P41440-1 | SLC19A1 | −0.68501 | true |
| Q96G01-1 | BICD1 | −0.68501 | false |
| Q96BK5-1 | PINX1 | −0.68501 | false |
| Q9NXV2 | KCTD5 | −0.68038 | false |
| O95900-1 | TRUB2 | −0.68038 | true |
| Q8NBI5-2 | SLC43A3 | −0.67807 | false |
| Q9Y2U9-1 | KLHDC2 | −0.67577 | false |
| Q8WXI2-1 | CNKSR2 | −0.67577 | false |
| Q96DU3-1 | SLAMF6 | −0.67577 | false |
| Q6P3S6 | FBXO42 | −0.60165 | false |
| Q5JTJ3-2 | COA6 | −0.60165 | false |
| Q8IUX1-1 | TMEM126B | −0.59946 | false |
| P28749-1 | RBL1 | −0.59946 | false |
| Q9NWH2 | TMEM242 | −0.59728 | false |
| Q96BZ8 | LENG1 | −0.5951 | false |
| O14757-1 | CHEK1 | −0.59292 | true |
| Q15049-1 | MLC1 | −0.59074 | false |
| Q8NDZ2-1 | SIMC1 | −0.58857 | false |
| Q14153-1 | FAM53B | −0.58641 | false |
| Q8N5I9 | C12orf45 | −0.58641 | true |
| Q9NSI2-1 | FAM207A | −0.58641 | false |
| Q5THK1-1 | PRR14L | −0.58641 | false |
| Q6AI12 | ANKRD40 | −0.58641 | false |
| Q9Y6A5 | TACC3 | −0.58424 | true |
| Q7Z417-1 | NUFIP2 | −0.58424 | false |
| A2RUB1-4 | MEIOC | −0.58424 | false |
| Q15223-1 | NECTIN1 | −0.58208 | false |
| Q9Y6M7-7 | SLC4A7 | −0.57992 | false |
| Q15758-1 | SLC1A5 | −0.57992 | false |
| Q99519 | NEU1 | −0.57992 | false |
| Q8WUH1-1 | CHURC1 | −0.57992 | false |
| Q9NSI8-1 | SAMSN1 | −0.57777 | false |
| Q6PI26-1 | SHQ1 | −0.57777 | true |
| Q9BVP2-1 | GNL3 | −0.57562 | true |
| Q69YH5-1 | CDCA2 | −0.57562 | false |
| Q9NYS0 | NKIRAS1 | −0.57562 | false |
| P00973-3 | OAS1 | −0.57347 | false |
| Q9C0F1-2 | CEP44 | −0.57132 | false |
| Q6P589 | TNFAIP8L2 | −0.56918 | false |
| Q14527-1 | HLTF | −0.56918 | false |
| O00311-1 | CDC7 | −0.56918 | true |
| P04921-1 | GYPC | −0.56918 | false |
| Q96CM3-1 | RPUSD4 | −0.56918 | true |
| P34910-2 | EVI2B | −0.56704 | false |
| P04264 | KRT1 | −0.56704 | false |
| Q8TCZ2-1 | CD99L2 | −0.5649 | false |
| Q2KHR2-1 | RFX7 | −0.5649 | false |
| Q96EA4-1 | SPDL1 | −0.5649 | false |
| Q01664 | TFAP4 | −0.56277 | true |
| O94854-1 | KIAA0754 | −0.56277 | false |
| P82094-1 | TMF1 | −0.56064 | false |
| P40855-1 | PEX19 | −0.56064 | false |
| Q8ND83-1 | SLAIN1 | −0.55852 | false |
| Q15468-2 | STIL | −0.55852 | true |
| O43768-4 | ENSA | −0.55639 | false |
| Q9HD26-1 | GOPC | −0.51664 | false |
| O94842-1 | TOX4 | −0.51457 | false |
| Q8N5L8 | RPP25L | −0.51251 | false |
| Q49B96 | COX19 | −0.51251 | false |
| O60291-2 | MGRN1 | −0.51046 | false |
| Q9NQY0-1 | BIN3 | −0.51046 | false |
| O14777 | NDC80 | −0.51046 | true |
| P10721-1 | KIT | −0.51046 | false |
| Q8N9M1-1 | C19orf47 | −0.51046 | false |
| PODPB5-1 | POLRID | −0.51046 | false |
| Q9Y2Y1 | POLR3K | −0.51046 | true |
| Q9BZD4 | NUF2 | −0.5084 | true |
| O95297-1 | MPZL1 | −0.5084 | false |
| Q9NPB0-1 | SAYSD1 | −0.5084 | false |
| O00559-2 | EBAG9 | −0.50635 | false |
| Q6FIF0-1 | ZFAND6 | −0.5043 | false |
| Q14CS0 | UBXN2B | −0.5043 | false |
| Q9Y6Y0 | IVNS1ABP | −0.50226 | false |
| P01130-1 | LDLR | −0.50226 | false |
| Q9NZN8-1 | CNOT2 | −0.50226 | false |
| Q15121-2 | PEA15 | −0.50226 | false |
| Q96L50-1 | LRR1 | −0.50226 | true |
| O95214-2 | LEPROTL1 | −0.50022 | false |
| Q9NVW2-1 | RLIM | −0.50022 | false |
| P49760-1 | CLK2 | −0.49818 | false |
| Q9NS56-1 | TOPORS | −0.49818 | false |
| Q9HDC5 | JPH1 | −0.49818 | false |
| Q9NU53 | GINM1 | −0.49818 | false |
| Q9BSF8-2 | BTBD10 | −0.49818 | false |
| Q99684 | GFI1 | −0.49614 | true |
| Q12841-1 | FSTL1 | −0.49411 | false |
| P06280 | GLA | −0.49208 | false |
| Q9Y597-1 | KCTD3 | −0.49005 | false |
| Q9BRS2 | RIOK1 | −0.48803 | false |
| O75386-2 | TULP3 | −0.48803 | false |
| Q13442 | PDAP1 | −0.48803 | true |
| O95926-1 | SYF2 | −0.48803 | true |
| Q9BVJ6-1 | UTP14A | −0.48803 | false |
| Q6P6B1-1 | ERICH5 | −0.486 | false |
| Q13501-1 | SQSTM1 | −0.486 | false |
| P78324-1 | SIRPA | −0.486 | false |
| Q8N0X7 | SPART | −0.486 | false |
| Q8IXQ3 | C9orf40 | −0.486 | false |
| Q9H3R5 | CENPH | −0.48398 | false |
| Q9NPA8-1 | ENY2 | −0.48398 | true |
| Q8TBM8-1 | DNAJB14 | −0.48398 | false |
| Q96A49 | SYAP1 | −0.45206 | false |
| P78330 | PSPH | −0.45206 | false |
| Q02742 | GCNT1 | −0.45206 | false |
| P48668 | KRT6C | −0.45206 | false |
| O75506 | HSBP1 | −0.45206 | false |
| O43766-1 | LIAS | −0.45008 | true |
| Q68D85 | NCR3LG1 | −0.45008 | false |
| P63146 | UBE2B | −0.45008 | false |
| Q9UL42 | PNMA2 | −0.44811 | false |
| Q9UMY1-1 | NOL7 | −0.44811 | true |
| Q16625-1 | OCLN | −0.44811 | false |
| P15151-1 | PVR | −0.44615 | false |
| P13612-1 | ITGA4 | −0.44615 | false |
| Q16342-1 | PDCD2 | −0.44615 | true |
| Q9H467 | CUEDC2 | −0.44615 | false |
| Q6ZWJ1-1 | STXBP4 | −0.44418 | false |
| P98179 | RBM3 | −0.44418 | false |
| Q15291-1 | RBBP5 | −0.44222 | true |
| Q07866-6 | KLC1 | −0.44222 | false |
| O15504-1 | NUPL2 | −0.44222 | false |
| Q13740-1 | ALCAM | −0.44222 | false |
| Q96AP0-1 | ACD | −0.44222 | false |
| P17535 | JUND | −0.44026 | false |
| P14317-1 | HCLS1 | −0.44026 | false |
| Q99607 | ELF4 | −0.44026 | false |
| Q9Y314 | NOSIP | −0.44026 | false |
| Q99704-1 | DOK1 | −0.44026 | false |
| O15318 | POLR3G | −0.43831 | false |
| Q9NVR7-1 | TBCCD1 | −0.43635 | false |
| Q9UHB6-1 | LIMA1 | −0.43635 | false |
| P48200-1 | IREB2 | −0.43635 | true |
| P04114 | APOB | −0.43635 | false |
| O15056-1 | SYNJ2 | −0.43635 | false |
| Q14444-1 | CAPRIN1 | −0.43635 | false |
| Q96F44-1 | TRIM11 | −0.43635 | false |
| Q7Z6K3 | PTAR1 | −0.43635 | false |
| Q9Y4B6-1 | DCAF1 | −0.43635 | false |
| Q96EZ8-2 | MCRS1 | −0.4344 | false |
| Q9BQE5 | APOL2 | −0.4344 | false |
| Q7Z5Y7-1 | KCTD20 | −0.4344 | false |
| Q99707-1 | MTR | −0.4344 | false |
| P49715-4 | CEBPA | −0.4344 | true |
| P84101-1 | SERF2 | −0.43245 | false |
| Q5JS54-2 | PSMG4 | −0.43245 | true |
| Q9Y421-1 | FAM32A | −0.43245 | false |

TABLE 6-continued

T6938051: 793 proteins
log2FC < −0.3 (142 essential proteins)

| Accession | Protein Name | log2FC (T6938051/DMSO) | essential |
|---|---|---|---|
| O43324-1 | EEF1E1 | −0.43245 | false |
| Q9BUP0-1 | EFHD1 | −0.41312 | false |
| P53794 | SLC5A3 | −0.41312 | true |
| O00161-1 | SNAP23 | −0.41312 | false |
| P30281-1 | CCND3 | −0.4112 | false |
| Q8WUM9 | SLC20A1 | −0.4112 | true |
| Q4AC94-5 | C2CD3 | −0.4112 | false |
| Q53EP0-1 | FNDC3B | −0.4112 | false |
| Q9Y3C1-1 | NOP16 | −0.4112 | true |
| Q8WVZ9 | KBTBD7 | −0.40928 | false |
| O75127 | PTCD1 | −0.40928 | true |
| P31785-1 | IL2RG | −0.40736 | false |
| Q9BWG6-1 | SCNM1 | −0.40736 | false |
| P59923 | ZNF445 | −0.40736 | false |
| Q9P2N7-5 | KLHL13 | −0.40736 | false |
| Q8IYL2-1 | TRMT44 | −0.40736 | false |
| P08195-1 | SLC3A2 | −0.40736 | true |
| P43007-1 | SLC1A4 | −0.40736 | false |
| Q6ZSR9 |  | −0.40736 | false |
| Q7Z591-1 | AKNA | −0.40545 | false |
| Q4VC05-1 | BCL7A | −0.40545 | false |
| P02533 | KRT14 | −0.40545 | false |
| Q99569-1 | PKP4 | −0.40545 | false |
| P30307-1 | CDC25C | −0.40545 | false |
| Q9BQE9-1 | BCL7B | −0.40354 | false |
| Q96SN8-1 | CDK5RAP2 | −0.40354 | true |
| Q13123 | IK | −0.40354 | false |
| Q96DN5-1 | TBC1D31 | −0.40354 | false |
| O75319-1 | DUSP11 | −0.40163 | false |
| P36894 | BMPR1A | −0.40163 | false |
| P16220-1 | CREB1 | −0.40163 | false |
| Q6P9H5-1 | GIMAP6 | −0.40163 | false |
| P05423 | POLR3D | −0.40163 | true |
| Q9NWT6 | HIF1AN | −0.39973 | false |
| Q9H649 | NSUN3 | −0.39973 | false |
| Q92698 | RAD54L | −0.39973 | false |
| Q6NYC1-3 | JMJD6 | −0.39973 | true |
| Q7Z4L5-1 | TTC21B | −0.39973 | false |
| Q9UQB8-1 | BAIAP2 | −0.39783 | false |
| Q9BWT6 | MND1 | −0.39783 | false |
| Q13111-1 | CHAF1A | −0.39783 | true |
| P52756-1 | RBM5 | −0.39783 | true |
| Q8IVD9 | NUDCD3 | −0.39783 | true |
| Q9NS18-2 | GLRX2 | −0.39783 | false |
| Q9H8U3 | ZFAND3 | −0.39593 | false |
| Q6NSJ2-1 | PHLDB3 | −0.39593 | false |
| Q9BZL1 | UBL5 | −0.39593 | true |
| Q8IWK6-1 | ADGRA3 | −0.37707 | false |
| O60315-1 | ZEB2 | −0.37707 | false |
| Q13491-4 | GPM6B | −0.37707 | false |
| Q14674-1 | ESPL1 | −0.37707 | true |
| Q9BVV6-3 | KIAA0586 | −0.37707 | false |
| Q9Y3A2-1 | UTP11 | −0.37707 | false |
| Q8NBR6-1 | MINDY2 | −0.37707 | false |
| Q8NHG7 | SVIP | −0.3752 | false |
| Q9GZU8 | FAM192A | −0.3752 | false |
| Q01826-2 | SATB1 | −0.3752 | false |
| O95707 | POP4 | −0.3752 | true |
| Q7L7V1-1 | DHX32 | −0.3752 | false |
| P17025-1 | ZNF182 | −0.37333 | false |
| P10276-1 | RARA | −0.37333 | true |
| Q96DX7 | TRIM44 | −0.37146 | false |
| Q9Y2Z2-6 | MTO1 | −0.37146 | false |
| Q9HCU4 | CELSR2 | −0.37146 | false |
| Q9BVC5-1 | C2orf49 | −0.37146 | false |
| O75478-1 | TADA2A | −0.36959 | false |
| P55085 | F2RL1 | −0.36959 | false |
| Q9Y250-1 | LZTS1 | −0.36959 | false |
| Q86XK2-5 | FBXO11 | −0.36959 | false |
| O60869-1 | EDF1 | −0.36773 | false |
| Q9Y3A4 | RRP7A | −0.36773 | false |
| Q92917 | GPKOW | −0.36773 | true |
| Q13573 | SNW1 | −0.36587 | true |
| P49642 | PRIM1 | −0.36587 | true |
| Q9BY77-1 | POLDIP3 | −0.36587 | false |
| Q86YQ8-1 | CPNE8 | −0.36587 | false |
| Q9HBM1 | SPC25 | −0.36401 | true |
| O75925-2 | PIAS1 | −0.36401 | false |
| Q9NUQ3-1 | TXLNG | −0.36401 | false |
| A6NDU8 | C5orf51 | −0.36401 | false |
| Q9H246 | C1orf21 | −0.36401 | false |
| Q96BD0-1 | SLCO4A1 | −0.36401 | false |
| Q9NR28-1 | DIABLO | −0.36401 | false |
| Q96E09 | FAM122A | −0.36401 | true |
| O14965 | AURKA | −0.36401 | true |
| Q8NBJ4-1 | GOLM1 | −0.36401 | false |
| Q9NXR1-1 | NDE1 | −0.36216 | false |
| Q13287 | NM1 | −0.36216 | false |
| O60784-2 | TOM1 | −0.36216 | false |
| Q9H9V9-1 | JMJD4 | −0.36216 | false |
| Q969T9-1 | WBP2 | −0.36216 | false |
| Q96Q83-1 | ALKBH3 | −0.36216 | false |
| Q15796-1 | SMAD2 | −0.36216 | false |
| Q96EX3 | WDR34 | −0.34008 | false |
| P10646-1 | TFP1 | −0.34008 | false |
| Q9H5U6-1 | ZCCHC4 | −0.34008 | false |
| Q9H300-1 | PARL | −0.34008 | false |
| O75197 | LRP5 | −0.33825 | false |
| Q9P013 | CWC15 | −0.33825 | false |
| O95997 | PTTG1 | −0.33825 | false |
| Q9BZR9 | TRIM8 | −0.33825 | false |
| P30520 | ADSS | −0.33825 | true |
| O43291-1 | SPINT2 | −0.33643 | false |
| Q9H967 | WDR76 | −0.33643 | false |
| Q8NDV7-1 | TNRC6A | −0.33643 | false |
| O94991-1 | SLITRK5 | −0.33643 | false |
| P10619-1 | CTSA | −0.33643 | false |
| Q0VD83-4 | APOBR | −0.33643 | false |
| Q9BSY4-1 | CHCHD5 | −0.33643 | false |
| Q6NW34-1 | NEPRO | −0.33461 | false |
| Q9C099-1 | LRRCC1 | −0.33461 | false |
| Q9POR6 | GSKIP | −0.33461 | false |
| Q8TB03-1 | CXorf38 | −0.33461 | false |
| Q8WYQ3 | CHCHD10 | −0.33461 | false |
| Q9UGP4 | LIMD1 | −0.33461 | false |
| P62487 | POLR2G | −0.33461 | true |
| Q96HC4-1 | PDLIM5 | −0.33461 | false |
| Q14687-1 | GSE1 | −0.33461 | false |
| Q8IWC1-1 | MAP7D3 | −0.33461 | false |
| P29084 | GTF2E2 | −0.33461 | false |
| Q13136-1 | PPFIA1 | −0.33279 | false |
| Q7Z3T8-1 | ZFYVE16 | −0.33279 | false |
| P23588-1 | EIF4B | −0.33279 | false |
| Q15032-2 | R3HDM1 | −0.33279 | false |
| Q8TAP6-1 | CEP76 | −0.33279 | false |
| Q15397 | PUM3 | −0.33279 | false |
| Q8IVQ6 | ZDHHC21 | −0.33279 | false |
| Q13445 | TMED1 | −0.33279 | false |
| Q96NB1-1 | FOPNL | −0.33279 | false |
| Q8N3R9-1 | MPP5 | −0.33279 | false |
| P02538 | KRT6A | −0.33279 | false |
| Q9BUB5-1 | MKNK1 | −0.33279 | false |
| Q96D70 | R3HDM4 | −0.33279 | false |
| Q96NL6-1 | SCLT1 | −0.33279 | false |
| Q9UQ49-2 | NEU3 | −0.33097 | false |
| Q9H6T3-1 | RPAP3 | −0.33097 | false |
| Q96II8-1 | LRCH3 | −0.33097 | false |
| Q9UBH6-1 | XPR1 | −0.33097 | false |
| Q6PII3 | CCDC174 | −0.33097 | false |
| Q01581 | HMGCS1 | −0.31833 | true |
| O00571-1 | DDX3X | −0.31833 | false |
| Q13480-2 | GAB1 | −0.31653 | false |
| Q9NZZ3-1 | CHMP5 | −0.31653 | true |
| Q8N884-1 | MB21D1 | −0.31653 | false |
| Q9UBF8-2 | PI4KB | −0.31653 | true |
| O15427 | SLC16A3 | −0.31653 | false |

TABLE 6-continued

T6938051: 793 proteins
log2FC < −0.3 (142 essential proteins)

| Accession | Protein Name | log2FC (T6938051/ DMSO) | essential |
|---|---|---|---|
| Q96T21-1 | SECISBP2 | −0.31653 | false |
| O60292 | SIPA1L3 | −0.31653 | false |
| Q8WU10-1 | PYROXD1 | −0.31473 | true |
| O15162-1 | PLSCR1 | −0.31473 | false |
| Q9UIV1-1 | CNOT7 | −0.31473 | false |
| Q96CX6 | LRRC58 | −0.31473 | false |
| Q6PL18-1 | ATAD2 | −0.31473 | false |
| Q8WXD5 | GEMIN6 | −0.31473 | false |
| Q6P4F7-1 | ARHGAP11A | −0.31473 | false |
| Q5TFE4-1 | NT5DC1 | −0.31294 | false |
| Q1RMZ1 | BMT2 | −0.31294 | false |
| Q92536 | SLC7A6 | −0.31294 | false |
| P30622-2 | CLIP1 | −0.31294 | false |
| Q8WUA2 | PPIL4 | −0.31294 | false |
| Q9HCM7 | FBRSL1 | −0.31294 | false |
| Q9BRT9-1 | GINS4 | −0.31294 | true |
| Q68DQ2-3 | CRYBG3 | −0.31294 | false |
| Q96GQ7 | DDX27 | −0.31294 | true |
| P49768-1 | PSEN1 | −0.31115 | false |
| Q53R41-1 | FASTKD1 | −0.31115 | false |
| P49207 | RPL34 | −0.31115 | true |
| Q06413-1 | MEF2C | −0.31115 | false |
| O75081-1 | CBFA2T3 | −0.31115 | false |
| Q9C0C2-1 | TNKS1BP1 | −0.30936 | false |
| Q14320 | FAM50A | −0.30936 | true |
| Q8N2W9 | PIAS4 | −0.30936 | false |
| O14786-1 | NRP1 | −0.30936 | false |
| Q9UGN4-1 | CD300A | −0.30936 | false |
| Q4VC31 | CCDC58 | −0.30936 | false |
| P43121-1 | MCAM | −0.30936 | false |
| Q53HL2 | CDCA8 | −0.30936 | true |
| Q8NAG6-2 | ANKLE1 | −0.30936 | false |
| Q5H9F3-3 | BCORL1 | −0.30936 | false |
| Q76L83-1 | ASXL2 | −0.30757 | false |
| P53611 | RABGGTB | −0.30757 | true |
| P42768 | WAS | −0.30757 | false |
| Q9H4Z2-1 | ZNF335 | −0.30757 | true |
| Q9NWZ8 | GEMIN8 | −0.30757 | false |
| Q86U06-1 | RBM23 | −0.85988 | false |
| Q9HBU6-1 | ETNK1 | −0.85465 | false |
| P28908-1 | TNFRSF8 | −0.84944 | false |
| Q9P021 | CRIPT | −0.84425 | false |
| Q99808-2 | SLC29A1 | −0.83393 | false |
| O75330-3 | HMMR | −0.82879 | false |
| Q9Y3Y2-3 | CHTOP | −0.82623 | false |
| Q9BR77-1 | CCDC77 | −0.82623 | false |
| Q6PIJ6-1 | FBXO38 | −0.82113 | false |
| P13598 | ICAM2 | −0.82113 | false |
| Q96PQ1-1 | SIGLEC12 | −0.82113 | false |
| Q9NZM5 | NOP53 | −0.81604 | false |
| P17544-6 | ATF7 | −0.81604 | false |
| Q14162-1 | SCARF1 | −0.8135 | false |
| Q56NI9-1 | ESCO2 | −0.81097 | false |
| A1XBS5-1 | FAM92A | −0.79837 | false |
| Q96QD8-1 | SLC38A2 | −0.79837 | false |
| Q9UKK3 | PARP4 | −0.79586 | false |
| Q9NY93-1 | DDX56 | −0.79336 | true |
| Q9H3C7-1 | GGNBP2 | −0.79336 | false |
| Q9NRY2-1 | INIP | −0.79086 | false |
| O75563 | SKAP2 | −0.78588 | false |
| Q9Y3B1-1 | PRELID3B | −0.78339 | false |
| Q06609-1 | RAD51 | −0.78339 | true |
| Q14004-2 | CDK13 | −0.78339 | true |
| Q9H3U5-6 | MFSD1 | −0.78091 | false |
| Q9BSI4-1 | TINF2 | −0.78091 | false |
| Q13137-4 | CALCOCO2 | −0.77596 | false |
| Q9NYJ1-2 | COA4 | −0.77349 | false |
| Q8TB72-1 | PUM2 | −0.77349 | false |
| Q9NUJ7 | PLCXD1 | −0.77103 | false |
| O43683-1 | BUB1 | −0.77103 | true |
| Q9HAW4-1 | CLSPN | −0.76857 | false |
| P31350-2 | RRM2 | −0.76611 | true |
| O75794 | CDC123 | −0.76366 | true |
| Q5T6F0 | DCAF12 | −0.76121 | false |
| Q5W0B1 | RNF219 | −0.76121 | false |
| Q6PGQ7-1 | BORA | −0.75877 | false |
| Q8NDD1-1 | C1orf131 | −0.75877 | false |
| Q9UKL3 | CASP8AP2 | −0.67577 | false |
| Q6ZQX7-4 | LIAT1 | −0.67346 | false |
| Q9BWL3-1 | C1orf43 | −0.67116 | false |
| O15182 | CETN3 | −0.66658 | false |
| Q9P0K1-1 | ADAM22 | −0.66429 | false |
| Q6GTX8-1 | LAIR1 | −0.66429 | true |
| O95229-1 | ZWINT | −0.65972 | true |
| Q86YC3 | NRROS | −0.65972 | false |
| O43164-1 | PJA2 | −0.65745 | false |
| Q3SXY8-1 | ARL13B | −0.65745 | false |
| Q9Y2G9-1 | SBNO2 | −0.65745 | false |
| P46013-2 | MKI67 | −0.6529 | false |
| Q9BVS4-1 | RIOK2 | −0.6529 | true |
| Q86W74-1 | ANKRD46 | −0.65063 | false |
| Q9UBE8 | NLK | −0.64837 | false |
| Q9Y620-1 | RAD54B | −0.64386 | false |
| Q86WX3 | RPS19BP1 | −0.64386 | false |
| Q96K31-1 | C8orf76 | −0.64386 | false |
| Q8N302-1 | AGGF1 | −0.6416 | false |
| Q155Q3-1 | DIXDC1 | −0.63935 | false |
| Q8IWD4-1 | CCDC117 | −0.63935 | false |
| P62328 | TMSB4X | −0.63711 | false |
| Q6PCD5 | RFWD3 | −0.63263 | false |
| P18850 | ATF6 | −0.63039 | false |
| Q969Q4 | ARL11 | −0.63039 | false |
| P17813-1 | ENG | −0.63039 | false |
| Q8NC42 | RNF149 | −0.62593 | false |
| Q14542-1 | SLC29A2 | −0.62593 | false |
| P52569-3 | SLC7A2 | −0.62593 | false |
| Q9H9Y2 | RPF1 | −0.62593 | true |
| Q9BVW5 | TIPIN | −0.62371 | false |
| Q15056-1 | EIF4H | −0.62149 | false |
| Q9BSR8 | YIPF4 | −0.61927 | false |
| E9PRG8 | C11orf98 | −0.61927 | false |
| Q9BRT7 | LLPH | −0.61927 | false |
| Q9BUL5-1 | PHF23 | −0.61706 | false |
| P09326-1 | CD48 | −0.61706 | false |
| Q8NC54 | KCT2 | −0.61264 | false |
| Q6DKI1-1 | RPL7L1 | −0.61264 | true |
| Q14207 | NPAT | −0.61264 | true |
| Q9Y6H1 | CHCHD2 | −0.61043 | false |
| P14635-1 | CCNB1 | −0.60823 | false |
| P16150 | SPN | −0.60823 | false |
| Q71RC2-4 | LARP4 | −0.60603 | false |
| Q15036-1 | SNX17 | −0.60384 | false |
| O60828-1 | PQBP1 | −0.60384 | false |
| Q969Z4 | RELT | −0.55639 | false |
| Q14164-1 | IKBKE | −0.55639 | false |
| Q9BU40-4 | CHRDL1 | −0.55427 | false |
| Q13823 | GNL2 | −0.55427 | true |
| Q96C01 | FAM136A | −0.55216 | false |
| Q9NYZ3 | GTSE1 | −0.55216 | true |
| Q03112-3 | MECOM | −0.55216 | false |
| Q9BZM6 | ULBP1 | −0.55004 | false |
| Q14126 | DSG2 | −0.54793 | false |
| Q9NVF7-1 | FBXO28 | −0.54793 | false |
| Q53EZ4-1 | CEP55 | −0.54582 | false |
| Q9BT23 | LIMD2 | −0.54582 | false |
| Q9ULT8 | HECTD1 | −0.54582 | false |
| Q4KWH8-1 | PLCH1 | −0.54372 | false |
| O60232 | SSSCA1 | −0.54372 | false |
| Q9C0D0-1 | PHACTR1 | −0.54372 | false |
| Q02224-1 | CENPE | −0.54162 | true |
| Q96E29-1 | MTERF3 | −0.54162 | false |
| Q16206-1 | ENOX2 | −0.54162 | false |
| Q8N128-2 | FAM177A1 | −0.54162 | false |
| Q8WUX9-1 | CHMP7 | −0.54162 | false |
| Q5T3I0-3 | GPATCH4 | −0.53952 | false |
| Q9UPP1-4 | PHF8 | −0.53742 | false |

TABLE 6-continued

T6938051: 793 proteins
log2FC < −0.3 (142 essential proteins)

| Accession | Protein Name | log2FC (T6938051/ DMSO) | essential |
|---|---|---|---|
| O15287 | FANCG | −0.53742 | true |
| Q3B7T1-1 | EDRF1 | −0.53324 | false |
| P58335-4 | ANTXR2 | −0.53324 | false |
| O00488 | ZNF593 | −0.53116 | false |
| Q1MSJ5-3 | CSPP1 | −0.53116 | false |
| Q96AT1 | KIAA1143 | −0.53116 | false |
| Q9Y4C2-1 | TCAF1 | −0.52907 | false |
| P61024 | CKS1B | −0.52907 | false |
| Q9Y289 | SLC5A6 | −0.52699 | false |
| Q00765-1 | REEP5 | −0.52699 | false |
| Q9C035-1 | TRIM5 | −0.52699 | false |
| Q6ZUT1-2 | NKAPDI | −0.52699 | false |
| Q5JUQ0 | FAM78A | −0.52699 | false |
| Q7Z7K0 | CMC1 | −0.52699 | false |
| Q96GE4-1 | CEP95 | −0.52699 | false |
| Q9BZM4 | ULBP3 | −0.52492 | false |
| Q9NUL7 | DDX28 | −0.52492 | true |
| P10242-4 | MYB | −0.52492 | true |
| Q8TF40-3 | FNIP1 | −0.52284 | false |
| Q9ULF5-1 | SLC39A10 | −0.52077 | false |
| Q99755-3 | PIP5K1A | −0.52077 | false |
| Q96SZ6-3 | CDK5RAP1 | −0.52077 | false |
| Q99941-1 | ATF6B | −0.5187 | false |
| Q15119-1 | PDK2 | −0.48398 | false |
| P42892-1 | ECE1 | −0.48398 | false |
| Q8N2K1-3 | UBE2J2 | −0.48398 | true |
| Q8IXZ2-1 | ZC3H3 | −0.48398 | true |
| A4D1E9-1 | GTPBP10 | −0.48197 | false |
| Q14135-4 | VGLL4 | −0.48197 | false |
| Q16254 | E2F4 | −0.47995 | false |
| Q5T2R2-1 | PDSS1 | −0.47995 | true |
| Q92686 | NRGN | −0.47995 | false |
| Q6PGN9-1 | PSRC1 | −0.47794 | false |
| P35527 | KRT9 | −0.47794 | false |
| Q9HAW0-1 | BRF2 | −0.47794 | true |
| Q8NFZ0-2 | FBXO18 | −0.47794 | false |
| Q86XR8-1 | CEP57 | −0.47794 | true |
| P14923 | JUP | −0.47594 | false |
| O00192-1 | ARVCF | −0.47594 | false |
| P42081-1 | CD86 | −0.47393 | false |
| P24864-1 | CCNE1 | −0.47393 | false |
| Q9H4K7-1 | MTG2 | −0.47393 | true |
| O00716-1 | E2F3 | −0.47193 | false |
| O43566-7 | RGS14 | −0.46993 | false |
| O60927 | PPP1R11 | −0.46793 | false |
| Q96BD8-1 | SKA1 | −0.46793 | true |
| Q9H5Z6-1 | FAM124B | −0.46793 | false |
| Q9Y5A9-1 | YTHDF2 | −0.46594 | false |
| Q7Z7C8-2 | TAF8 | −0.46594 | true |
| Q9BQD3 | KXD1 | −0.46395 | false |
| P0CG12-1 | CHTF8 | −0.46395 | true |
| Q9H8N7 | ZNF395 | −0.46395 | false |
| O00220 | TNFRSF10A | −0.46395 | false |
| Q4J6C6-1 | PREPL | −0.46395 | false |
| Q96BH1 | RNF25 | −0.46196 | false |
| Q96MN5-1 | TCEANC2 | −0.46196 | false |
| P57076 | C21orf59 | −0.45997 | true |
| Q96EU6-1 | RRP36 | −0.45799 | false |
| Q8WUD4 | CCDC12 | −0.45799 | false |
| Q86WP2-2 | GPBP1 | −0.45799 | false |
| Q9H0K1 | SIK2 | −0.45799 | false |
| Q9BXS6-1 | NUSAP1 | −0.45799 | false |
| Q9NRP4 | SDHAF3 | −0.45799 | false |
| Q8NC26-1 | ZNF114 | −0.45799 | false |
| Q86V81 | ALYREF | −0.45601 | true |
| Q9UBT7-1 | CTNNAL1 | −0.45601 | false |
| Q8TD30-1 | GPT2 | −0.45601 | false |
| Q96B01-1 | RAD51AP1 | −0.45403 | false |
| Q8TCG1-1 | KIAA1524 | −0.45403 | false |
| Q6UWB1 | IL27RA | −0.43245 | false |
| Q8WUX2 | CHAC2 | −0.43051 | false |
| P61244-1 | MAX | −0.43051 | false |
| Q9BVC3 | DSCC1 | −0.43051 | true |
| O60779-1 | SLC19A2 | −0.43051 | false |
| Q86WA8-1 | LONP2 | −0.43051 | false |
| Q8IZT6-1 | ASPM | −0.43051 | false |
| Q15080-1 | NCF4 | −0.43051 | false |
| P25774-1 | CTSS | −0.43051 | false |
| Q14249 | ENDOG | −0.43051 | false |
| O60427-1 | FADS1 | −0.43051 | false |
| O60603 | TLR2 | −0.42857 | false |
| Q9NXG0-2 | CNTLN | −0.42857 | false |
| O95249-1 | GOSR1 | −0.42857 | false |
| Q8WW33 | GTSF1 | −0.42857 | false |
| Q5VTB9-3 | RNF220 | −0.42857 | false |
| Q49A88-1 | CCDC14 | −0.42857 | false |
| O60353-1 | FZD6 | −0.42857 | false |
| Q96L73-1 | NSD1 | −0.42857 | false |
| Q9UPN9-1 | TRIM33 | −0.42663 | false |
| P35790-1 | CHKA | −0.42663 | true |
| O95343 | SIX3 | −0.42663 | false |
| Q93096 | PTP4A1 | −0.42469 | false |
| O95159 | ZFPL1 | −0.42469 | false |
| P67809 | YBX1 | −0.42469 | false |
| Q9BW61 | DDA1 | −0.42469 | false |
| Q6Y7W6-1 | GIGYF2 | −0.42275 | true |
| Q8WUX1-1 | SLC38A5 | −0.42275 | true |
| P47224 | RABIF | −0.42082 | false |
| O75387-2 | SLC43A1 | −0.41889 | false |
| Q8N567 | ZCCHC9 | −0.41889 | false |
| Q8NBT0-1 | POC1A | −0.41889 | false |
| P15924-1 | DSP | −0.41889 | false |
| Q96BR5 | COA7 | −0.41889 | false |
| O75354-1 | ENTPD6 | −0.41889 | false |
| Q9NXW2-1 | DNAJB12 | −0.41696 | false |
| Q9H3S4-1 | TPK1 | −0.41696 | false |
| Q8IWZ8-1 | SUGP1 | −0.41696 | false |
| Q9H2H9 | SLC38A1 | −0.41696 | false |
| Q9NPF2-1 | CHST11 | −0.41696 | false |
| O43716 | GATC | −0.41504 | true |
| Q92834-1 | RPGR | −0.41504 | false |
| Q6NUS6-1 | TCTN3 | −0.41504 | false |
| Q86Y07-1 | VRK2 | −0.41504 | false |
| P20336 | RAB3A | −0.41504 | false |
| Q9NSA3 | CTNNBIP1 | −0.41504 | false |
| P38398-7 | BRCA1 | −0.39593 | true |
| P19256-1 | CD58 | −0.39593 | false |
| Q8WTV0-2 | SCARB1 | −0.39403 | false |
| Q96CS2-1 | HAUS1 | −0.39403 | true |
| Q9Y605 | MRFAP1 | −0.39403 | false |
| P37268-1 | FDFT1 | −0.39214 | false |
| Q14651 | PLS1 | −0.39214 | false |
| Q5MIZ7-1 | PPP4R3B | −0.39025 | false |
| Q96RT1-8 | ERBIN | −0.39025 | false |
| Q9NS28 | RGS18 | −0.38836 | false |
| O60266-1 | ADCY3 | −0.38836 | false |
| O43900-1 | PRICKLE3 | −0.38836 | false |
| O43805 | SSNA1 | −0.38836 | false |
| O94964-2 | SOGA1 | −0.38836 | false |
| Q9H8K7 | C10orf88 | −0.38647 | false |
| Q2TAL8 | QRICH1 | −0.38647 | true |
| Q9Y6N7-2 | ROBO1 | −0.38647 | false |
| Q17RS7 | GEN1 | −0.38647 | false |
| Q8TF74-1 | WIPF2 | −0.38647 | false |
| Q06547-1 | GABPB1 | −0.38647 | true |
| Q96R06 | SPAG5 | −0.38458 | true |
| Q6UWY0 | ARSK | −0.38458 | false |
| Q9H5V9-1 | CXorf56 | −0.38458 | false |
| Q9UQ84-1 | EXO1 | −0.38458 | false |
| Q9NVR5-1 | DNAAF2 | −0.38458 | false |
| Q9HC44 | GPBPIL1 | −0.38458 | false |
| Q9H078-2 | CLPB | −0.3827 | true |
| Q9H0W8-1 | SMG9 | −0.3827 | false |
| Q13490-1 | BIRC2 | −0.3827 | false |
| Q8NB14-1 | USP38 | −0.3827 | false |
| Q12899 | TRIM26 | −0.3827 | false |

TABLE 6-continued

T6938051: 793 proteins
log2FC < −0.3 (142 essential proteins)

| Accession | Protein Name | log2FC (T6938051/ DMSO) | essential |
|---|---|---|---|
| Q86Y91-2 | KIF18B | −0.3827 | false |
| Q96Q89-3 | KIF20B | −0.3827 | false |
| P25686-3 | DNAJB2 | −0.3827 | false |
| P54760-1 | EPHB4 | −0.3827 | false |
| P16070-1 | CD44 | −0.38082 | false |
| Q9UHQ1-2 | NARF | −0.38082 | false |
| Q9H3L0 | MMADHC | −0.38082 | false |
| O43791 | SPOP | −0.38082 | true |
| P08174-7 | CD55 | −0.37894 | false |
| Q9NRX1 | PNO1 | −0.37894 | false |
| Q9NW81-4 | DMAC2 | −0.37894 | false |
| Q9NY35-1 | CLDND1 | −0.37894 | false |
| Q7Z7F0-1 | KIAA0907 | −0.37894 | false |
| Q86U28-1 | ISCA2 | −0.37894 | true |
| P05067-1 | APP | −0.37707 | false |
| Q08357 | SLC20A2 | −0.3603 | false |
| Q7Z3K6-2 | MIER3 | −0.3603 | false |
| Q9UBR2 | CTSZ | −0.3603 | false |
| Q96EP9 | SLC10A4 | −0.3603 | false |
| P61966-1 | AP1S1 | −0.35845 | false |
| Q9BQI3-1 | EIF2AK1 | −0.35845 | false |
| P57060 | RWDD2B | −0.35845 | false |
| Q8NHQ1-1 | CEP70 | −0.35661 | false |
| O00308-1 | WWP2 | −0.35661 | false |
| Q9BV40 | VAMP8 | −0.35661 | false |
| Q9H501 | ESF1 | −0.35661 | false |
| Q8IV50-1 | LYSMD2 | −0.35476 | false |
| Q9Y4C8 | RBM19 | −0.35476 | true |
| P04183 | TK1 | −0.35476 | false |
| Q9UL33-1 | TRAPPC2L | −0.35292 | false |
| Q7Z5L9-1 | IRF2BP2 | −0.35292 | true |
| Q9UNY4-1 | TTF2 | −0.35292 | false |
| Q8TCB7-1 | METTL6 | −0.35292 | false |
| O95684-1 | FGFRIOP | −0.35107 | true |
| P00374-1 | DHFR | −0.35107 | true |
| O43592 | XPOT | −0.35107 | false |
| Q8WXW3-1 | PIBF1 | −0.35107 | false |
| O15145 | ARPC3 | −0.35107 | false |
| O95456-1 | PSMG1 | −0.35107 | true |
| Q5T3J3-1 | LRIF1 | −0.35107 | false |
| Q9UKA4 | AKAP11 | −0.35107 | false |
| Q8NA72-1 | POC5 | −0.35107 | false |
| Q9BRP8-1 | PYM1 | −0.35107 | false |
| O43715 | TRIAP1 | −0.35107 | true |
| P98082-1 | DAB2 | −0.34924 | false |
| Q9HD47-1 | RANGRF | −0.34924 | false |
| Q10589-1 | BST2 | −0.34924 | false |
| Q15527 | SURF2 | −0.3474 | false |
| Q9Y2J4-4 | AMOTL2 | −0.3474 | false |
| Q969K3-2 | RNF34 | −0.3474 | false |
| Q96DF8 | DGCR14 | −0.3474 | true |
| Q99550-1 | MPHOSPH9 | −0.34556 | false |
| Q14192-1 | FHL2 | −0.34556 | false |
| Q9BRT3 | MIEN1 | −0.34556 | false |
| Q96NB3 | ZNF830 | −0.34556 | true |
| Q53FT3 | HIKESHI | −0.34373 | false |
| P18124 | RPL7 | −0.34373 | true |
| P54132 | BLM | −0.34373 | false |
| P07108-5 | DBI | −0.3419 | false |
| Q5EBL8-2 | PDZD11 | −0.34008 | false |
| Q13614-1 | MTMR2 | −0.34008 | false |
| Q9NRN9 | METTL5 | −0.33097 | false |
| Q8WTP8-2 | AEN | −0.33097 | false |
| Q49ANO-1 | CRY2 | −0.33097 | false |
| P10586-1 | PTPRF | −0.32916 | false |
| Q92854-1 | SEMA4D | −0.32916 | false |
| Q9NW68-1 | BSDC1 | −0.32916 | false |
| Q5QP82-1 | DCAF10 | −0.32916 | false |
| Q9Y6V7-1 | DDX49 | −0.32735 | true |
| Q9NW13-1 | RBM28 | −0.32735 | true |
| Q12894-2 | IFRD2 | −0.32735 | false |
| Q12834 | CDC20 | −0.32735 | true |
| Q9Y5V0 | ZNF706 | −0.32735 | false |
| Q9Y5P8-1 | PPP2R3B | −0.32735 | false |
| Q8ND24-1 | RNF214 | −0.32735 | false |
| O14628-1 | ZNF195 | −0.32735 | false |
| O14545-1 | TRAFD1 | −0.32735 | false |
| Q01196-8 | RUNX1 | −0.32554 | true |
| Q969Q6-1 | PPP2R3C | −0.32554 | true |
| Q9NZ72-1 | STMN3 | −0.32554 | false |
| Q13188-2 | STK3 | −0.32554 | false |
| Q9H981-1 | ACTR8 | −0.32554 | true |
| P49366-1 | DHPS | −0.32554 | true |
| Q9PO31 | CCDC59 | −0.32554 | true |
| Q68CQ7-1 | GLT8D1 | −0.32373 | false |
| Q8ND25-1 | ZNRF1 | −0.32373 | false |
| Q969P6-1 | TOP1MT | −0.32373 | false |
| Q49AR2-1 | C5orf22 | −0.32373 | false |
| P48509 | CD151 | −0.32373 | false |
| O95619 | YEATS4 | −0.32373 | false |
| Q6PID6 | TTC33 | −0.32373 | false |
| Q8N6N3-1 | C1orf52 | −0.32193 | false |
| Q8WVP5 | TNFAIP8L1 | −0.32193 | false |
| Q86VI3 | IQGAP3 | −0.32193 | false |
| Q6IQ49-1 | SDE2 | −0.32193 | true |
| P49459-1 | UBE2A | −0.32193 | false |
| O95243-1 | MBD4 | −0.32013 | false |
| Q9Y3B9 | RRP15 | −0.32013 | false |
| Q6FI81-1 | CIAPIN1 | −0.32013 | false |
| Q96ES7 | SGF29 | −0.32013 | false |
| Q9H9L3 | ISG20L2 | −0.32013 | true |
| Q6NUJ5-1 | PWWP2B | −0.31833 | false |
| Q9BX70-1 | BTBD2 | −0.31833 | false |
| Q9H446-1 | RWDD1 | −0.31833 | false |
| Q96C57 | C12orf43 | −0.31833 | false |
| O95801 | TTC4 | −0.31833 | false |
| Q969W8-2 | ZNF566 | −0.31833 | false |
| Q96LB3-1 | IFT74 | −0.30757 | false |
| Q99614 | TTC1 | −0.30579 | true |
| Q6ULP2-1 | AFTPH | −0.30579 | false |
| Q8IVU3-1 | HERC6 | −0.30579 | false |
| O95858 | TSPAN15 | −0.30579 | false |
| Q9ULH7-5 | MKL2 | −0.30579 | false |
| Q13686 | ALKBH1 | −0.30579 | false |
| Q9Y2R4 | DDX52 | −0.30579 | true |
| O75528-1 | TADA3 | −0.30579 | true |
| Q1ED39 | KNOP1 | −0.30579 | false |
| Q9NS87-1 | KIF15 | −0.30579 | false |
| Q56P03 | EAPP | −0.30401 | false |
| Q9UJJ7 | RPUSD1 | −0.30401 | false |
| Q9BTL3 | FAM103A1 | −0.30401 | false |
| Q96EC8-1 | YIPF6 | −0.30401 | false |
| Q15050 | RRS1 | −0.30401 | true |
| P08670 | VIM | −0.30401 | false |
| Q460N5-6 | PARP14 | −0.30401 | false |
| Q9H4D5-1 | NXF3 | −0.30401 | false |
| Q8IX90-1 | SKA3 | −0.30401 | true |
| Q8IY63-1 | AMOTL1 | −0.30223 | false |
| Q96GX2 | ATXN7L3B | −0.30223 | false |
| Q96A57-2 | TMEM230 | −0.30223 | false |
| Q9P2W1-1 | PSMC3IP | −0.30045 | false |
| Q14692 | BMS1 | −0.30045 | true |
| Q3V6T2-1 | CCDC88A | −0.30045 | false |
| Q96T68-1 | SETDB2 | −0.30045 | false |
| O95166 | GABARAP | −0.30045 | false |
| Q9UG63-2 | ABCF2 | −0.30045 | false |

The invention claimed is:

1. An in vitro method for identifying a compound having the ability to degrade one or more protein(s),
the method comprising contacting a compound with a wild-type cell and with a mutated cell, wherein the mutated cell comprises a hypomorphic mutation or inactivation of at least one member or regulator of an E3 ubiquitin ligase complex;
wherein the compound is determined to degrade one or more protein(s) if the level of the one or more protein(s) of the wild-type cell is decreased compared to the mutated cell.

2. The method of claim 1, wherein the compound is determined to degrade one or more protein(s) if the viability of the wild-type cell is decreased compared to the viability of the mutated cell.

3. The method of claim 2, wherein the viability is determined by measuring the $LC_{50}$ value.

4. The method of claim 2, wherein the compound is determined to degrade one or more protein(s) if the viability of the wild-type cell is decreased by at least 2 fold compared to the mutant cell.

5. The method of claim 1, wherein the ability to degrade one or more protein(s) comprises a decreased level of the one or more protein(s) by at least 2-fold compared to the level of the one or more protein(s) in the mutant cell.

6. The method of claim 1, wherein the hypomorphic mutation or inactivation of the at least one member or regulator of the E3 ubiquitin ligase complex results in a decreased functionality of said E3 ubiquitin ligase compared to the functionality of a E3 ubiquitin ligase in the wild-type cell.

7. The method of claim 1, wherein the at least one member of the E3 ubiquitin ligase complex is selected from the group consisting of CUL4B, DDB1, RBX1, UBE2G1, and CUL4A; and wherein the at least one regulator of the E3 ubiquitin ligase complex is selected from the group consisting of UBE2M, UBA3, UBE2F, COPS1, COPS2, COPS3, COPS4, COPS5, COPS6, COPS7A, COPS7B, COPS8, DCUN1D1, DCUN1D2, DCUN1D3, DCUN1D4, DCUN1D5.

8. The method of claim 1, wherein the at the at least one member or regulator of the E3 ubiquitin ligase complex is CUL4B or DDB1.

9. The method of claim 1, wherein the hypomorphic mutation or inactivation is induced by Cas9/CRISPR, inhibitors, antibodies, monobodies, nanobodies, nucleic acid molecules, or any combinations thereof or by a knock out.

10. The method of claim 1, wherein the wild-type cell and the mutated cell are each a cancer cell.

11. The method of claim 10, wherein the cancer cell is selected from the group consisting of a leukemia cell; a pancreatic cancer cell; a lung cancer cell; a gastric cancer cell; a melanoma cell; a sarcoma cell; a colon cancer cell; or a neuroblastoma cell.

12. The method of claim 1, wherein the one or more protein(s) is one or more protein(s) associated with cancer, metabolic disorders, neurologic disorders or infectious diseases.

13. The method of claim 12, wherein the one or more protein(s) associated with cancer are selected from the group consisting of DNA-binding proteins; RNA binding proteins; scaffolding proteins; GTPases; solute carriers; kinases; phosphatases; bromodomain- and chromodomain containing proteins; G-protein coupled receptors; anti-apoptotic proteins; immune regulators; and combinations thereof;
wherein the one or more protein(s) associated with metabolic disorders are selected from the group consisting of ARX, SUR, DPP4 and SGLT;
wherein the one or more protein(s) associated with neurologic disorders are selected from the group consisting of Tau and beta-amyloid; and
wherein the one or more protein(s) associated with infectious diseases are selected from the group consisting of CCR5 and PLA2G16.

14. The method of claim 1, wherein the wild-type cell and the mutated cell are of the same cell type.

15. The method of claim 1, wherein the only difference between the wild-type cell and the mutated cell is the hypomorphic mutation or inactivation of at least one member or regulator of an E3 ubiquitin ligase complex comprised in the mutated cell, which results in a reduced activity or impairment of the E3 ubiquitin ligase complex in the mutated cell compared to the wild-type cell.

16. The method of claim 9, wherein the nucleic acid molecules are selected from the group consisting of antisense oligonucleotides, siRNA, shRNA, and miRNA.

17. The method of claim 11, wherein the cancer cell is a KBM-7 cell.

18. The method of claim 13, wherein the one or more protein(s) associated with cancer are selected from the group consisting of ESR1, AR, MYB, MYC, HRAS, NRAS, KRAS, CCNK, CDK12, CDK13, CDK4, CDK6, CDK9, EGFR, SRC, PDGFR, ABL1, HER2, HER3, BCR-ABL, MEK1, ARAF, BRAF, CRAF, BRD2, BRD3, BRD4, CBP, p300, ATAD2, SMARCA2, SMARCA4, PBRM1, SHP2, PTPN1, PTPN12, PDL1, and combinations thereof.

* * * * *